(12) United States Patent
Lo et al.

(10) Patent No.: US 12,247,029 B2
(45) Date of Patent: Mar. 11, 2025

(54) HETEROCYCLIC COMPOUNDS AS CLASS II PHOSPHOINOSITIDE 3-KINASE INHIBITORS

(71) Applicant: Forschungsverbund Berlin e.V., Berlin (DE)

(72) Inventors: Wen-Ting Lo, Berlin (DE); Hassane Belabed, Paris (FR); Volker Haucke, Kleinmachnow (DE); Marc Nazare, Berlin (DE); Murat Kucukdisli, Berlin (DE)

(73) Assignee: Forschungsverbund Berlin e.V., Berlin (DE)

( * ) Notice: Subject to any disclaimer, the term of this patent is extended or adjusted under 35 U.S.C. 154(b) by 1052 days.

(21) Appl. No.: 16/972,501

(22) PCT Filed: Jun. 7, 2019

(86) PCT No.: PCT/EP2019/065009
§ 371 (c)(1),
(2) Date: Dec. 4, 2020

(87) PCT Pub. No.: WO2019/234237
PCT Pub. Date: Dec. 12, 2019

(65) Prior Publication Data
US 2022/0332717 A1    Oct. 20, 2022

(30) Foreign Application Priority Data

Jun. 7, 2018 (EP) .................................. 18176603

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ............................ C07D 487/04; C07D 239/72
See application file for complete search history.

(56) References Cited

FOREIGN PATENT DOCUMENTS

WO    WO 2005/049613 A1    6/2005
WO    WO 2016/040951 A1    3/2016

OTHER PUBLICATIONS

International Search Report and Written Opinion in PCT/EP2019/065009, issued Jul. 26, 2019.
Database Registry [Online], Chemical Abstracts Service, Columbus, Ohio, US; Apr. 19, 2007 (Apr. 19, 2007), XP002784072, retrieved from STN Database accession No. 930848-79-6, abstract.
Database Registry [Online], Chemical Abstracts Service, Columbus, Ohio, US; Dec. 24, 2008 (Dec. 24, 2008), XP002784073, retrieved from STN Database accession No. 1089571-23-2, abstract.
Database Registry [Online] 1,5, Chemical Abstracts Service, Columbus, Ohio, US; Dec. 25, 2008 (Dec. 25, 2008), XP002784074, retrieved from STN Database accession No. 1089999-59-6, abstract.
Database Registry [Online] 1,5, Chemical Abstracts Service, Columbus, Ohio, US; Dec. 28, 2008, XP002784075, retrieved from STN Database accession No. 1090939-76-6, abstract.
Mountford, Simon J., et al., "Class II but Not Second Class-Prospects for the Development of Class II PI3K Inhibitors," ACS Medicinal Chemistry Letters, vol. 6, No. 1, Jan. 8, 2015, pp. 3-6.
Falasca, Marco, et al., "Class II Phosphoinositide 3-Kinases as Novel Drug Targets" Journal of Medicinal Chemistry, vol. 60, No. 1, Oct. 21, 2016, pp. 47-65.
Chauhan, Prem M.S., et al., "Syntheses of novel heterocycles as anticancer agents," Bioorganic & Medicinal Chemistry, 13 (2005) 3513-3518.

*Primary Examiner* — Susanna Moore
(74) *Attorney, Agent, or Firm* — Knobbe, Martens, Olson & Bear, LLP

(57) ABSTRACT

Compounds of the following formula:

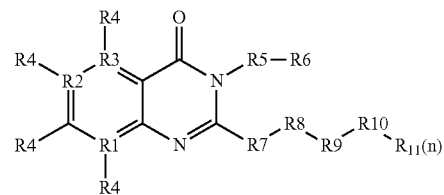

having defined substituents. The compounds can inhibit class II phosphoinositide 3-kinase (PI3K) signaling and are useful for the treatment of a medical condition associated with defective PI3K signaling, such as myopathy, cancer, diabetes, thrombosis or cardiovascular disease.

15 Claims, 15 Drawing Sheets

Class I PI3K – lipid product PI(3,4,5)P$_3$ and/or PI(3,4)P$_2$

Class IA (p110α, β, δ)

Regulatory subunit

Class IB (p110γ)

Regulatory subunit
p101
p87

Class II PI3K – lipid product PI(3,4)P$_2$ and/or PI(3,4)P

PI3K-C2α, β

PI3K-C2γ

Class III PI3K – lipid product PI(3)P

Vps34

Complex I
• Beclin 1
• Atg14
• NRBF2

Complex II
• Beclin 1
• UVRAG

Regulatory subunit
Vps15

MYRISTOYLATION

Scale  — = 100 amino acids   —//— = 400 amino acids

A

Wortmannin
Steroid

PI-103
Pyridinylfuranopyrimidine

PIK-93
Phenylthiazole

PIK-124
Aryl thiazolidinone

KU-55933
Morpholinopyranone

PIK-75
Imidazopyridine

LY294002 (TGX-115, PIK-108)
Morpholinochromone

PIK-90
Imidazoquinazoline

AMA-37 (IC60211, IC86621)
Morpholinopehnol

PIK-39 (IC87114, PIK-23)
Quinazolinone purine

TGX-286
Pyridinylchromone

Fig. 2 (cont.)

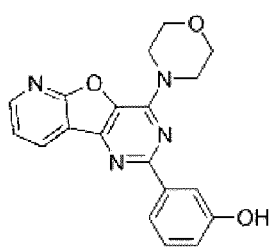

PI-103
p110α: IC$_{50}$ = 0.002 μM
p110β: IC$_{50}$ = 0.003 μM
p110δ: IC$_{50}$ = 0.003 μM
p110γ: IC$_{50}$ = 0.015 μM
mTOR: IC$_{50}$ = 0.030 μM
PI3KC2α: IC$_{50}$ = 1 μM
PI3KC2β: IC$_{50}$ = 0.026 μM

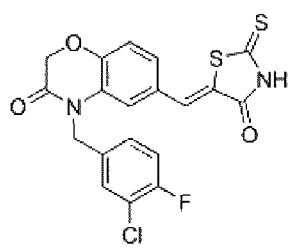

PIK124
p110α: IC$_{50}$ = 0.023 μM
p110β: IC$_{50}$ = 1.1 μM
p110δ: IC$_{50}$ = 0.34 μM
p110γ: IC$_{50}$ = 0.054 μM
mTOR: IC$_{50}$ = 9 μM
PI3KC2α: IC$_{50}$ = 0.14 μM
PI3KC2β: IC$_{50}$ = 0.37 μM

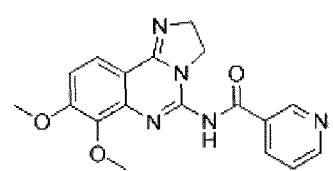

PIK90
p110α: IC$_{50}$ = 0.011 μM
p110β: IC$_{50}$ = 0.350 μM
p110δ: IC$_{50}$ = 0.058 μM
p110γ: IC$_{50}$ = 0.018 μM
mTOR: IC$_{50}$ = 1.05 μM
PI3KC2α: IC$_{50}$ = 0.047 μM
PI3KC2β: IC$_{50}$ = 0.064 μM

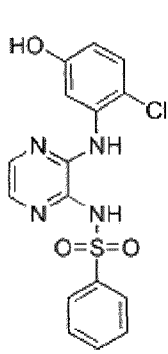

Freitag 30
p110α: IC$_{50}$ = >10 μM
p110β: IC$_{50}$ = >10 μM
p110δ: IC$_{50}$ = >10 μM
p110γ: IC$_{50}$ = >10 μM
mTOR: IC$_{50}$ = n.d.
PI3KC2α: IC$_{50}$ = >10 μM
PI3KC2β: IC$_{50}$ = 2.71 μM

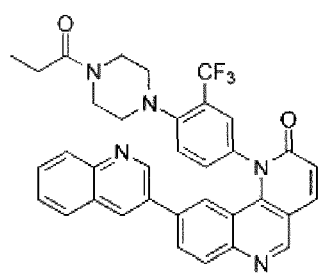

Torin1
p110α: IC$_{50}$ = 0.250 μM
p110β: IC$_{50}$ = n.d.
p110δ: IC$_{50}$ = 0.564 μM
p110γ: IC$_{50}$ = 0.171 μM
mTOR: IC$_{50}$ = 0.004 μM
PI3KC2α: IC$_{50}$ = 0.176 μM
PI3KC2β: IC$_{50}$ = 0.549 μM

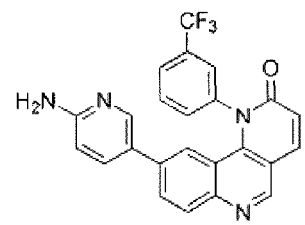

Torin2
p110α: IC$_{50}$ = 0.005 μM
p110β: IC$_{50}$ = n.d.
p110δ: IC$_{50}$ = 0.018 μM
p110γ: IC$_{50}$ = 0.006 μM
mTOR: IC$_{50}$ = 0.003 μM
PI3KC2α: IC$_{50}$ = 0.028 μM
PI3KC2β: IC$_{50}$ = 0.025 μM

1
PI3KC2α: IC$_{50}$ = 2.6 μM

C2a_Inh1

2
PI3KC2α: IC$_{50}$ = 4.2 μM

6
PI3KC2α: IC$_{50}$ = 0.56 μM

C2a_Inh2

B

PI3KC2α: IC$_{50}$ = 16.9μM

PI3KC2α: IC$_{50}$ = 50% inhibition at ca 50μM

PI3KC2α: IC$_{50}$ = 45μM

PI3KC2α: IC$_{50}$ = 10.5μM

C

Dihydropteridinones

Torins

Quinolones

| Example compound 1 | Example compound 2 | Example compound 11 |
|---|---|---|
| 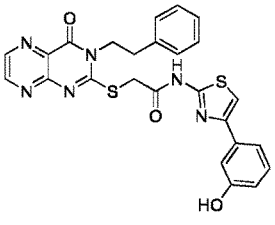 | 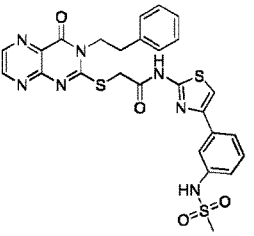 | 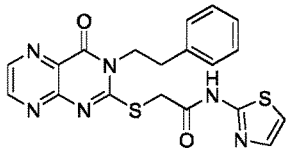 |
| Inhibition @10μM PI3KC2α: 98%<br>Inhibition @3μM PI3KC2α: 93%<br>Inhibition @1μM PI3KC2α: 89%<br>Inhibition @10μM PI3KC2β: 81%<br>Inhibition @3μM PI3KC2β: 56%<br>Inhibition @1μM PI3KC2β: 41%<br>Inhibition @10μM PI3KC2γ: 19%<br>Inhibition @3μM PI3KC2γ: 16%<br>Inhibition @1μM PI3KC2γ: 10%<br><br>Lipid kinase panel @10μM: no inhibition >50% inhibition | Inhibition @10μM PI3KC2α: 96%<br>Inhibition @3μM PI3KC2α: 96%<br>Inhibition @1μM PI3KC2α: 86%<br>Inhibition @10μM PI3KC2β: 19%<br>Inhibition @3μM PI3KC2β: 12%<br>Inhibition @1μM PI3KC2β: 12%<br>Inhibition @10μM PI3KC2γ: 16%<br>Inhibition @3μM PI3KC2γ: 14%<br>Inhibition @1μM PI3KC2γ: 17%<br><br>Lipid kinase panel @10μM: no inhibition >50% inhibition<br><br>General kinase panel @10μM, no inhibition >20% inhibition. | Inhibition @10μM PI3KC2α: 97%<br>Inhibition @3μM PI3KC2α: 95%<br>Inhibition @1μM PI3KC2α: 88%<br>Inhibition @10μM PI3KC2β: 68%<br>Inhibition @3μM PI3KC2β: 49%<br>Inhibition @1μM PI3KC2β: 13%<br>Inhibition @10μM PI3KC2γ: 76%<br>Inhibition @3μM PI3KC2γ: 58%<br>Inhibition @1μM PI3KC2γ: 32%<br><br>Lipid kinase panel @10μM: no inhibition >50% inhibition<br><br>General kinase panel @10μM, no inhibition >20% inhibition. |

HETEROCYCLIC COMPOUNDS AS CLASS II PHOSPHOINOSITIDE 3-KINASE INHIBITORS

The invention relates to chemical compounds useful as inhibitors of class II phosphoinositide 3-kinase (PI3K) signalling. The invention further relates to the medical use of inhibitors of class II phosphoinositide 3-kinase (PI3K) signalling in the treatment of medical conditions associated with defective and/or pathologic class II phosphoinositide 3-kinase (PI3K) signaling, such as myopathy, cancer, diabetes and cardiovascular disease.

BACKGROUND OF THE INVENTION

The phosphoinositide 3-kinases (PI3Ks) are a family of lipid kinases central to regulating a wide range of important intracellular processes. PI3Ks orchestrate cell responses including mitogenic signaling, cell survival and growth, metabolic control, vesicular trafficking, degranulation, cytoskeletal rearrangement and migration. PI3Ks catalyze the phosphorylation of the 3-OH group on the inositol ring of phosphatidylinositol. Based on substrate preference, amino acid sequence, and structure, three classes of PI3Ks are identified (FIG. 1).

Class I PI3Ks are the earliest discovered PI3Ks. They form hetero-dimers by association of a catalytic subunit and a regulatory subunit that produce $PI(3,4,5)P_3$. Class I PI3Ks are further classified into class IA (p110α, β, and δ) and class IB (p110γ), based on distinct regulatory subunits (FIG. 1). The structural similarity between kinase domains of class I PI3Ks and protein kinases implies that PI3Ks have protein kinase activity in addition to lipid kinase activity.

In contrast to class I, relatively little is known about class II PI3K. Class II PI3Ks produce $PI(3)P$ or $PI(3,4)P_2$, with varying levels of efficiency that may be related to isoform and cell type. There are three class II PI3K isoforms (PI3KC2α, PI3KC2β, and PI3KC2γ) in vertebrates, but only one member exists in worm and fly. Similar to the catalytic subunit of class I PI3Ks, all class II isoforms contain a Ras binding domain (RBD), a C2 domain (C2), a helical domain (HD), and a kinase domain, but have unique disordered regions in their N-terminus and are extended by two lipid binding domains (PX and C2 domain) at their C-terminus (FIG. 1). Unlike class I PI3K, class II PI3K kinases lack regulatory subunits and act as monomers.

Class II PI3K isoforms have been demonstrated to couple signaling to membrane traffic. This indicates that distinct mechanisms serve to recruit PI3KII and that their lipid product has unique roles [$PI(3)P$ and/or $PI(3,4)P_2$]. Recently, the α isoform has been shown to synthesize $PI(3,4)P_2$ on endocytic pits at the plasma membrane, where $PI(3,4)P_2$ is required for membrane constriction prior to vesicle fission (Posor et al, Nature, 2013, July 11; 499(7457):233-7) and is required to internalize VEGF receptor in endothelial cells (Yoshioka et al., Nat. Med. 2012, 18, 1560-1569).

Besides, PI3KC2a knock-down impairs autophagy at least in some cells and the maturation of endocytic vesicles. PI3KC2a can also generate $PI(3)P$ and regulate the formation of a $PI(3)P$ pool at pericentriolar recycling endosomes (PRE) required for Rab11 and Shh pathway activation and primary cilia formation. Moreover, the C2β isoform regulates nutrient signaling by suppressing mTORC1 signaling via local production of $PI(3,4)P_2$ at late endosomes or lysosomes (Marat et al, Science, 2017, June 2; 356(6341): 968-972).

Endothelial-specific PI3KC2a knock-out mice display a vascular barrier function defect indicating that PI3KC2a is involved in angiogenesis (Yoshioka et al., Endothelial PI3K-C2alpha, a class II PI3K, has an essential role in angiogenesis and vascular barrier function. Nat. Med. 2012, 18, 1560-1569). In addition, the liver-specific C2γ isoform has recently been shown to produce an endosomal $PI(3,4)P_2$ pool needed for sustained Akt2 activation following insulin stimulation (Braccini et al., 2015, Nat. Commun. 2015, 6, 7400). Based on data accumulated to this point in time, class II PI3Ks appear to be involved in cancer, cardiovascular disease, and diabetes, amongst other diseases (Falasca et al, 2016, J. Med. Chem. 60, 1, 47-65).

There is only one member of class III PI3K (also termed Vps34) in eukaryotes. It was initially identified as a kinase regulating endosome/lysosome sorting in yeast. Vps34 shares the same PI3K core domain with class I PI3Ks, but lacks the ABD and Ras binding domains (FIG. 1).

Cell permeable small-molecule inhibitors of kinases are excellent tools to directly and quickly unravel the functional consequences of kinase inactivity and represent useful medical agents. A key challenge for the generation of such inhibitors is their specificity. For PI3Ks, the two widely used primary pharmacological tools available, wortmannin and LY294002, have off-target effects on other members of this family. Therefore, during the past decade more chemotypically diverse small molecule inhibitors have been developed in order to specifically target specific PI3K isoforms.

For a spectrum of PI3K inhibitors with different degrees of selectivity, different chemotypes have been observed. The most selective compounds include the quinazolinone purine inhibitors (e.g. TGX-115, TGX286, and PIK-108) for PI3K δ and imidazopyridine inhibitors (e.g. PIK75) for PI3K α (FIG. 2A). These compounds exhibit >100-fold selectivity between their primary targets and other class I PI3Ks. Other chemotypes of inhibitors (i.e. aryl thiazolidinones, pyridinylfuranopyrimidines, phenylthiazoles, and imidazoquinazolines) were found to inhibit multiple PI3Ks to a variable extent. Additional class I PI3K inhibitors are described in Falasca et al, 2016, J. Med. Chem. 60, 1, 47-65.

Recently, the class III PI3K (Vps34) specific inhibitors, SAR304/VPS34IN1 and SAR405, have been developed. These were shown to affect late endosomal/lysosomal compartments, to inhibit autophagy and to rescue defective endosomal exocytosis in absence of the PI(3)P phosphatase MTM1 (Ketel et al, Nature, 2016 Jan. 21; 529(7586):408-12).

In contrast to class I and III PI3Ks, for class II PI3Ks few specific inhibitors exist, also because of the lack of structural information. At present, only a limited number of lead inhibitors targeting class II PI3K specific (3 and j isoforms have been identified. They act in a low µM to high nM range, but the compound/kinase binding mode and the biological effects of these compounds remain questionable. Furthermore, specific PI3KC2a inhibitors have not yet been identified. A number of compounds that show class II PI3K inhibitory activity in vitro are also disclosed in Mountford, S. J. et al, (ACS Med. Chem. Lett. 2015, 6, 3-6), as shown in FIG. 2B.

A number of compounds have been disclosed in the art with a structure similar to those compounds of the present invention. For example, chemical compound structures are disclosed in the Chemical Abstracts Service under XP002784072 (Database accession no. 930848-79-6), XP002784073 (Database accession no. 1089571-23-2), XP002784074 (Database accession no. 1089999-59-6) and XP002784075 (Database accession no. 1090939-76-6).

However, no indications are made regarding the activity of the compounds or whether these structures could exhibit activity as inhibitors of class II phosphoinositide 3-kinase (PI3K) signalling.

WO 2005/049613 and WO 2016/040951 disclose various heterocyclic derivatives, described as Vanilloid-1-Receptor (VRI)-Modulators and Hedgehog-inhibitors, respectively, with some structural similarity to the compounds of the present invention. No mention is made of a possible activity as inhibitors of class II phosphoinositide 3-kinase (PI3K) signalling.

Mountford et al (Medicinal Chemistry Letters, vol. 6, no. 1, 2015, p. 3-6) and Falasca et al (Journal of Medicinal Chemistry, vol. 60, no. 1, 2016, p. 47-65) are review articles that present comments on prospects for the development of inhibitors of class II phosphoinositide 3-kinase (PI3K) signalling and class II phosphoinositide 3-kinases as potential drug targets. The chemical structures disclosed therein are distinct from those of the present invention.

In light of the lack of established class II PI3Ks, the present invention sought the development of class II PI3Ks inhibitors, in particular specific inhibitors of PI3KC2α-mediated PI(3,4)P$_2$ production, in order to provide novel compounds useful in research and medical treatment. In light of the prior art, and considering the relevance of class II PI3Ks in multiple medical conditions, there remains a significant need in the art to provide compounds for the inhibition of class II PI3Ks.

SUMMARY OF THE INVENTION

In light of the prior art the technical problem underlying the present invention is to provide means for the inhibition of class II PI3Ks.

This problem is solved by the features of the independent claims. Preferred embodiments of the present invention are provided by the dependent claims.

The present invention therefore relates to a compound according to Formula 1,

Formula 1

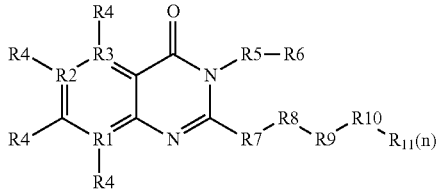

wherein
R1: N or C;
R2: N or C;
R3: N or C;
wherein at least one of R1, R2 and R3 is N; preferably wherein R1 and R3 are N and R2 is C;
R4: can be the same or different, H, halogen (preferably Cl, Br, F), C1-C5 alkyl (preferably C1-C3 alkyl), C1-C5 haloalkyl, hydroxyl, alkoxy (preferably —OCH$_3$, —OCH$_2$CH$_3$), cycloalkyl (preferably C3-C6 cycloalkyl), —CN, carbonyl, carboxyl, carboxy ester, alkoxy, aldehyde, trihalide methyl ester, primary, secondary or tertiary amine, amide, imide, carbamate, carboxamide, nitro, sulfide, sulfurtrihalide, sulfurpentahalide, sulfinyl, sulfonyl, sulfino, or sulfo, sulfonamide, —OCF$_3$;
wherein when R1, R2, R3 is N, R4 attached thereto is absent;
R5: absent (covalent bond to R6), C1-C5 alkyl (preferably C2 alkyl), cycloalkyl (preferably C3-C6 cycloalkyl), aryl (preferably phenyl or napthyl), C1-C5 alkyl-cycloalkyl, C1-C5 alkyl-aryl, partially saturated bicyclic aryl (preferably indenyl, a benzene ring fused with a cyclopentane ring, which is bonded to the adjacent N of Formula 1);
wherein R5 is optionally substituted with one or more halogens (preferably Cl, Br, F), C1-C5 alkyl (preferably C1-C3 alkyl), C1-C5 haloalkyl, hydroxyl, alkoxy (preferably OCH$_3$, OCH$_2$CH$_3$);
wherein R5 is optionally substituted with at least two substituents, said two substituents forming R6, attached to adjacent atoms of R5, to form as R6 a 5- to 8-membered saturated, partially unsaturated or aromatic cyclic group comprising said adjacent two atoms of R5 (preferably wherein R5-R6 is indanyl or fluorenyl);
R6: H, alkyl (preferably C1-C5 alkyl), cycloalkyl (preferably C3-C6 cycloalkyl), aryl (preferably phenyl), heterocyclyl, heteroaryl,
wherein R6 is optionally substituted with one or more halogens (preferably Cl, Br, F), C1-C5 alkyl (preferably C1-C3 alkyl), C1-C5 haloalkyl, hydroxyl, alkoxy (preferably OCH$_3$, OCH$_2$CH$_3$), C2-C10 alkynyl, C3-C8 cycloalkyl, a 5- or 6-membered heterocyclyl or heteroaryl comprising one or more of N, O and/or S (preferably tetrazole), carbonyl, C0-C5 alkyl carboxyester (preferably —(CO)O—CH$_3$ or —(CO)O—C(CH$_3$)$_3$), carboxamide, C0-C5 alkyl carboxamide, primary, secondary or tertiary amine, carbamate, amide amine, nitro, —CN, O, sulfide, amine sulfoxide, sulfonamide, said sulfonamide optionally substituted with a 5- or 6-membered heterocyclyl or heteroaryl comprising one or more of N, O and/or S (preferably thiadiazole), sulfonamide amine, sulfoxide, sulfone, sulfonamide haloalkyl, cyano (preferably CN), —OCF$_3$, carbamate, imide, —SF$_3$, —SF$_5$;
R7: S, absent (covalent bond to R8), NR, wherein R is H, C1-C5 alkyl (preferably C1-C3 alkyl), C1-C5 haloalkyl, alkoxy (preferably OCH$_3$, OCH$_2$CH$_3$);
R8: C1-C5 alkyl (preferably C1 alkyl), cycloalkyl (preferably C3-C6 cycloalkyl), wherein R8 is optionally substituted with one or more halogens (preferably Cl, Br, F), C1-C5 alkyl (preferably C1 alkyl), C1-C5 haloalkyl, hydroxyl, alkoxy (preferably OCH$_3$, OCH$_2$CH$_3$);
R9: absent (covalent bond to R10), amide (preferably —CONH—), amine (preferably —NH—), urea (preferably —NHCONH—), sulfonamide (preferably —SO$_2$NH—), carbonyl (preferably —CO—);
R10: 5-membered heterocyclyl or heteroaryl (except for pyrazolyl, tetrahydrofurfuryl), preferably a 5-membered aromatic heterocycle comprising one or more of N, O and/or S, more preferably comprising N and S, or N and O;
wherein optionally a C1-C5 (preferably C1-C2) alkyl is positioned between R9 and R10;
R11(n): n is 0-5 (preferably 1), may be the same or different, halogen (preferably Cl, Br, F), C1-C5 alkyl (preferably C1 alkyl), CN, C1-C5 haloalkyl, hydroxyl, alkoxy (preferably OCH$_3$, OCH$_2$CH$_3$), alkoxycarbonyl (preferably —COOCH$_3$, —CH$_2$COOCH$_3$, —CH$_2$CH$_2$COOCH$_3$), cycloalkyl (preferably C3-C6 cycloalkyl), aryl (preferably phenyl), C1-C5 alkyl-cycloalkyl, C1-C5 alkyl-aryl, heterocyclyl, heteroaryl, carboxamide, C0-C5 alkyl carboxamide (preferably $CON(CH_2CH_2)_2O$);
wherein optionally, two R11 form, together with two carbon atoms of R10 to which they are attached, a 5-, 6-, 7- or 8-membered cyclic residue, (preferably forming with R10 a condensed bicyclic aromatic group) comprising two carbon atoms of R10 and optionally further comprising 0, 1, 2, 3 or 4 heteroatoms, said heteroatoms selected independently from nitrogen, sulfur or oxygen, wherein said cyclic residue as R11 is saturated, partially unsaturated or aromatic, and optionally substituted by one or more substituents,
wherein optionally, when R11 is aryl (preferably phenyl), heterocyclyl or heteroaryl and R11 is substituted with at least two substituents, two substituents of R11 attached to adjacent atoms of R11 form a 5- to 8-membered saturated, partially unsaturated or aromatic cyclic group (preferably a condensed bicyclic aromatic group) comprising two atoms of R11 and further comprising 0, 1, 2, 3 or 4 heteroatoms, said heteroatoms selected independently from nitrogen, sulfur or oxygen, wherein said saturated, partially unsaturated or aromatic cyclic group is optionally substituted by one or more of R, wherein R is independently selected from the group consisting of H, alkyl, haloalkyl, alkoxy, or amine,
wherein R11 is optionally substituted with one or more substituents selected from the group consisting of one or more halogens (preferably Cl, Br, F), C1-C5 alkyl (preferably C1 alkyl), C1-C5 haloalkyl, hydroxyl, alkoxy (preferably $OCH_3$, $OCH_2CH_3$), C2-C10 alkynyl, C3-C8 cycloalkyl, carbonyl, C0-C5 alkyl carboxyester (preferably $—(CO)O—CH_3$), carboxamide, C0-C5 alkyl carboxamide (preferably $CON(CH_2CH_2)_2O$), primary, secondary or tertiary amine, carbamate, amide amine, nitro, —CN, O, sulfide, amine sulfoxide, sulfonamide, alkyl sulfonamide (preferably $N(SO_2CH_3)_2$), sulfonamide amine, sulfoxide, sulfone, sulfonamide haloalkyl, —$OCF_3$, carbamate, imide, —$SF_3$, —$SF_5$.

In one aspect, the present invention therefore also relates to a compound according to Formula 1, as outlined above, wherein the substituents R1-R11 are defined as follows:
R1: N or C;
R2: N or C;
R3: N or C;
wherein at least one of R1, R2 and R3 is N; preferably wherein R1 and R3 are N and R2 is C;
R4: can be the same or different, H, halogen (preferably Cl, Br, F), C1-C5 alkyl (preferably C1-C3 alkyl), C1-C5 haloalkyl, hydroxyl, alkoxy (preferably —$OCH_3$, —$OCH_2CH_3$), cycloalkyl (preferably C3-C6 cycloalkyl), —CN, carbonyl, carboxyl, carboxy ester, alkoxy, aldehyde, trihalide methyl ester, primary, secondary or tertiary amine, amide, imide, carbamate, carboxamide, nitro, sulfide, sulfurtrihalide, sulfurpentahalide, sulfinyl, sulfonyl, sulfino, or sulfo, sulfonamide, —$OCF_3$;
wherein when R1, R2, R3 is N, R4 attached thereto is absent;
R5: C1-C5 alkyl (preferably C2 alkyl), cycloalkyl (preferably C3-C6 cycloalkyl), aryl (preferably phenyl or napthyl), C1-C5 alkyl-cycloalkyl, C1-C5 alkyl-aryl, partially saturated bicyclic aryl (preferably indenyl, a benzene ring fused with a cyclopentane ring, which is bonded to the adjacent N of Formula 1);
wherein R5 is optionally substituted with one or more halogens (preferably Cl, Br, F), C1-C5 alkyl (preferably C1-C3 alkyl), C1-C5 haloalkyl, hydroxyl, alkoxy (preferably $OCH_3$, $OCH_2CH_3$);
R6: H, alkyl (preferably C1-C5 alkyl), cycloalkyl (preferably C3-C6 cycloalkyl), aryl (preferably phenyl), heterocyclyl, heteroaryl,
wherein R6 is optionally substituted with one or more halogens (preferably Cl, Br, F), C1-C5 alkyl (preferably C1-C3 alkyl), C1-C5 haloalkyl, hydroxyl, alkoxy (preferably $OCH_3$, $OCH_2CH_3$), C2-C10 alkynyl, C3-C8 cycloalkyl, carbonyl, C0-C5 alkyl carboxyester, C0-C5 alkyl carboxamide, primary, secondary or tertiary amine, carbamate, amide amine, nitro, —CN, O, sulfide, amine sulfoxide, sulfonamide, sulfonamide amine, sulfoxide, sulfone, sulfonamide haloalkyl, —$OCF_3$, carbamate, imide, —$SF_3$, —$SF_5$;
R7: S, absent (covalent bond to R8), NR, wherein R is H, C1-C5 alkyl (preferably C1-C3 alkyl), C1-C5 haloalkyl, alkoxy (preferably $OCH_3$, $OCH_2CH_3$);
R8: C1-C5 alkyl (preferably C1 alkyl), cycloalkyl (preferably C3-C6 cycloalkyl),
wherein R8 is optionally substituted with one or more halogens (preferably Cl, Br, F), C1-C5 alkyl (preferably C1 alkyl), C1-C5 haloalkyl, hydroxyl, alkoxy (preferably $OCH_3$, $OCH_2CH_3$);
R9: amide (preferably —CONH—), amine (preferably —NH—), urea (preferably —NHCONH—), sulfonamide (preferably —$SO_2NH$—), carbonyl (preferably —CO—);
R10: 5-membered heterocyclyl or heteroaryl (except for pyrazolyl, tetrahydrofurfuryl), preferably a 5-membered aromatic heterocycle comprising one or more of N, O and/or S, more preferably comprising N and S, or N and O;
R11(n): n is 0-5 (preferably 1), may be the same or different, halogen (preferably Cl, Br, F), C1-C5 alkyl (preferably C1 alkyl), CN, C1-C5 haloalkyl, hydroxyl, alkoxy (preferably $OCH_3$, $OCH_2CH_3$), alkoxycarbonyl (preferably —$COOCH_3$, —$CH_2COOCH_3$, —$CH_2CH_2COOCH_3$), cycloalkyl (preferably C3-C6 cycloalkyl), aryl (preferably phenyl), C1-C5 alkyl-cycloalkyl, C1-C5 alkyl-aryl, heterocyclyl, heteroaryl, carboxamide, C0-C5 alkyl carboxamide (preferably $CON(CH_2CH_2)_2O$);
wherein optionally, when R11 is aryl (preferably phenyl), heterocyclyl or heteroaryl and R10 is substituted with at least two substituents, two substituents or members of R11 attached to adjacent atoms of R10 form a 5- to 8-membered saturated, partially unsaturated or aromatic cyclic group (preferably a condensed bicyclic aromatic group) comprising two atoms of R10 and optionally further comprising 0, 1, 2, 3 or 4 heteroatoms, said heteroatoms selected independently from nitrogen, sulfur or oxygen, wherein said saturated, partially unsaturated or aromatic cyclic group is optionally substituted by one or more of R, wherein R is independently selected from the group consisting of H, alkyl, haloalkyl, alkoxy, or amine.
wherein optionally, when R11 is aryl (preferably phenyl), heterocyclyl or heteroaryl and R11 is substituted with at least two substituents, two substituents of R11 attached to adjacent atoms of R11 form a 5- to 8-membered saturated, partially unsaturated or aromatic cyclic group (preferably a condensed bicyclic aromatic group) comprising two atoms of R11 and further comprising 0, 1, 2, 3 or 4 heteroatoms, said heteroatoms selected independently from nitrogen, sulfur or oxygen, wherein said saturated, partially unsaturated or aromatic cyclic group is optionally substituted by one or more of R, wherein R is independently selected from the group consisting of H, alkyl, haloalkyl, alkoxy, or amine.

wherein R11 is optionally substituted with one or more substituents selected from the group consisting of one or more halogens (preferably Cl, Br, F), C1-C5 alkyl (preferably C1 alkyl), C1-C5 haloalkyl, hydroxyl, alkoxy (preferably $OCH_3$, $OCH_2CH_3$), C2-C10 alkynyl, C3-C8 cycloalkyl, carbonyl, C0-C5 alkyl carboxyester, carboxamide, C0-C5 alkyl carboxamide (preferably $CON(CH_2CH_2)_2O$), primary, secondary or tertiary amine, carbamate, amide amine, nitro, —CN, O, sulfide, amine sulfoxide, sulfonamide, sulfonamide amine, sulfoxide, sulfone, sulfonamide haloalkyl, —$OCF_3$, carbamate, imide, —$SF_3$, —$SF_5$.

In one embodiment the compound according to Formula 1 is characterized in that preferably R4 can be the same or different, H, halogen (preferably Cl, Br, F), C1-C5 alkyl (preferably C1-C3 alkyl), C1-C5 haloalkyl, hydroxyl, alkoxy (preferably —$OCH_3$, —$OCH_2CH_3$), cycloalkyl (preferably C3-C6 cycloalkyl), CN, carbonyl (—C(O)R), carboxyl (—C(O)OH), carboxy ester ($CO_2R$), alkoxy (—O— alkyl), aldehyde (—C(O)H), trihalide methyl ester (—$C(O)OCX_3$), primary, secondary or tertiary amine (—NR(R')), amide (—N(R)—C(O)—R), imide (—C(O)—N(R)—C(O)—R'), carbamate (—N(R)—C(O)—OR'), carboxamide (—C(O)N(R)R'), nitro (—$NO_2$), sulfide (—SR), sulfurtrihalide (—$SX_3$), sulfurpentahalide (—$SX_5$), sulfinyl (—S(O)R), sulfonyl (—$SO_2R$), sulfino (—$SO_2H$), or sulfo (—$SO_3H$), wherein R, R' is independently selected from the group consisting of H, alkyl, haloalkyl, alkoxy, or amine, and wherein X is halogen.

In one embodiment the compound according to Formula 1 is characterized in that preferably R4 can be the same or different, H, halogen (preferably Cl, Br, F), C1-C5 alkyl (preferably C1-C3 alkyl), C1-C5 haloalkyl, hydroxyl, alkoxy (preferably —$OCH_3$, —$OCH_2CH_3$), cycloalkyl (preferably C3-C6 cycloalkyl), more preferably H, alkyl, cycloalkyl or alkoxy.

In a preferred embodiment according to Formula 1, R4 is H and R1 and R3 are N and R2 is C, optionally in combination with another preferred embodiment according to Formula 1, in which R7 is S, R8 is $CH_2$ (optionally substituted with $CH_3$) and R9 is an amide (preferably —CONH—).

According to the knowledge of the inventors, the definition of R10 as a 5-membered heterocyclyl or heteroaryl (with the exception of pyrazolyl, tetrahydrofurfuryl, which are hereby excluded as potential substituents at R10), preferably a 5-membered aromatic heterocycle comprising one or more of N, O and/or S, more preferably comprising N and S, or N and O, the compounds represent a novel structure never previously described.

In one embodiment the compound according to Formula 1 is characterized in that preferably R11(n): n is 1, cycloalkyl (preferably C3-C6 cycloalkyl), aryl (preferably phenyl), C1-C5 alkyl-cycloalkyl, C1-C5 alkyl-aryl, heterocyclyl, heteroaryl, with an optional substitution as described above.

In one embodiment the compound according to Formula 1 is characterized in that preferably R11 is optionally substituted with one or more substituents selected from the group consisting of one or more halogens (preferably Cl, Br, F), C1-C5 alkyl (preferably C1 alkyl), C1-C5 haloalkyl, hydroxyl, alkoxy (preferably $OCH_3$, $OCH_2CH_3$), sulfone (preferably —$SO_2CH_3$), C2-C10 alkynyl, C3-C8 cycloalkyl, carbonyl (—C(O)—R), carboxyester (—C(O)—O—R), carboxamide (—C(O)—N(R)—R), C0-C5 alkyl carboxyester, C0-C5 alkyl carboxamide (preferably $CON(CH_2CH_2)_2O$), primary, secondary or tertiary amine (—N(R)—R), carbamate (—NR—C(O)—O—R), amide amine (NH—C(O)—NH—R), nitro (—$NO_2$), —CN, O, sulfide (S—R), amine sulfoxide, sulfonamide, sulfonamide amine (preferably —N(R)—$S(O)_u$—R, wherein u is 1 or 2, or —$S(O)_v$—N(R)—R, wherein v is 1 or 2, preferably —$NHSO_2CH_3$, —$SO_2NHCH_3$, —$NHSO_2N(CH_3)_2$), sulfoxide (preferably —$SO_r$—R, wherein r is 1-3, preferably —S(O)R, —$SO_2R$, —$SO_2H$, and —$SO_3H$), sulfonamide haloalkyl (preferably —$NHSO_2CF_3$, —$NHSO_2CH_2CF_3$), —$OCF_3$, carbamate (—N(R)—C(O)—R), imide (—C(O)—N(R)—C(O)—R'), —$SF_3$, —$SF_5$, wherein R is independently selected from the group consisting of H, alkyl, haloalkyl, alkoxy, or amine, wherein optionally when R11 is aryl (preferably phenyl), heterocyclyl or heteroaryl and R11 is substituted with at least two substituents, two substituents of R11 attached to adjacent atoms of R11 form a 5- to 8-membered cyclic group comprising two atoms of R11 and further comprising 1.2, 3 or 4 heteroatoms, said heteroatoms selected independently from nitrogen, sulfur or oxygen, wherein said cyclic group is optionally substituted by one or more of R, wherein R is independently selected from the group consisting of H, alkyl, haloalkyl, alkoxy, or amine.

In one embodiment the compound according to Formula 1 is characterized in that preferably R11 is optionally substituted with one or more substituents selected from the group consisting of one or more halogens (preferably Cl, Br, F), C1-C5 alkyl (preferably C1 alkyl), C1-C5 haloalkyl, hydroxyl, alkoxy (preferably $OCH_3$, $OCH_2CH_3$), sulfone (preferably —$SO_2CH_3$), carboxamide, primary, secondary or tertiary amine, carbamate, amide amine, —CN, sulfide, amine sulfoxide, sulfonamide, sulfonamide amine, sulfoxide, sulfonamide haloalkyl, wherein optionally when R11 is aryl (preferably phenyl), heterocyclyl or heteroaryl and R11 is substituted with at least two substituents, two substituents of R11 attached to adjacent atoms of R11 form a 5- to 8-membered cyclic group comprising two atoms of R11 and further comprising 1, 2, 3 or 4 heteroatoms, said heteroatoms selected independently from nitrogen, sulfur or oxygen, wherein said cyclic group is optionally substituted by one or more of R, wherein R is independently selected from the group consisting of H, alkyl, haloalkyl, alkoxy, or amine.

In one embodiment, R10 and R11 together form a bicyclic structure. Examples are presented below with respect to specific non-limiting structures for R10-R11.

In some embodiments, R10 is a 5- or 6-membered cyclic structure. Preferred are 5- or 6-membered heterocyclyl or heteroaryl, or 5- or 6-membered heterocycles comprising one or more of N, O and/or S, more preferably comprising N and S, or N and O.

In some embodiments, R11 is a cyclic structure, as described above with respect to the feature: wherein optionally, two R11 form, together with two carbon atoms of R10 to which they are attached, a 5-, 6-, 7- or 8-membered cyclic residue, (preferably forming with R10 a condensed bicyclic aromatic group) comprising two carbon atoms of R10 and optionally further comprising 0, 1.2, 3 or 4 heteroatoms, said heteroatoms selected independently from nitrogen, sulfur or oxygen, wherein said cyclic residue is saturated, partially unsaturated or aromatic, and optionally substituted by one or more of R, wherein R is independently selected from the group consisting of H, alkyl, haloalkyl, alkoxy, or amine.

This combination of R10 and R11 results in a bicyclic structure, in which R10 and R11 share e.g. 2 atoms, as shown for example in the structures of compounds 56, 57, 62, 63, 65, 66, 69, 71, etc (e.g. bicyclic heteroaryl groups as R10-R11 with or without an amide linkage at R9, R9 can be amide or absent).

Such R10-R11 bicyclic groups may also be defined as:

Two R11 form, together with the two carbon atoms of R10 to which they are attached, a 5-, 6-7- or 8-membered cyclic residue, containing up to 0, 1, 2, or 3 additional heteroatoms chosen from nitrogen, sulfur or oxygen, wherein said cyclic residue is saturated, partially unsaturated or aromatic and unsubstituted or substituted one, two, three or four times, independent of one another. The substitution of R11 may occur, for example, with one or more substituents selected from the group consisting of one or more halogens (preferably Cl, Br, F), C1-C5 alkyl (preferably C1 alkyl), C1-C5 haloalkyl, hydroxyl, alkoxy (preferably $OCH_3$, $OCH_2CH_3$), C2-C10 alkynyl, C3-C8 cycloalkyl, carbonyl, C0-C5 alkyl carboxyester (preferably —(CO)O—$CH_3$), carboxamide, C0-C5 alkyl carboxamide (preferably $CON(CH_2CH_2)_2O$), primary, secondary or tertiary amine, carbamate, amide amine, nitro, —CN, O, sulfide, amine sulfoxide, sulfonamide, alkyl sulfonamide (preferably $NHSO_2CH_3$, $SO_2N(CH_2CH_3)_2$, $N(SO_2CH_3)_2$), sulfonamide amine, sulfoxide, sulfone, sulfonamide haloalkyl, —$OCF_3$, carbamate, imide, —$SF_3$, —$SF_5$.

In other words, R11 (n), wherein n=2, such that R10 is substituted with R11 at two positions of the ring structure, preferably adjacent carbon atoms of R10, to form a cyclic structure fused with R10 to produce a bicyclic (preferably bicyclic aromatic group) structure R10-R11.

In one embodiment, the compound according to Formula 1 is characterized in that preferably R1 is N.

In one embodiment, the compound according to Formula 1 is characterized in that preferably R3 is N. In one embodiment, the compound according to Formula 1 is characterized in that preferably R3 is C or N.

In a further embodiment, the compound according to Formula 1 is characterized in that preferably R5 is C1-C5 alkyl (preferably C2 alkyl), wherein R5 is optionally substituted with one or more halogens (preferably Cl, Br, F), C1-C5 alkyl (preferably C1-C3 alkyl), C1-C5 haloalkyl, hydroxyl, alkoxy (preferably $OCH_3$, $OCH_2CH_3$).

In one embodiment, the compound according to Formula 1 is characterized in that preferably R6 is a cyclic group, such as cycloalkyl (preferably C3-C6 cycloalkyl), aryl (preferably phenyl), heterocyclyl or heteroaryl.

In one embodiment, the compound according to Formula 1 is characterized in that preferably R7 is S or $CH_2$.

In one embodiment, the compound according to Formula 1 is characterized in that R9 is amide (preferably —CONH—) or carbonyl (preferably —CO—), and R10 is aryl (preferably phenyl) or heteroaryl.

In one embodiment, the compound according to Formula 1 is characterized in that R1 is N, R3 is N, R5 is C1-C5 alkyl (preferably C2 alkyl), wherein R5 is optionally substituted with one or more halogens (preferably Cl, Br, F), C1-C5 alkyl (preferably C1-C3 alkyl), C1-C5 haloalkyl, hydroxyl, alkoxy (preferably $OCH_3$, $OCH_2CH_3$), and R6 is a cyclic group, such as cycloalkyl (preferably CO—CO cycloalkyl), aryl (preferably phenyl), heterocyclyl or heteroaryl.

In one embodiment, the compound according to Formula 1 is characterized in that R1 is N, R3 is N, R5 is C1-C5 alkyl (preferably C2 alkyl), wherein R5 is optionally substituted with one or more halogens (preferably Cl, Br, F), C1-C5 alkyl (preferably C1-C3 alkyl), C1-C5 haloalkyl, hydroxyl, alkoxy (preferably $OCH_3$, $OCH_2CH_3$), R6 is a cyclic group, such as cycloalkyl (preferably C3-C6 cycloalkyl), aryl (preferably phenyl), heterocyclyl or heteroaryl, R9 is amide (preferably —CONH—) or carbonyl (preferably —CO—), and R10 is aryl (preferably phenyl) or heteroaryl.

Combinations of the various preferred embodiments are themselves considered preferred embodiments according to Formula 1 of the present invention.

The present invention therefore relates to a compound according to Formula 2,

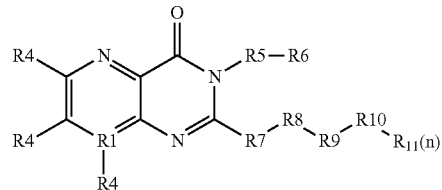

Formula 2 wherein R1: N or C, preferably N, wherein when R1 is N, R4 attached thereto is absent; and R4 to R11 are as recited in the embodiments above for Formula 1.

The present invention therefore relates to a compound according to Formula 2a,

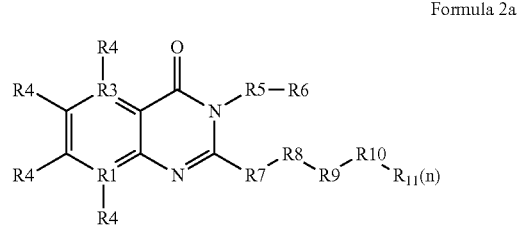

Formula 2a wherein R1 and R3: N or C, preferably N, wherein when R1 or R3 is N, R4 attached thereto is absent; and R4 to R11 are as recited in the embodiments above for Formula 1. In preferred embodiments, when R1 or R3 is N, R4 attached thereto is absent, and R4 is H.

The present invention therefore relates to a compound according to Formula 2b,

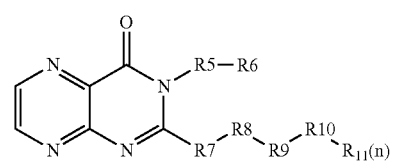

Formula 2b wherein R5 to R11 are as recited in the embodiments above for Formula 1.

The present invention therefore relates to a compound according to Formula 2c,

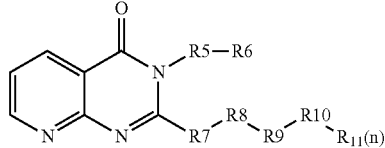

Formula 2c wherein R5 to R11 are as recited in the embodiments above for Formula 1.

The present invention therefore relates to a compound according to Formula 2d,

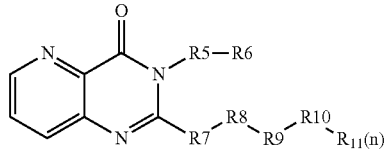

Formula 2d wherein R5 to R11 are as recited in the embodiments above for Formula 1.

In preferred embodiments the present invention relates to a compound according to Formula 1 or 2 or 4, wherein R5-R6 is one of:

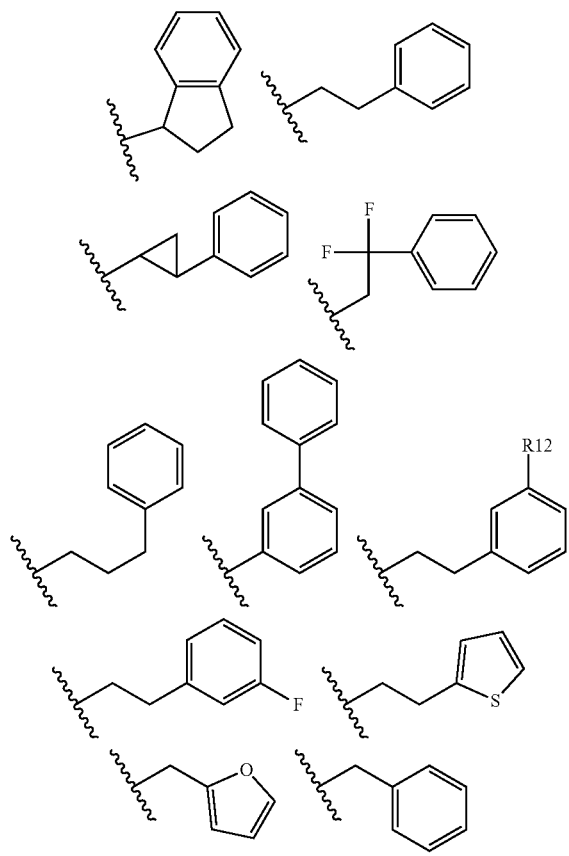

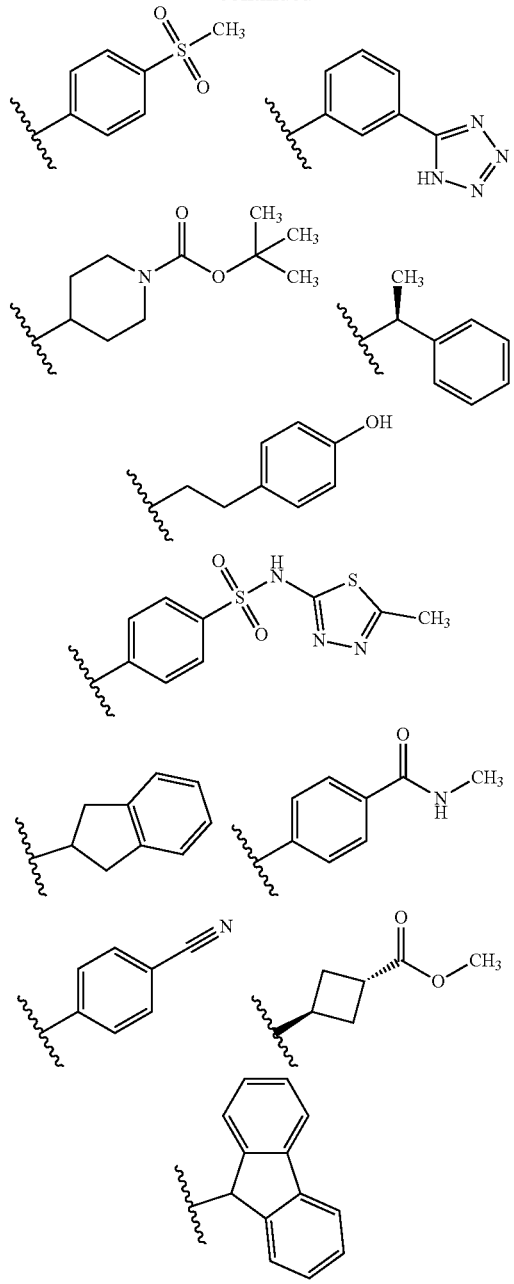

wherein R12: halogen (preferably Cl, Br, F), C1-C5 haloalkyl (preferably $CF_3$).

In these embodiments the particular substituents represented above are to be considered as combined substituents of R5 and R6. R5 is therefore considered preferably to represent the initial atom or group bound directly to backbone structure of Formula 1 or 2, and R6 is the adjacent atom or group. For example, R5 may be C2-alkyl and R6 a phenyl group, or R5 may be C3-cyloalkyl and R6 a phenyl, or R5 may be $CH_2$ and R6 a furyl group. In some embodiments R6 may be absent. The preferred substituents of R5-R6 may be combined preferentially with the preferred embodiments as described above for Formula 1. In some embodiments, R5 may be absent (or represent a covalent bond to R6), and the definitions of R6 are those above.

The present invention therefore relates to a compound according to Formula 3,

Formula 3

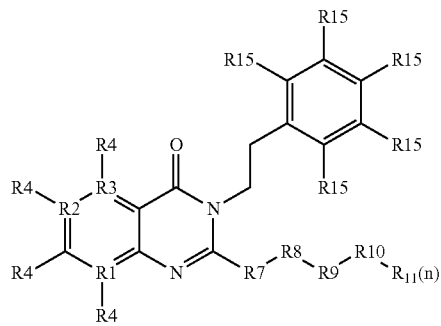

wherein
R15: may be the same or different, H, halogen (preferably Cl, Br, F) C1-C5 alkyl (preferably C1-C3 alkyl), C1-C5 haloalkyl, hydroxyl, alkoxy (preferably OCH$_3$, OCH$_2$CH$_3$);
and R1 to R4 and R7 to R11 are as recited in the embodiments above for Formula 1, 2 or 3.

The present invention therefore relates to a compound according to Formula 4,

Formula 4

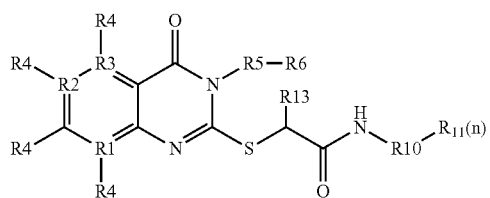

wherein
R13: H or CH$_3$, and
R1 to R6 and R10 and R11 are as recited in the embodiments above for Formula 1.

In one embodiment, the compound according to Formula 4 is characterized in that preferably R1 is N.

In one embodiment, the compound according to Formula 4 is characterized in that preferably R3 is N. In one embodiment, the compound according to Formula 4 is characterized in that preferably R3 is C or N.

In a further embodiment, the compound according to Formula 4 is characterized in that preferably R5 is C1-C5 alkyl (preferably C2 alkyl), wherein R5 is optionally substituted with one or more halogens (preferably Cl, Br, F), C1-C5 alkyl (preferably C1-C3 alkyl), C1-C5 haloalkyl, hydroxyl, alkoxy (preferably OCH$_3$, OCH$_2$CH$_3$).

In one embodiment, the compound according to Formula 4 is characterized in that preferably R6 is a cyclic group, such as cycloalkyl (preferably C3-C6 cycloalkyl), aryl (preferably phenyl), heterocyclyl or heteroaryl.

In one embodiment, the compound according to Formula 4 is characterized in that R1 is N, R3 is N, R5 is C1-C5 alkyl (preferably C2 alkyl), wherein R5 is optionally substituted with one or more halogens (preferably Cl, Br, F), C1-C5 alkyl (preferably C1-C3 alkyl), C1-C5 haloalkyl, hydroxyl, alkoxy (preferably OCH$_3$, OCH$_2$CH$_3$), and R6 is a cyclic group, such as cycloalkyl (preferably C3-C6 cycloalkyl), aryl (preferably phenyl), heterocyclyl or heteroaryl.

In preferred embodiments the present invention relates to a compound according to Formula 1, 2, 3 and/or 4, wherein R10-R11 is one of:

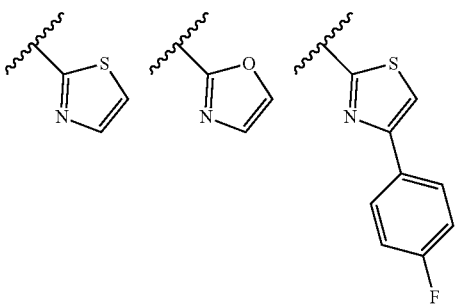

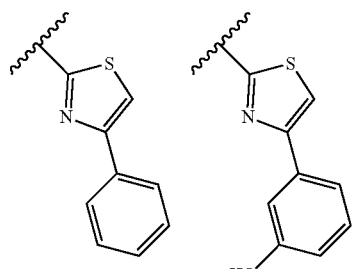

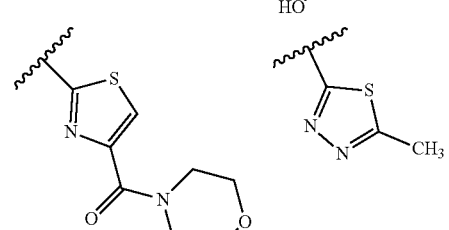

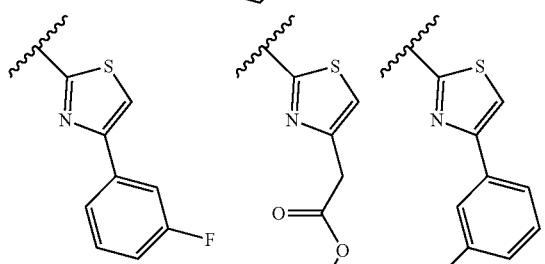

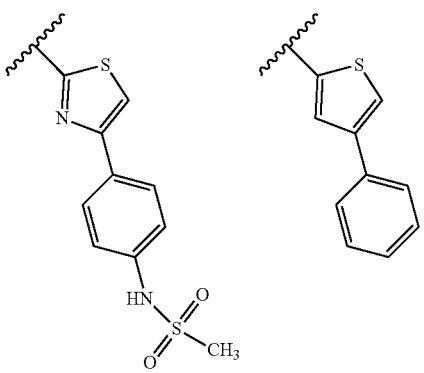

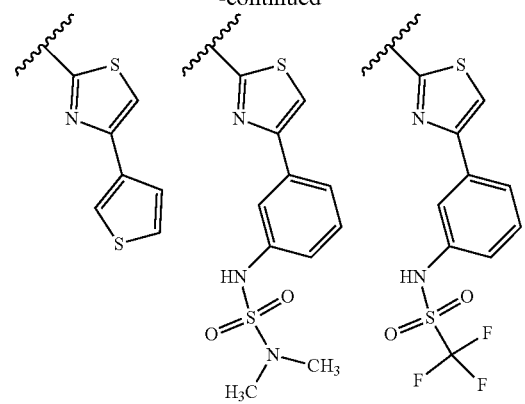
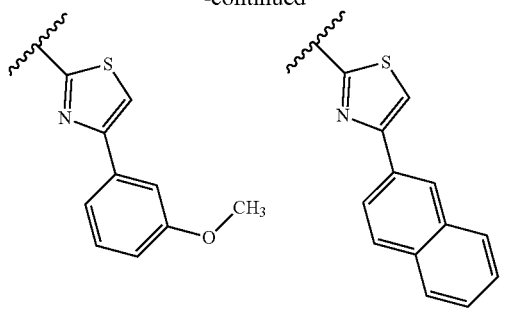
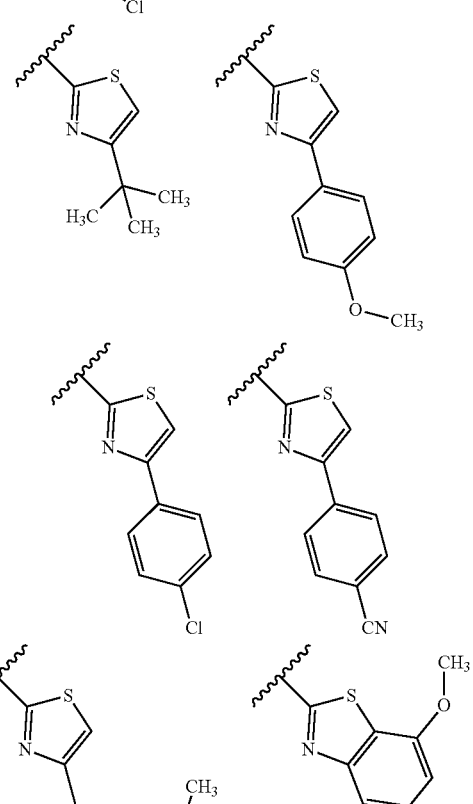
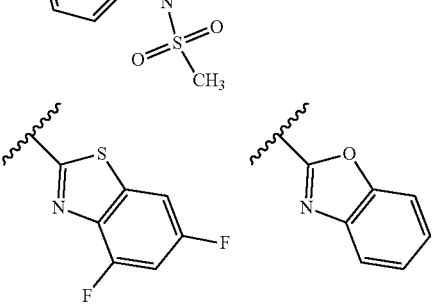

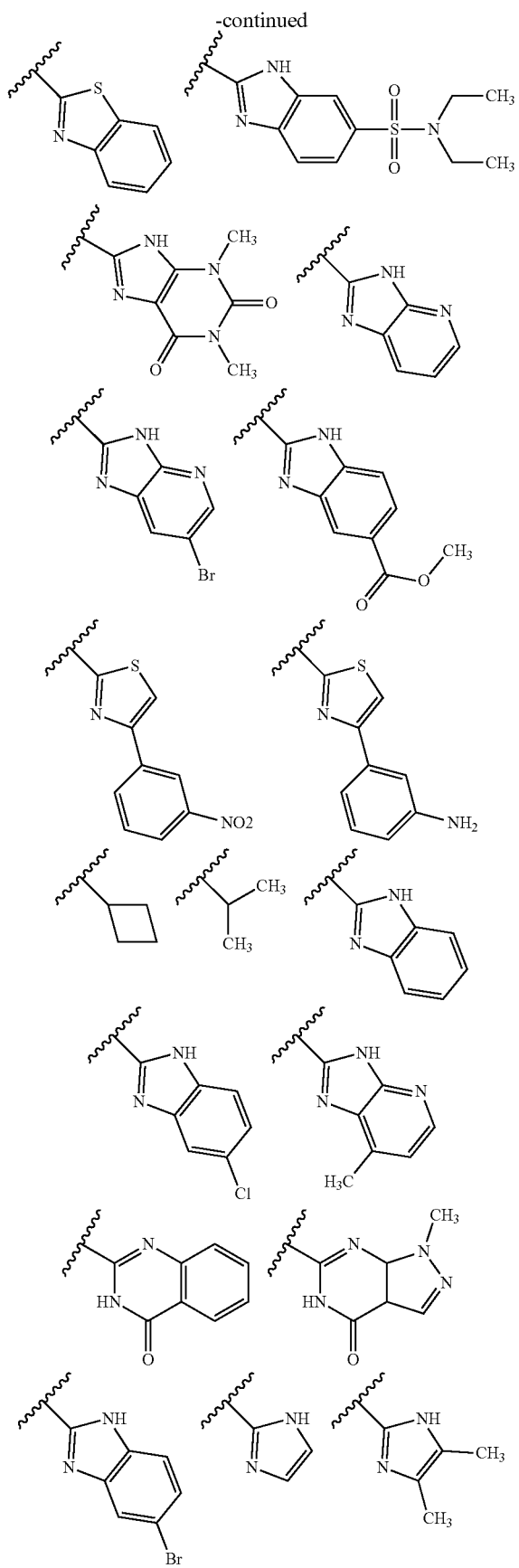

In these embodiments the particular substituents represented above are to be considered as combined substituents of R10 and R11. R10 is therefore considered preferably to represent the initial atom or group bound directly to R9 or to the amide of Formula 4, and R11 is a substituent of R10. For example, R10 may be thiazole and R11 a phenyl group. The preferred substituents of R10-R11 above may be combined preferentially with the preferred embodiments as described above for Formula 1 or 4. In some embodiments, R9 may be absent (or represent a covalent bond to R10), and the definitions of R10-R11 are those above.

The present invention therefore relates to a compound according to Formula 5,

Formula 5

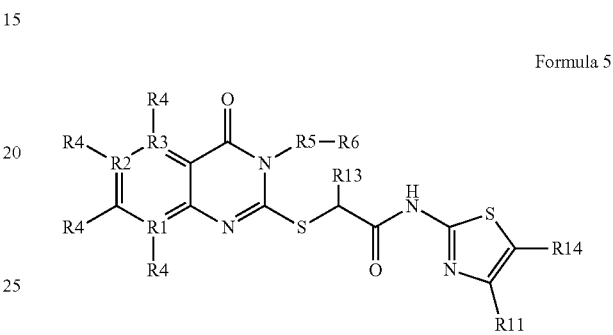

wherein R1 to R6 are as recited in the embodiments above for Formula 1 and R13 is as recited for Formula 4; wherein the positions of R11 and R14 may optionally be exchanged;

R14: H, halogen (preferably Cl, Br, F), C1-C5 alkyl (preferably C1 alkyl);

R11: halogen (preferably Cl, Br, F), C1-C5 alkyl (preferably C1 alkyl), CN, C1-C5 haloalkyl, hydroxyl, alkoxy (preferably $OCH_3$, $OCH_2CH_3$), alkoxycarbonyl (preferably —$COOCH_3$, —$CH_2COOCH_3$, —$CH_2CH_2COOCH_3$), cycloalkyl (preferably C3-C6 cycloalkyl), aryl (preferably phenyl), C1-C5 alkyl-cycloalkyl, C1-C5 alkyl-aryl, heterocyclyl, heteroaryl, carboxamide, C0-C5 alkyl carboxamide (preferably $CON(CH_2CH_2)_2O$);

wherein R11 is optionally substituted with one or more substituents selected from the group consisting of one or more halogens (preferably Cl, Br, F), C1-C5 alkyl (preferably C1 alkyl), C1-C5 haloalkyl, hydroxyl, alkoxy (preferably $OCH_3$, $OCH_2CH_3$), C2-C10 alkynyl, C3-C8 cycloalkyl, carbonyl, C0-C5 alkyl carboxyester, carboxamide, C0-C5 alkyl carboxamide (preferably $CON(CH_2CH_2)_2O$), primary, secondary or tertiary amine, carbamate, amide amine, nitro, —CN, O, sulfide, amine sulfoxide, sulfonamide, sulfonamide amine, sulfoxide, sulfone, sulfonamide haloalkyl, —$OCF_3$, carbamate, imide, —$SF_3$, —$SF_5$, wherein optionally, when R11 is aryl (preferably phenyl), heterocyclyl or heteroaryl and R11 is substituted with at least two substituents, two substituents of R11 attached to adjacent atoms of R11 form a 5- to 8-membered saturated, partially unsaturated or aromatic cyclic group (preferably a condensed bicyclic aromatic group) comprising two atoms of R11 and further comprising 0, 1, 2, 3 or 4 heteroatoms, said heteroatoms selected independently from nitrogen, sulfur or oxygen, wherein said saturated, partially unsaturated or aromatic cyclic group is optionally substituted by one or more of R, wherein R is independently selected from the group consisting of H, alkyl, haloalkyl, alkoxy, or amine, wherein optionally, R11 and R14 form, together with the two carbon atoms of the adjacent 5-membered ring structure to which they are attached, a 5-, 6-7- or 8-membered cyclic residue (preferably forming a condensed bicyclic aromatic group), optionally further comprising 0, 1, 2, 3 or 4 heteroatoms, said heteroatoms selected independently from nitrogen, sulfur or oxygen, wherein said cyclic residue is saturated, partially unsaturated or aromatic, and optionally substituted with the substituents above for R11.

The present invention therefore relates to a compound according to Formula 6,

Formula 6

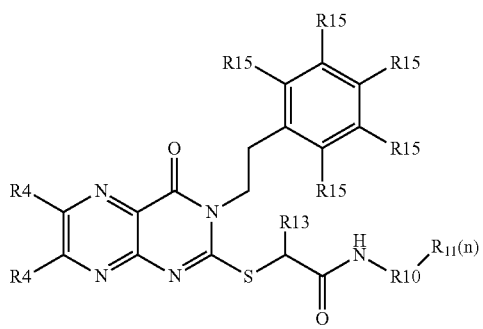

wherein
R4: as recited in the embodiments above for Formula 1;
R10, R11: as recited in the embodiments above for Formula 1 or 4, or preferred embodiments for R10-R11 as above;
R13: as recited in the embodiments above for Formula 4;
R15: as recited in the embodiments above for Formula 3.

The present invention therefore relates to a compound according to Formula 7,

Formula 7

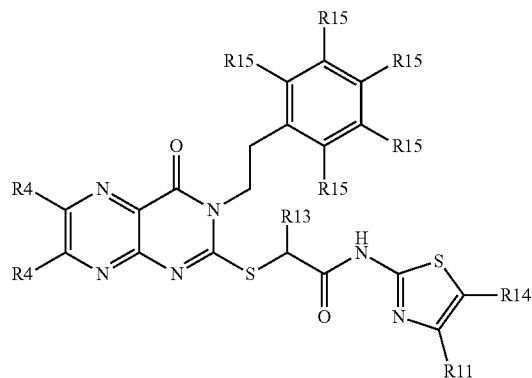

wherein
R4, R13, R15 are as recited in the embodiments above for Formula 1, 3 and/or 4; and
wherein the positions of R11 and R14 may optionally be exchanged;
R14: H, halogen (preferably Cl, Br, F), C1-C5 alkyl (preferably C1 alkyl);

R11: halogen (preferably Cl, Br, F), C1-C5 alkyl (preferably C1 alkyl), CN, C1-C5 haloalkyl, hydroxyl, alkoxy (preferably $OCH_3$, $OCH_2CH_3$), alkoxycarbonyl (preferably —$COOCH_3$, —$CH_2COOCH_3$, —$CH_2CH_2COOCH_3$), cycloalkyl (preferably C3-C6 cycloalkyl), aryl (preferably phenyl), C1-C5 alkyl-cycloalkyl, C1-C5 alkyl-aryl, heterocyclyl, heteroaryl, carboxamide, C0-C5 alkyl carboxamide (preferably $CON(CH_2CH_2)_2O$);

wherein R11 is optionally substituted with one or more substituents selected from the group consisting of one or more halogens (preferably Cl, Br, F), C1-C5 alkyl (preferably C1 alkyl), C1-C5 haloalkyl, hydroxyl, alkoxy (preferably $OCH_3$, $OCH_2CH_3$), C2-C10 alkynyl, C3-C8 cycloalkyl, carbonyl, C0-C5 alkyl carboxyester, carboxamide, C0-C5 alkyl carboxamide (preferably $CON(CH_2CH_2)_2O$), primary, secondary or tertiary amine, carbamate, amide amine, nitro, —CN, O, sulfide, amine sulfoxide, sulfonamide, sulfonamide amine, sulfoxide, sulfone, sulfonamide haloalkyl, —$OCF_3$, carbamate, imide, —$SF_3$, —$SF_5$, wherein optionally, when R11 is aryl (preferably phenyl), heterocyclyl or heteroaryl and R11 is substituted with at least two substituents, two substituents of R11 attached to adjacent atoms of R11 form a 5- to 8-membered saturated, partially unsaturated or aromatic cyclic group (preferably a condensed bicyclic aromatic group) comprising two atoms of R11 and further comprising 0, 1, 2, 3 or 4 heteroatoms, said heteroatoms selected independently from nitrogen, sulfur or oxygen, wherein said saturated, partially unsaturated or aromatic cyclic group is optionally substituted by one or more of R, wherein R is independently selected from the group consisting of H, alkyl, haloalkyl, alkoxy, or amine, wherein optionally, R11 and R14 form, together with the two carbon atoms of the adjacent 5-membered ring structure to which they are attached, a 5-, 6-7- or 8-membered cyclic residue (preferably forming a condensed bicyclic aromatic group), optionally further comprising 0, 1, 2, 3 or 4 heteroatoms, said heteroatoms selected independently from nitrogen, sulfur or oxygen, wherein said cyclic residue is saturated, partially unsaturated or aromatic, and optionally substituted with the substituents above for R11.

In one embodiment the compound according to Formula 5 or 7 is characterized in that preferably R11: cycloalkyl (preferably C3-C6 cycloalkyl), aryl (preferably phenyl), C1-C5 alkyl-cycloalkyl, C1-C5 alkyl-aryl, heterocyclyl, heteroaryl, with an optional substitution as described herein.

In one embodiment the compound according to Formula 5 or 7 is characterized in that preferably R11 is optionally substituted with one or more substituents selected from the group consisting of one or more halogens (preferably Cl, Br, F), C1-C5 alkyl (preferably C1 alkyl), C1-C5 haloalkyl, hydroxyl, alkoxy (preferably $OCH_3$, $OCH_2CH_3$), sulfone (preferably —$SO_2CH_3$), C2-C10 alkynyl, C3-C8 cycloalkyl, carbonyl (—C(O)—R), carboxyester (—C(O)—O—R), carboxamide (—C(O)—N(R)—R), C0-C5 alkyl carboxyester, C0-C5 alkyl carboxamide (preferably $CON(CH_2CH_2)_2O$), primary, secondary or tertiary amine (—N(R)—R), carbamate (—NR—C(O)—O—R), amide amine (NH—C(O)—NH—R), nitro (—$NO_2$), —CN, O, sulfide (S—R), amine sulfoxide, sulfonamide, sulfonamide amine (preferably —N(R)—S(O)$_u$—R, wherein u is 1 or 2, or —S(O)$_v$—N(R)—R, wherein v is 1 or 2, preferably —$NHSO_2CH_3$, —$SO_2NHCH_3$, —$NHSO_2N(CH_3)_2$), sulfoxide, sulfone (preferably —SO$_r$R, wherein r is 1-3, preferably —S(O)R, —SO₂R, —SO₂H, and —SO₃H), sulfonamide haloalkyl (preferably —NHSO₂CF₃, —NHSO₂CH₂CF₃), —OCF₃, carbamate (—N(R)—C(O)—R), imide (—C(O)—N(R)—C(O)—R'), —SF₃, —SF₅, wherein R is independently selected from the group consisting of H, alkyl, haloalkyl, alkoxy, or amine, wherein optionally when R11 is aryl (preferably phenyl), heterocyclyl or heteroaryl and R11 is substituted with at least two substituents, two substituents of R11 attached to adjacent atoms of R11 form a 5- to 8-membered cyclic group comprising two atoms of R11 and further comprising 1, 2, 3 or 4 heteroatoms, said heteroatoms selected independently from nitrogen, sulfur or oxygen, wherein said cyclic group is optionally substituted by one or more of R, wherein R is independently selected from the group consisting of H, alkyl, haloalkyl, alkoxy, or amine.

In one embodiment the compound according to Formula 5 or 7 is characterized in that preferably R11 is optionally substituted with one or more substituents selected from the group consisting of one or more halogens (preferably Cl, Br, F), C1-C5 alkyl (preferably C1 alkyl), C1-C5 haloalkyl, hydroxyl, alkoxy (preferably OCH₃, OCH₂CH₃), sulfone (preferably —SO₂CH₃), carboxamide, C0-C5 alkyl carboxyester, C0-C5 alkyl carboxamide (preferably CON(CH₂CH₂)₂O), primary, secondary or tertiary amine, carbamate, amide amine, —CN, sulfide, amine sulfoxide, sulfonamide, sulfonamide amine, sulfoxide, sulfone, sulfonamide haloalkyl, wherein optionally when R11 is aryl (preferably phenyl), heterocyclyl or heteroaryl and R11 is substituted with at least two substituents, two substituents of R11 attached to adjacent atoms of R11 form a 5- to 8-membered cyclic group comprising two atoms of R11 and further comprising 1, 2, 3 or 4 heteroatoms, said heteroatoms selected independently from nitrogen, sulfur or oxygen, wherein said cyclic group is optionally substituted by one or more of R, wherein R is independently selected from the group consisting of H, alkyl, haloalkyl, alkoxy, or amine.

In further embodiments the invention relates to those compounds disclosed in Table 1 and FIGS. 5 and 6.

A further aspect of the invention relates to the use of the compounds above as a medicament in the treatment of a medical condition associated with defective and/or pathologic class II phosphoinositide 3-kinase (PI3K) signaling. The invention therefore relates to a method of treating and/or preventing a medical condition associated with defective and/or pathologic class II phosphoinositide 3-kinase (PI3K) signaling, said method comprising the administration of one or more of the above compounds or compounds falling under the formulae described above to a subject in need thereof.

Compounds for Medical Use According to Formula 1a;

A further aspect of the invention relates to a compound according to Formula 1a for use as a medicament in the treatment of a medical condition associated with defective and/or pathologic class II phosphoinositide 3-kinase (PI3K) signaling, Formula 1a

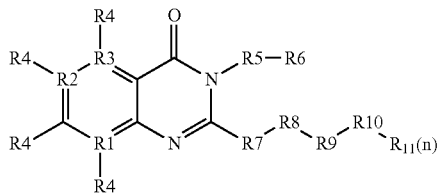

wherein

R1: N or C;
R2: N or C;
R3: N or C;
wherein at least one of R1, R2 and R3 is N; preferably wherein R1 and R3 are N and R2 is C; R4: can be the same or different, H, halogen (preferably Cl, Br, F), C1-C5 alkyl (preferably C1-C3 alkyl), C1-C5 haloalkyl, hydroxyl, alkoxy (preferably —OCH₃, —OCH₂CH₃), cycloalkyl (preferably C3-C6 cycloalkyl), —CN, carbonyl, carboxyl, carboxy ester, alkoxy, aldehyde, trihalide methyl ester, primary, secondary or tertiary amine, amide, imide, carbamate, carboxamide, nitro, sulfide, sulfurtrihalide, sulfurpentahalide, sulfinyl, sulfonyl, sulfino, or sulfo, sulfonamide, —OCF₃;
wherein when R1, R2, R3 is N, R4 attached thereto is absent;
R5: absent (covalent bond to R6), C1-C5 alkyl (preferably C2 alkyl), cycloalkyl (preferably C0—C0 cycloalkyl), aryl (preferably phenyl or napthyl), C1-C5 alkyl-cycloalkyl, C1-C5 alkyl-aryl, partially saturated bicyclic aryl (preferably indenyl, a benzene ring fused with a cyclopentane ring, which is bonded to the adjacent N of Formula 1);
wherein R5 is optionally substituted with one or more halogens (preferably Cl, Br, F), C1-C5 alkyl (preferably C1-C3 alkyl), C1-C5 haloalkyl, hydroxyl, alkoxy (preferably OCH₃, OCH₂CH₃);
wherein R5 is optionally substituted with at least two substituents, said two substituents forming R6, attached to adjacent atoms of R5, to form as R6 a 5- to 8-membered saturated, partially unsaturated or aromatic cyclic group comprising said adjacent two atoms of R5 (preferably wherein R5-R6 is indanyl or fluorenyl);
R6: H, alkyl (preferably C1-C5 alkyl), cycloalkyl (preferably C3-C6 cycloalkyl), aryl (preferably phenyl), heterocyclyl, heteroaryl,
wherein R6 is optionally substituted with one or more halogens (preferably Cl, Br, F), C1-C5 alkyl (preferably C1-C3 alkyl), C1-C5 haloalkyl, hydroxyl, alkoxy (preferably OCH₃, OCH₂CH₃), C2-C10 alkynyl, C3-C8 cycloalkyl, a 5- or 6-membered heterocyclyl or heteroaryl comprising one or more of N, O and/or S (preferably tetrazole), carbonyl, C0-C5 alkyl carboxyester (preferably —(CO)O—CH₃ or —(CO)O—C(CH₃)₃), carboxamide, C0-C5 alkyl carboxamide, primary, secondary or tertiary amine, carbamate, amide amine, nitro, —CN, O, sulfide, amine sulfoxide, sulfonamide, said sulfonamide optionally substituted with a 5- or 6-membered heterocyclyl or heteroaryl comprising one or more of N, O and/or S (preferably thiadiazole), sulfonamide amine, sulfoxide, sulfone, sulfonamide haloalkyl, cyano (preferably CN), —OCF₃, carbamate, imide, —SF₃, —SF₅;
R7: S, absent (covalent bond to R8), NR, wherein R is H, C1-C5 alkyl (preferably C1-C3 alkyl), C1-C5 haloalkyl, alkoxy (preferably OCH₃, OCH₂CH₃);
R8: C1-C5 alkyl (preferably C1 alkyl), cycloalkyl (preferably C3-C6 cycloalkyl),
wherein R8 is optionally substituted with one or more halogens (preferably Cl, Br, F), C1-C5 alkyl (preferably C1 alkyl), C1-C5 haloalkyl, hydroxyl, alkoxy (preferably OCH₃, OCH₂CH₃);
R9: absent (covalent bond to R10), amide (preferably —CONH—), amine (preferably —NH—), urea (preferably —NHCONH—), sulfonamide (preferably —SO$_2$NH—), carbonyl (preferably —CO—);

R10: cycloalkyl (preferably C3-C6 cycloalkyl), aryl (preferably phenyl), heterocyclyl, heteroaryl (preferably 5- or 6-membered heterocyclyl, heteroaryl), more preferably a 5- or 6-membered aromatic heterocycle, comprising one or more of N, O and/or S, wherein a C atom of of R10 is optionally substituted with =O;

wherein optionally a C1-C5 (preferably C1-C2) alkyl is positioned between R9 and R10;

R11(n): n is 0-5 (preferably 1), may be the same or different, halogen (preferably Cl, Br, F), C1-C5 alkyl (preferably C1 alkyl), CN, C1-C5 haloalkyl, hydroxyl, alkoxy (preferably OCH$_3$, OCH$_2$CH$_3$), alkoxycarbonyl (preferably —COOCH$_3$, —CH$_2$COOCH$_3$, —CH$_2$CH$_2$COOCH$_3$), cycloalkyl (preferably C3-C6 cycloalkyl), aryl (preferably phenyl), C1-C5 alkyl-cycloalkyl, C1-C5 alkyl-aryl, heterocyclyl, heteroaryl, carboxamide, C0-C5 alkyl carboxamide (preferably CON(CH$_2$CH$_2$)$_2$O);

wherein optionally, two R11 form, together with two carbon atoms of R10 to which they are attached, a 5-, 6-, 7- or 8-membered cyclic residue, (preferably forming with R10 a condensed bicyclic aromatic group) comprising two carbon atoms of R10 and optionally further comprising 0, 1, 2, 3 or 4 heteroatoms, said heteroatoms selected independently from nitrogen, sulfur or oxygen, wherein said cyclic residue as R11 is saturated, partially unsaturated or aromatic, and optionally substituted by one or more substituents, wherein optionally, when R11 is aryl (preferably phenyl), heterocyclyl or heteroaryl and R11 is substituted with at least two substituents, two substituents of R11 attached to adjacent atoms of R11 form a 5- to 8-membered saturated, partially unsaturated or aromatic cyclic group (preferably a condensed bicyclic aromatic group) comprising two atoms of R11 and further comprising 0, 1, 2, 3 or 4 heteroatoms, said heteroatoms selected independently from nitrogen, sulfur or oxygen, wherein said saturated, partially unsaturated or aromatic cyclic group is optionally substituted by one or more of R, wherein R is independently selected from the group consisting of H, alkyl, haloalkyl, alkoxy, or amine, wherein R11 is optionally substituted with one or more substituents selected from the group consisting of one or more halogens (preferably Cl, Br, F), C1-C5 alkyl (preferably C1 alkyl), C1-C5 haloalkyl, hydroxyl, alkoxy (preferably OCH$_3$, OCH$_2$CH$_3$), C2-C10 alkynyl, C3-C8 cycloalkyl, carbonyl, C0-C5 alkyl carboxyester (preferably —(CO)O—CH$_3$), carboxamide, C0-C5 alkyl carboxamide (preferably CON(CH$_2$CH$_2$)$_2$O), primary, secondary or tertiary amine, carbamate, amide amine, nitro, —CN, O, sulfide, amine sulfoxide, sulfonamide, alkyl sulfonamide (preferably N(SO$_2$CH$_3$)$_2$), sulfonamide amine, sulfoxide, sulfone, sulfonamide haloalkyl, —OCF$_3$, carbamate, imide, —SF$_3$, —SF$_5$.

In one embodiment, the invention therefore also relates to a compound according to Formula 1a for use as a medicament in the treatment of a medical condition associated with defective and/or pathologic class II phosphoinositide 3-kinase (PI3K) signaling, as outlined above, wherein the substituents R1-R11 are defined as follows:

wherein

R1: N or C;
R2: N or C;
R3: N or C;

wherein at least one of R1, R2 and R3 is N; preferably wherein R1 and R3 are N and R2 is C;

R4: can be the same or different, H, halogen (preferably Cl, Br, F), C1-C5 alkyl (preferably C1-C3 alkyl), C1-C5 haloalkyl, hydroxyl, alkoxy (preferably —OCH$_3$, —OCH$_2$CH$_3$), cycloalkyl (preferably C3-C6 cycloalkyl), —CN, carbonyl, carboxyl, carboxy ester, alkoxy, aldehyde, trihalide methyl ester, primary, secondary or tertiary amine, amide, imide, carbamate, carboxamide, nitro, sulfide, sulfurtrihalide, sulfurpentahalide, sulfinyl, sulfonyl, sulfino, or sulfo, sulfonamide, —OCF$_3$;

wherein when R1, R2, R3 is N, R4 attached thereto is absent;

R5: C1-C5 alkyl (preferably C2 alkyl), cycloalkyl (preferably C3-C6 cycloalkyl), aryl (preferably phenyl or napthyl), C1-C5 alkyl-cycloalkyl, C1-C5 alkyl-aryl, partially saturated bicyclic aryl (preferably indenyl, a benzene ring fused with a cyclopentane ring, which is bonded to the adjacent N of Formula 1);

wherein R5 is optionally substituted with one or more halogens (preferably Cl, Br, F), C1-C5 alkyl (preferably C1-C3 alkyl), C1-C5 haloalkyl, hydroxyl, alkoxy (preferably OCH$_3$, OCH$_2$CH$_3$);

R6: H, alkyl (preferably C1-C5 alkyl), cycloalkyl (preferably C3-C6 cycloalkyl), aryl (preferably phenyl), heterocyclyl, heteroaryl, wherein R6 is optionally substituted with one or more halogens (preferably Cl, Br, F), C1-C5 alkyl (preferably C1-C3 alkyl), C1-C5 haloalkyl, hydroxyl, alkoxy (preferably OCH$_3$, OCH$_2$CH$_3$), C2-C10 alkynyl, C3-C8 cycloalkyl, carbonyl, C0-C5 alkyl carboxyester, C0-C5 alkyl carboxamide, primary, secondary or tertiary amine, carbamate, amide amine, nitro, —CN, O, sulfide, amine sulfoxide, sulfonamide, sulfonamide amine, sulfoxide, sulfone, sulfonamide haloalkyl, —OCF$_3$, carbamate, imide, —SF$_3$, —SF$_5$;

R7: S, absent (covalent bond to R8), NR, wherein R is H, C1-C5 alkyl (preferably C1-C3 alkyl), C1-C5 haloalkyl, alkoxy (preferably OCH$_3$, OCH$_2$CH$_3$);

R8: C1-C5 alkyl (preferably C1 alkyl), cycloalkyl (preferably C3-C6 cycloalkyl), wherein R8 is optionally substituted with one or more halogens (preferably Cl, Br, F), C1-C5 alkyl (preferably C1 alkyl), C1-C5 haloalkyl, hydroxyl, alkoxy (preferably OCH$_3$, OCH$_2$CH$_3$);

R9: amide (preferably —CONH—), amine (preferably-NH—), urea (preferably-NHCONH—), sulfonamide (preferably —SO$_2$NH—), carbonyl (preferably —CO—);

R10: cycloalkyl (preferably C3-C6 cycloalkyl), aryl (preferably phenyl), heterocyclyl, heteroaryl (preferably 5- or 6-membered heterocyclyl, heteroaryl), more preferably a 5- or 6-membered aromatic heterocycle, comprising one or more of N, O and/or S, wherein a C atom of of R10 is optionally substituted with O;

R11(n): n is 0-5 (preferably 1), may be the same or different, halogen (preferably Cl, Br, F), C1-C5 alkyl (preferably C1 alkyl), CN, C1-C5 haloalkyl, hydroxyl, alkoxy (preferably OCH$_3$, OCH$_2$CH$_3$), alkoxycarbonyl (preferably —COOCH$_3$, —CH$_2$COOCH$_3$, —CH$_2$CH$_2$COOCH$_3$), cycloalkyl (preferably C3-C6 cycloalkyl), aryl (preferably phenyl), C1-C5 alkyl-cycloalkyl, C1-C5 alkyl-aryl, heterocyclyl, heteroaryl, carboxamide, C0-C5 alkyl carboxamide (preferably CON(CH$_2$CH$_2$)$_2$O);

wherein optionally, when R11 is aryl (preferably phenyl), heterocyclyl or heteroaryl and R10 is substituted with at least two substituents, two substituents or members of R11 attached to adjacent atoms of R10 form a 5- to 8-membered saturated, partially unsaturated or aromatic cyclic group (preferably a condensed bicyclic aromatic group) comprising two atoms of R10 and optionally further comprising 0, 1, 2, 3 or 4 heteroatoms, said heteroatoms selected independently from nitrogen, sulfur or oxygen, wherein said saturated, partially unsaturated or aromatic cyclic group is optionally substituted by one or more of R, wherein R is independently selected from the group consisting of H, alkyl, haloalkyl, alkoxy, or amine.

wherein optionally, when R11 is aryl (preferably phenyl), heterocyclyl or heteroaryl and R11 is substituted with at least two substituents, two substituents of R11 attached to adjacent atoms of R11 form a 5- to 8-membered saturated, partially unsaturated or aromatic cyclic group (preferably a condensed bicyclic aromatic group) comprising two atoms of R11 and further comprising 0, 1, 2, 3 or 4 heteroatoms, said heteroatoms selected independently from nitrogen, sulfur or oxygen, wherein said saturated, partially unsaturated or aromatic cyclic group is optionally substituted by one or more of R, wherein R is independently selected from the group consisting of H, alkyl, haloalkyl, alkoxy, or amine.

wherein R11 is optionally substituted with one or more substituents selected from the group consisting of one or more halogens (preferably Cl, Br, F), C1-C5 alkyl (preferably C1 alkyl), C1-C5 haloalkyl, hydroxyl, alkoxy (preferably OCH$_3$, OCH$_2$CH$_3$), C2-C10 alkynyl, C3-C8 cycloalkyl, carbonyl, C0-C5 alkyl carboxyester, carboxamide, C0-C5 alkyl carboxamide (preferably CON(CH$_2$CH$_2$)$_2$O), primary, secondary or tertiary amine, carbamate, amide amine, nitro, —CN, O, sulfide, amine sulfoxide, sulfonamide, sulfonamide amine, sulfoxide, sulfone, sulfonamide haloalkyl, —OCF$_3$, carbamate, imide, —SF$_3$, —SF$_5$.

In one embodiment the compound according to Formula 1a is characterized in that preferably R4 can be the same or different, H, halogen (preferably Cl, Br, F), C1-C5 alkyl (preferably C1-C3 alkyl), C1-C5 haloalkyl, hydroxyl, alkoxy (preferably —OCH$_3$, —OCH$_2$CH$_3$), cycloalkyl (preferably C3-C6 cycloalkyl), CN, carbonyl (—C(O)R), carboxyl (—C(O)OH), carboxy ester (CO$_2$R), alkoxy (—O— alkyl), aldehyde (—C(O)H), trihalide methyl ester (—C(O)OCX$_3$), primary, secondary or tertiary amine (—NR(R')), amide (—N(R)—C(O)—R), imide (—C(O)—N(R)—C(O)—R'), carbamate (—N(R)—C(O)—OR'), carboxamide (—C(O)N(R)R'), nitro (—NO$_2$), sulfide (—SR), sulfurtrihalide (—SX$_3$), sulfurpentahalide (—SX$_5$), sulfinyl (—S(O)R), sulfonyl (—SO$_2$R), sulfino (—SO$_2$H), or sulfo (—SO$_3$H), wherein R, R' is independently selected from the group consisting of H, alkyl, haloalkyl, alkoxy, or amine, and wherein X is halogen.

In one embodiment the compound according to Formula 1a is characterized in that preferably R4 can be the same or different, H, halogen (preferably Cl, Br, F), C1-C5 alkyl (preferably C1-C3 alkyl), C1-C5 haloalkyl, hydroxyl, alkoxy (preferably —OCH$_3$, —OCH$_2$CH$_3$), cycloalkyl (preferably C3-C6 cycloalkyl), more preferably H, alkyl, cycloalkyl or alkoxy.

In a preferred embodiment according to Formula 1a, R4 is H and R1 and R3 are N and R2 is C, optionally in combination with another preferred embodiment according to Formula 1a, in which R7 is S, R8 is CH$_2$ (optionally substituted with CH$_3$) and R9 is an amide (preferably —CONH—).

In one embodiment the compound according to Formula 1a is characterized in that preferably R11(n): n is 1, cycloalkyl (preferably C3-C6 cycloalkyl), aryl (preferably phenyl), C1-C5 alkyl-cycloalkyl, C1-C5 alkyl-aryl, heterocyclyl, heteroaryl, with an optional substitution as described above.

In one embodiment the compound according to Formula 1a is characterized in that preferably R11 is optionally substituted with one or more substituents selected from the group consisting of one or more halogens (preferably Cl, Br, F), C1-C5 alkyl (preferably C1 alkyl), C1-C5 haloalkyl, hydroxyl, alkoxy (preferably OCH$_3$, OCH$_2$CH$_3$), sulfone (preferably —SO$_2$CH$_3$), C2-C10 alkynyl, C3-C8 cycloalkyl, carbonyl (—C(O)—R), carboxyester (—C(O)—O—R), carboxamide (—C(O)—N(R)—R), C0-C5 alkyl carboxamide (preferably CON(CH$_2$CH$_2$)$_2$O), primary, secondary or tertiary amine (—N(R)—R), carbamate (—NR—C(O)—O—R), amide amine (NH—C(O)—NH—R), nitro (—NO$_2$), —CN, O, sulfide (S—R), amine sulfoxide, sulfonamide, sulfonamide amine (preferably —N(R)—S(O)$_u$—R, wherein u is 1 or 2, or —S(O)$_v$—N(R)—R, wherein v is 1 or 2, preferably —NHSO$_2$CH$_3$, —SO$_2$NHCH$_3$, —NHSO$_2$N(CH$_3$)$_2$), sulfoxide (preferably —SO$_r$R, wherein r is 1-3, preferably —S(O)R, —SO$_2$R, —SO$_2$H, and —SO$_3$H), sulfonamide haloalkyl (preferably -NHSO$_2$CF$_3$, —NHSO$_2$CH$_2$CF$_3$), —OCF$_3$, carbamate (—N(R)—C(O)—R), imide (—C(O)—N(R)—C(O)—R'), —SF$_3$, —SF$_5$, wherein R is independently selected from the group consisting of H, alkyl, haloalkyl, alkoxy, or amine, wherein optionally when R11 is aryl (preferably phenyl), heterocyclyl or heteroaryl and R11 is substituted with at least two substituents, two substituents of R11 attached to adjacent atoms of R11 form a 5- to 8-membered cyclic group comprising two atoms of R11 and further comprising 1, 2, 3 or 4 heteroatoms, said heteroatoms selected independently from nitrogen, sulfur or oxygen, wherein said cyclic group is optionally substituted by one or more of R, wherein R is independently selected from the group consisting of H, alkyl, haloalkyl, alkoxy, or amine.

In one embodiment the compound according to Formula 1a is characterized in that preferably R11 is optionally substituted with one or more substituents selected from the group consisting of one or more halogens (preferably Cl, Br, F), C1-C5 alkyl (preferably C1 alkyl), C1-C5 haloalkyl, hydroxyl, alkoxy (preferably OCH$_3$, OCH$_2$CH$_3$), sulfone (preferably —SO$_2$CH$_3$), carboxamide, C0-C5 alkyl carboxamide (preferably CON(CH$_2$CH$_2$)$_2$O), primary, secondary or tertiary amine, carbamate, amide amine, —CN, sulfide, amine sulfoxide, sulfonamide, sulfonamide amine, sulfoxide, sulfonamide haloalkyl, wherein optionally when R11 is aryl (preferably phenyl), heterocyclyl or heteroaryl and R11 is substituted with at least two substituents, two substituents of R11 attached to adjacent atoms of R11 form a 5- to 8-membered cyclic group comprising two atoms of R11 and further comprising 1, 2, 3 or 4 heteroatoms, said heteroatoms selected independently from nitrogen, sulfur or oxygen, wherein said cyclic group is optionally substituted by one or more of R, wherein R is independently selected from the group consisting of H, alkyl, alkoxy, or amine.

In one embodiment, the compound according to Formula 1a is characterized in that preferably R1 is N. In one embodiment, the compound according to Formula 1a is characterized in that preferably R3 is N.

In a further embodiment, the compound according to Formula 1a is characterized in that preferably R5 is C1-C5 alkyl (preferably C2 alkyl), wherein R5 is optionally substituted with one or more halogens (preferably Cl, Br, F), C1-C5 alkyl (preferably C1-C3 alkyl), C1-C5 haloalkyl, hydroxyl, alkoxy (preferably $OCH_3$, $OCH_2CH_3$).

In one embodiment, the compound according to Formula 1a is characterized in that preferably R6 is a cyclic group, such as cycloalkyl (preferably C3-C6 cycloalkyl), aryl (preferably phenyl), heterocyclyl or heteroaryl.

In one embodiment, the compound according to Formula 1a is characterized in that R9 is amide (preferably —CONH—) or carbonyl (preferably —CO—), and R10 is aryl (preferably phenyl) or heteroaryl.

In one embodiment, the compound according to Formula 1a is characterized in that R1 is N, R3 is N, R5 is C1-C5 alkyl (preferably C2 alkyl), wherein R5 is optionally substituted with one or more halogens (preferably Cl, Br, F), C1-C5 alkyl (preferably C1-C3 alkyl), C1-C5 haloalkyl, hydroxyl, alkoxy (preferably $OCH_3$, $OCH_2CH_3$), and R6 is a cyclic group, such as cycloalkyl (preferably C3-C6 cycloalkyl), aryl (preferably phenyl), heterocyclyl or heteroaryl.

In one embodiment, the compound according to Formula 1a is characterized in that R1 is N, R3 is N, R5 is C1-C5 alkyl (preferably C2 alkyl), wherein R5 is optionally substituted with one or more halogens (preferably Cl, Br, F), C1-C5 alkyl (preferably C1-C3 alkyl), C1-C5 haloalkyl, hydroxyl, alkoxy (preferably $OCH_3$, $OCH_2CH_3$), R6 is a cyclic group, such as cycloalkyl (preferably C3-C6 cycloalkyl), aryl (preferably phenyl), heterocyclyl or heteroaryl, R9 is amide (preferably —CONH—) or carbonyl (preferably —CO—), and R10 is aryl (preferably phenyl) or heteroaryl.

Combinations of the various preferred embodiments are themselves considered preferred embodiments according to Formula 1a of the present invention.

The present invention therefore relates to a compound according to Formula 4a for use as a medicament in the treatment of a medical condition associated with defective and/or pathologic class II phosphoinositide 3-kinase (PI3K) signaling, Formula 4a

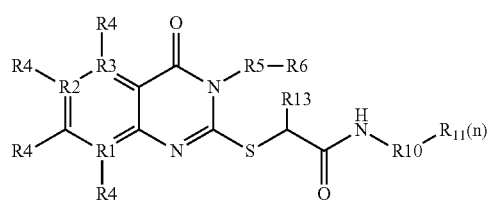

wherein R13: H or $CH_3$, and R1 to R6 and R10 and R11 are as recited in embodiments of Formula 1a, wherein R10-R11 is preferably one of:

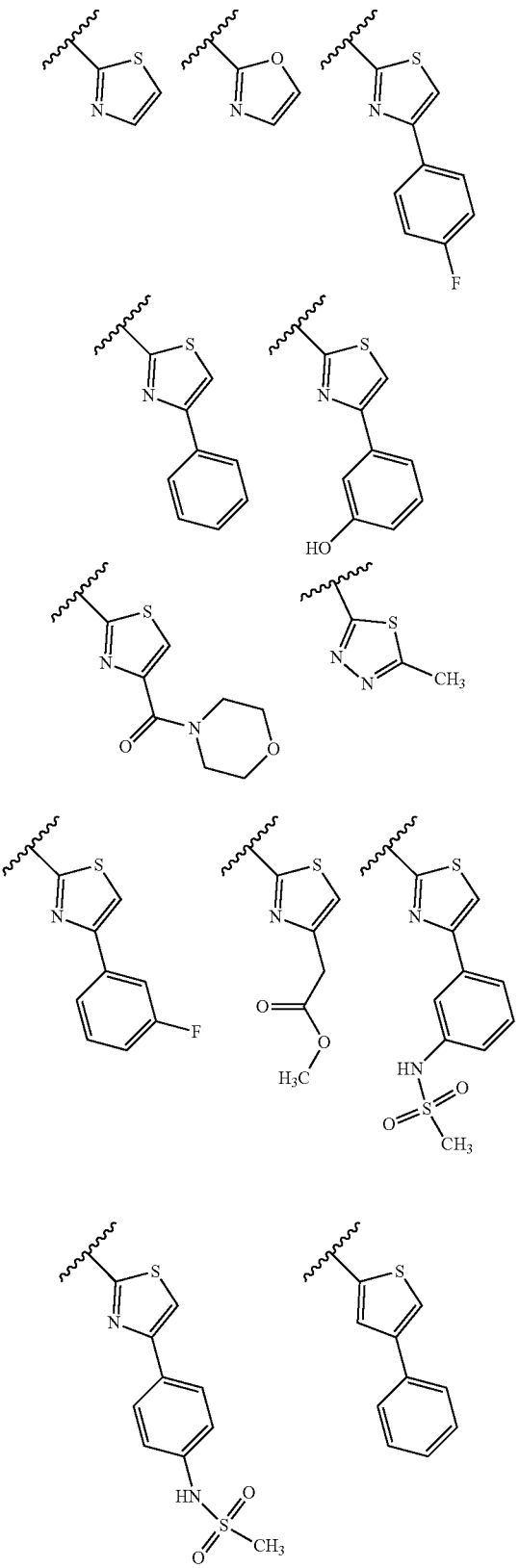

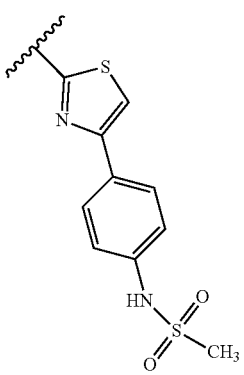

-continued
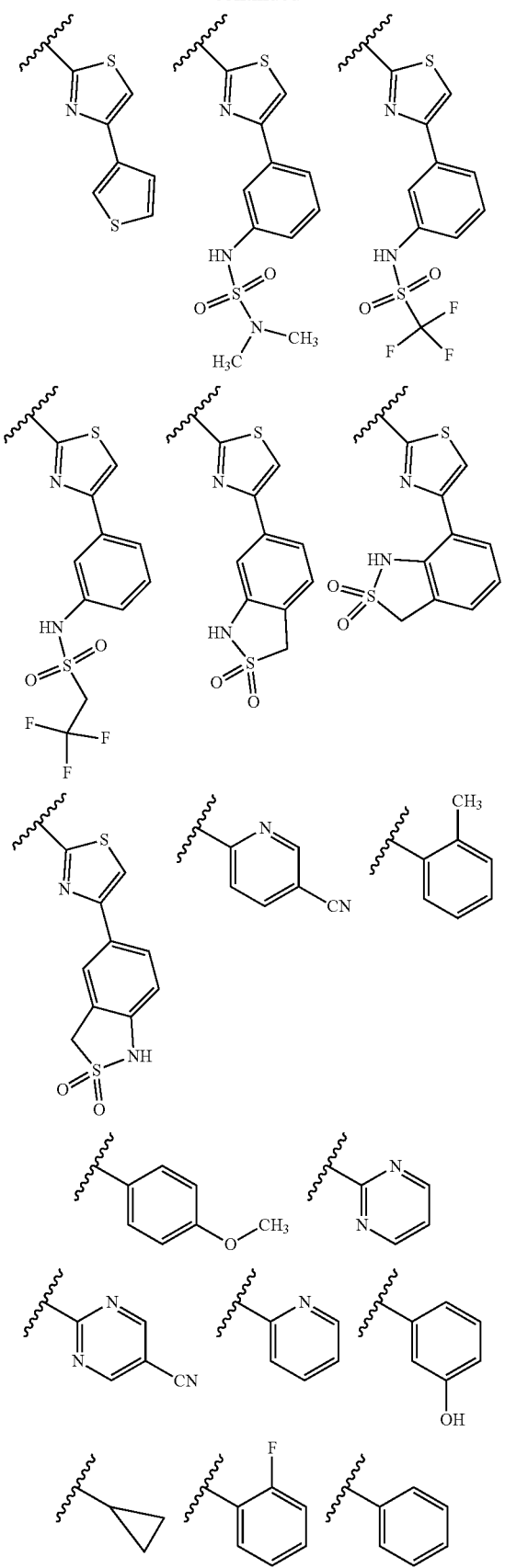
-continued
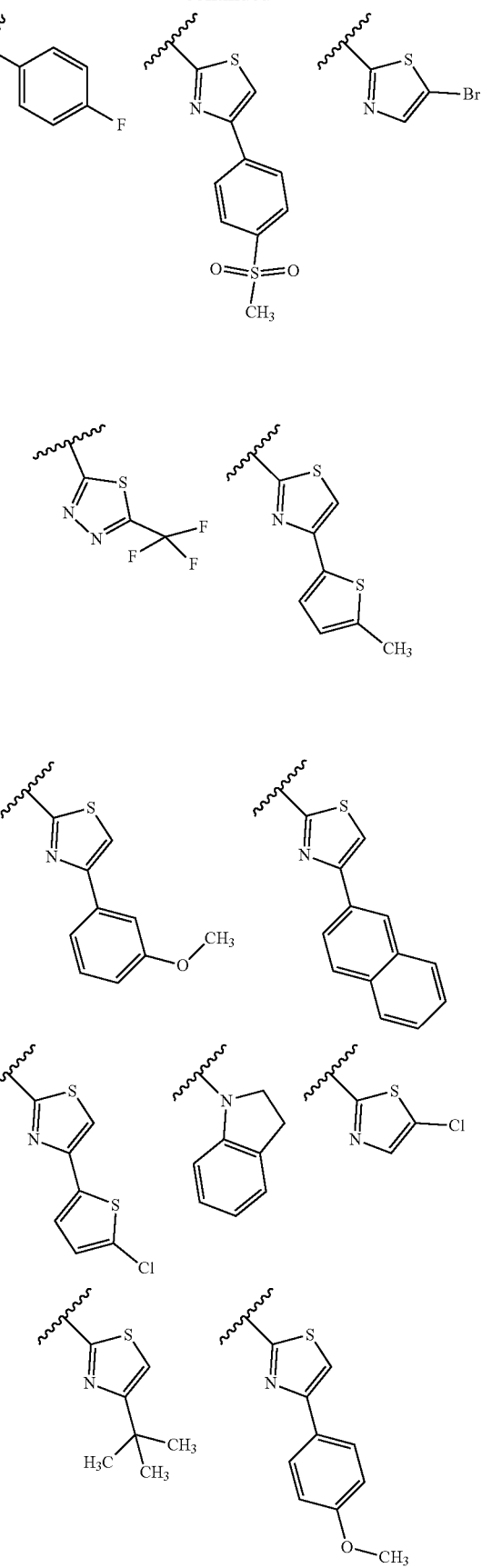

-continued

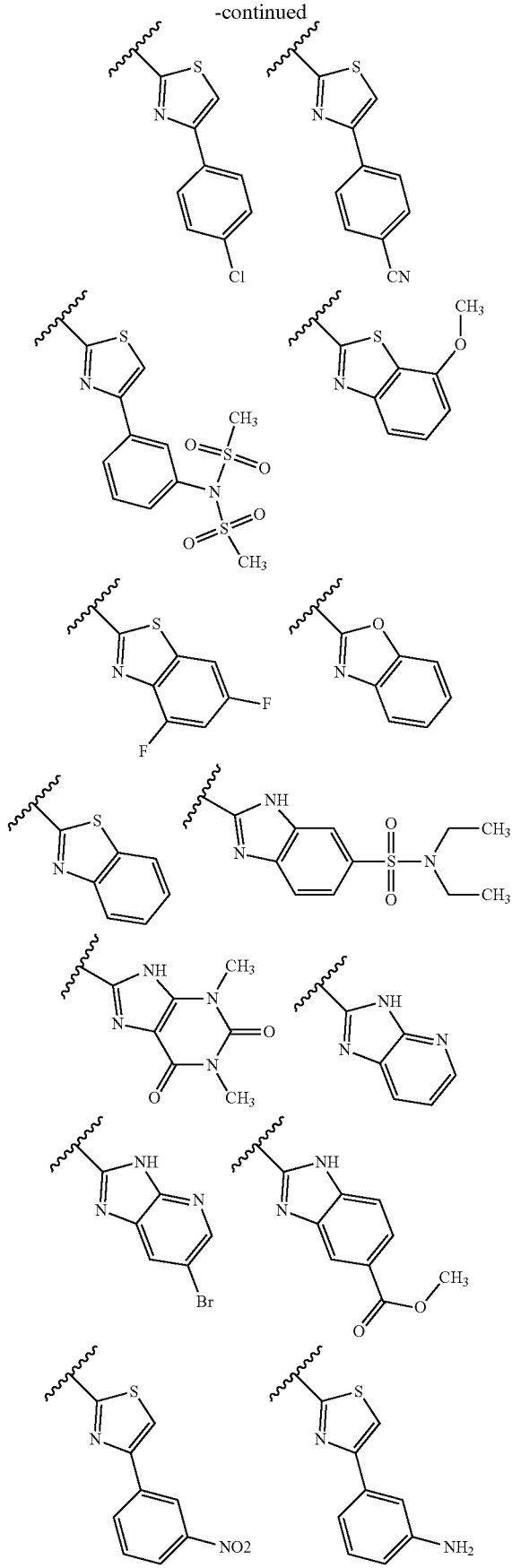

-continued

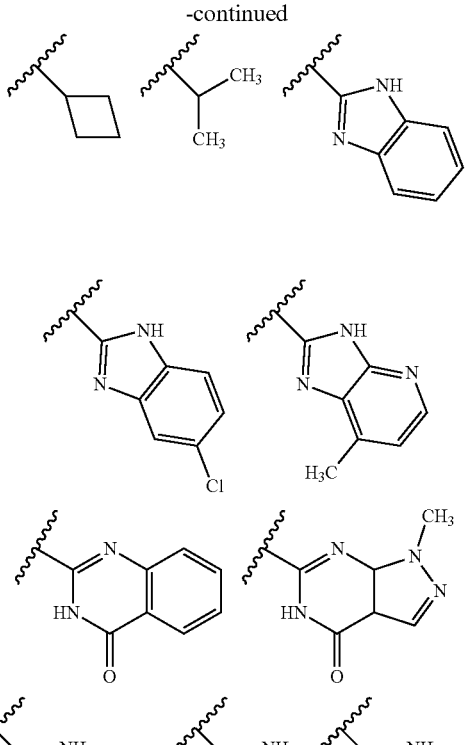

In one embodiment, the compound according to Formula 4a is characterized in that preferably R1 is N. In one embodiment, the compound according to Formula 4a is characterized in that preferably R3 is N.

In a further embodiment, the compound according to Formula 4a is characterized in that preferably R5 is C1-C5 alkyl (preferably C2 alkyl), wherein R5 is optionally substituted with one or more halogens (preferably Cl, Br, F), C1-C5 alkyl (preferably C1-C3 alkyl), C1-C5 haloalkyl, hydroxyl, alkoxy (preferably $OCH_3$, $OCH_2CH_3$).

In one embodiment, the compound according to Formula 4a is characterized in that preferably R6 is a cyclic group, such as cycloalkyl (preferably C3-C6 cycloalkyl), aryl (preferably phenyl), heterocyclyl or heteroaryl.

In one embodiment, the compound according to Formula 4a is characterized in that R1 is N, R3 is N, R5 is C1-C5 alkyl (preferably C2 alkyl), wherein R5 is optionally substituted with one or more halogens (preferably Cl, Br, F), C1-C5 alkyl (preferably C1-C3 alkyl), C1-C5 haloalkyl, hydroxyl, alkoxy (preferably $OCH_3$, $OCH_2CH_3$), and R6 is a cyclic group, such as cycloalkyl (preferably CO—CO cycloalkyl), aryl (preferably phenyl), heterocyclyl or heteroaryl.

The present invention therefore relates to a compound according to Formula 6a for use as a medicament in the treatment of a medical condition associated with defective and/or pathologic class II phosphoinositide 3-kinase (PI3K) signaling, Formula 6a

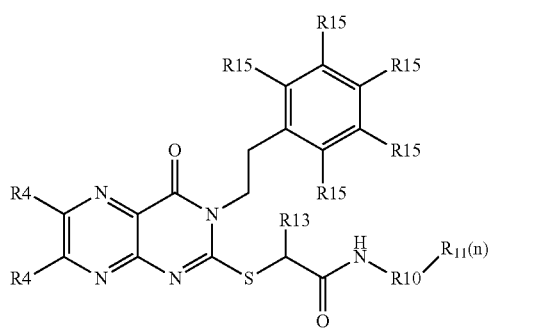

wherein
R4: as recited in embodiments of Formula 1a;
R10, R11: as recited in embodiments of Formula 1a or 4a;
R13: H or CH$_3$;
R15: may be the same or different, H, halogen (preferably Cl, Br, F) C1-C5 alkyl (preferably C1-C3 alkyl), C1-C5 haloalkyl, hydroxyl, alkoxy (preferably OCH$_3$, OCH$_2$CH$_3$).

The present invention therefore relates to a compound according to Formula 8a for use as a medicament in the treatment of a medical condition associated with defective and/or pathologic class II phosphoinositide 3-kinase (PI3K) signaling, Formula 8a

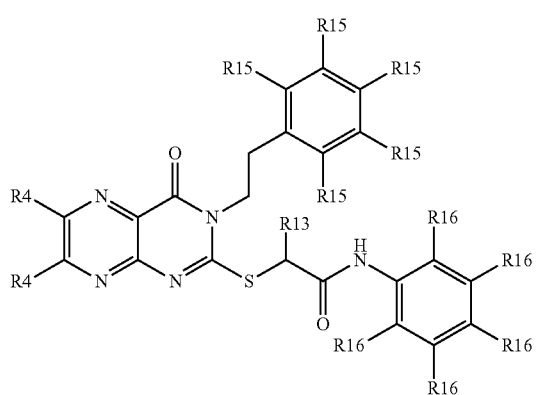

wherein
R4: as recited in embodiments of Formula 1a;
R13: H or CH$_3$;
R15: may be the same or different, H, halogen (preferably Cl, Br, F) C1-C5 alkyl (preferably C1-C3 alkyl), C1-C5 haloalkyl, hydroxyl, alkoxy (preferably OCH$_3$, OCH$_2$CH$_3$);
R16: may be the same or different, H, halogen (preferably Cl, Br, F), C1-C5 alkyl (preferably C1 alkyl), C1-C5 haloalkyl, hydroxyl, alkoxy (preferably OCH$_3$, OCH$_2$CH$_3$), CN.

In further embodiments, the compounds described under Formula 1a, 4a, 6a and 8a are defined by an alternative R10 substituent in comparison to the Formula 1, 4 and 6. In particular, the medical use of the compound relates to compounds with R10: cycloalkyl (preferably C3-C6 cycloalkyl), aryl (preferably phenyl), heterocyclyl, heteroaryl (preferably 5- or 6-membered heterocyclyl, heteroaryl), more preferably a 5- or 6-membered aromatic heterocycle, comprising one or more of N, O and/or S.

Accordingly, for the sake of completeness, the present invention therefore further relates to compounds according to Formula 2 or 3, as described above, wherein R10 is defined as for Formula 1a, for use as a medicament as described herein.

The invention therefore relates to a method of treating and/or preventing a medical condition associated with defective and/or pathologic class II phosphoinositide 3-kinase (PI3K) signaling, said method comprising the administration of one or more of the above compounds or compounds falling under the formulae described above to a subject in need thereof, in particular the compounds of Formula 1, 1a, 2, 3, 4, 4a, 5, 6, 6a, 7 and 8, and preferred embodiments and combinations thereof described above.

In one embodiment, the medical condition to be treated is myopathy, preferably myotubular myopathy, more preferably X-linked centronuclear myopathy. Preferred embodiments relate to myopathies associated with defective and/or pathologic phosphoinositide 3-kinase (PI3K) signaling. For example, it has been shown that X-linked centronuclear myopathy phenotypes in mouse models are rescued by deletion of class II PI3KC2b and partially ameliorated by application of the non-selective PI3K inhibitor wortmannin.

In one embodiment, the medical condition to be treated is cancer, preferably solid tumors, more preferably wherein the compound targets pathological tumor angiogenesis. Preferred embodiments relate to cancers associated with defective and/or pathologic class II phosphoinositide 3-kinase (PI3K) signaling.

In one embodiment, the medical condition to be treated is diabetes. Preferred embodiments relate to subjects with diabetes in which it can be shown the disease is associated with defective and/or pathologic class II phosphoinositide 3-kinase (PI3K) signaling.

In one embodiment, the medical condition to be treated is thrombosis and/or cardiovascular disease. Preferred embodiments relate to cardiovascular diseases associated with defective and/or pathologic class II phosphoinositide 3-kinase (PI3K) signaling.

The invention therefore relates to a pharmaceutical composition for use as a medicament in the treatment of a medical condition associated with defective and/or pathologic class II phosphoinositide 3-kinase (PI3K) signaling comprising one or more compounds as described herein with a pharmaceutically acceptable carrier.

The invention therefore also relates to an in vitro method for modulating (preferably inhibiting) class II phosphoinositide 3-kinase (PI3K) signaling comprising the administration of a compound as disclosed herein, or a composition comprising said compound, to a cell in which PI3K signaling is to be modulated.

Table 1 shows a number of exemplary compounds of the invention, suitable for the medical use described herein.

Table 1: Preferred compounds of the invention

TABLE 1

| Entry | Example-IUPAC NAME | Structure | IC$_{50}$ (PI3KC2α; ADP-Glo ™ assay) [μM] |
|---|---|---|---|
| 1 | Example compound 1: N-(4-(3-Hydroxyphenyl)thiazol-2-yl)-2-((4-oxo-3-phenethyl-3,4-dihydropteridin-2-yl)thio)acetamide | 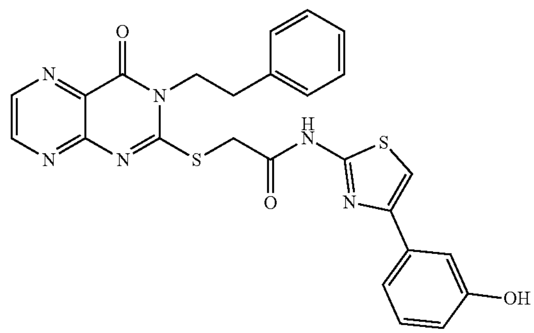 [SMILES: O=C(CSc1nc2nccnc2c(=O)n1CCc1ccccc1)Nc1nc(-c2cccc(O)c2)cs1] | 0.12 |
| 2 | Example compound 2: N-(4-(4-(Methylsulfonamido)phenyl)thiazol-2-yl)-2-((4-oxo-3-phenethyl-3,4-dihydropteridin-2-yl)thio)acetamide | 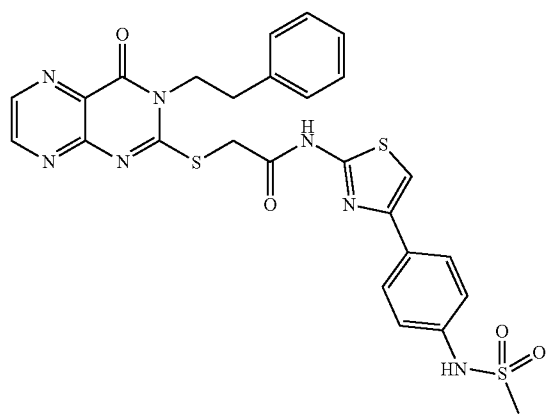 [SMILES: CS(=O)(=O)Nc1ccc(-c2csc(NC(=O)CSc3nc4nccnc4c(=O)n3CCc3ccccc3)n2)cc1] | 1.70 |
| 3 | Example compound 3: 2-((3-(3-Fluorophenethyl)-4-oxo-3,4-dihydropteridin-2-yl)thio)-N-(oxazol-2-yl)acetamide | 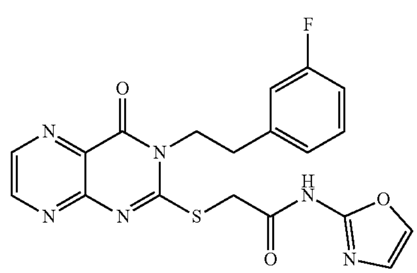 [SMILES: O=C(CSc1nc2nccnc2c(=O)n1CCc1cccc(F)c1)Nc1ncco1] | 2.10 |
| 4 | Example compound 4: 2-((3-(3-Fluorophenethyl)-4-oxo-3,4-dihydropteridin-2-yl)thio)-N-(thiazol-2-yl)acetamide | 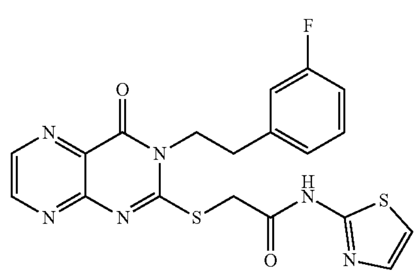 [SMILES: O=C(CSc1nc2nccnc2c(=O)n1CCc1cccc(F)c1)Nc1nccs1] | 0.84 |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 5 | Example compound 5: 2-((3-(3-Fluorophenethyl)-4-oxo-3,4-dihydropteridin-2-yl)thio)-N-(5-methyl-1,3,4-thiadiazol-2-yl)acetamide | 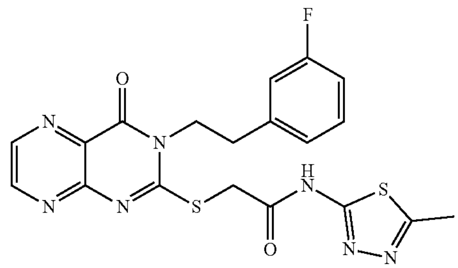 [SMILES: Cc1nnc(NC(=O)CSc2nc3nccnc3c(=O)n2CCc2cccc(F)c2)s1] | 6.30 |
| 6 | Example compound 6: 2-((3-(3-Fluorophenethyl)-4-oxo-3,4-dihydropteridin-2-yl)thio)-N-(4-(4-fluorophenyl)thiazol-2-yl)acetamide | 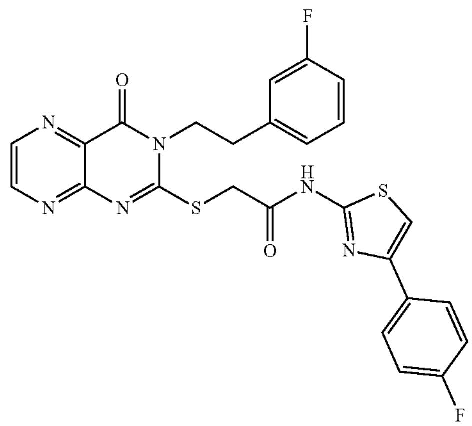 [SMILES: O=C(CSc1nc2nccnc2c(=O)n1CCc1cccc(F)c1)Nc1nc(-c2ccc(F)cc2)cs1] | 0.61 |
| 7 | Example compound 7: N-Cyclopropyl-2-((3-(3-fluorophenethyl)-4-oxo-3,4-dihydropteridin-2-yl)thio)acetamide | 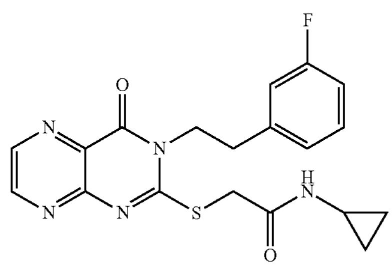 [SMILES: O=C(CSc1nc2nccnc2c(=O)n1CCc1cccc(F)c1)NC1CC1] | 7.10 |
| 8 | Example compound 8: 2-((4-Oxo-3-(2-(thiophen-2-yl)ethyl)-3,4-dihydropteridin-2-yl)thio)-N-(thiazol-2-yl)acetamide | 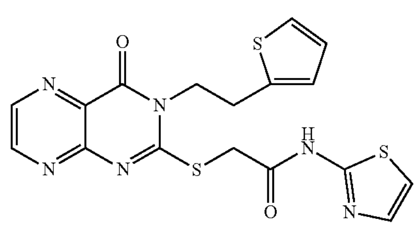 [SMILES: O=C(CSc1nc2nccnc2c(=O)n1CCc1cccs1)Nc1nccs1] | 1.10 |
| 9 | Example compound 9: 2-((4-Oxo-3-(3-(trifluoromethyl)phenethyl)-3,4-dihydropteridin-2-yl)thio)-N-(thiazol-2-yl)acetamide | 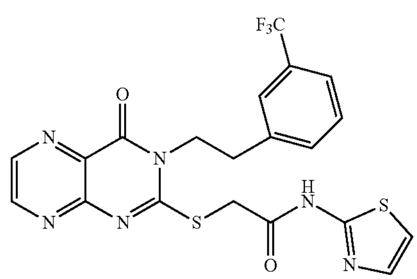 [SMILES: O=C(CSc1nc2nccnc2c(=O)n1CCc1cccc(C(F)(F)F)c1)Nc1nccs1] | 1.50 |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 10 | Example compound 10: 2-((4-Oxo-3-phenethyl-3,4-dihydropteridin-2-yl)thio)-N-(4-phenylthiazol-2-yl)acetamide | 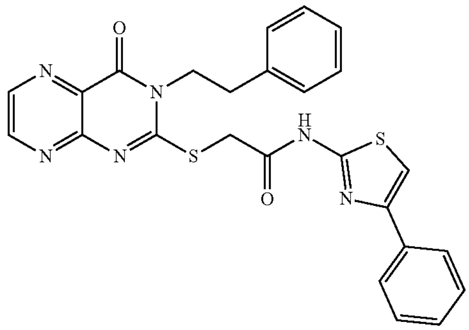 | 1.26 |
| 11 | Example compound 11: 2-((4-Oxo-3-phenethyl-3,4-dihydropteridin-2-yl)thio)-N-(thiazol-2-yl)acetamide | 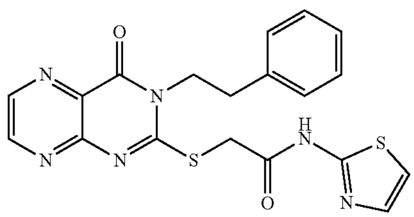 [SMILES: O=C(CSc1nc2nccnc2c(=O)n1CCc1ccccc1)Nc1nccs1] | 0.10 |
| 12 | Example compound 12: N-(4-(3-(Methylsulfonamido)phenyl)thiazol-2-yl)-2-((4-oxo-3-phenethyl-3,4-dihydropteridin-2-yl)thio)acetamide | 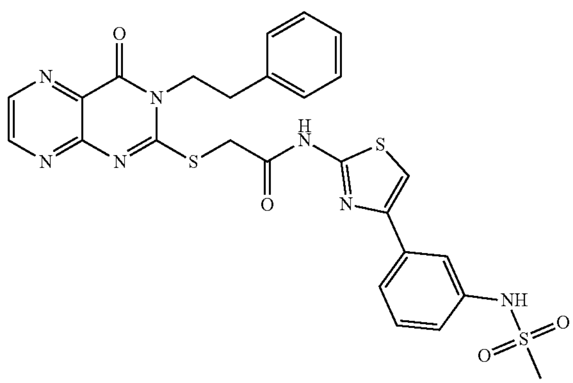 [SMILES: CS(=O)(=O)Nc1cccc(-c2csc(NC(=O)CSc3nc4nccnc4c(=O)n3CCc3ccccc3)n2)c1] | 0.13 |
| 13 | Example compound 13: 2-((4-Oxo-3-phenethyl-3,4-dihydropyrido[3,2-d]pyrimidin-2-yl)thio)-N-(thiazol-2-yl)acetamide | 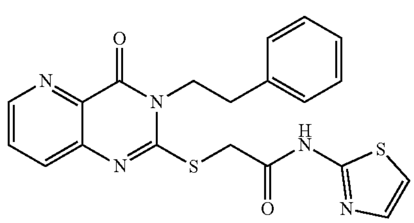 [SMILES: O=C(CSc1nc2nccnc2c(=O)n1CCc1ccccc1)Nc1ncco1] | 13.0 |
| 14 | Example compound 14: N-(Oxazol-2-yl)-2-((4-oxo-3-phenethyl-3,4-dihydropteridin-2-yl)thio)acetamide | 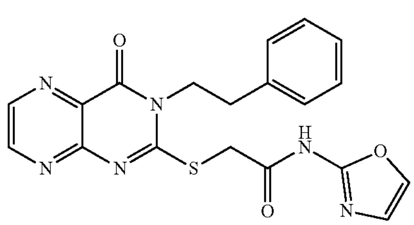 | 2.80 |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 15 | Example compound 15: N-(2-Fluorophenyl)-2-((4-oxo-3-phenethyl-3,4-dihydropteridin-2-yl)thio)acetamide | 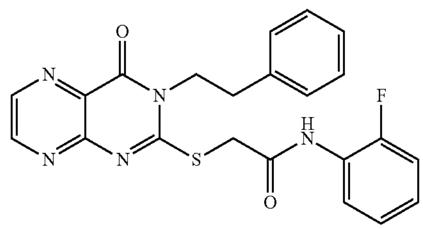 [SMILES: O=C(CSc1nc2nccnc2c(=O)n1CCc1ccccc1)Nc1ccccc1F] | 6.0 |
| 16 | Example compound 16: 2-((3-(3-Fluorophenethyl)-4-oxo-3,4-dihydropteridin-2-yl)thio)-N-(thiazol-2-yl)propenamide | 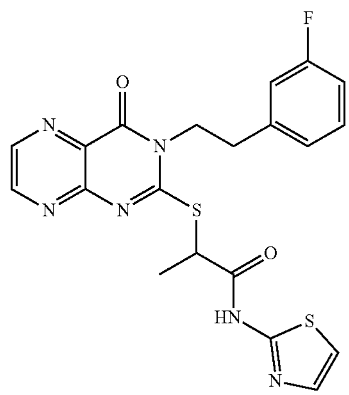 [SMILES: CC(Sc1nc2nccnc2c(=O)n1CCc1cccc(F)c1)C(=O)Nc1nccs1] | 5.2 |
| 17 | Example compound 17: 2-((3-([1,1'-Biphenyl]-3-yl)-4-oxo-3,4-dihydropteridin-2-yl)thio)-N-(thiazol-2-yl)acetamide | 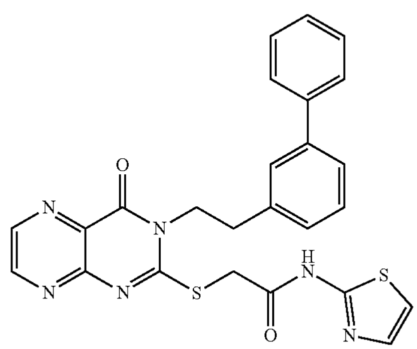 [SMILES: O=C(CSc1nc2nccnc2c(=O)n1CCc1cccc(-c2ccccc2)c1)Nc1nccs1] | 9.0 |
| 18 | Example compound 18: 2-((3-(2,2-Difluoro-2-phenylethyl)-4-oxo-3,4-dihydropteridin-2-yl)thio)-N-(thiazol-2-yl)acetamide | 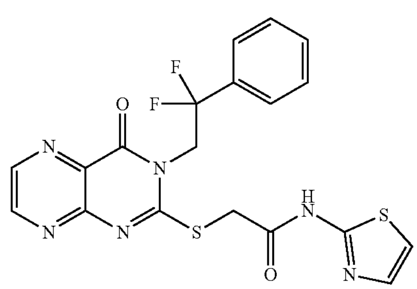 [SMILES: O=C(CSc1nc2nccnc2c(=O)n1CC(F)(F)c1ccccc1)Nc1nccs1] | 2.30 |
| 19 | Example compound 19: 2-((3-(2,3-dihydro-1H-inden-1-yl)-4-oxo-3,4-dihydropteridin-2-yl)thio)-N-(thiazol-2-yl)acetamide | 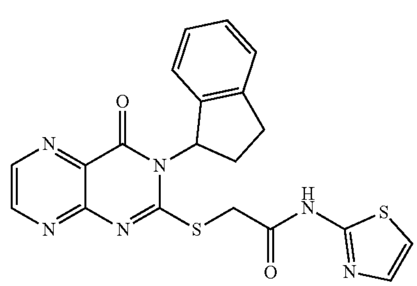 [SMILES: O=C(CSc1nc2nccnc2c(=O)n1C1CCc2ccccc21)Nc1nccs1] | 1.60 |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 20 | Example compound 20: 2-((4-Oxo-3-phenethyl-3,4-dihydropteridin-2-yl)thio)-N-(pyrimidin-2-yl)acetamide | 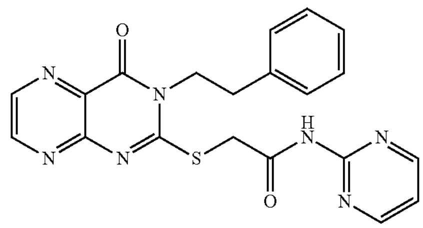 [SMILES: O=C(CSc1nc2nccnc2c(=O)n1CCc1ccccc1)Nc1ncccn1] | 2.00 |
| 21 | Example compound 21: 2-((4-Oxo-3-(2-phenylcyclopropyl)-3,4-dihydropteridin-2-yl)thio)-N-(thiazol-2-yl)acetamide | 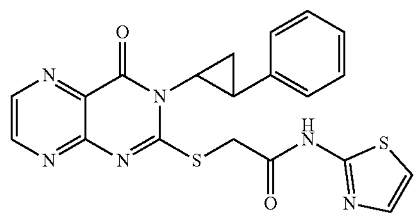 [SMILES: O=C(CSc1nc2nccnc2c(=O)n1C1CC1c1ccccc1)Nc1nccs1] | 12 |
| 22 | Example compound 22: 2-((4-Oxo-3-phenethyl-3,4-dihydropteridin-2-yl)thio)-N-phenylacetamide | 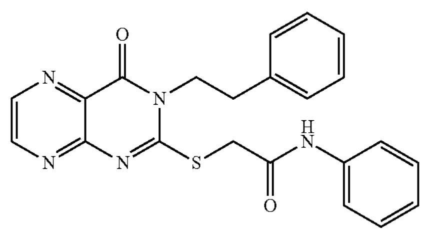 [SMILES: O=C(CSc1nc2nccnc2c(=O)n1CCc1ccccc1)Nc1ccccc1] | 3.3 |
| 23 | Example compound 23: 2-((4-Oxo-3-phenethyl-3,4-dihydropteridin-2-yl)thio)-N-(4-(thiophen-3-yl)thiazol-2-yl)acetamide | 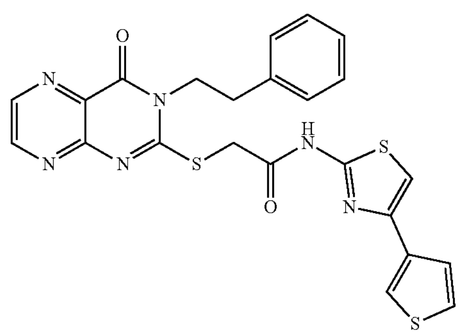 [SMILES: O=C(CSc1nc2nccnc2c(=O)n1CCc1ccccc1)Nc1nc(-c2ccsc2)cs1] | 0.76 |
| 24 | Example compound 24: Methyl 2-(2-(2-((4-oxo-3-phenethyl-3,4-dihydropteridin-2-yl)thio)acetamido)thiazol-4-yl)acetate | 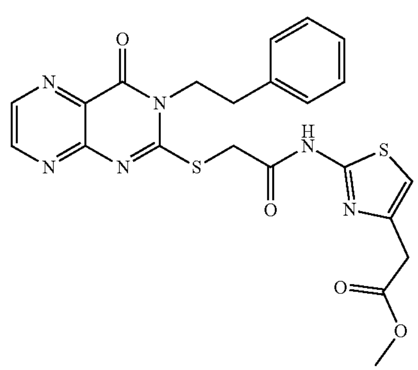 [SMILES: COC(=O)Cc1csc(NC(=O)CSc2nc3nccnc3c(=O)n2CCc2ccccc2)n1] | 2.20 |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 25 | Example compound 25: N-(4-(Morpholine-4-carbonyl)thiazol-2-yl)-2-((4-oxo-3-phenethyl-3,4-dihydropteridin-2-yl)thio)acetamide | 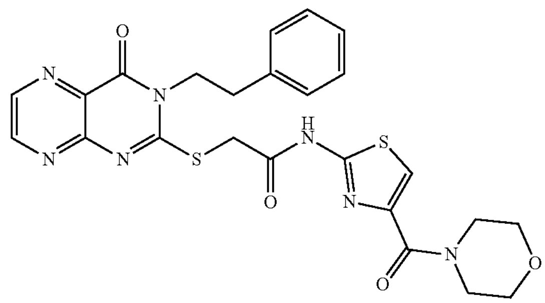 [SMILES: O=C(CSc1nc2nccnc2c(=O)n1CCc1ccccc1)Nc1nc(C(=O)N2CCOCC2)cs1] | 3.50 |
| 26 | Example compound 26: N-(4-(3-Fluorophenyl)thiazol-2-yl)-2-((4-oxo-3-phenethyl-3,4-dihydropteridin-2-yl)thio)acetamide | 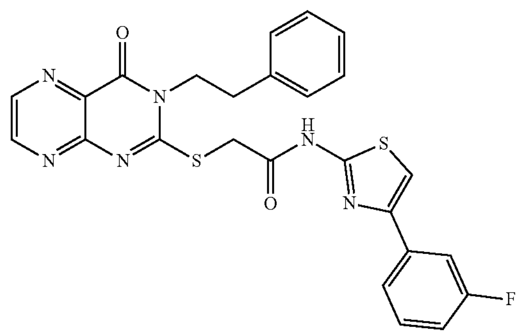 [SMILES: O=C(CSc1nc2nccnc2c(=O)n1CCc1ccccc1)Nc1nc(-c2cccc(F)c2)cs1] | 1.50 |
| 27 | Example compound 27: 2-((4-Oxo-3-phenethyl-3,4-dihydropteridin-2-yl)thio)-N-(4-phenylthiophen-2-yl)acetamide | 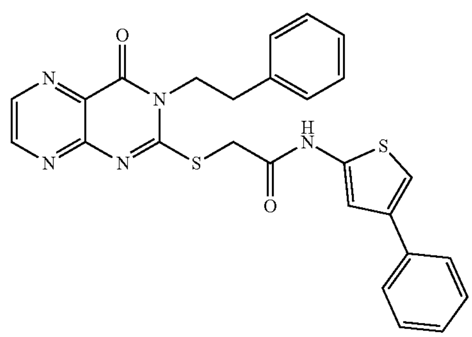 [SMILES: O=C(CSc1nc2nccnc2c(=O)n1CCc1ccccc1)Nc1cc(-c2ccccc2)cs1] | 17.2 |
| 28 | Example compound 28: N-(5-Cyanopyridin-2-yl)-2-((4-oxo-3-phenethyl-3,4-dihydropteridin-2-yl)thio)acetamide | 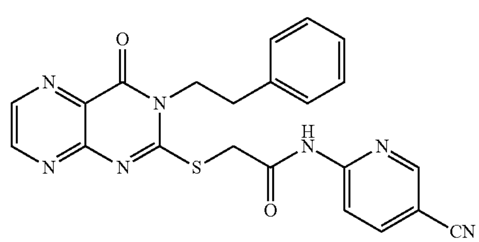 [SMILES: N#Cc1ccc(NC(=O)CSc2nc3nccnc3c(=O)n2CCc2ccccc2)nc1] | 7.6 |
| 29 | Example compound 29: N-(5-Bromothiazol-2-yl)-2-((4-oxo-3-phenethyl-3,4-dihydropteridin-2-yl)thio)acetamide | 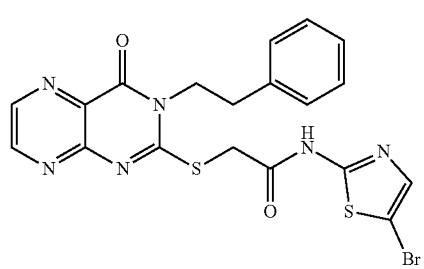 [SMILES: O=C(CSc1nc2nccnc2c(=O)n1CCc1ccccc1)Nc1ncc(Br)s1] | 6.6 |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 30 | Example compound 30: N-(4-(5-Methylthiophen-2-yl)thiazol-2-yl)-2-((4-oxo-3-phenethyl-3,4-dihydropteridin-2-yl)thio)acetamide | 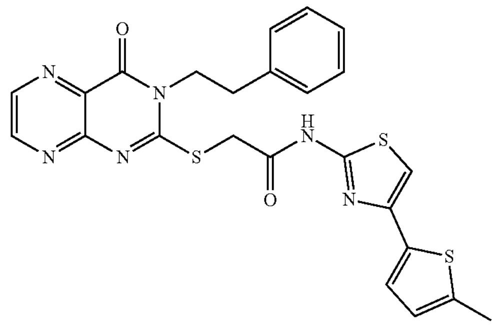 [SMILES: Cc1ccc(-c2csc(NC(=O)CSc3nc4nccnc4c(=O)n3CCc3ccccc3)n2)s1] | 5.8 |
| 31 | Example compound 31: N-(4-(3-Methoxyphenyl)thiazol-2-yl)-2-((4-oxo-3-phenethyl-3,4-dihydropteridin-2-yl)thio)acetamide | 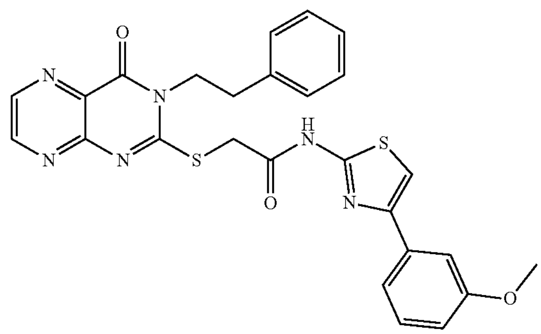 [SMILES: COc1cccc(-c2csc(NC(=O)CSc3nc4nccnc4c(=O)n3CCc3ccccc3)n2)c1] | 2.4 |
| 32 | Example compound 32: 2-((3-(Furan-2-ylmethyl)-4-oxo-3,4-dihydropteridin-2-yl)thio)-N-(thiazol-2-yl)acetamide | 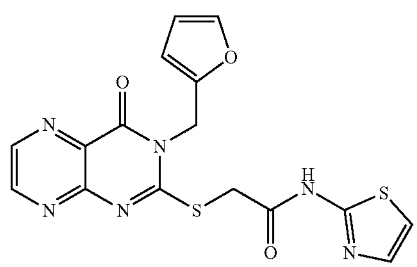 [SMILES: O=C(CSc1nc2nccnc2c(=O)n1Cc1ccco1)Nc1nccs1] | 1.8 |
| 33 | Example compound 33: N-(2-Fluorophenyl)-2-((3-(furan-2-ylmethyl)-4-oxo-3,4-dihydropteridin-2-yl)thio)acetamide | 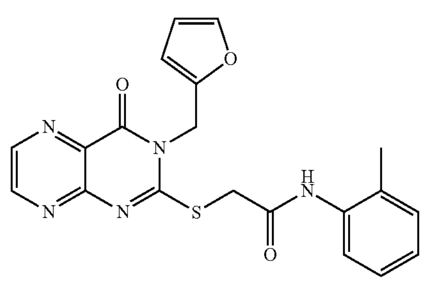 [SMILES: Cc1ccccc1NC(=O)CSc1nc2nccnc2c(=O)n1Cc1ccco1] | 7.9 |
| 34 | Example compound 34: 2-((4-Oxo-3-phenethyl-3,4-dihydropyrido[3,2-d]pyrimidin-2-yl)thio)-N-(5-(trifluoromethyl)-1,3,4-thiadiazol-2-yl)acetamide | 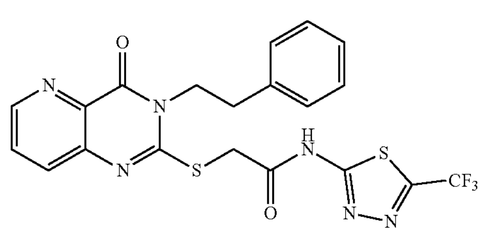 [SMILES: O=C(CSc1nc2cccnc2c(=O)n1CCc1ccccc1)Nc1nnc(C(F)(F)F)s1] | |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 35 | Example compound 35: 2-((2-(Indolin-1-yl)-2-oxoethyl)thio)-3-phenethylpteridin-4(3H)-one | 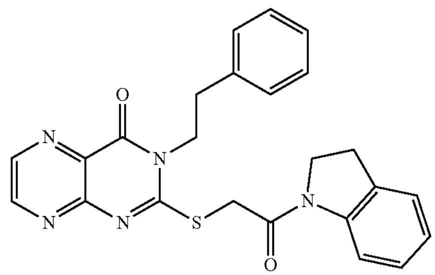 [SMILES: O=C(CSc1nc2nccnc2c(=O)n1CCc1ccccc1)N1CCc2ccccc21] | |
| 36 | Example compound 36: N-(oxazol-2-yl)-2-((4-oxo-3-phenethyl-3,4-dihydropyrido[3,2-d]pyrimidin-2-yl)thio)acetamide | 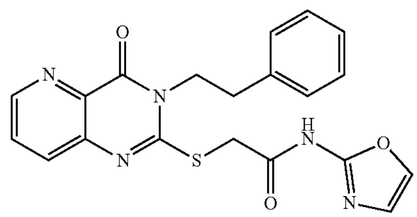 [SMILES: O=C(CSc1nc2cccnc2c(=O)n1CCc1ccccc1)Nc1ncco1] | |
| 37 | Example compound 37: 2-Methyl-2-((4-oxo-3-phenethyl-3,4-dihydropteridin-2-yl)thio)-N-(thiazol-2-yl)propanamide | 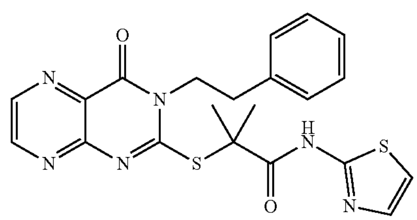 [SMILES: CC(C)(Sc1nc2nccnc2c(=O)n1CCc1ccccc1)C(=O)Nc1nccs1] | |
| 38 | Example compound 38: N-Methyl-2-((4-oxo-3-phenethyl-3,4-dihydropteridin-2-yl)thio)-N-phenylacetamide | 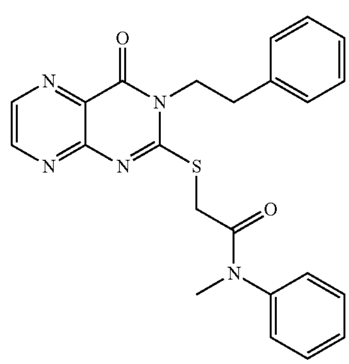 [SMILES: CN(C(=O)CSc1nc2nccnc2c(=O)n1CCc1ccccc1)c1ccccc1] | |
| 39 | Example compound 39: 2-((2-(4-Methoxyphenyl)-2-oxoethyl)thio)-3-phenethylpteridin-4(3H)-one | 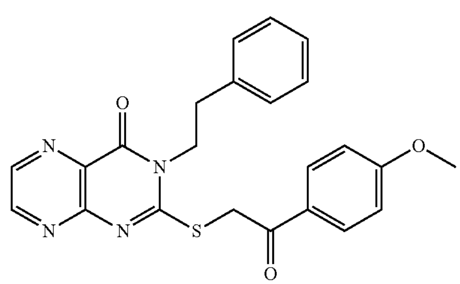 [SMILES: COc1ccc(C(=O)CSc2nc3nccnc3c(=O)n2CCc2ccccc2)cc1] | |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 40 | Example compound 40: 2-((4-Oxo-3-phenyl-3,4-dihydropteridin-2-yl)thio)-N-(thiazol-2-yl)acetamide | 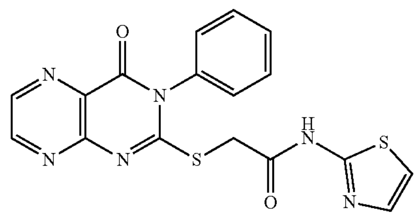 [SMILES: O=C(CSc1nc2nccnc2c(=O)n1-c1ccccc1)Nc1nccs1] | 6.6 |
| 41 | Example compound 41: 4-(4-Oxo-2-((2-oxo-2-(thiazol-2-ylamino)ethyl)thio)pteridin-3(4H)-yl)benzamide | 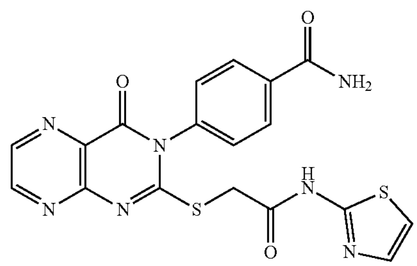 [SMILES: NC(=O)c1ccc(-n2c(SCC(=O)Nc3nccs3)nc3nccnc3c2=O)cc1] | 0.051 |
| 42 | Example compound 42: 2-((3-Benzyl-4-oxo-3,4-dihydropteridin-2-yl)thio)-N-(thiazol-2-yl)acetamide | 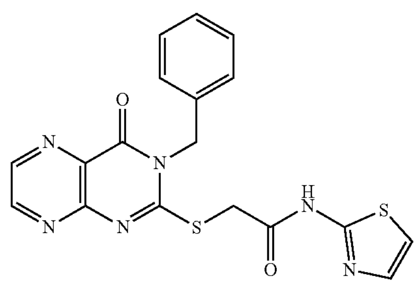 [SMILES: O=C(CSc1nc2nccnc2c(=O)n1Cc1ccccc1)Nc1nccs1] | <50 |
| 43 | Example compound 43: 2-((3-(2-((3r,5r,7r)-Adamantan-1-yl)ethyl)-4-oxo-3,4-dihydropteridin-2-yl)thio)-N-(thiazol-2-yl)acetamide | 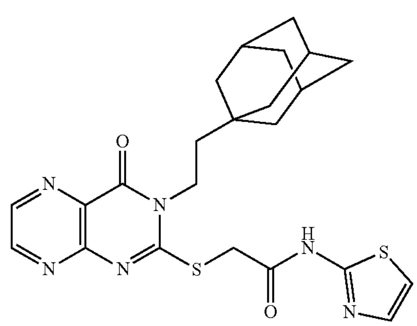 [SMILES: O=C(CSc1nc2nccnc2c(=O)n1CCC12CC3CC(CC(C3)C1)C2)Nc1nccs1] | |
| 44 | Example compound 44: 2-((3-(2-Cyclohexylethyl)-4-oxo-3,4-dihydropteridin-2-yl)thio)-N-(thiazol-2-yl)acetamide | 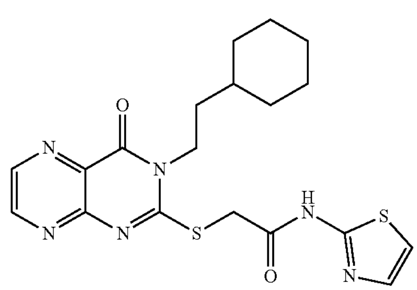 [SMILES: O=C(CSc1nc2nccnc2c(=O)n1CCC1CCCCC1)Nc1nccs1] | 0.59 |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 45 | Example compound 45: N-(5-Chlorothiazol-2-yl)-2-((4-oxo-3-phenethyl-3,4-dihydropteridin-2-yl)thio)acetamide | 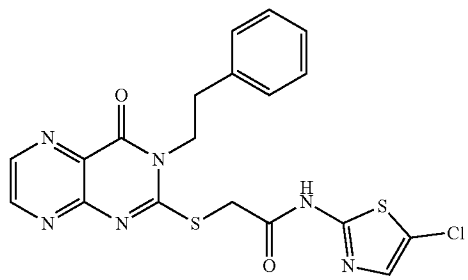 [SMILES: O=C(CSc1nc2nccnc2c(=O)n1CCc1ccccc1)Nc1ncc(Cl)s1] | 35 |
| 46 | Example compound 46: 2-((6-Methyl-4-oxo-3-phenethyl-3,4-dihydropteridin-2-yl)thio)-N-(thiazol-2-yl)acetamide | 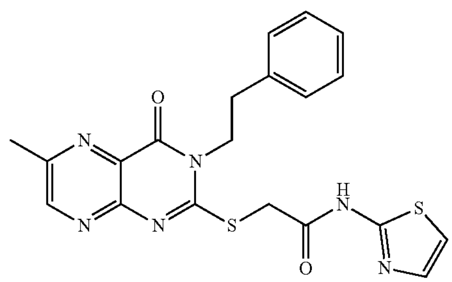 [SMILES: Cc1cnc2nc(SCC(=O)Nc3nccs3)n(CCc3ccccc3)c(=O)c2n1] | 23 |
| 47 | Example compound 47: N-(4-(4-Methoxyphenyl)thiazol-2-yl)-2-((4-oxo-3-phenethyl-3,4-dihydropteridin-2-yl)thio)acetamide | 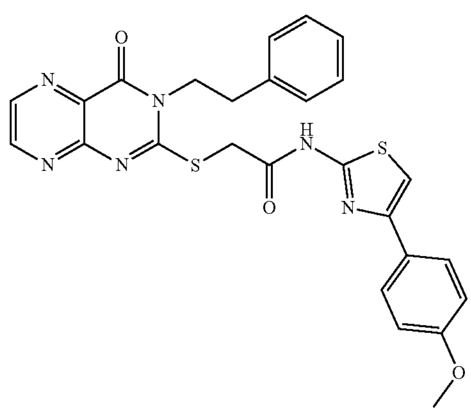 [SMILES: COc1ccc(-c2csc(NC(=O)CSc3nc4nccnc4c(=O)n3CCc3ccccc3)n2)cc1] | |
| 48 | Example compound 48: N-(4-(Naphthalen-2-yl)thiazol-2-yl)-2-((4-oxo-3-phenethyl-3,4-dihydropteridin-2-yl)thio)acetamide | 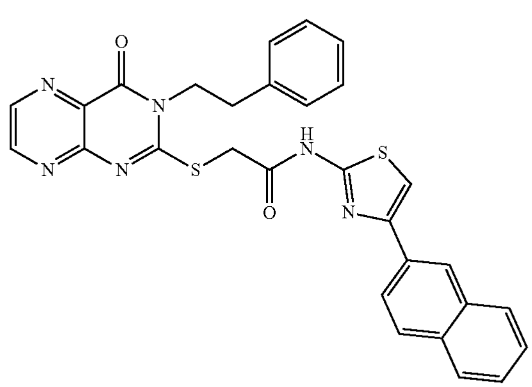 [SMILES: O=C(CSc1nc2nccnc2c(=O)n1CCc1ccccc1)Nc1nc(-c2ccc3ccccc3c2)cs1] | 26 |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 49 | Example compound 49: N-(4-(4-Chlorophenyl)thiazol-2-yl)-2-((4-oxo-3-phenethyl-3,4-dihydropteridin-2-yl)thio)acetamide | 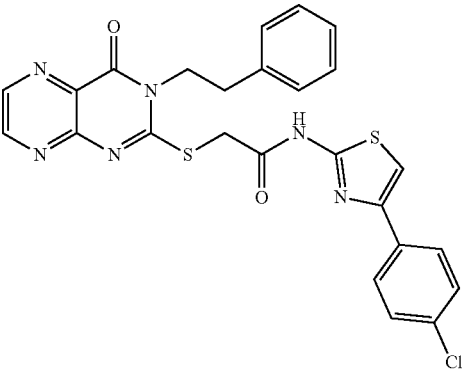 [SMILES: O=C(CSc1nc2nccnc2c(=O)n1CCc1ccccc1)Nc1nc(-c2ccc(Cl)cc2)cs1] | 7.1 |
| 50 | Example compound 50: N-(4-(4-Cyanophenyl)thiazol-2-yl)-2-((4-oxo-3-phenethyl-3,4-dihydropteridin-2-yl)thio)acetamide | 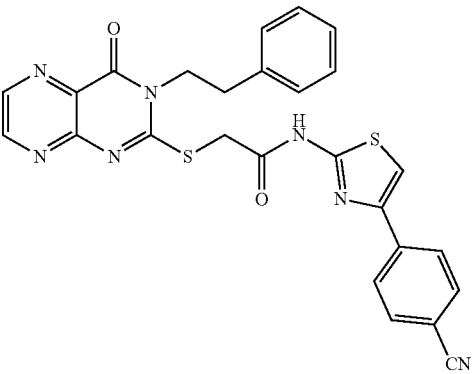 [SMILES: N#Cc1ccc(-c2csc(NC(=O)CSc3nc4nccnc4c(=O)n3CCc3ccccc3)n2)cc1] | 2.9 |
| 51 | Example compound 51: N-(4-(Tert-butyl)thiazol-2-yl)-2-((4-oxo-3-phenethyl-3,4-dihydropteridin-2-yl)thio)acetamide | 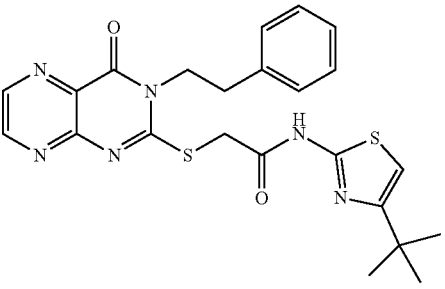 [SMILES: CC(C)(C)c1csc(NC(=O)CSc2nc3nccnc3c(=O)n2CCc2ccccc2)n1] | |
| 52 | Example compound 52: N-(4-(5-Chlorothiophen-2-yl)thiazol-2-yl)-2-((4-oxo-3-phenethyl-3,4-dihydropteridin-2-yl)thio)acetamide | 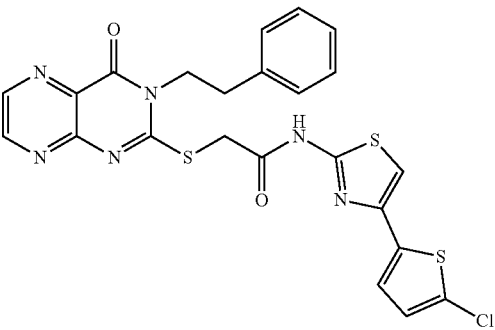 [SMILES: O=C(CSc1nc2nccnc2c(=O)n1CCc1ccccc1)Nc1nc(-c2ccc(Cl)s2)cs1] | |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 53 | Example compound 53: N-(4-(4-(Methylsulfonyl)phenyl)thiazol-2-yl)-2-((4-oxo-3-phenethyl-3,4-dihydropteridin-2-yl)thio)acetamide | 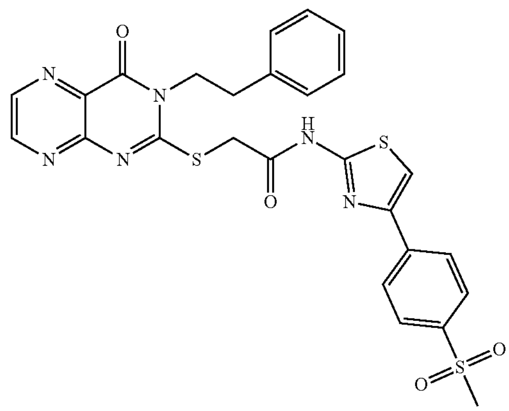 [SMILES: CS(=O)(=O)c1ccc(-c2csc(NC(=O)CSc3nc4nccnc4c(=O)n3CCc3ccccc3)n2)cc1] | 1.3 |
| 54 | Example compound 54: 2-((4-oxo-3-phenethyl-3,4-dihydropyrido[2,3-d]pyrimidin-2-yl)thio)-N-(thiazol-2-yl)acetamide | 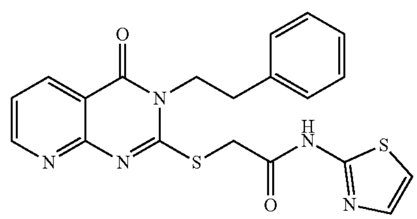 [SMILES: O=C(CSc1nc2ncccc2c(=O)n1CCc1ccccc1)Nc1nccs1] | 0.82 |
| 55 | Example compound 55: N-(4-(3-(N-(methylsulfonyl)methyl-sulfonamido)phenyl)thiazol-2-yl)-2-((4-oxo-3-phenethyl-3,4-dihydropteridin-2-yl)thio)acetamide | 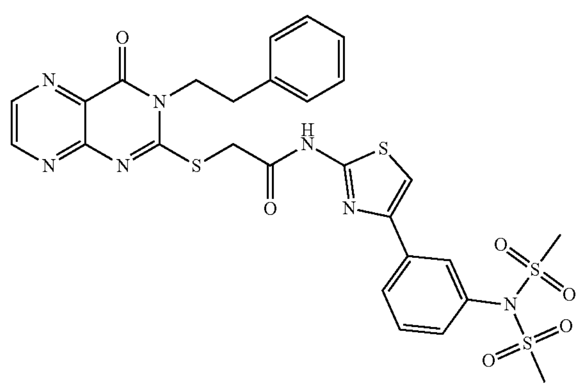 [SMILES: CS(=O)(=O)N(c1cccc(-c2csc(NC(=O)CSc3nc4nccnc4c(=O)n3CCc3ccccc3)n2)c1)S(C)(=O)=O] | 0.20 |
| 56 | Example compound 56: N-(7-methoxybenzo[d]thiazol-2-yl)-2-((4-oxo-3-phenethyl-3,4-dihydropteridin-2-yl)thio)acetamide | 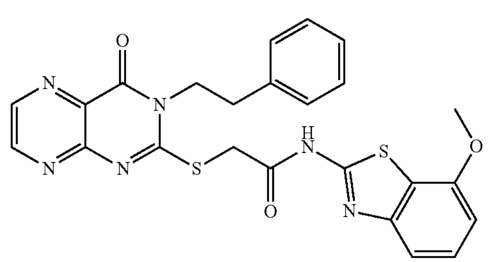 [SMILES: COc1cccc2nc(NC(=O)CSc3nc4nccnc4c(=O)n3CCc3ccccc3)sc12] | 3.1 |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 57 | Example compound 57: N-(4,6-difluorobenzo[d]thiazol-2-yl)-2-((4-oxo-3-phenethyl-3,4-dihydropteridin-2-yl)thio)acetamide | 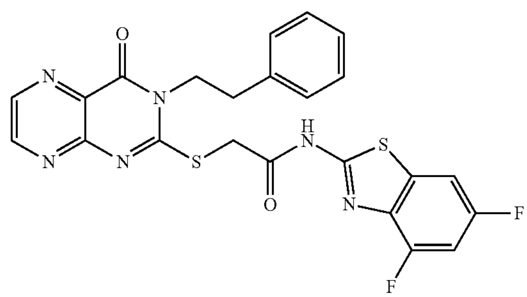 [SMILES: O=C(CSc1nc2nccnc2c(=O)n1CCc1ccccc1)Nc1nc2c(F)cc(F)cc2s1] | 3.4 |
| 58 | Example compound 58: N-(4-(3-Nitrophenyl)thiazol-2-yl)-2-((4-oxo-3-phenethyl-3,4-dihydropteridin-2-yl)thio)acetamide | 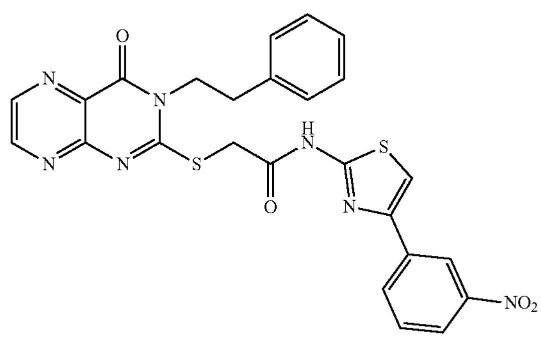 | 100% inhibition at 10 μM |
| 59 | Example compound 59: N-(4-(3-aminophenyl)thiazol-2-yl)-2-((4-oxo-3-phenethyl-3,4-dihydropteridin-2-yl)thio)acetamide | 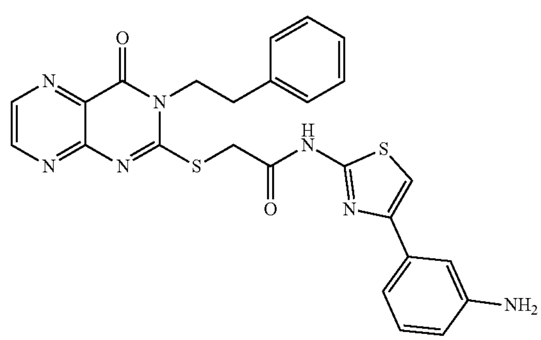 [SMILES: O=C(CSc1nc2nccnc2c(=O)n1CCc1ccccc1)Nc1nc(-c2cccc([N+](=O)[O-])c2)cs1] | 0.15 |
| 60 | Example compound 60: N-cyclobutyl-2-((4-oxo-3-phenethyl-3,4-dihydropteridin-2-yl)thio)acetamide | 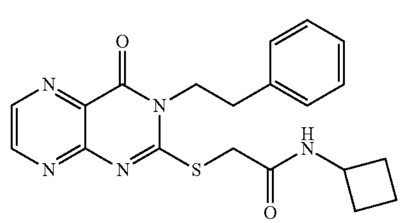 [SMILES: O=C(CSc1nc2nccnc2c(=O)n1CCc1ccccc1)NC1CCC1] | 5.9 |
| 61 | Example compound 61: N-Isopropyl-2-((4-oxo-3-phenethyl-3,4-dihydropteridin-2-yl)thio)acetamide | 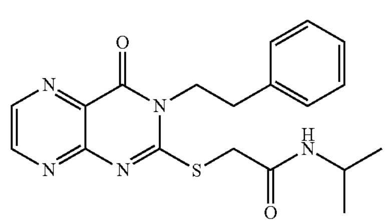 [SMILES: CC(C)NC(=O)CSc1nc2nccnc2c(=O)n1CCc1ccccc1] | 30% inhibition at 10 μM |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 62 | Example compound 62: 2-((benzo[d]thiazol-2-ylmethyl)thio)-3-phenethylpteridin-4(3H)-one | 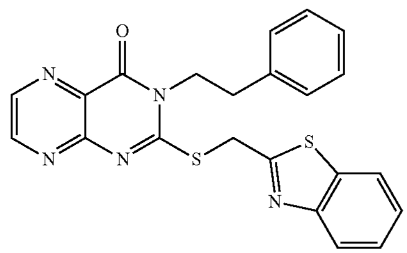 [SMILES: O=c1c2nccnc2nc(SCc2nc3ccccc3s2)n1CCc1ccccc1] | 4.0 |
| 63 | Example compound 63: 2-((benzo[d]oxazol-2-ylmethyl)thio)-3-phenethylpteridin-4(3H)-one | 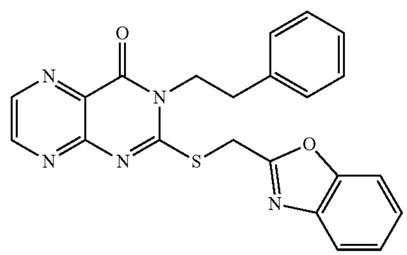 [SMILES: O=c1c2nccnc2nc(SCc2nc3ccccc3o2)n1CCc1ccccc1] | 5.7 |
| 64 | Example compound 64: 2-((2-(2-Fluorophenyl)-2-oxoethyl)thio)-3-phenethylpteridin-4(3H)-one | 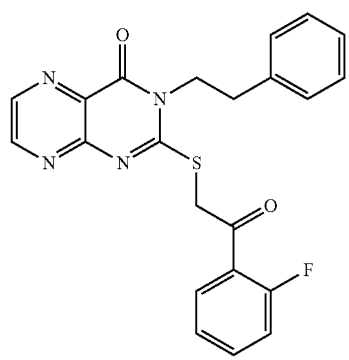 [SMILES: O=C(CSc1nc2nccnc2c(=O)n1CCc1ccccc1)c1ccccc1F] | 35% inhibition at 10 μM |
| 65 | Example compound 65: 2-(((1H-benzo[d]imidazol-2-yl)methyl)thio)-3-phenethylpteridin-4(3H)-one | 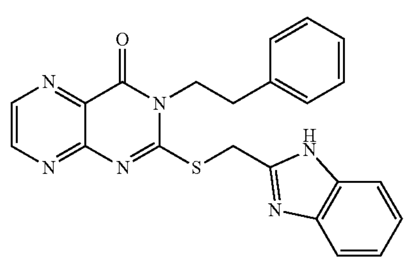 [SMILES: O=c1c2nccnc2nc(SCc2nc3ccccc3[nH]2)n1CCc1ccccc1] | 0.17 |
| 66 | Example compound 66: N,N-Diethyl-2-(((4-oxo-3-phenethyl-3,4-dihydropteridin-2-yl)thio)methyl)-1H-benzo[d]imidazole-6-sulfonamide | 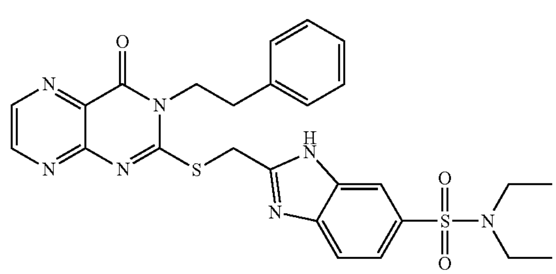 [SMILES: CCN(CC)S(=O)(=O)c1ccc2nc(CSc3nc4nccnc4c(=O)n3CCc3ccccc3)[nH]c2c1] | |

TABLE 1-continued

Preferred compounds of the invention

| Entry | Example-IUPAC NAME | Structure | IC$_{50}$ (PI3KC2α; ADP-Glo ™ assay) [µM] |
|---|---|---|---|
| 67 | Example compound 67: 2-(((4-Oxo-3,4-dihydroquinazolin-2-yl)methyl)thio)-3-phenethylpteridin-4(3H)-one | 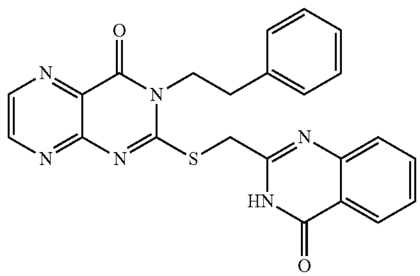 [SMILES: O=c1[nH]c(CSc2nc3nccnc3c(=O)n2CCc2ccccc2)nc2ccccc12] | 1.9 |
| 68 | Example compound 68: 1,3-Dimethyl-8-(((4-oxo-3-phenethyl-3,4-dihydropteridin-2-yl)thio)methyl)-3,9-dihydro-1H-purine-2,6-dione | 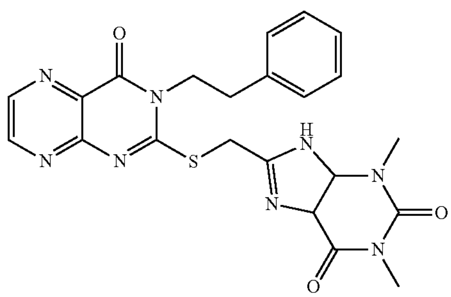 [SMILES: CN1C(=O)C2N=C(CSc3nc4nccnc4c(=O)n3CCc3ccccc3)NC2N(C)C1=O] | 1.4 |
| 69 | Example compound 69: 2-(((5-Chloro-1H-benzo[d]imidazol-2-yl)methyl)thio)-3-phenethylpteridin-4(3H)-one | 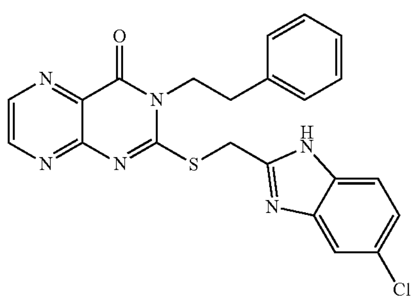 | 27 |
| 70 | Example compound 70: 2-(((7-Methyl-3H-imidazo[4,5-b]pyridin-2-yl)methyl)thio)-3-phenethylpteridin-4(3H)-one | 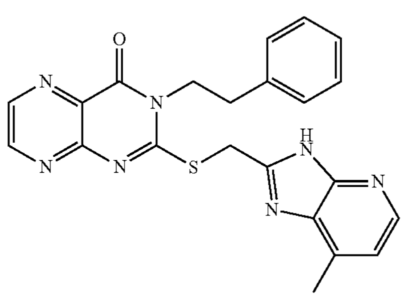 [SMILES: Cc1ccnc2[nH]c(CSc3nc4nccnc4c(=O)n3CCc3ccccc3)nc12] | 42 |
| 71 | Example compound 71: 2-(((1-Methyl-4-oxo-4,5-dihydro-1H-pyrazolo[3,4-d]pyrimidin-6-yl)methyl)thio)-3-phenethylpteridin-4(3H)-one | 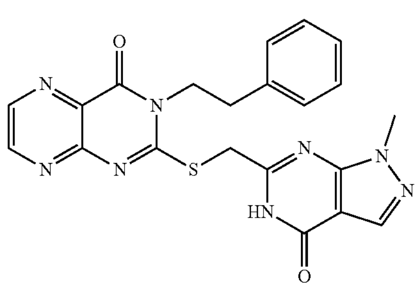 [SMILES: Cn1ncc2c(=O)[nH]c(CSc3nc4nccnc4c(=O)n3CCc3ccccc3)nc21] | 1.5 |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 72 | Example compound 72: 2-(((5-Bromo-1H-benzo[d]imidazol-2-yl)methyl)thio)-3-phenethylpteridin-4(3H)-one | 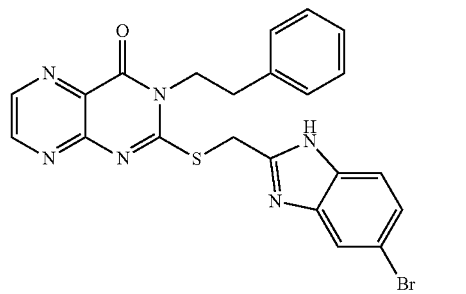 [SMILES: O=c1c2nccnc2nc(SCc2nc3cc(Br)ccc3[nH]2)n1CCc1ccccc1] | 51 |
| 73 | Example compound 73: 2-(((3H-Imidazo[4,5-b]pyridin-2-yl)methyl)thio)-3-phenethylpteridin-4(3H)-one | 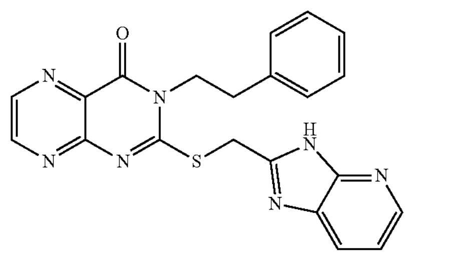 [SMILES: O=c1c2nccnc2nc(SCc2nc3cccnc3[nH]2)n1CCc1ccccc1] | 0.61 |
| 74 | Example compound 74: 2-(((6-Bromo-3H-imidazo[4,5-b]pyridin-2-yl)methyl)thio)-3-phenethylpteridin-4(3H)-one | 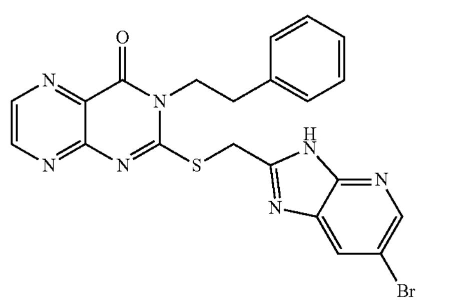 [SMILES: O=c1c2nccnc2nc(SCc2nc3cc(Br)cnc3[nH]2)n1CCc1ccccc1] | 0.91 |
| 75 | Example compound 75: Methyl 2-(((4-oxo-3-phenethyl-3,4-dihydropteridin-2-yl)thio)methyl)-1H-benzo[d]imidazole-5-carboxylate | 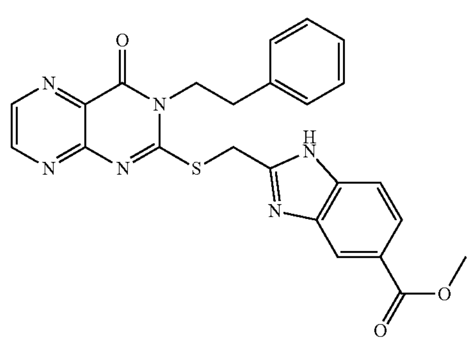 [SMILES: COC(=O)c1ccc2[nH]c(CSc3nc4nccnc4c(=O)n3CCc3ccccc3)nc2c1] | 2.6 |
| 76 | Example compound 76: 2-(((1H-Imidazol-2-yl)methyl)thio)-3-phenethylpteridin-4(3H)-one | 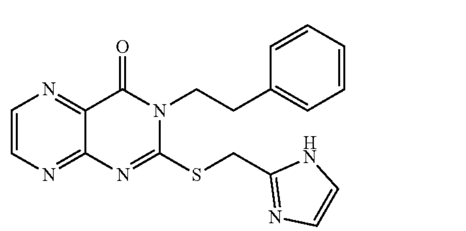 [SMILES: O=c1c2nccnc2nc(SCc2ncc[nH]2)n1CCc1ccccc1] | 22 |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 77 | Example compound 77: 2-(((4,5-Dimethyl-1H-imidazol-2-yl)methyl)thio)-3-phenethylpteridin-4(3H)-one | 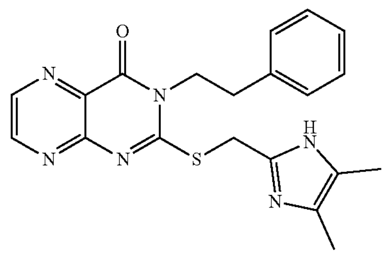 [SMILES: Cc1nc(CSc2nc3nccnc3c(=O)n2CCc2ccccc2)[nH]c1C] | 23 |
| 78 | Example compound 78: 2-((3-(4-(Methylsulfonyl)phenyl)-4-oxo-3,4-dihydropteridin-2-yl)thio)-N-(thiazol-2-yl)acetamide | 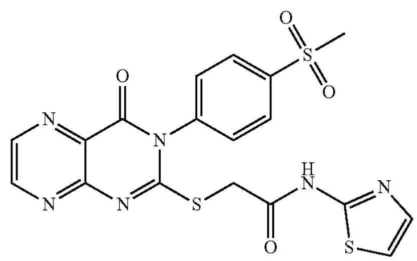 [SMILES: CS(=O)(=O)c1ccc(-n2c(SCC(=O)Nc3nccs3)nc3nccnc3c2=O)cc1] | 9.5 |
| 79 | Example compound 79: 2-(((1H-Benzo[d]imidazol-2-yl)methyl)thio)-3-(4-(methylsulfonyl)phenyl)pteridin-4(3H)-one | 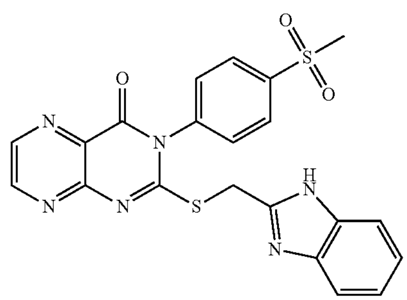 [SMILES: CS(=O)(=O)c1ccc(-n2c(SCc3nc4ccccc4[nH]3)nc3nccnc3c2=O)cc1] | 0.92 |
| 80 | Example compound 80: 2-((3-(4-(N-(5-Methyl-1,3,4-thiadiazol-2-yl)sulfamoyl)phenyl)-4-oxo-3,4-dihydropteridin-2-yl)thio)-N-(thiazol-2-yl)acetamide | 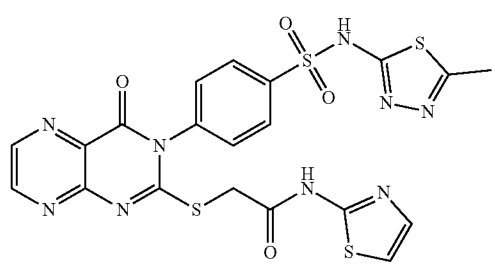 [SMILES: Cc1nnc(NS(=O)(=O)c2ccc(-n3c(SCC(=O)Nc4nccs4)nc4nccnc4c3=O)cc2)s1] | 0.28 |
| 81 | Example compound 81: 4 N-Methyl-4-(4-oxo-2-((2-oxo-2-(thiazol-2-ylamino)ethyl)thio)pteridin-3(4H)-yl)benzamide | 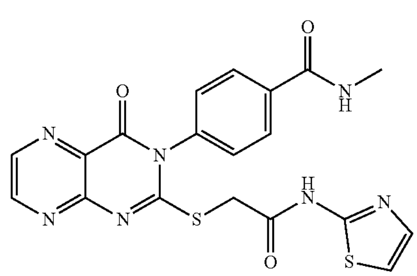 [SMILES: CNC(=O)c1ccc(-n2c(SCC(=O)Nc3nccs3)nc3nccnc3c2=O)cc1] | 0.62 |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 82 | Example compound 82: 4-(2-(((1H-Benzo[d]imidazol-2-yl)methyl)thio)-4-oxopteridin-3(4H)-yl)-N-methylbenzamide | 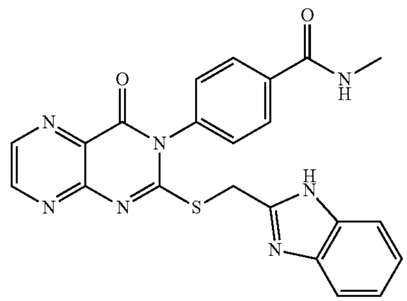 [SMILES: CNC(=O)c1ccc(-n2c(SCc3nc4ccccc4[nH]3)nc3nccnc3c2=O)cc1] | 0.61 |
| 83 | Example compound 83: 2-((3-(3-(1H-Tetrazol-5-yl)phenyl)-4-oxo-3,4-dihydropteridin-2-yl)thio)-N-(thiazol-2-yl)acetamide | 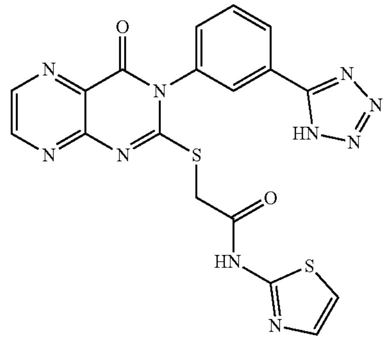 [SMILES: O=C(CSc1nc2nccnc2c(=O)n1-c1cccc(-c2nnn[nH]2)c1)Nc1nccs1] | |
| 84 | Example compound 84: 2-(((1H-Benzo yl)methyl)thio)-3-(3-(1H-tetrazol-5-yl)phenyl)pteridin-4(3H)-one | 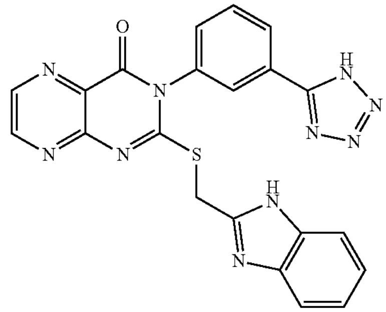 [SMILES: O=c1c2nccnc2nc(SCc2nc3ccccc3[nH]2)n1-c1cccc(-c2nnn[nH]2)c1] | |
| 85 | Example compound 85: 2-((3-(4-Cyanophenyl)-4-oxo-3,4-dihydropteridin-2-yl)-thio)-N-(thiazol-2-yl)acetamide | 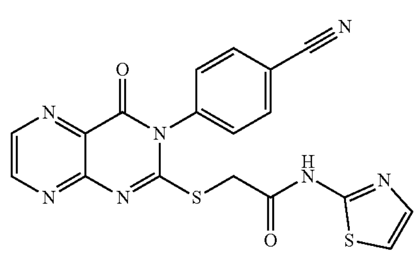 [SMILES: N#Cc1ccc(-n2c(SCC(=O)Nc3nccs3)nc3nccnc3c2=O)cc1] | 1.2 |
| 86 | Example compound 86: 4-(2-(((1H-Benzo[d]imidazol-2-yl)methyl)thio)-4-oxopteridin-3(4H)-yl)benzonitrile | 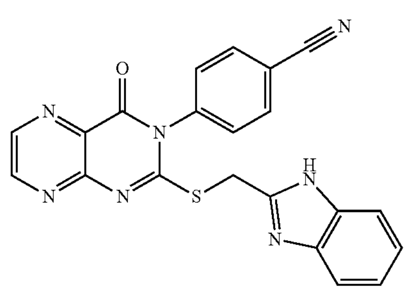 [SMILES: N#Cc1ccc(-n2c(SCc3nc4ccccc4[nH]3)nc3nccnc3c2=O)cc1] | 1.1 |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 87 | Example compound 87: 2-((3-(2,3-Dihydro-1H-inden-2-yl)-4-oxo-3,4-dihydropteridin-2-yl)thio)-N-(thiazol-2-yl)acetamide | 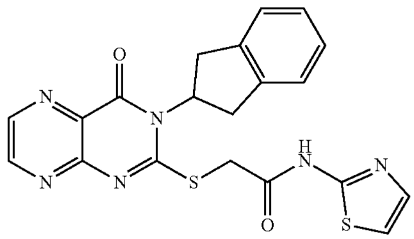 [SMILES: O=C(CSc1nc2nccnc2c(=O)n1C1Cc2ccccc2C1)Nc1nccs1] | 0.17 |
| 88 | Example compound 88: 2-(((1H-Benzo[d]imidazol-2-yl)methyl)thio)-3-(2,3-dihydro-1H-inden-2-yl)pteridin-4(3H)-one | 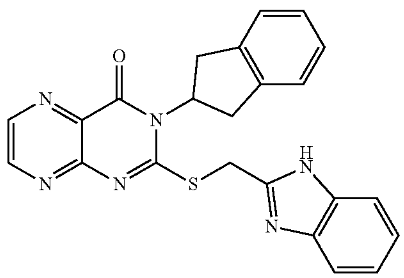 [SMILES: O=c1c2nccnc2nc(SCc2nc3ccccc3[nH]2)n1C1Cc2ccccc2C1] | 0.13 |
| 89 | Example compound 89: (S)-2-((4-Oxo-3-(1-phenylethyl)-3,4-dihydropteridin-2-yl)-thio)-N-(thiazol-2-yl) acetamide | 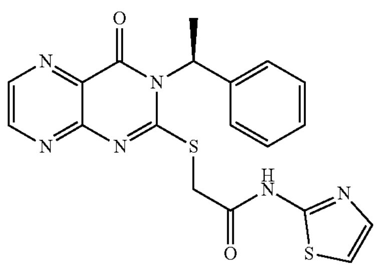 [SMILES: C[C@@H](c1ccccc1)n1c(SCC(=O)Nc2nccs2)nc2nccnc2c1=O] | 1.7 |
| 90 | Example compound 90: (S)-2-(((1H-Benzo[d]imidazol-2-yl)methyl)thio)-3-(1-phenylethyl)pteridin-4(3H)-one | 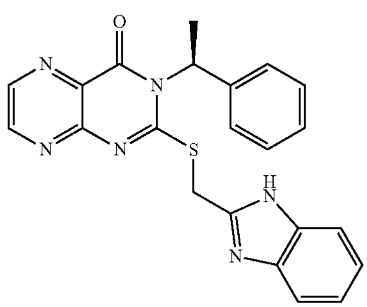 [SMILES: C[C@@H](c1ccccc1)n1c(SCc2nc3ccccc3[nH]2)nc2nccnc2c1=O] | 16 |
| 91 | Example compound 91: trans-Methyl 3-(4-oxo-2-((2-oxo-2-(thiazol-2-ylamino)ethyl)thio)pteridin-3(4H)-yl)cyclobutane-1-carboxylate | 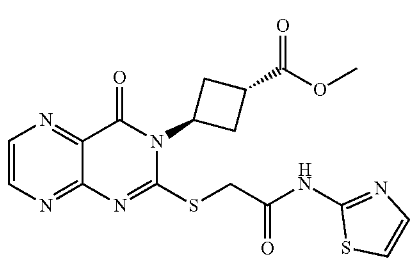 [SMILES: COC(=O)[C@H]1C[C@H](n2c(SCC(=O)Nc3nccs3)nc3nccnc3c2=O)C1] | 0.37 |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 92 | Example compound 92: trans-Methyl-3-(2-(((1H-benzo[d]imidazol-2-yl)methyl)thio)-4-oxo-pteridin-3(4H)-yl)cyclobutane-1-carboxylate | 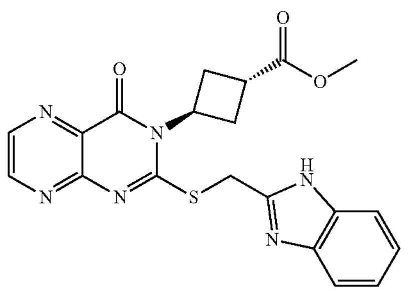 [SMILES: COC(=O)[C@H]1C[C@H](n2c(SCc3nc4ccccc4[nH]3)nc3nccnc3c2=O)C1] | 0.32 |
| 93 | Example compound 93: tert-Butyl 4-(4-oxo-2-((2-oxo-2-(thiazol-2-ylamino)ethyl)thio)pteridin-3(4H)-yl)piperidine-1-carboxylate | 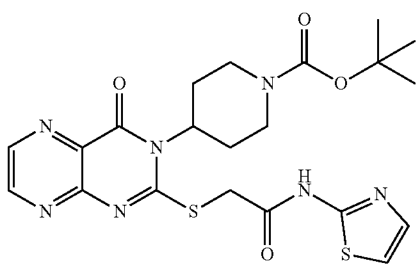 [SMILES: CC(C)(C)OC(=O)N1CCC(n2c(SCC(=O)Nc3nccs3)nc3nccnc3c2=O)CC1] | 3.6 |
| 94 | Example compound 94: tert-Butyl 4-(2-(((1H-benzo[d]imidazol-2-yl)methyl)thio)4-oxopteridin-3(4H)-yl)piperidine-1-carboxylate | 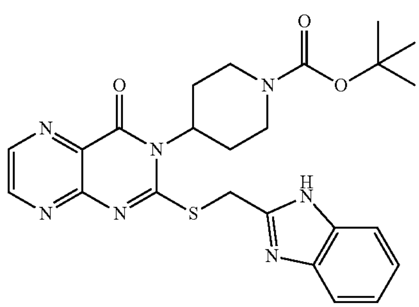 [SMILES: CC(C)(C)OC(=O)N1CCC(n2c(SCc3nc4ccccc4[nH]3)nc3nccnc3c2=O)CC1] | 1.2 |
| 95 | Example compound 95: 2-((3-(4-Hydroxyphenethyl)-4-oxo-3,4-dihydropteridin-2-yl) thio)-N-(thiazol-2-yl)acetamide | 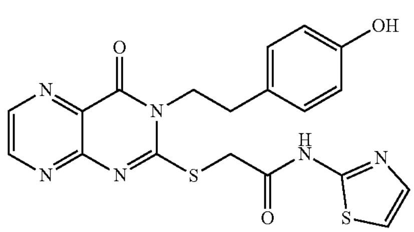 [SMILES: O=C(CSc1nc2nccnc2c(=O)n1CCc1ccc(O)cc1)Nc1nccs1] | 0.21 |
| 96 | Example compound 96: 2-(((1H-Benzo[d]imidazol-2-yl)methyl)thio)-3-(4-hydroxyphenethyl)pteridin-4(3H)-one | 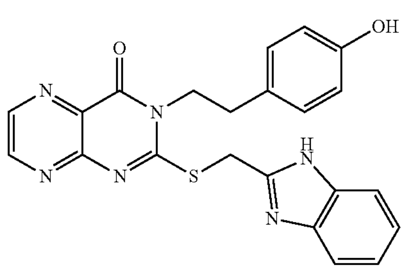 [SMILES: O=c1c2nccnc2nc(SCc2nc3ccccc3[nH]2)n1CCc1ccc(O)cc1] | 0.1 |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 97 | Example compound 97: 2-((3-(9H-Fluoren-9-yl)-4-oxo-3,4-dihydropteridin-2-yl)-thio)-N-(thiazol-2-yl)acetamide | 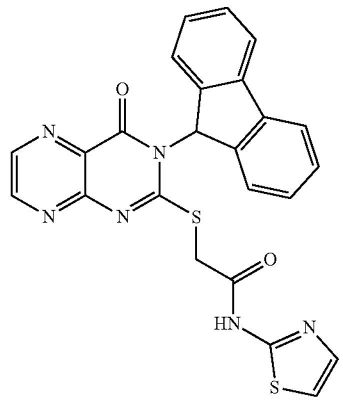 [SMILES: O=C(CSc1nc2nccnc2c(=O)n1C1c2ccccc2-c2ccccc21)Nc1nccs1] | |
| 98 | Example compound 98: 2-(((1H-Benzo[d]imidazol-2-yl)methyl)thio)-3-(9H-fluoren-9-yl)pteridin-4(3H)-one | 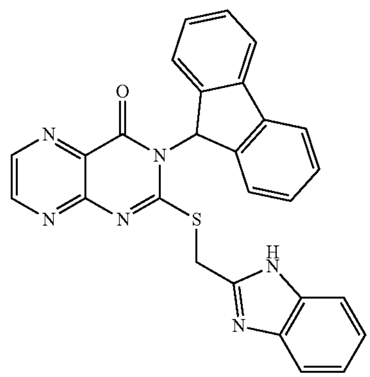 [SMILES: O=c1c2nccnc2nc(SCc2nc3ccccc3[nH]2)n1C1c2ccccc2-c2ccccc21] | |
| 99 | Example compound 99: trans-2-(((1H-Benzo[d]imidazol-2-yl)methyl)thio)-3-(2-phenylcyclopropyl)pteridin-4(3H)-one | 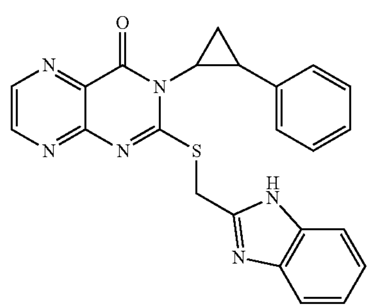 [SMILES: O=c1c2nccnc2nc(SCc2nc3ccccc3[nH]2)n1C1CC1c1ccccc1] | 1.8 |
| 100 | Example compound 100: 3-(4-Oxo-3-phenethyl-3,4-dihydropteridin-2-yl)-N-phenylpropanamide | 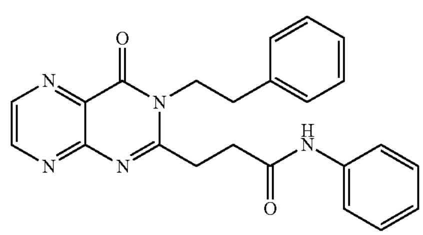 | 31% inhibition at 10 μM |
| 101 | Example compound 101: N-Benzyl-3-(4-oxo-3-phenethyl-3,4-dihydropteridin-2-yl)propanamide | 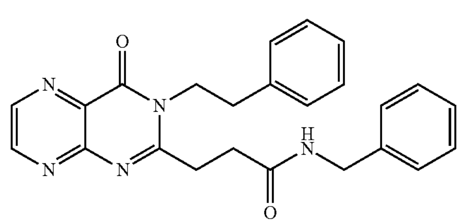 [SMILES: O=C(CCc1nc2nccnc2c(=O)n1CCc1ccccc1)NCc1ccccc1] | 28% inhibition at 10 μM |

TABLE 1-continued

Preferred compounds of the invention

| Entry | Example-IUPAC NAME | Structure | IC$_{50}$ (PI3KC2α; ADP-Glo ™ assay) [μM] |
|---|---|---|---|
| 102 | Example compound 102: 3-(4-Oxo-3-phenethyl-3,4-dihydropteridin-2-yl)-N-phenethylpropanamide | 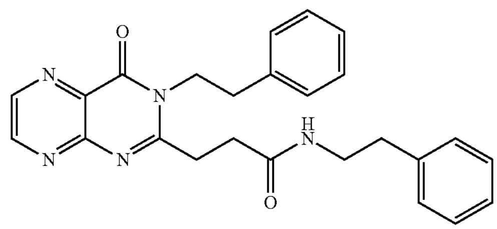 [SMILES: O=C(CCc1nc2nccnc2c(=O)n1CCc1ccccc1)NCCc1ccccc1] | 36% inhibition at 10 μM |

DETAILED DESCRIPTION OF THE INVENTION

The invention relates to chemical compounds useful as inhibitors of class II phosphoinositide 3-kinase (PI3K) signalling. The invention further relates to the medical use of inhibitors of class II phosphoinositide 3-kinase (PI3K) signalling in the treatment of medical conditions associated with defective and/or pathologic class II phosphoinositide 3-kinase (PI3K) signaling, such as myopathy, cancer, diabetes and cardiovascular disease.

Medical Use;

According to the invention, "medical conditions associated with defective and/or pathologic class II phosphoinositide 3-kinase (PI3K) signaling" relate to any medical condition, illness, disease or other medical state in which class II phosphoinositide 3-kinase (PI3K) signaling is aberrant or associated with a defect in signaling, such as reduced signaling, enhanced signaling and/or any change in signaling associated with or responsible for the cause of a medical condition.

The term "class II phosphoinositide 3-kinase (PI3K) signaling" relates to a signaling pathway as understood by a skilled person, in preferred embodiments relating to aberrations in class II phosphoinositide 3-kinase (PI3K) activity, thereby leading to disruptions in associated signaling pathways. A review of PI3K signaling is provided in Vanhaesebroeck et al (Nat. Rev. Mol. Cel. Biol. May 2010, Vol 11).

In preferred embodiments, without limitation thereto, the "defective and/or pathologic class II phosphoinositide 3-kinase (PI3K) signaling" relates to elevated activity, gene copy number, or expression of class II phosphoinositide 3-kinases. Established tests are available for a skilled person to determine whether cII PI3K signaling is disrupted, for example by obtaining pathologic cells, such as cancer cells, and assessing these for said signaling, or directly assessing elevated activity, gene copy number, or expression of class II phosphoinositide 3-kinases in tumor or other biological samples, depending on the disease to be tested.

PI3KC2α is broadly expressed in human cells. In vitro studies have shown that PI3KC2α can be activated by a range of molecules, including clathrin, cytokines, chemokines, integrins, as well as insulin and other growth factors.

A number of mouse models targeting PI3KC2α have been developed over the past 5 years. Importantly, Yoshioka et al. detailed the involvement of endothelial cell PI3KC2α in angiogenesis and vascular development (Yoshioka, et al. Endothelial PI3K-C2alpha, a class II PI3K, has an essential role in angiogenesis and vascular barrier function. Nat. Med. 2012, 18, 1560-1569). Mountford et al. (Nat. Commun. 2015, 6, 6535) uncovered a role for platelet PI3KC2α in thrombosis, while Franco et al. reported that PI3KC2α is important in cilia function (Dev. Cell 2014, 28, 647-658).

A number of medical indications have been well-established as being linked to signalling. Reviews are provided in Mazza and Maffucci, Int J Biochem Mol Biol 2011; 2(2): 168-182 and in Falasca et al, 2016, J. Med. Chem. 60, 1, 47-65. As outlined below, these reviews describe an involvement in diabetes, cancer and cardiovascular disease Diabetes:

The fact that PI3K-C2α contributes to both glucose disposal into muscle cells and insulin secretion shows that deregulation of signalling pathways controlled by this enzyme may ultimately have a role in Type 2 diabetes. Based on the data accumulated so far, it appears deregulation of PI3K-C2α-dependent signalling may result in inhibition of glucose disposal, a hallmark of insulin resistance, and in reduced insulin secretion, indicative of pancreatic p cell dysfunction.

The first mouse model in which there is combined deficiency of both PI3KC2α and PI3KC2p has been described, and suggests that at least some of the key functions of these two highly related enzymes do not overlap. The first significant phenotype observed in PI3KC2β-deficient mice points to a role for PI3KC2β in insulin sensitivity and glucose tolerance. Furthermore, PI3KC2βD1212A/D1212A mice were protected from high-fat diet-induced steatosis, indicating that this regulatory role of insulin signaling is particularly important in the liver. These results suggest that PI3KC2β may be a potential drug target for the treatment of type 2 diabetes, as well as other insulin-resistant conditions such as nonalcoholic fatty liver diseases.

Cancer:

Thorpe et al, (Nat. Rev. Cancer, Volume 15, January 2015) provides an extensive review of potential cancer targets in PI3K signaling.

In addition, in vitro data, in particular on the potential role of PI3K-C2α in regulation of survival, indicates that PI3K-C2α specifically has a role in cancer. A number of studies have investigated the potential association of PI3K-C2α expression level and cancer. For instance, a decrease in the DNA copy number but an increase in mRNA levels was reported in 19 hepatitis B-positive hepatocellular carcinoma compared to matched nontumour counterparts (Ng S K, et al. Biochem Biophys Res Commun, 2009; 387:310-15).

The expression and localisation of all PI3K isoforms in pancreatic ductal adenocarcinoma specimens compared to normal tissues by immunohistochemistry has been recently tested (Edling C E, et al. Clin Cancer Res 2010; 16:4928-37). PI3K-C2α was expressed in a subset of the samples and it was found localised in acini and ducts in cancer tissue. A higher expression was detected in acini with high cellular atypia and in dysplastic ducts.

Amplification of Pik3c2a has also been observed in colon, cervical, ovarian, thyroid, and non-small-cell lung cancers, and alterations in Pik3c2a have been found in medulloblastomas and anaplastic oligodendrioglomas. An increase in PI3KC2α mRNA levels has been observed in a subset of B-positive hepatocellular cancer samples when compared to nontumorigenic tissues. The expression of PI3KC2α has also been attributed to the survival of HeLa cells. Additionally, a significant increase in PI3KC2α expression has been observed in a population of MCF7 cells, enriched in cancer stemlike cells, compared to normal breast cells. These data suggest an involvement of PI3KC2α in breast cancer development (Falasca et al, 2016, J. Med. Chem. 60, 1, 47-65).

An interesting observation was made in a study which characterised the side-population of the breast cancer cell line MCF7, a rare cell population enriched in cancer stem-like cells with increased tumourigenicity in vivo (Zhou J, et al. Proc Natl Acad Sci USA 2007; 104:16158-63). The authors showed that PI3KC2A, the gene encoding for PI3K-C2α, was one of the genes expressed at higher levels in the side population compared to the normal population.

A potential involvement of PI3KC2α in tumor angiogenesis favoring lung cancer and melanoma has also been proposed. Indeed, in PIK3C2A knockout mice injected with Lewis lung carcinoma or B16-BL6 melanoma a significant reduction in microvessel density, tumor weight, and volume could be observed, compared to control mice (Yoshioka, K. et al. Nat. Med. 2012, 18, 1560-1569). Endothelial-cell-specific deficiency of PI3KC2α in mice results in markedly reduced retinal angiogenesis and postischemic hindlimb revascularization due to impaired endothelial cell migration and proliferation. Furthermore, the microvessel density and overall volume of solid tumors implanted into the mice were reduced in a mouse model.

Amplification of the gene encoding PI3KC2β, PIK3C2B, has been reported in several tumors, such as glioblastoma multiforme and glioblastoma histological sections, and in 90 ovarian cancer specimens pointed to a similar, significant increase in PIK3C2B copy number in these cells. The observed increase in PI3KC2β expression in ovarian cancer cells was significantly higher than of other PI3K classes. Amplification of PIK3C2B, together with MDM4, was also detected in oligodendroglia tumors. Overexpression of PI3KC2β has been observed in different cancer cell lines and specimens, such as acute myeloid leukemia, medulloblastoma, glioblastoma multiforme. PIK3C2B was identified as one of the genes mutated in non-small-cell lung cancer samples, compared to nontumorigenic tissues. Overexpression of negative PI3KC2β considerably inhibited growth and growthfactor-induced Akt activation in small cell lung cancer. Increased expression of PI3KC2β was also demonstrated in myeloid leukemia and acute lymphocytic leukemia. Its inhibition showed high antiproliferative activity, especially in AML cell lines, in which reduced proliferation, as well as considerable increase in apoptosis, was observed.

Taken together, these observations suggest that PI3KC2α and/or PI3KC2β inhibition has value as a therapeutic strategy for the treatment of cancer, including solid tumors, with PI3KC2α and/or PI3KC2β as a drug target for reducing pathologic tumor metastasis, angiogenesis and growth/survival.

In a preferred embodiment the present invention relates to cancer as a disease to be treated. Cancer according to the present invention refers to all types of cancer or neoplasm or malignant tumors found in mammals, including leukemias, lymphomas, sarcomas, melanomas and carcinomas. Examples of cancers are cancer of the breast, pancreas, colon, lung, non-small cell lung, ovary, and prostate.

In the context of the present invention, leukemias include, but are not limited to acute non-lymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

According to the present invention, lymphomas include Hodgkin and non-Hodgkin lymphoma (B-cell and T-cell lymphoma) including, but not limited to Diffuse large B-cell lymphoma (DLBCL), primary mediastinal B-cell lymphoma, Follicular lymphoma, Chronic lymphocytic leukemia, small lymphocytic lymphoma, Mantle cell lymphoma, Marginal zone B-cell lymphomas, Extranodal marginal zone B-cell lymphomas, also known as mucosa-associated lymphoid tissue (MALT) lymphomas, Nodal marginal zone B-cell lymphoma and Splenic marginal zone B-cell lymphoma, Burkitt lymphoma, Lymphoplasmacytic lymphoma (Waldenstrom macroglobulinemia), Hairy cell leukemia Primary central nervous system (CNS) lymphoma, Precursor T-lymphoblastic lymphoma/leukemia, Peripheral T-cell lymphomas, Cutaneous T-cell lymphomas (mycosis fungoides, Sezary syndrome, and others), Adult T-cell leukemia/lymphoma including the smoldering, the chronic, the acute and the lymphoma subtype, Angioimmunoblastic T-cell lymphoma, Extranodal natural killer/T-cell lymphoma, nasal type, Enteropathy-associated intestinal T-cell lymphoma (EATL), Anaplastic large cell lymphoma (ALCL), and unspecified Peripheral T-cell lymphoma.

Sarcomas as defined in the context of the present invention include, but are not limited to a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Melanomas according to the present invention include, but are not limited to include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

Carcinomas as defined by the present inventin include, but are not limited to acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma exulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticurn, carcinoma telangiectodes, transitional cell carcinoma, carcinoma tuberosum, tuberous carcinoma, verrucous carcinoma, and carcinoma villosum.

Additional cancers according to the present invention include, but are not limited to multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, esophageal cancer, genitourinary tract cancer, malignant hypercalcemia, cervical cancer, endometrial cancer, adrenal cortical cancer, and prostate cancer.

Cardiovascular Diseases:

As discussed above, PI3K-C2α activity increases in aortae from SHRs, which is paralleled by increased Rho activity, MYPT1 phosphorylation and systolic blood pressure (Seok Y M, et al. Hypertension 2010; 56:934-41). It is noteworthy that not only treatment with the calcium blocker nicardipine but also infusion with high concentrations of wortmannin (which inhibited PI3K-C2α activity) also strongly reduced systolic blood pressure in aortas and mesenteric arteries of SHRs. These data indicate a role for PI3K-C2α in hypertension.

Cardiovascular disease (CVD) is a class of diseases that involve the heart or blood vessels. Cardiovascular disease includes, but is not limited to, coronary artery diseases (CAD) such as angina and myocardial infarction (commonly known as a heart attack). Other CVDs include stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, and venous thrombosis.

Thrombosis:

Two recent studies identified a role for PI3KC2α in platelet function and suggested that PI3KC2α is a suitable drug target for the prevention and treatment of thrombosis and cardiovascular disease Mountford et al. (ACS Med. Chem. Lett. 2015, 6, 3-6) and Valet et al. (Blood 2015, 126, 1128-1137) both observed that PI3KC2α is involved in the regulation of platelet membrane structure that is sufficient to cause significant platelet functional consequences in the setting of thrombosis. Taken together, these two studies point to a key role for PI3KC2α in platelet function and highlight the potential of this enzyme as an antithrombotic drug target. Given the global burden of cardiovascular diseases and the limitations of currently available treatments, new antiplatelet approaches are critically needed.

Myopathy:

It has been demonstrated that PIK3C2B inhibition improves function and prolongs survival in myotubular myopathy animal models (Sabha et al, J Clin Invest. 2016; 126(9):3613-3625). Myotubular myopathy (MTM) is a pediatric neuromuscular disorder of hosphoinositide (PIP) metabolism resulting from mutations of the PIP phosphatase MTM1 for which there are presently no established treatments. Class II and III PI3 kinases were targeted (PI3Ks) in an MTM1-deficient mouse model. Muscle-specific ablation of Pik3c2b, but not Pik3c3, resulted in complete prevention of the MTM phenotype, and postsymptomatic targeting promoted a striking rescue of disease. The PI3K inhibitor wortmannin also improved motor function and prolonged lifespan of the Mtm1-deficient mice. This evidence speaks strongly for a therapeutic effect of PIK3 inhibitors in treating myopathy.

Chemical Compounds

With respect to the chemical compounds described herein, the term "alkyl" refers to a branched or unbranched saturated hydrocarbon group of preferably 1 to 7 carbon atoms, such as methyl, ethyl, n-propyl, isopropyl, n-butyl, isobutyl, sec-butyl, pentyl, hexyl, heptyl, and the like. Preferred alkyl groups have 1-7 carbon atoms, more preferably 1-6, 1-5, 1-4 or 1-3, 2 or 1 carbon atoms. Any one or more of the alkyl groups described herein may be "substituted alkyls", wherein one or more hydrogen atoms are substituted with a substituent such as halogen, cycloalkyl, alkoxy, hydroxyl, aryl, or carboxyl.

The term "alkenyl" refers to a straight, branched or cyclic hydrocarbon configuration and combinations thereof, including preferably 2 to 7 carbon atoms, more preferably 2 to 4 carbon atoms, that would form if a hydrogen atom is removed from an alkene, for example resulting in ethenyl, or the like.

The term "alkynyl" refers a straight, branched or cyclic hydrocarbon configuration and combinations thereof, including preferably 2 to 7 carbon atoms, more preferably 2 to 4 carbon atoms, that would form if a hydrogen atom is removed from an alkyne, for example resulting in ethynyl, or the like.

The term "cycloalkyl" refers to a configuration derived from a cycloalkane by removal of an atom of hydrogen, thereby forming preferably cyclopropyl, cyclobutyl, cyclopentyl, cyclohexyl or cycloheptyl, or the like.

The term "alkoxy" refers to a straight, branched or cyclic hydrocarbon configuration and combinations thereof, including preferably 1-7 carbon atoms, more preferably 1-6, 1-5, 1-4 or 1-3 carbon atoms, that include an oxygen atom at the point of attachment (such as O-alkyl). An example of an "alkoxy group" is represented by the formula —OR, or —ROR, where R can be an alkyl group, optionally substituted with halogen, aryl, cycloalkyl, halogenated alkyl. Suitable alkoxy groups include methoxy, ethoxy, n-propoxy, i-propoxy, n-butoxy, i-butoxy, sec-butoxy, cyclohexyloxy, and the like.

The term "aryl" refers to any carbon-based aromatic group including, but not limited to, benzene, naphthalene, and the like. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur. The aryl group can be substituted with one or more groups including, but not limited to, alkyl, aryl, halogen, nitro, hydroxy, carboxylic acid, or alkoxy, or the aryl group can be unsubstituted.

The term "heteroaryl" is understood to mean saturated (heterocycloalkyl), partly unsaturated (heterocycloalkenyl) or unsaturated (heteroaryl) hydrocarbon rings containing from 3 to 15 carbon atoms in a mono- or bicyclic, fused, bridged or spirocyclic ring in which 1 to 5 carbon atoms of the 3 to 15 ring carbon atoms are replaced by heteroatoms such as nitrogen, oxygen or sulfur in which further the heteroatoms can be oxidized, for example N=O, S=O, $SO_2$. Non-limiting examples of heterocycles are acridinyl, azaindole (1H-pyrrolopyridinyl), azabenzimidazolyl, azaspirodecanyl, azepinyl, azetidinyl, aziridinyl, benzimidazolyl, benzofuranyl, dihydrobenzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The term "amine" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above. A suitable amido group is acetamido.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine, phenyl, a substituted phenyl (substituted with, for example, halogen, C1-C3 alkyl, alkoxy, amine), carboxyl, alkoxycarbonyl, amine, aryl.

The term "alkyl amino" refers to alkyl groups as defined above where at least one hydrogen atom is replaced with an amino group.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H) or —C(O)—N(R).

"Carboxyl" refers to a —COOH radical. Substituted carboxyl refers to —COOR where R is aliphatic, heteroaliphatic, alkyl, heteroalkyl, or a carboxylic acid or ester.

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

The term "aralkyl" refers to an aryl group having an alkyl group, as defined above, attached to the aryl group, as defined above. An example of an aralkyl group is a benzyl group.

Optionally substituted groups, such as "optionally substituted alkyl," refers to groups, such as an alkyl group, that when substituted, have from 1-5 substituents, typically 1, 2 or 3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, halogen, optionally substituted heteroaryl, optionally substituted heterocyclyl, hydroxy, sulfonyl, thiol and thioalkoxy.

In particular, optionally substituted alkyl groups include, by way of example, haloalkyl groups, such as fluoroalkyl groups, including, without limitation, trifluoromethyl groups. These potential optional substituents apply to any group of the formula disclosed herein where an optional substituent is recited. Preferable optional substituents are hydroxyl, alkyl, alkoxy, carbonyl, alkoxycarbonyl, NO2, amine.

The term "aldehyde" is represented by the formula —CHO, consisting of a carbonyl center (a carbon double-bonded to oxygen) with the carbon atom also bonded to hydrogen and to an R group, preferably the backbone of the formula.

The term "carboxyester" is represented by the formula —C(O)—O—R.

The term "carboxamide" is represented by the formula —C(O)—N(R)—R.

The term "primary, secondary or tertiary amine" is represented by the formula —N(R)—R.

The term "carbamate" is represented by the formula —NR—C(O)—O—R.

The term "amide amine" is represented by the formula —NH—C(O)—NH—R,

The term "sulfide" is represented by the formula —S—R

The terms "amine sulfoxide", "sulfonamide", "sulfonamide amine" are preferably selected from the groups —N(R)—S(O)$_u$—R, wherein u is 1 or 2, or —S(O)$_v$—N(R)—R, wherein v is 1 or 2, preferably from the groups —NHSO$_2$CH$_3$, —SO$_2$NHCH$_3$, —NHSO$_2$N(CH$_3$)$_2$).

The terms "sulfoxide" or "sulfone are preferably selected from the groups —SO$_r$R, wherein r is 1-3, preferably from the groups —S(O)R, —SO$_2$R, —SO$_2$H, and —SO$_3$H.

The term "sulfonamide haloalkyl" is preferably selected from —NHSO$_2$CF$_3$, —NHSO$_2$CH$_2$CF$_3$.

The term "carbamate" is represented by the formula —N(R)—C(O)—R.

The term "imide" is represented by the formula —C(O)—N(R)—C(O)—R'.

The term "sulfide" is represented by the formula —SR.

The term "sulfurtihalide" is represented by the formula —SX$_3$.

The term "sulfurpentahalide" is represented by the formula —SX$_5$.

The term "sulfinyl" is represented by the formula —S(O)R.

The term "sulfonyl" is represented by the formula —SO$_2$R.

The term "sulfino" is represented by the formula —SO$_2$H.

The term "sulfo" is represented by the formula —SO$_3$H.

For the definitions above, preferably the terms R, R' are independently selected from the group of H, alkyl, alkylhalo, alkoxy, or amine, and wherein X is halogen. The terms R, R' also comprise the possibility of any given group being appended to R.

The term "nitro" refers to an NO$_2$ group.

Optionally substituted groups, such as "optionally substituted" refers to groups, such as an alkyl group, that when substituted, have from 1-5 substituents, typically 1, 2 or 3 substituents.

The term "5-membered heterocyclyl or heteroaryl" refers to a configuration comprising a 5-membered heterocyclic optionally aromatic ring structure, comprising preferably C and one or more of N, O and/or S, preferably selected from a configuration if a hydrogen atom is removed from furan, pyrrole, oxazole, thiophene, thiazole, pyrazole, imidazole, and the like.

In some embodiments, the 5-membered heterocyclyl or heteroaryl, comprising preferably one or more of N, O and/or S, is selected from the list, or a sub-group of the list, from Table 2 below:

TABLE 2

| 5-membered heterocyclyl or heteroaryl substituents | |
|---|---|
|  | Furan |
|  | 1,2,4-oxadiazole |
|  | Pyrrole |
|  | 1,2,5-oxadiazole |
|  | Imidazole |
|  | 1 3,4-oxadiazole |
|  | Pyrazole |
|  | 1,2-thiazole |
|  | 1,3,4-triazole |
|  | 1,3-thiazole |
|  | 1,2,3-triazole |
|  | 1,2,3-thiadiazole |
|  | 1,2,4-triazole |
|  | 1,2,4-thiadiazole |
|  | Tetrazole |

TABLE 2-continued 5-membered heterocyclyl or heteroaryl substituents

| Structure | Name |
|---|---|
| | 1,2,5-thiadiazole |
| | Thiophene |
| | 1,3,4-thiadiazole |
| | Isoxazole |
| | 1,2,3-oxadiazole |
| | Oxazole |

The "5- or 6-membered heterocyclyl or heteroaryl" as described herein relates preferably to a cycloalkyl, cycloalkane non-aromatic cyclic structures, such as cyclopentyl or cyclohexyl, and optionally to aromatic cyclic structures, such as phenyl, and the like.

The "6-membered heterocycle" as described herein relates preferably to a cycloalkyl, cycloalkane non-aromatic cyclic structures, such as cyclohexyl, or to aromatic cyclic structures, such as phenyl, and the like.

The "6-membered aromatic heterocycle, comprising one or more of N, O and/or S" as described herein refers to a configuration comprising a 6-membered ring structure comprising C and one or more of N, O and/or S, preferably selected from a configuration if a hydrogen atom is removed from pyridine, pyridazine, pyrimidine, pyrazine, pyran, triazine, thiazine, thiopyran, oxazine, and the like.

In some embodiments, the "6-membered aromatic heterocycle" comprises 1 or 2 N atoms, referring to a configuration comprising a 6-membered ring structure comprising C and 1 or 2 N atoms, preferably selected from pyridine, pyridazine, pyrimidine, pyrazine, triazine, thiazine, oxazine, and the like. Preferred heterocycles comprise only 1 or 2 N atoms.

Where reference is made to "C1-C7, C1-C5 or C1-C3" alkyl, cycloalkyl, alkoxy, aryl, or the like, the number of carbon atoms C1-C7 preferably refers to each of the substituents mentioned, although in some embodiments the shorter substituents of C1-C5 or C1-C3 apply to the alkyl, cycloalkyl and/or alkoxy groups, whereby aryl may remain preferably C1-C7, such as C6 phenyl. Protected derivatives of the disclosed compound also are contemplated, for example for use in the synthesis of the disclosed compounds. A variety of suitable protecting groups for use with the disclosed compounds are disclosed in Greene and Wuts Protective Groups in Organic Synthesis; 3rd Ed.; John Wiley & Sons, New York, 1999. In general, protecting groups are removed under conditions which will not affect the remaining portion of the molecule. These methods are well known in the art and include acid hydrolysis, hydrogenolysis and the like.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures.

The compounds of the invention may also exist in various polymorphous forms, for example as amorphous and crystalline polymorphous forms. All polymorphous forms of the compounds of the invention belong within the framework of the invention and are a further aspect of the invention.

The compound of the invention may also comprise deuterium replacing hydrogen. This replacement may in some circumstances lead to improved metabolic stability (Nature Reviews Drug Discovery 15, 219-221 (2016)).

It is understood that substituents and substitution patterns of the compounds described herein can be selected by one of ordinary skill in the art to provide compounds that are chemically stable and that can be readily synthesized by techniques known in the art and further by the methods set forth in this disclosure.

The present invention relates further to pharmaceutically acceptable salts of the compounds described herein. The term "pharmaceutically acceptable salt" refers to salts or esters of the compounds described herein prepared by conventional means that include basic salts of inorganic and organic acids. "Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002).

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

Compositions and Modes of Treatment:

Another aspect of the disclosure includes pharmaceutical compositions prepared for administration to a subject and which include a therapeutically effective amount of one or more of the compounds disclosed herein. In certain embodiments, the pharmaceutical compositions are useful for treating medical conditions associated with defective and/or pathologic class II phosphoinositide 3-kinase (PI3K) signaling, such as myopathy, cancer, diabetes and cardiovascular disease.

The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. Remington's Pharmaceutical Sciences, by E. W. Martin, Mack Publishing Co., Easton, PA, 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The pharmaceutical compositions can be administered to subjects by a variety of mucosal administration modes, including by oral, rectal, intraocular, intranasal, intrapulmonary, or transdermal delivery, or by topical delivery to other surfaces. Optionally, the compositions can be administered by non-mucosal routes, including by intramuscular, intraocular, subcutaneous, intravenous, intra-arterial, intra-articular, intraperitoneal, intrathecal, intracerebroventricular, or parenteral routes.

The compositions of the disclosure can alternatively contain as pharmaceutically acceptable carrier substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

In a preferred embodiment the invention comprise the topical and/or local administration of a compound as described herein and/or a composition comprising a compound as described herein to a subject. The term "topical administration" refers to the delivery of a pharmacologically active agent to the skin or mucosa of a patient. Topical administration can provide a local rather than a systemic effect. The terms "topical administration" and "transdermal administration" are used interchangeably to mean administration of a pharmacologically active agent to the skin or mucosa of a patient to achieve a therapeutic effect in treating or preventing a medical disorder of the invention or discomfort at the site of topical or transdermal administration. Preferred administration modes relate to a topical solution, lotion, shake lotion, cream, ointment, gel, foam, transdermal patch, powder, solid form, sponge, tape, paste or tincture. Preferred embodiments relate to creams, foams, gels, lotions, and ointments.

Various additives, known to those skilled in the art, may be included in topical compositions of the present disclosure. For example, solvents, including relatively small amounts of alcohol, may be used to solubilize a compound of the invention. Other optional additives include antioxidants, fragrances, colorant, gelling agents, emulsifiers, thickening agents, stabilizers, surfactants, buffers, cooling agents (e.g., menthol) and the like. Other agents may also be added, such as antimicrobial agents, to prevent spoilage upon storage, i.e., to inhibit growth of microbes such as yeasts and molds. Examples of suitable antimicrobial agents include methyl and propyl esters of p-hydroxybenzoic acid (i.e., methyl and propyl paraben), sodium benzoate, sorbic acid, imidurea, and the like. When applied to skin, a topical composition of the present disclosure can be covered with an occlusive or non-occlusive dressing, which may be porous or non-porous, so as to protect the composition from mechanical removal during the period of treatment, e.g. a plastic film food wrap or other non-absorbent film. Various inert coverings may be employed. Non-woven or woven coverings may be employed, particularly elastomeric coverings, which allow for heat and vapor transport. These coverings can allow for cooling of the diseased site, which can provide for greater comfort, while protecting the composition from mechanical removal.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

"Administration of" and "administering a" compound should be understood to mean providing a compound, a prodrug of a compound, or a pharmaceutical composition as described herein. The compound or composition can be administered by another person to the subject (e.g., intravenously, gel, cream, spray) or it can be self-administered by the subject (e.g., tablets, gel, cream, spray).

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The term "subject" includes both human and veterinary subjects. The term "treatment" refers to a therapeutic intervention that ameliorates a sign or symptom of a disease or pathological condition after it has begun to develop.

As used herein, the term "ameliorating", with reference to a disease or pathological condition, refers to any given beneficial effect of the treatment. The beneficial effect can be evidenced, for example, by a delayed onset of clinical symptoms of the disease in a subject, a reduction in severity of some or all clinical symptoms of the disease, a slower progression of the disease, an improvement in the overall health or well-being of the subject, or by other parameters well known in the art that are specific to the particular disease.

The present invention encompasses both therapeutic treatment and prophylactic treatment of a subject. A "prophylactic" treatment is a treatment administered to a subject, who does not exhibit signs of the medical condition or who preferably exhibits indications of developing or developing further any given medical condition, for the purpose of decreasing the risk of developing pathology or clinical symptoms. A prophylactic administration may comprise the administration of the compounds in advance of developing symptoms, thereby avoiding or reducing the subsequent occurrence of a disease. The present invention also relates to a method of treatment of subjects suffering from the various medical conditions disclosed herein. The method of treatment comprises preferably the administration of a therapeutically effective amount of a compound disclosed herein to a subject in need thereof.

A "therapeutically effective amount" refers to a quantity of a specified agent sufficient to achieve a desired effect in a subject being treated with that agent. For example, this may be the amount of a compound disclosed herein useful in alleviating the symptoms of one or more of the medical conditions described herein in a subject. The therapeutically effective amount or diagnostically effective amount of an agent will be dependent on the subject being treated, the severity of illness, and the manner of administration of the therapeutic composition. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects.

A non-limiting range for a therapeutically effective amount of a compound and/or other biologically active agent within the methods and formulations of the disclosure is about 0.001 mg/kg body weight to 50 mg/kg body weight, 0.01 mg/kg body weight to about 20 mg/kg body weight, such as about 0.05 mg kg to about 5 mg/kg body weight, or about 0.2 mg/kg to about 2 mg/kg body weight.

The instant disclosure also includes kits, packages and multi-container units containing the herein described pharmaceutical compositions, active ingredients, and/or means for administering the same for use in the prevention and treatment of diseases and other conditions in mammalian subjects.

FIGURES

The invention is further described by the following figures. These are not intended to limit the scope of the invention, but represent preferred embodiments of aspects of the invention provided for greater illustration.

DETAILED DESCRIPTION OF THE FIGURES

Figure 1:
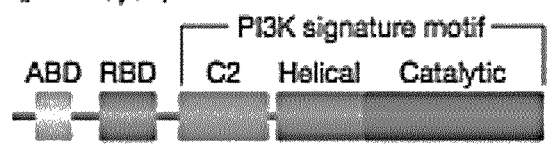
FIG. 1: Domain organization of PI3 kinases.
Figure 1:
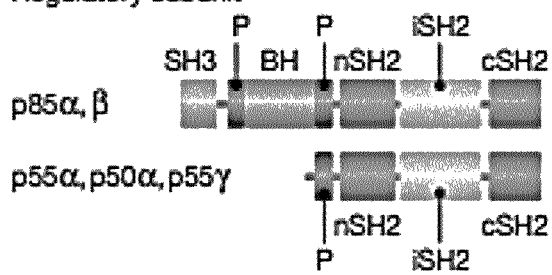
Figure 1:
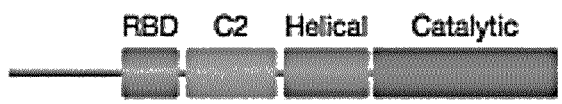
Figure 1:
Figure 1:
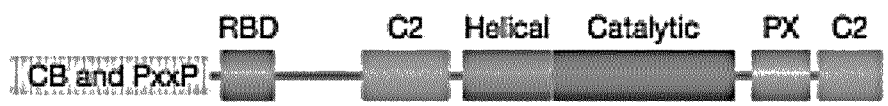
Figure 1:
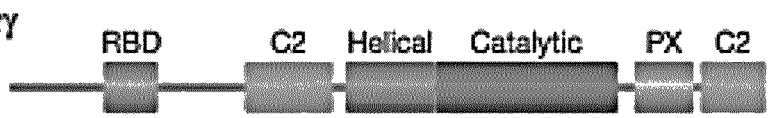
Figure 1:
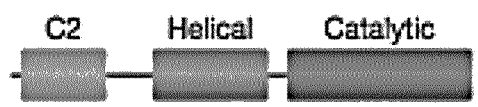
Figure 1:
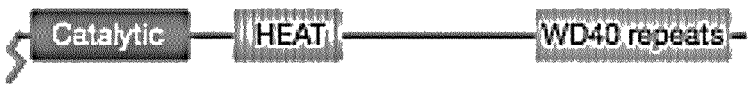

FIG. 1: Domain organization of PI3 kinases. PI3 kinases are classified according to their function and diversity of sequence. Class I and III kinases form heterodimers with a regulatory subunit (p85 or p55 for class IA, p101 or p87 for class IB, and Vps15 for Vps34). All three classes of PI3 kinases share a conserved PI3K core region (C2, Helical, and catalytic domain). Class I PI3K contains unique ABD domain for regulatory subunit interaction. Class II PI3K contains unique N-terminal disorder region for protein-protein interaction, and C-terminal lipid binding domain, which binds to phosphoinositide.

Figure 2:
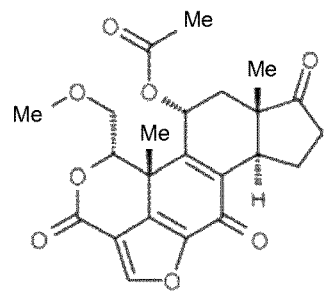
FIG. 2: Inhibitors of PI3Ks.
Figure 2:
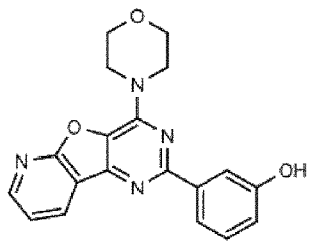
Figure 2:
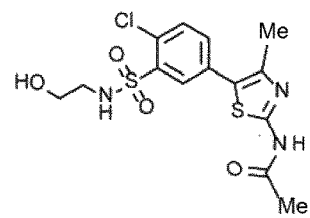
Figure 2:
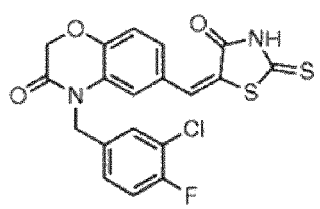
Figure 2:
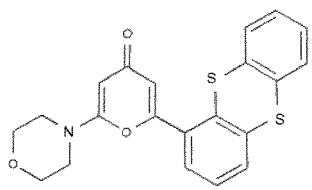
Figure 2:
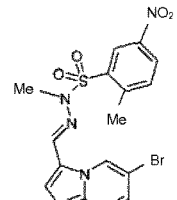
Figure 2:
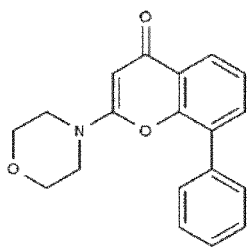
Figure 2:
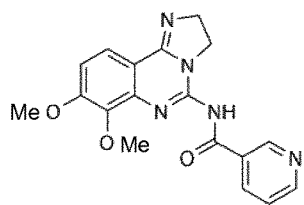
Figure 2:
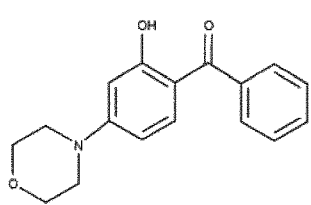
Figure 2:
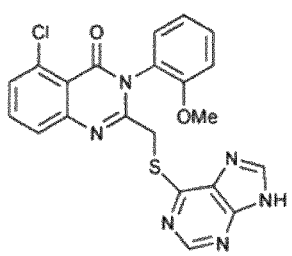
Figure 2:
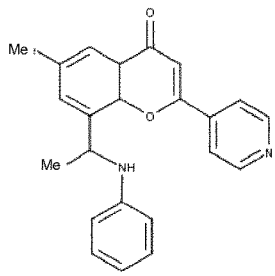

FIG. 2: Inhibitors of PI3Ks. Structures of different chemotypes of PI3K inhibitors described previously are demonstrated as comparative examples.

Figure 3:
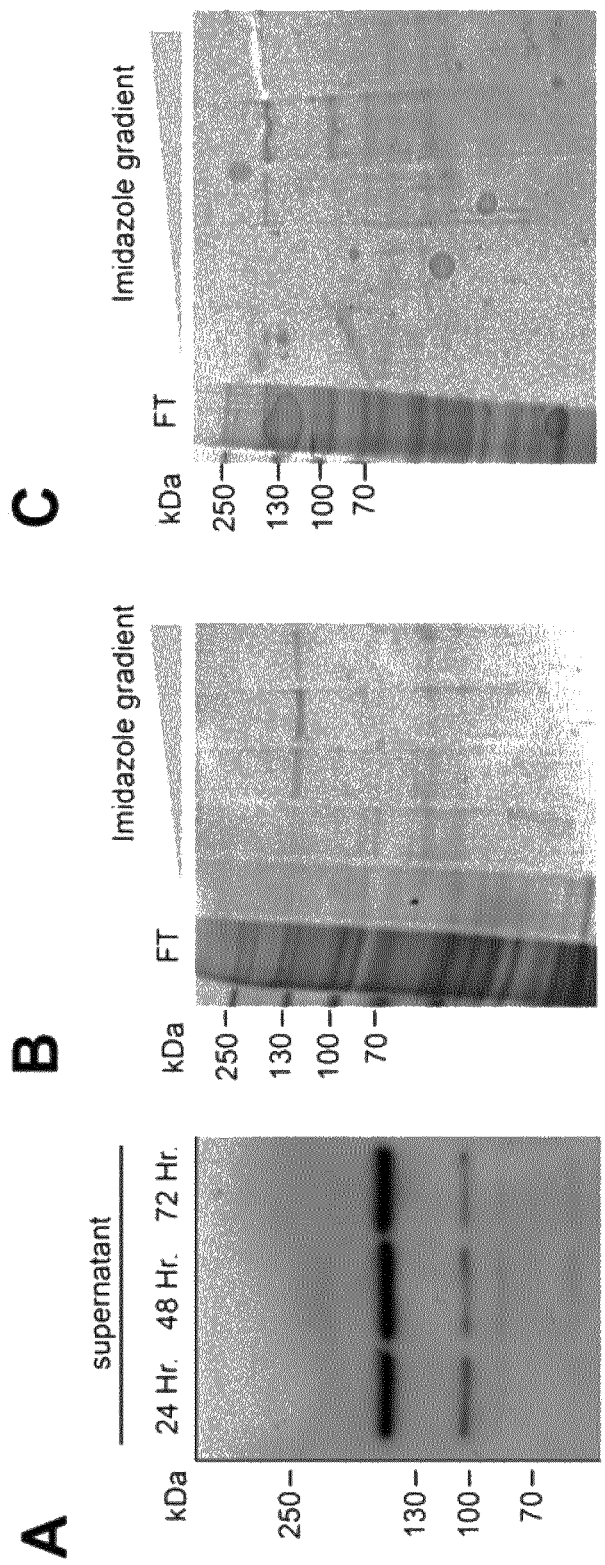
FIG. 3: Expression and purification of PI3KC2α Δ1-298 from baculovirus-insect cell expression system.

FIG. 3: Expression and purification of PI3KC2α Δ1-298 from baculovirus-insect cell expression system. (A) Time dependent infection and expression of PI3KC2α Δ1-298. The immunoblot was performed with mouse anti-His$_6$ antibody followed by HRP coupled anti-mouse IgG. (B)—(C) Purification of PI3KC2α Δ1-298 from baculovirus-infected S/21 cells (B) and Hi5 cells (C). The fractions were collected from buffer containing imidazole gradients from 20 to 300 mM. The purity of protein was verified by 10% SDS-PAGE and Coomassie blue staining.

Figure 4:
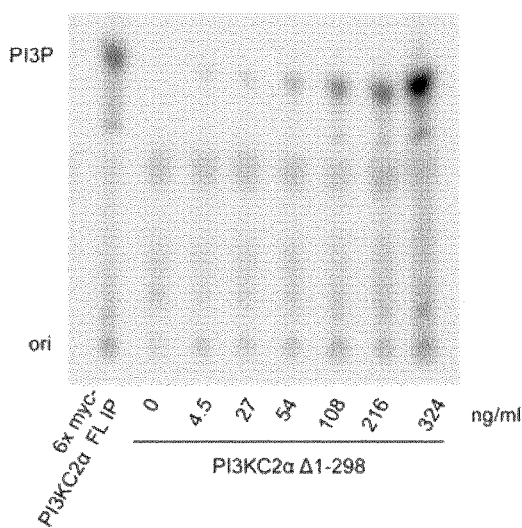
FIG. 4: Kinase activity of purified PI3KC2α Δ1-298.
Figure 4:
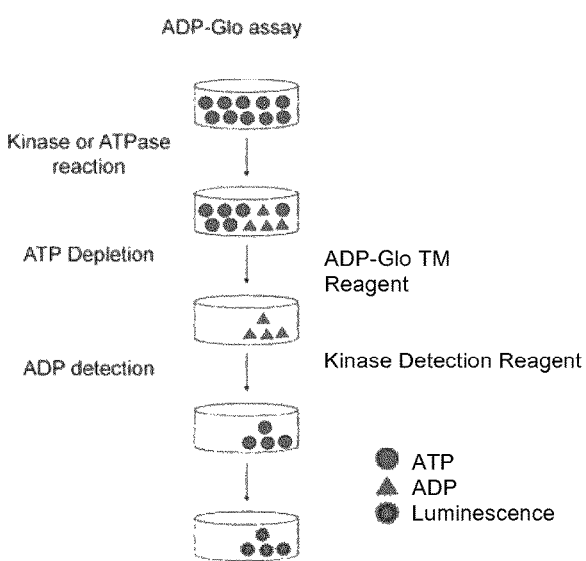
Figure 4:
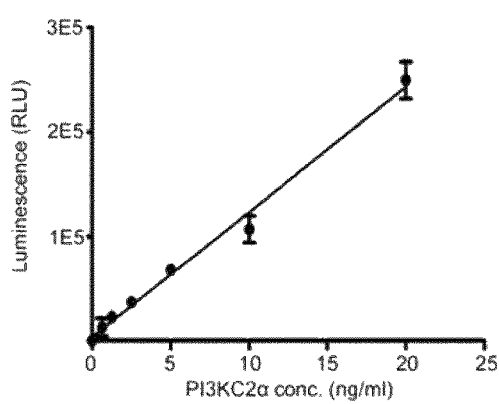
Figure 4:
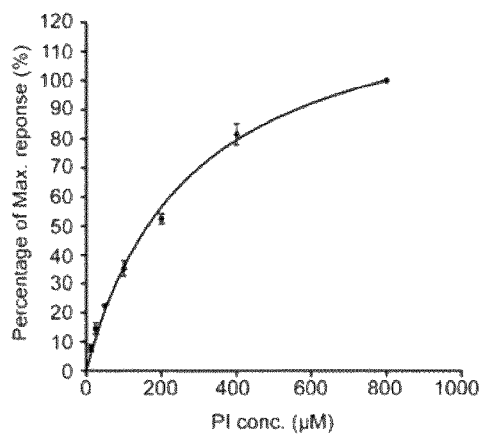
Figure 4:
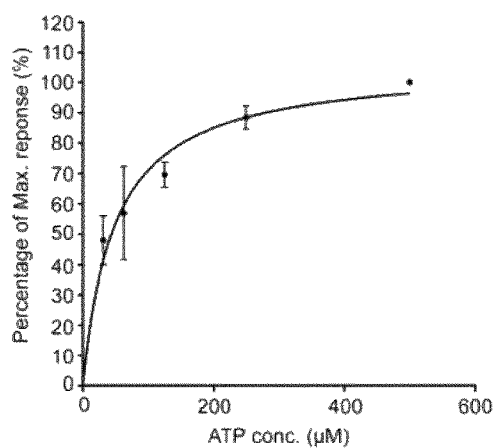

FIG. 4: Kinase activity of purified PI3KC2α Δ1-298. (A) Isotopic kinase assay of purified PI3KC2α Δ1-298. Dilution series of purified PI3KC2α carboxamide, nitro, sulfide, sulfurtrihalide, sulfurpentahalide, sulfinyl, sulfonyl, sulfino, or sulfo, Δ1-298 incubated with 100 μM ATP/200 μM PI, containing 10 μCi of ATP γ-$^{32}$P in kinase reaction buffer. Immunoprecipitated, HEK cell-expressed myc$_6$-PI3KC2α FL was used as positive control. Isotopic lipid products were separated by TLC. (B) Scheme for measuring kinase activity with ADP-Glo™ assay. (C) Activity of purified PI3KC2α Δ1-298 using 100 μM ATP/200 μM PI as substrates assayed by ADP-Glo™. Triple experiments were performed with a series of concentrations of purified PI3KC2α Δ1-298. The luminescence intensity was plotted versus the amount of kinase. (D)-(E) Enzymatic characterization of purified PI3KC2α Δ1-298. The experiment was performed in duplicate to measure the Km for PI (D) or for ATP (E) incubating PI3KC2α Δ1-298 with titrated amounts of PI and ATP. All data were normalized to the maximal response. The curves were fitted using the Michealis-Menten equation, yielding a Km for ATP of 50 μM and a Km for PI of 300 μM.

Figure 5:
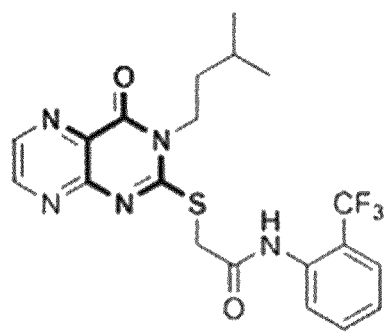
FIG. 5. Inhibitor scaffolds of PI3KC2α.
Figure 5:
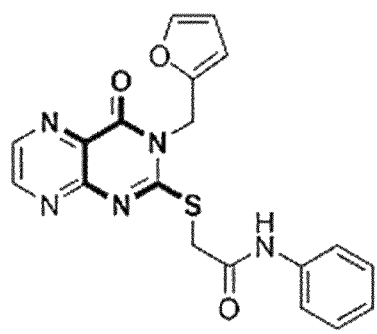
Figure 5:
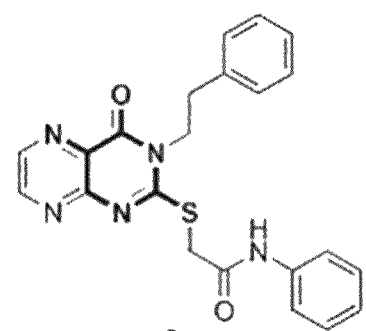
Figure 5:
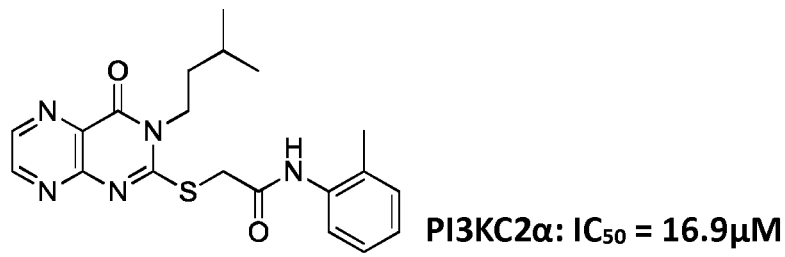
Figure 5:
Figure 5:
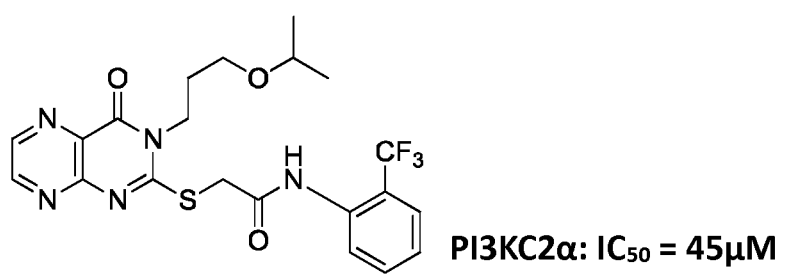
Figure 5:
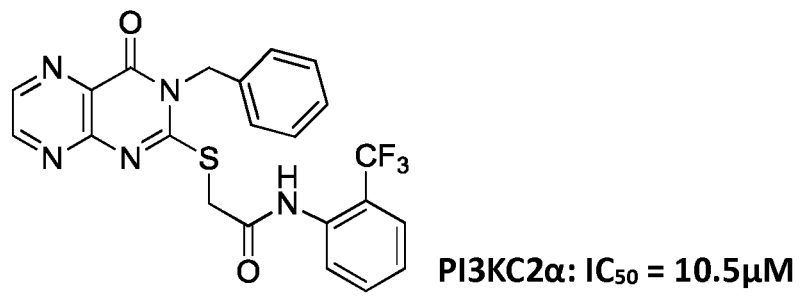
Figure 5:
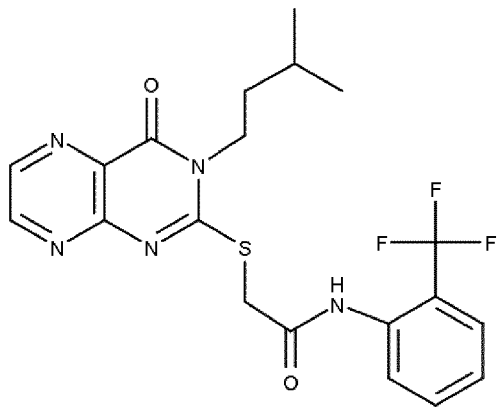
Figure 5:
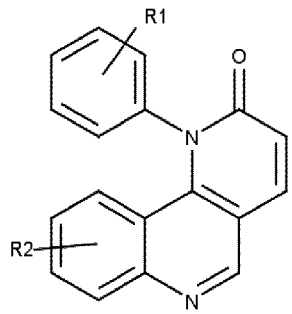
Figure 5:
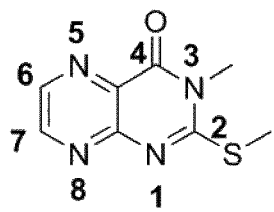
Figure 5:
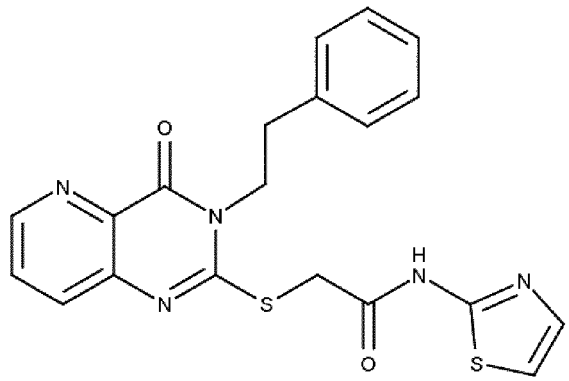

FIG. 5. Inhibitor scaffolds of PI3KC2α. (A)-(B) Active compounds share a pyrimidone scaffold and a sulfur linker (indicated in bold), and show different activities towards PI3KC2α. (C) Three main chemical scaffolds of the hits (dihydropteridinone, torin, and quinolone) were found from screening. (D) Numbering of the dihydropteridinone scaffold.

Figure 6:
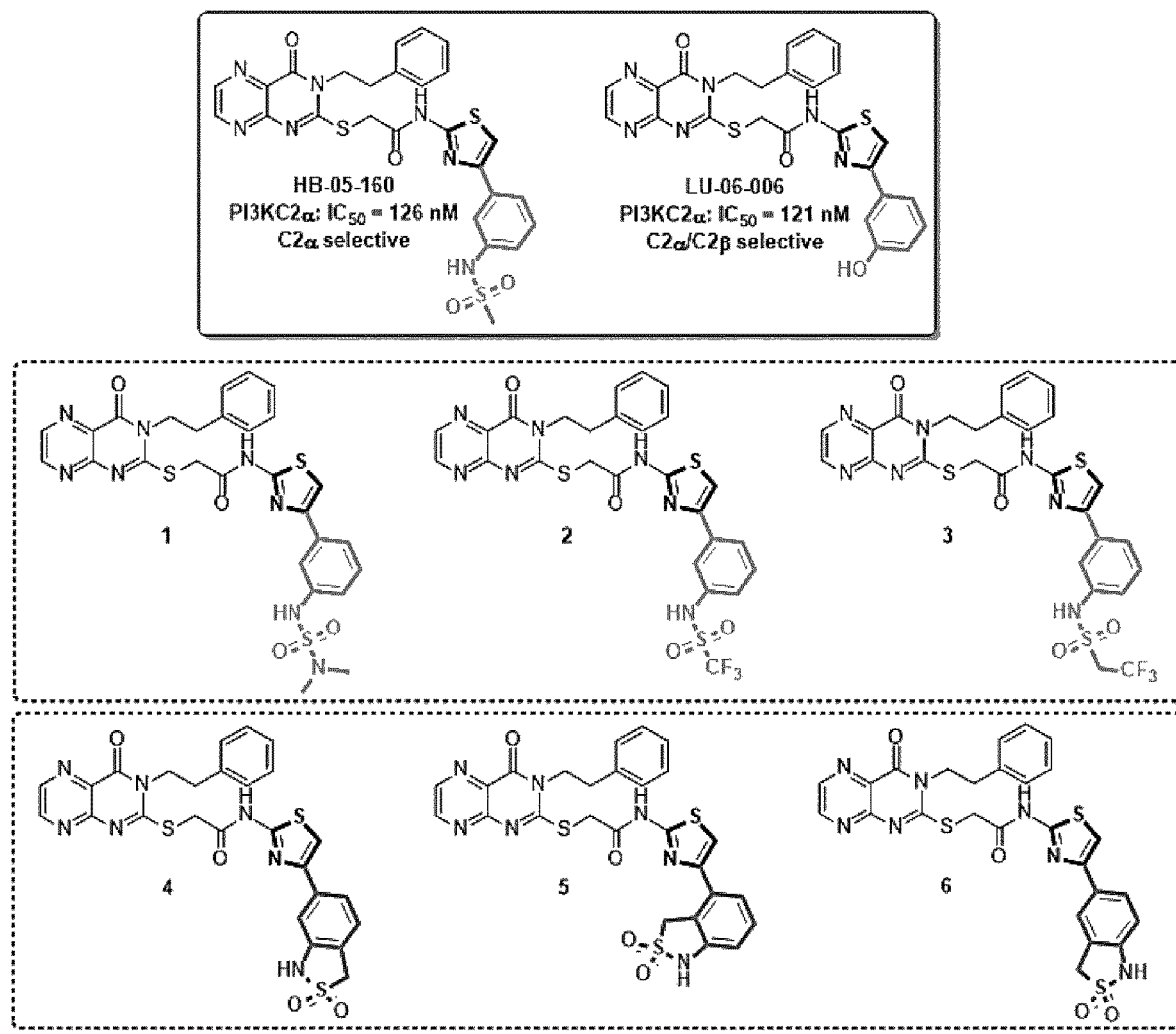
FIG. 6. Additional compounds of the invention.

FIG. 6. Additional compounds of the invention. Additional derivation of the R4, R10 and R11 positions lead to compounds with the desired inhibitory activity.

Figure 7:
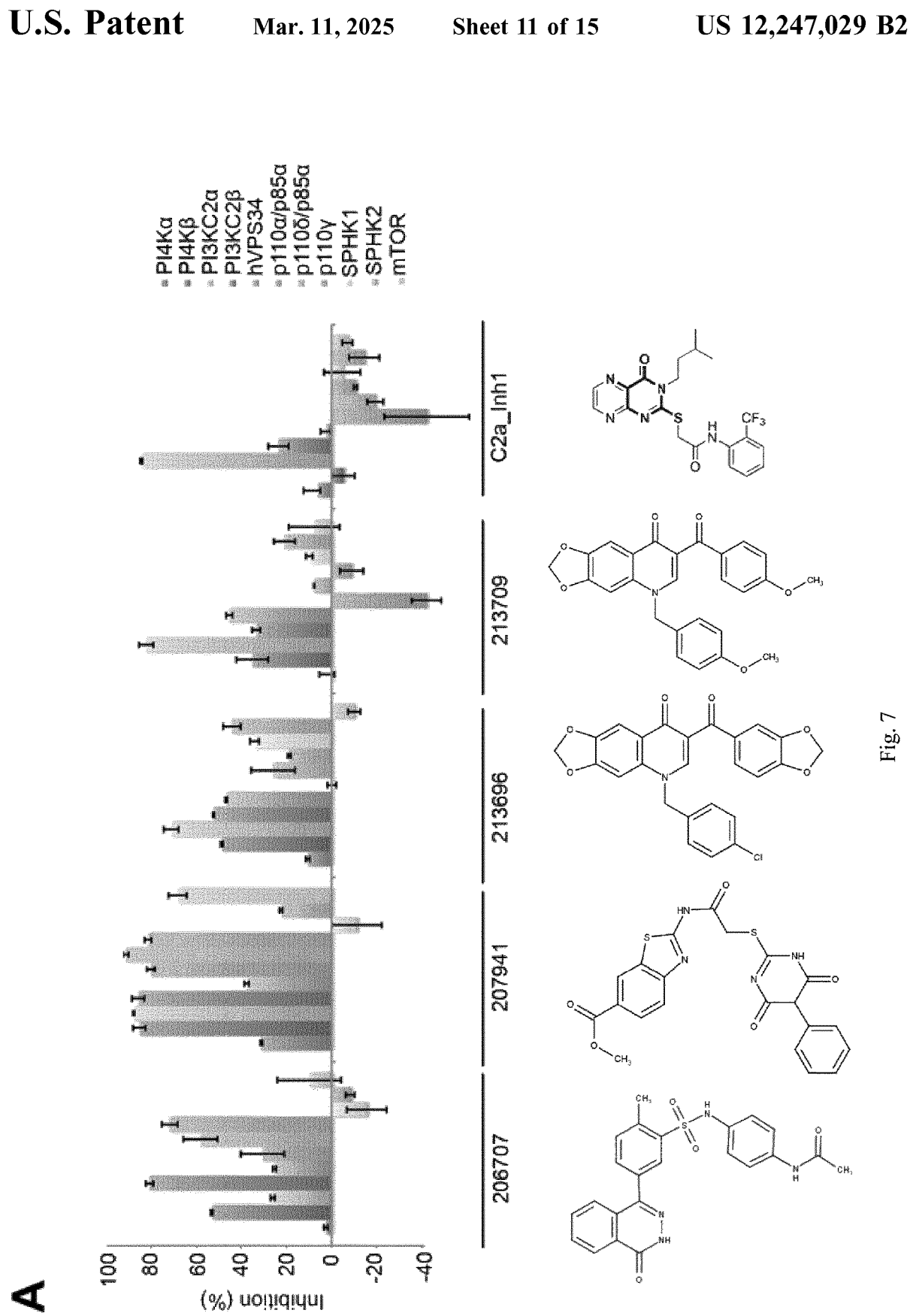
FIG. 7. In vitro kinase activity in presence of 10 μM compounds.
Figure 7:
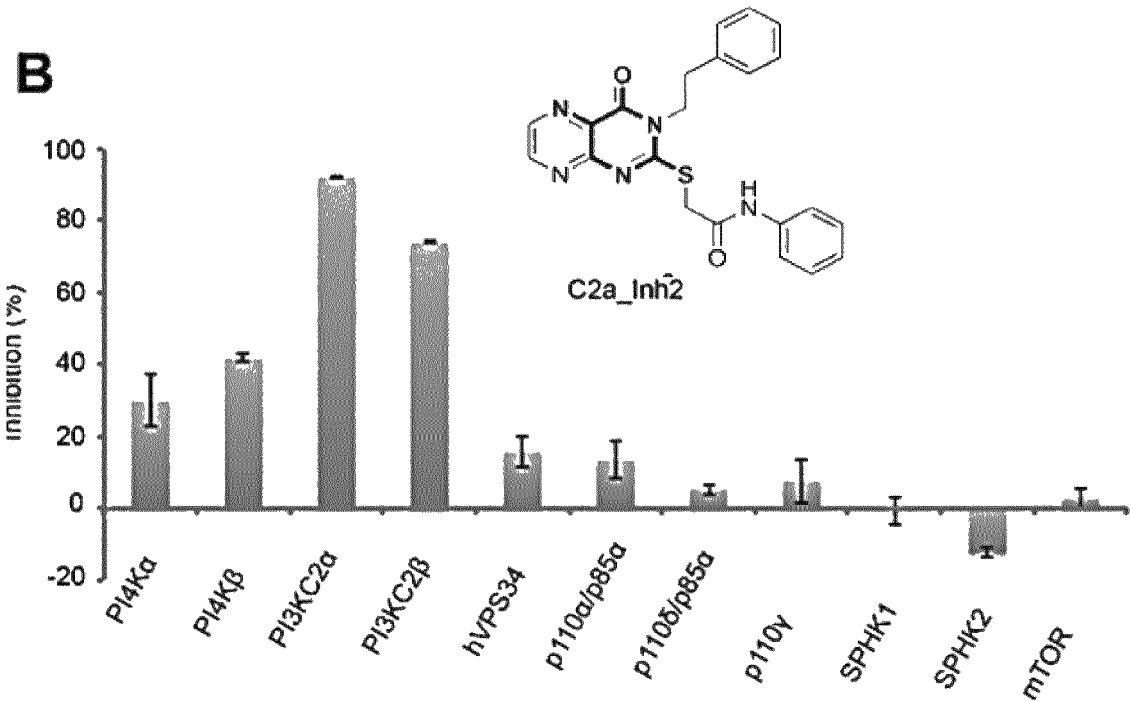
Figure 7:
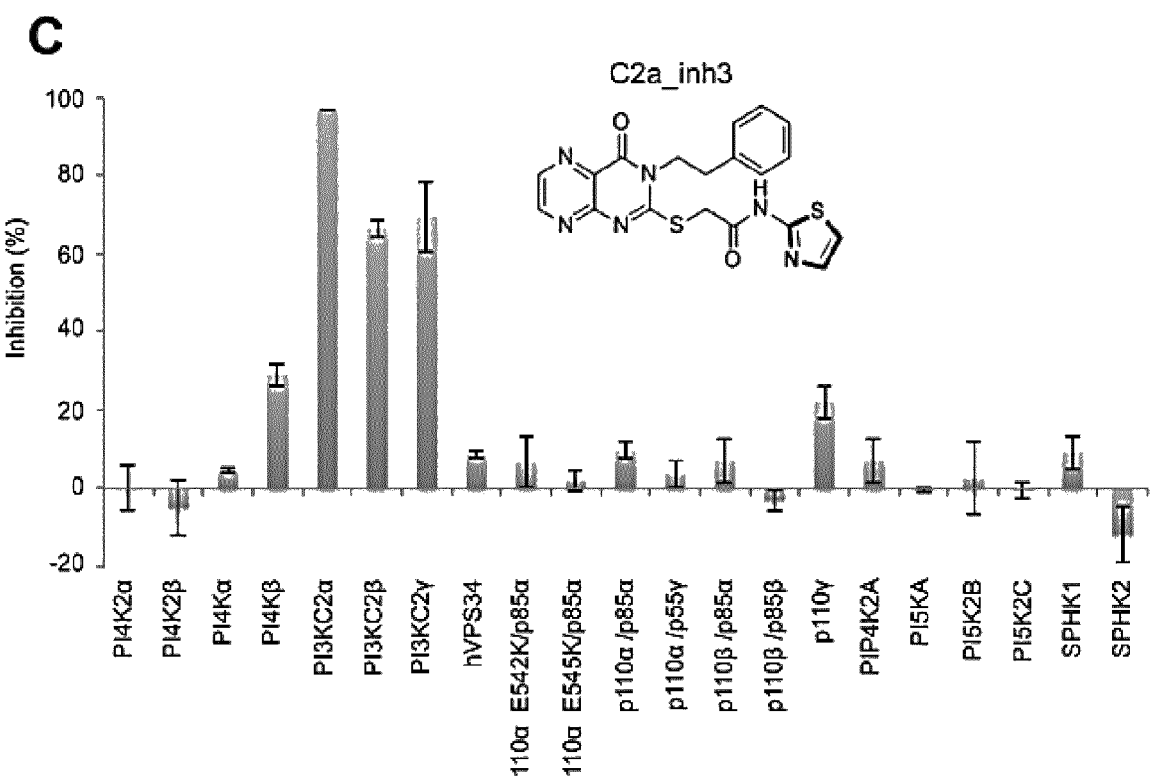

FIG. 7. In vitro kinase activity in presence of 10 μM compounds. (A-C) The specificity of initial screening hits and C2a_inh1-3 was validated by incubation with available lipid kinases. (A) The specificity of initial screening hits and C2a_inh1 indicates C2a_Inh1 (IC50=2.6 μM) is a highly specific inhibitor. (B—C) C2a_Inh2, 3 specifically inhibited class II PI3Ks, and displayed selectivity for PI3KC2α to a variable extent. For note, C2a_Inh2, 3 are modified based on C2a_Inh1 (IC50 of C2a_Inh2=0.76 μM; IC50 of C2a_Inh3=0.49 μM). (D) Selectivity may be modulated by modifying the R11 substituent of Formula 1.

Lipid kinase panel: PI4K2A (PI4K2 alpha), PI4K2B (PI4K2 beta), PI4KA (PI4K alpha), PI4KB (PI4K beta), PIK3C3 (hVPS34), PIK3CA E542K/PIK3R1 (p110 alpha E542K/p85 alpha), PIK3CA E545K/PIK3R1 (p110 alpha E545K/p85 alpha), PIK3CA/PIK3R1 (p110 alpha/p85 alpha), PIK3CA/PIK3R3 (p110 alpha/p55 gamma), PIK3CB/PIK3R1 (p110 beta/p85 alpha), PIK3CB/PIK3R2 (p110 beta/p85 beta), PIK3CG (p110 gamma), PIP4K2A, PIP5K1A, PIP5K1B, PIP5K1C, SPHK1, SPHK2, FRAP1 (mTOR).

General kinase panel: ABL1, ABL1 E255K, ABL1 T3151, ACVR1B (ALK4), ADCK3, AKT1 (PKB alpha), AKT2 (PKB beta), ALK, AURKA (Aurora A), AURKB (Aurora B), AXL, BMPR2, BRAF, BRAF V599E, BTK, CAMKK2 (CaMKK beta), CDK11/cyclin C, CDK16 (PCTK1)/cyclin Y, CDK2/cyclin 0, CDK3/cyclin E1, CDK9/cyclin K, CHEK1 (CHK1), CSF1R (FMS), CSK, CSNK1D (CK1 delta), CSNK1G2 (CK1 gamma 2), DCAMKL1 (DCLK1), DNA-PK, DYRK1B, EGFR (ErbB1), EGFR (ErbB1) L858R, EPHA2, ERBB2 (HER2), ERBB4 (HER4), FGFR2, FGFR3, FLT3, GSK3B (GSK3 beta), IGF1R, IKBKB (IKK beta), INSR, IRAK4, JAK1, JAK2, JAK2 JH1 JH2, JAK3, KDR (VEGFR2), KIT, KIT D816V, KIT V559D T6701, LYN A, MAP2K1 (MEK1), MAP2K2 (MEK2), MAP3K7/MAP3K7IP1 (TAK1-TAB1), MAP3K8 (COT), MAPK11 (p38 beta), MAPK14 (p38 alpha), MAPKAPK2, MAPKAPK5 (PRAK), MARK3, MET (cMet), MKNK1 (MNK1), MKNK2 (MNK2), PAK1, PAK2 (PAK65), PAK4, PDGFRA (PDGFR alpha), PDGFRB (PDGFR beta), PDK1, PIM1, PIM2, PIM3, PKN1 (PRK1), PLK1, PLK3, PRKACA (PKA), PRKCA (PKC alpha), PRKCE (PKC epsilon), PTK2 (FAK), RAF1 (cRAF) Y340D Y341 D, RET, ROCK2, SRC, STK17B (DRAK2), STK32C (YANK3), SYK, TEK (Tie2), TGFBR1 (ALK5), TNIK, TYK2, ULK2, WNK1, ZAP70.

Figure 8:
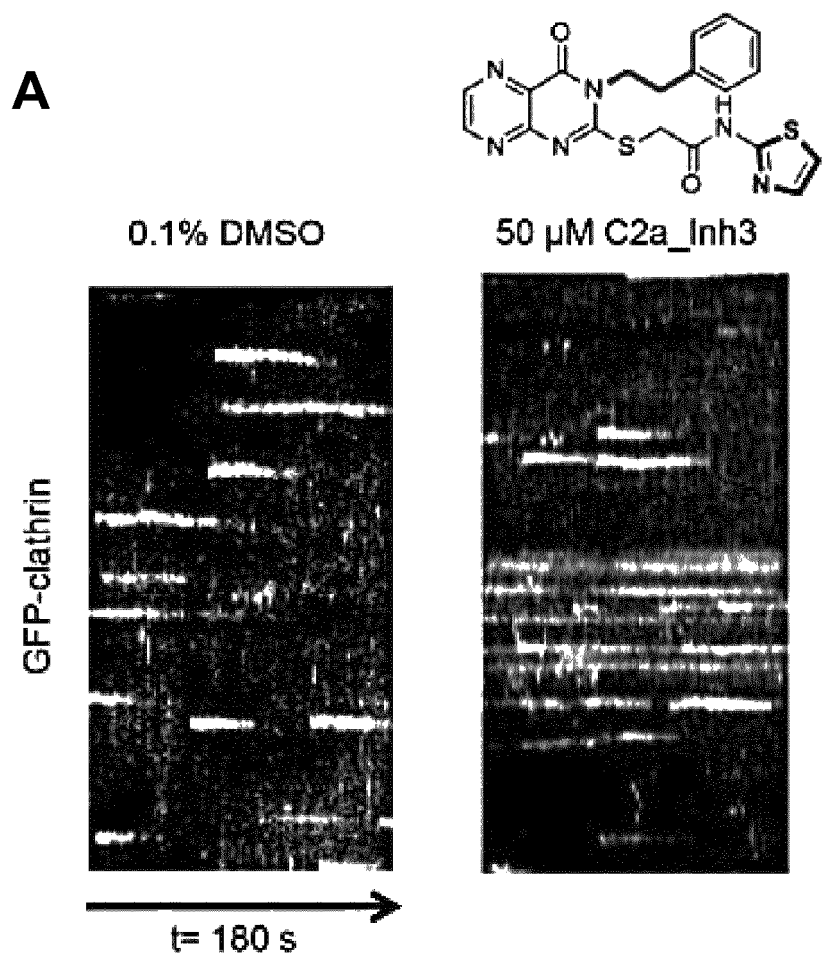
FIG. 8. Inhibition of PI3KC2α in living cells upon treatment with C2a_inh1 to 3.
Figure 8:
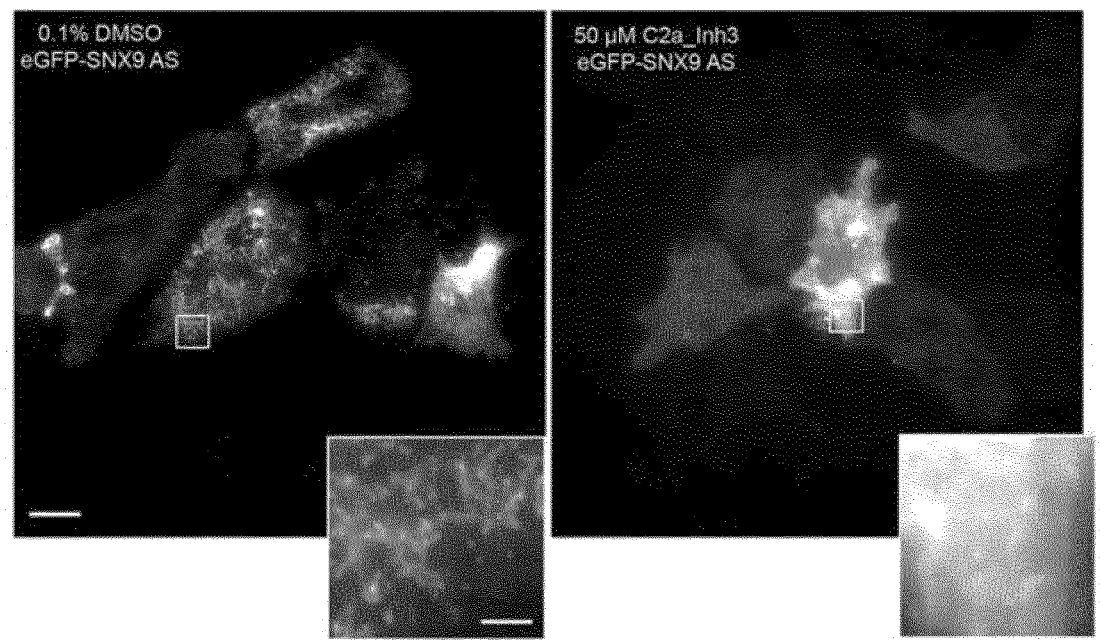
Figure 8:
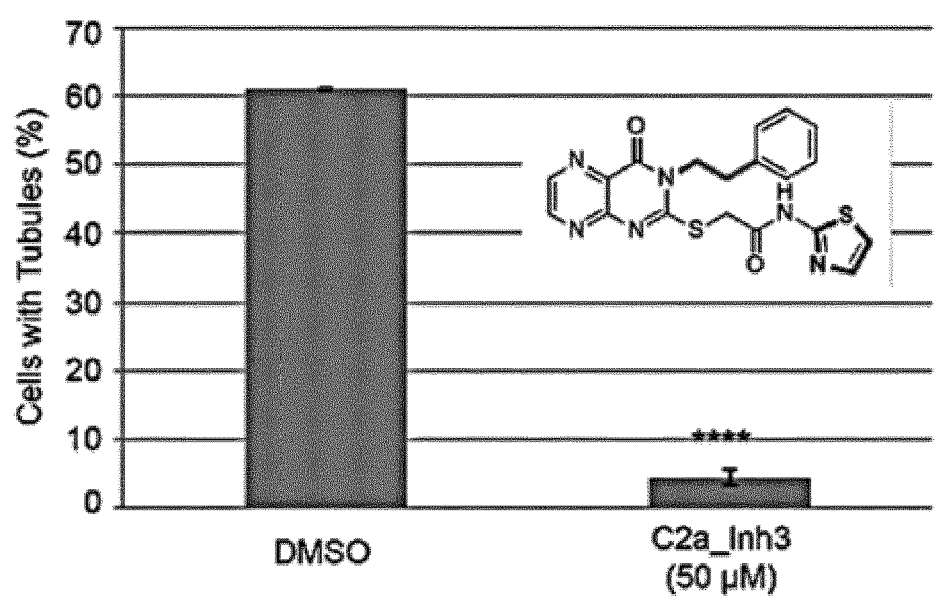

FIG. 8. Inhibition of PI3KC2α in living cells upon treatment with C2a_inh1-3. (A) PI3KC2α inhibition impairs CCP dynamics analyzed by TIRF microscope. eGFP-clathrin expressing Cos7 cells were treated by DMSO or C2a_Inh3 for 1 h and imaged by TIRF microscope. Kymographs show increased CCP-lifetimes in C2a_Inh3-treated cells. (B) C2a_Inh3 treatment of eGFP-SNX9 AS OE HeLa cells. DMSO control treatment, as shown in the left panel, reveals a high percentage of cells with membrane tubules. C2a_Inh3 treatment cells reduced the recruitment of SNX9 to the membrane, and the number of tubules in the cell. Scale bar, 10 μm or 2 μm (inset). (C) Quantification of the results depicted in B, indicating the percentage of cells containing membrane tubules (N=3, statistical analysis with one-way ANOVA, **** is for p<0.0001).

EXAMPLES

The invention is further described by the following examples. These are not intended to limit the scope of the invention, but represent preferred embodiments of aspects of the invention provided for greater illustration.

Example 1: Inhibitor Development and Structural Characterization of PI3KC2α

Functional data indicate that class II PI3K activity is under tight spatiotemporal control but how this is accomplished at the molecular level has remained largely elusive. Apart from the PX and C2 domains of PI3KC2α, class II PI3Ks are structurally unresolved, largely owed to the lack of pure soluble and enzymatically active recombinant protein. Moreover, no specific inhibitors of PI3KC2α have been described. One object of the invention is therefore the development of novel small molecule inhibitors of PI3KC2α.

Example 2: Expression and Purification of PI3KC2α Δ1-298

To overcome limitations with respect to the availability of pure recombinant enzyme the inventors developed protocols to obtain purified recombinant PI3KC2α from insect cells. The expression and purification of class II PI3 kinases (PI3KC2) is notoriously difficult as variants containing the long N-terminal disordered regions and *E. coli*-expressed PI3KC2 resulted in formation of inclusion bodies. The inventors therefore decided to probe whether an N-terminally truncated variant of human PI3KC2α can be expressed in baculovirus-transduced insect cells. To this aim, S/21 cells were infected with a virus for recombinant expression of human PI3KC2α Δ1-298 (e.g. a truncated variant lacking the N-terminal 298 amino acids). The optimal expression time was tested by measuring the amount of soluble protein every 24 hours post-infection. Soluble protein content increased within the initial 48 hours, while no further increase was detectable after this time point (FIG. 3A). Thus, expression for 48-72 hours appears to be a suitable time window for expression of soluble recombinant protein. To test, which insect cell line is more efficient for PI3KC2α Δ1-298 expression, Sf21 and Hi5 cells were infected with a virus encoding PI3KC2α Δ1-298 and harvested at 48 hours post-infection. Small-scale purification with Ni-NTA beads showed that S/21 cells gave a higher yield and less degradation product compared to Hi5 cells (FIG. 3B-C). These results establish suitable conditions for the expression and purification of PI3KC2α Δ1-298 from baculovirus-infected insect cells.

Example 3: Enzymatic Activity and Assay Development for Purified PI3KC2α

Previous studies have shown that PI3KC2α can utilize phosphatidylinositol (PI) or phosphatidylinositol 4-phosphate [PI(4)P] to produce PI(3)P or PI(3,4)P$_2$ respectively but with a preference for PI(3,4)P$_2$ production. To verify that purified PI3KC2α Δ1-298 is active, a radioactive kinase assay was performed with PI as a substrate and different amounts of purified PI3KC2α Δ1-298. The lipid product [PI(3)P] was separated on TLC plates, and the PI(3)P signal was correlated with the amount of PI3KC2α used (FIG. 4A). The result indicates that purified PI3KC2α Δ1-298 from baculovirus-infected insect cells is folded and catalytically active. After having confirmed the activity of purified PI3KC2α Δ1-298, an assay suitable for high content screens in multiwell format (ADP-Glo™ assay) was established. The ADP-Glo™ assay has been used for universal detection of ATP hydrolysis. This assay measures ATP hydrolysis occurring during a kinase reaction. For detection, generated ADP is re-converted into ATP with the Glo™ reagent and converted into light by the Ultra-Glo™ Luciferase reagent. The luminescent signal reports kinase activity (FIG. 4B).

The ADP-Glo™ assay was first used to determine the linear correlation range of signal with different amounts of kinase, and then to assess the $K_m$s for ATP and for PI. The signals showed a linear correlation for a broad range of PI3KC2α concentrations (FIG. 4C). Lipid titration experiments with fixed ATP concentration (200 μM) revealed a Km for PI of around 300 μM, and ATP titration experiments with 400 μM PI indicated a Km for ATP of about 50 μM (FIG. 4D, E). These results provide important parameters for establishing high content inhibitor screening. Further optimization of this assay allowed us to carry out medium-to-high throughput screening using low amounts of purified enzyme (at fixed concentrations of: ATP=40 μM, PI=200 μM, PI3KC2α Δ1–298=10 ng/μl).

Example 4: Chemical Compound Library Screening

Primary screens were performed using the ADP-Glo™ assay in a 384-well format. 37, 224 small molecules were screened for their ability to inhibit kinase activity of PI3KC2α Δ1-298. The concentration of each compound used in the primary screens was 10 μM. Kinase incubations with ATP but without PI were used as negative control samples. This primary screen turned out to be robust with an average z' factor of 0.57, and therefore judged as successful.

Example 5: Primary Hits Validation from Inhibitor Screening

Following initial screening, 408 hits were found, 348 of which were chosen for validation by dose-response ($IC_{50}$) analysis from 10 to 0.1 μM. 30 out of 345 compounds proved to be PI3KC2α inhibitors. Based on the structures of these 30 hits, three main chemical scaffolds (dihydropteridinone, torin, and quinolone) were classified (FIG. 5C). However, torin- and quinolone-derived inhibitors have known activity towards mTOR or class I PI3K. The inventors therefore focused on the dihydropteridinone scaffold, which share a pyrimidone scaffold and a sulfur linker hinge. The numbering scheme of the dihyfropteridinone scaffold is shown in FIG. 5D.

Two of these compounds, hereafter termed C2a_Inh1 (FIG. 5A; compound 1) and C2a_Inh2 (FIG. 5A; compound 6), inhibited PI3KC2α with an $IC_{50}$ about 2.6 μM and 0.5-0.6 μM. These results reveal a chemical scaffold for PI3KC2α inhibitors. Four additional compounds of related structure were also shown to inhibit PI3KC2α, namely those shown in FIG. 5B.

Example 6: Structure-Activity-Relationship (SAR) Validation

The inventors further validated the compound activity using the established ADP-Glo™ assay. The shared pyrimidone scaffold and sulfur linker hinge in dihydropteridinone-derived compounds provided the basis for further chemical modification and structure-activity-relationship (SAR) validation.

To further investigate if the nitrogen at position 8 of dihydropteridinone (R1 of Formula 1) is important for compound activity, compound variants were generated missing the nitrogen at position 8, in combination with variation of the ring structure at R10 of Formula 1. Interestingly, this modification gave rise to the compound in FIG. 5E, which showed excellent activity, with an $IC_{50}$ of 13 μM. This suggests that a thiazole at R10 of Formula 1 might increase the activity of dihydropteridinone-based inhibitors.

Based on the above results, we introduced a thiazole at R10 of Formula 1 into C2a_Inh2, giving rise to C2a_Inh3 (Example Compound 11, see Table 1) that displayed an $IC_{50}$ of 0.1 μM, a considerable improvement over C2a_Inh2. The water solubility of C2a_Inh3 is much higher than C2a_Inh2 (C2a_Inh3: 100-50 μM and C2a_Inh2: 25-10 μM in water), thereby facilitating experiments in aqueous solution.

Further optimizations of the compound were based on C2a_Inh3, switching the hinge on the $3^{rd}$ position of the dihydropteridionone moiety, leading to further functional compounds (see Table 1). p-fluorophenyl substitution of C2a_Inh3 (leading to Example Compound 9, see Table 1; named C2a_Inh4) showed similar activity as C2a_Inh3. This compound, was considered as another inhibitor for further validation.

Modification of the carbon linker at the $2^{nd}$ hinge position with a branched carbon chain did not disrupt the activity of inhibitor (Example Compound 16, see Table 1).

Variation of the amide substitution was further carried out to assess SAR. A number of compounds with substituted phenyl rings or 5- or 6-membered heterocycles at position R10 of Formula 1 showed activity (see Table 1).

Further substitution of the thiazole group of C2a_Inh3 corresponding to R10 of Formula 1 was carried out in order to explore additional structural variation. A bromo derivative (Example Compound 29; Table 1), phenyl derivative (Example Compound 10; Table 1) and halo-substituted phenyl derivatives (Example Compound 6; Table 1) of the thiazole group at R10 lead to functional compounds. In addition, alkoxy- and hydroxy-substituted phenyl substituents and a thiophene substituent of R10 also lead to active compounds (see Table 1).

Additional compounds of the invention relate to those disclosed in FIG. 6, and the additional compounds shown in Table 1.

Example 7: Specificity of PI3KC2α Inhibitors

It was addressed whether the newly identified compounds exhibit selectivity towards class II PI3Ks or even isoform specificity for PI3KC2α. We firstly analyzed the specificity of C2a_inh1 (dihydropteridinone derived compound) and other initial screening hits (eg. quinolone derived compound) in vitro. As PI3KC2α like other lipid kinases belong to the Ser/Thr kinase superfamily and given the extensive structural conservation of the kinase domains of PI3Ks and mTOR, we profiled all inhibitors at a fixed concentration of 10 μM for their activities towards commercially available lipid kinases and the related mTOR protein kinase. C2a_Inh1 showed higher specificity in comparison to other initial hits (FIG. 7A). With elevation of activity, C2a_Inh2, 3 showed relatively high off-targeting activity towards other class II kinase isoforms compared to C2a_Inh1 (FIG. 7A-C).

These results indicate that the identified dihydropteridinone derived compounds are PI3KC2α-specific inhibitors, that display some activity towards other class II PI3K isoforms, at least when applied at high doses (>10 μM).

Furthermore, modification of substituent R11 of the R10 thiazole group appears to allow modulation of specificity, as indicated by comparisons in class II PI3K inhibition of three compounds shown in FIG. 7D.

Example 8: Biological Activity of PI3KC2α Inhibitors

A previous study indicated that knockdown of PI3KC2α decreases clathrin-mediated transferrin uptake by about 50% and retard the CCP dynamics. To test if the validated compounds are cell membrane permeable and, thus, can be used as medicaments and in cell-based experiments, the inventors analyzed clathrin-mediated endocytosis of transferrin in the presence of PI3KC2α inhibitors or DMSO as a solvent control. Treatment of HeLa cells with C2a_inh1 and 2 resulted in a moderate 20-30% reduction in transferrin uptake. Similar results were obtained for C2a_Inh_3 (FIG. 8A). Further, the inventors monitored the CCP dynamics in cells with PI3KC2α inhibitor (C2a_Inh3) treatment for 1 h. In contrast to control cells, CCP dynamics in C2a_Inh_3 showed increase of lifetime (FIG. 8B).

SNX9 is a main effector protein of PI3KC2α dependent $PI(3,4)P_2$ production. The inventors, therefore, made use of a hyper-active SNX9 mutant (SNX9 AS) that is recruited to PI(3,4)P2-enriched membranes and displays strong membrane tubulation activity (FIG. 8C). HeLa cells overexpressing SNX9 AS were treated with C2a_inh_3 or DMSO as a control. In control cells SNX9 AS displayed was found on tubular structures (FIG. 8 C), whereas in presence of inh_3 SNX9 AS remained largely cytosolic, indicating that C2a_Inh3 led to a decrease in cellular/plasmalemmal PI(3, 4)$P_2$ levels. Of note, this result is consistent with what has been shown for PI3KC2a-knockdown cells. These results suggest that our PI3KC2α inhibitors (C2a_inh1, 2, and 3) are cell membrane permeable and inhibit PI3KC2α kinase activity in living cells.

Discussion of the Examples

The results outlined above present novel, first-in-class PI3KC2α inhibitors, termed C2a_Inh_1, C2a_Inh_2, and C2a_Inh3, in addition to other derivatives, based on a dihydropteridinone scaffold. In vitro these compounds inhibited PI3KC2α activity with an $IC_{50}$ in the low μM to high nM range. In vivo, these compounds inhibited the PI(3,4)$P_2$-dependent recruitment of SNX9 to CCPs, and as a consequence transferrin uptake.

According to SAR analysis with different modified variants, the inventors have found the atoms in the main scaffold (dihydropteridinone) region, the length, and conformation of two extended hinge regions to be important for compound activity. The phenyl group appears in hinge of C2a_Inh2 and C2a_Inh3, increasing (although not essential for) compound activity when comparing them to C2a_Inh1. This potentially indicates that C2a_inh2 and C2a_inh3 targets specific aromatic amino acid residues of PI3KC2α and/or Class II PI3Ks, contained in the binding pocket through hydrophobic-hydrophobic interactions. From the kinase profiling results, C2a_inh1 to 3 at a concentration of 10 μM are highly specific to class II PI3 kinases, and preferentially act on PI3KC2α.

There has been demonstration of a role for PI3KC2α in human disease. Accumulating evidence indicates that PI3KC2α is involved in cell survival, mitosis, angiogenesis, and cilliogenesis, suggesting a role for PI3KC2α in cancer. Additionally, PI3KC2α activity increases in aortae from spontaneously hypertensive rats, which increases systolic blood pressure, indicating a role in cardiovascular diseases. PI3KC2α-specific inhibitors or activators represent promising compounds for the treatment of these and other diseases related to defective and/or pathogenic class 2PI3K signaling.

Methods Employed for Protein Expression, Isotopic Kinase Assay and ADP-Glo Kinase Assay Protein Expression and Purification:

Human PI3KC2α Δ1-298 was expressed in baculovirus infected S/21 cells. 1.6 l of suspension S/21 cells (cell viability more than 95%) were cultured in four 2 L Pyrex® narrow-mouth Erlenmeyer flasks at a cell density of 2.0 million cell/ml and infected with 16 ml V1 virus. The cells were harvested 72 h post-infection. PI3KC2α expressing cell pellets were collected in 8×50 ml falcon tubes and resuspended in 50 ml lysis buffer (50 mM Tris pH 7.5, 300 mM NaCl, 10 mM imidazole, 1 mM DTT, 0.5% Triton X-100, 1 tablet EDTA free protease inhibitor cocktail/50 ml buffer) per falcon tube. Cells were opened by sonification at 30% max power for 1 min at 4° C. Purification was performed with 0.5 ml Ni-NTA beads (Sigma). Bead-bound $His_{10}$-tagged PI3KC2α was washed once with lysis buffer, then 5× with 10 resin volumes of wash buffer (50 mM Tris pH 7.5, 300 mM NaCl, 20 mM imidazole, 1 mM DTT), and finally eluted by 3× consecutive addition of 0.5 ml elution buffer (50 mM Tris pH 7.5, 300 mM NaCl, 300 mM imidazole, 5 mM DTT). The eluted fractions were pooled. The purity of samples was validated by SDS-PAGE and Comassie blue staining. The samples were transferred to dialysis tubes (10 kDa) for buffer exchange into stock buffer (50 mM Tris pH 7.5, 300 mM NaCl, 5 mM DTT, 50% Glycerol). The samples were stocked in −20° C. and used within 1 week.

Human PI3KC2α (amino acid (aa) 376 based truncated mutant) and homologs (mouse: aa 377 based truncated mutants; rat: aa 377 based truncated mutants; zebrafish: aa 374 based truncated mutants) were expressed in baculovirus-infected S/21 cells. 800 ml of suspension S/21 cells (cell viability more than 95%) were cultured in two 2 L Pyrex® narrow-mouth Erlenmeyer flasks at a cell density of 1.5 million cell/ml and infected with 8 ml V1 virus. The cells were harvested at 48 h to 72 h post-infection depending on the time of cell viability decrease from more than 95 to around 90-80%. PI3KC2α expressing cell pellets were collected in 4×50 ml falcon tubes and were resuspended in 40 ml lysis buffer (50 mM Tris pH 7.2, 300 mM NaCl, 10 mM imidazole, 1 mM DTT, 0.5% Triton X-100, 1 tablet EDTA free protease inhibitor cocktail/50 ml buffer, DNase) per falcon tube. The cells were open with sonifier with 30% max power and 1 min sonification at 4° C. Purification was performed with 1 ml Ni-NTA beads (Sigma). The beads bound $His_{10}$ tagged PI3KC2α were washed with lysis buffer once, then 10 resin volumes of wash buffer (50 mM Tris pH 7.2, 300 mM NaCl, 20 mM imidazole, 1 mM DTT) for 5 times and finally eluted with 4× elution in 2 ml elution buffer each (50 mM Tris pH 7.2, 300 mM NaCl, 300 mM imidazole, 5 mM DTT). The N-terminal His-tag was released with 200 μg tobacco etch virus (TEV) protease during dialysis against SEC buffer (20 mM Tris pH 7.5, 300 mM NaCl, 5 mM DTT) at 4° C. Size exclusion chromatography was performed to isolate homogeneous and pure fractions of PI3KC2α. All PI3KC2α samples were concentrated to reach a concentration from 2.5 to 10 mg/ml, depending on solubility of homologues. Samples were snap frozen in liquid nitrogen and stocked in −80 until used for further applications.

Expression of SNX9 WT and mutants were performed with *E. coli* BL21 (DE3). The *E. coli* cells are grown in 2×YT medium at 37° C. and shaken at 180 rpm until $OD_{600\ nm}$=0.8-0.9. The cultures are equilibrated to 20° C., and protein expression was induced by applying IPTG to a final concentration of 0.05 mM. The cells are harvested 20 h post-induction. Purification of SNX9 WT, SNX9 AS (161-168mutation), APA/W2A2 (106DPW108; 165W169W/APA; A2) was performed with nickel NTA beads (Sigma). The N-terminal $His_{10}$-tag was released with TEV. SNX9 WT, AS and APA/W2A2 was further purified by size exclusion chromatography (Superdex S200 10/30). SNX9 PX-BAR (amino acids 204-595) was purified using GST-Bind™ resin (Novagen), followed on-beads cleavage with HRV3-C protease. The flow through fractions were pooled and concentrated for further purification by size exclusion chromatography (Superdex S200). For full-length SNX9 samples (SNX9 WT, AS, and APA/W2A2) the protein purification buffers were HBS (20 mM HEPES, pH 7.5, 300 mM NaCl, 1 mM DTT) with a 10-300 mM imidazole concentration gradient. For SNX9 PX-BAR, HBS supplied with 0.5 mM EDTA was used.

Expression of AP2 α-ear was done in *E. coli* BL21 (DE3). *E. coli* cells were grown in 2×YT medium at 37° C. and shaken at 180 rpm until $OD_{600\ nm}$=0.6-0.8. The cultures were equilibrated to 20° C. and protein expression was induced by applying IPTG to a final concentration of 0.5 mM. The cells are harvested 16 h post-induction. Purification of the AP2 α-ear was performed with with nickel NTA beads and PBS supplied with 20% glycerol and a 10-300 mM imidazole concentration gradient. The N-terminal $His_6$-tag was released with thrombin (GE Healthcare). The protein was further purified by size exclusion chromatography (Superdex S75 10/30).

All SNX9 and AP2 α-ear samples were snap-frozen in liquid nitrogen and stocked in size exclusion chromatography buffer (20 mM HEPES pH 7.5, 200 mM NaCl, 5 mM DTT) at −80° C.

Isotopic Kinase Assay

Isotopic kinase assay was performed with either immunoprecipitated (IPed) kinase or $His_{10}$ tag purified PI3KC2α Δ1-298. To IPed kinase, a 80-90% confluent 10 cm dish of Hek293 cells transiently expressing 6×Myc-PI3KC2α were harvested in 500 µl IP Buffer (20 mM HEPES, 100 mM KCl, 2 mM MgCl2, 1% CHAPS, 1 mM PMSF, 0.3% protease inhibitor cocktail). Cells were incubated on ice for 30 min, cell debris was removed by centrifuging for 10 min at 13,000 rpm and 4° C. 20 µl of protein A/G agarose bead slurry were incubated with about 10 µg of mouse-anti-c-myc antibody in 500 µl PBS for 1 h at room temperature and washed with IP buffer. Hek cell extract was added and incubated at 4° C. for 1 h. Beads were washed using 0.5 ml IP buffer three times and removed using a Hamilton syringe. Beads were resuspended in 100 µl kinase buffer (5 mM HEPES/KOH pH 7.2, 25 mM KCl, 2.5 mM MgOAc, 150 mM KGlu, 10 µM CaCl2, 0.2% CHAPS) and 25 µl beads were aliquoted to each kinase assay tube for kinase reaction. The reactions were started by applying substrate mixture to final concentrations of: 200 µM liver PI (Avanti) and 100 µM ATP/10 µCi of $\gamma$-$^{32}$P-ATP. For $His_{10}$ tag purified PI3KC2α Δ1-298, the titrated amount of purified kinase was applied in kinase reaction buffer containing the substrates mixture described above.

ADP-Glo™ Kinase Assay

ADP-Glo kinase assay was performed as described by the manufacturer's protocol. Briefly, the kinase assay was performed with a 5 mixture of liver PI/ATP/purified PI3KC2α for 20 min in kinase reaction buffer described above. To deplete the remaining ATP from the reaction, 5 µl of Glo™ reagent was added to the kinase reaction mixture and incubated for 40 min. For detection, the generated ADP is re-converted into ATP and converted into light by the Ultra-Glo™ luciferase in kinase detection reagent. The luminescent signal positively correlates with kinase activity. All reactions are performed in Corning® 384 well-white plates.

Synthesis and Analytical Chemistry:

General Procedure:

In general, compounds of the invention can be prepared, for example in the course of a convergent synthesis, by linking two or more fragments which can be derived retrosynthetically from any one of formula 1, 1a, 2, 3, 4, 4a, 5, 6, 6a, 7 and 8. More specifically, suitably substituted starting 4-oxodihydropteridine derivatives are employed as building blocks in the preparation of the compounds of the invention. If not commercially available, such 4-oxodihydropteridine derivatives can be prepared according to the well-known standard procedures for the formation of the 4-oxodihydropteridine ring system. By choosing suitable precursor molecules, these 4-oxodihydropteridine syntheses allow the introduction of a variety of substituents into the various positions of the 4-oxodihydropteridine system, which can be chemically modified in order to finally arrive at the molecule of the invention having the desired substituent pattern.

In one synthetic approach for the preparation of compounds of the invention, a compound of the formula S1 are transformed to give a compound of the formula S2, which can then further cyclized to give compounds S3. Intermediate S3 can then be reacted with S4 to give S5 which can already be the final compound of the formula I, or which is converted into the desired final compound of the formula I.

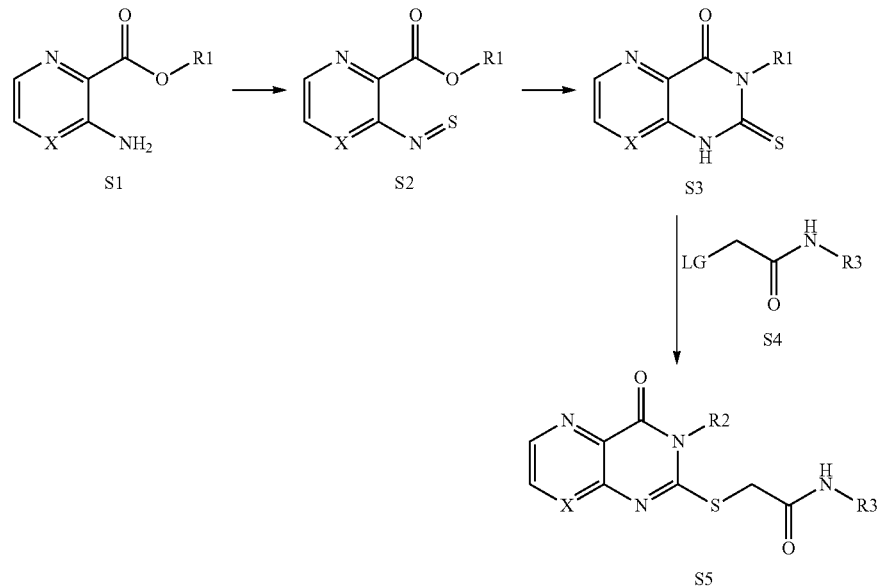

The groups R1, R2 and R3, in the compounds of the formulae S1, S2, S3, S4 and S5 are defined as in the corresponding compounds of the formula 1, 1a, 2, 3, 4, 4a, 5, 6, 6a, 7 or 8, and additionally functional groups may be present in protected form or in the form of a precursor group which is subsequently converted into the final group. The group LG attached to residue S4 is a leaving group, such as a halogen, in particular bromine or chlorine, or a sulfonyloxy group, in particular trifluoromethanesulfonyloxy, methanesulfonyloxy, benzenesulfonyloxy or tosyloxy.

The starting compounds in the synthesis of the compounds of the invention can also be employed, and the intermediates obtained and/or employed, in the form of salts, for example acid addition salts in case of basic compounds. The intermediates can also be present in another tautomeric form.

The reaction of the compounds of the invention are, in general, extensively described in textbooks of peptide chemistry and synthesis. A plethora of methods for the formation of the peptide bond have been reported. The most successful approaches known today involve active ester formation with uronium/guanidinium salts. The most popular members of this family are peptide synthesis reagents based on benzotriazole derivatives such as HOBt or HOAt, both of which are also commonly used as additives in carbodiimide mediated peptide coupling like (TBTU, HBTU, HATU, EDC, BtFFH, ByPOP) in situ with an organic or inorganic base such as an amine like triethylamine, ethyldiisopropylamine, N-methylmorpholine or 1,8-diazabicyclo[5.4.0]unde-7-ene is used for activation of the corresponding carboxylic acid.

Functional groups can be present in the form of precursor groups or of derivatives, for example in protected form. In the course of the preparation of the compounds of the invention it can generally be advantageous or necessary to introduce functional groups which reduce or prevent undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). Protective groups can also have the meaning of a solid phase, and cleavage from the solid phase stands for the removal of the protective group. The use of such techniques is known to those skilled in the art (Burgess K (Ed.) Solid Phase Organic Synthesis, New York, Wiley, 2000).

Nitro groups can be reduced to amino groups with various reducing agents, such as sulfides, dithionites, complex hydrides or by catalytic hydrogenation. A reduction of a nitro group may also be carried out at a later stage of the synthesis of a compound of the formula 1, 1a, 2, 3, 4, 4a, 5, 6, 6a, 7 or 8, and a reduction of a nitro group to an amino group may also occur simultaneously with a reaction performed on another functional group, for example when reacting a group like a cyano group with hydrogen sulfide or when hydrogenating a group. In order to introduce these residues, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides.

Ester groups can be hydrolyzed to the corresponding carboxylic acids under basic conditions in NaOH/MeOH and/or water, which after activation can then be reacted with amines or alcohols under standard conditions. Furthermore, these esters can be hydrolyzed under acid conditions with HBr/AcOH.

The previously-mentioned reactions for the conversion of functional groups are furthermore, in general, extensively described in textbooks of organic chemistry in which details on the reactions and primary source literature can be found. Due to the fact that in the present case the functional groups are attached to 4-oxodihydropteridine derivatives it may in certain cases become necessary to specifically adapt reaction conditions or to choose specific reagents from a variety of reagents that can in principle be employed in a conversion reaction, or otherwise to take specific measures for achieving a desired conversion, for example to use protection group techniques. However, finding suitable reaction variants and reaction conditions in such cases does not cause any problems for one skilled in the art.

Halogens, hydroxy groups (via the triflate or nonaflate) or primary amines (via the diazonium salt) or after interconversion to the corresponding stannane, or boronic acid—present in the 4-oxodihydropteridine structure can be converted into a variety of other functional groups like for example —CN, —CF3, —C2F5, ethers, acids, amides, amines, alkyl- or aryl-groups mediated by means of transition metals, such as palladium or nickel catalysts or copper salts and reagents for example referred to below (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996)

The structural elements present in the residues at the R1, R2 and R3 according to the scheme above of the 4-oxodihydropteridine derivatives and precursors of the formulae of the invention can be introduced for example at the stage of a suitable precursor or the using the methods outlined above by consecutive reaction steps using parallel synthesis methodologies like those outlined below using procedures which per se are well known to one skilled in the art.

In the course of the preparation of the compounds of the invention it can generally be advantageous or necessary to introduce functional groups which reduce or prevent undesired reactions or side reactions in the respective synthesis steps, in the form of precursor groups which are later converted into the desired functional groups, or to temporarily block functional groups by a protective group strategy suited to the synthesis problem. Such strategies are well known to those skilled in the art. Examples of precursor groups are cyano groups and nitro groups. The cyano group can, in a later step, be transformed into carboxylic acid derivatives or by reduction into aminomethyl groups. Nitro groups may be transformed by reduction like catalytic hydrogenation into amino groups. Protective groups can also have the meaning of a solid phase, and cleavage from the solid phase stands for the removal of the protective group. The use of such techniques is known to those skilled in the art. For example, a phenolic hydroxy group can be attached to a trityl-polystyrene resin, which serves as a protecting group, and the molecule is cleaved from this resin by treatment with TFA or other acids at a later stage of the synthesis.

If a residue of the 4-oxodihydropteridine derivatives of the invention are present in protected form or in the form of a precursor group, which have not already been introduced during a preceding step, for example during a synthesis of the 4-oxodihydropteridine derivative nucleus, these residues can, for example, be introduced by standard alkylation procedures well-known to one skilled in the art. Alkylation of the aforementioned atom can, for example, be performed under standard conditions, preferably in the presence of a base like potassium carbonate, cesium carbonate, sodium hydride or potassium tert-butoxide, using an alkylating reagent containing a leaving group, like for example halogen like chlorine, bromine or iodine, or a sulfonyloxy group like tosyloxy, mesyloxy or trifluormethylsulfonyloxy. These standard procedures are known to the skilled person.

As it is usual and applies to all reactions performed in the course of the synthesis of a compound of the invention, appropriate details of the conditions applied in a specific preparation process, including the solvent, a base or acid, the temperature, the order of addition, the molar ratios and other parameters, are routinely chosen by the skilled person in view of the characteristics of the starting compounds and the target compound and the other particularities of the specific case. As is also known by the skilled person, not all processes described herein will in the same way be suitable for the preparation of all compounds of the invention and their intermediates, and adaptations have to be made. In all processes for the preparation of the compounds of the invention, workup of the reaction mixture and the purification of the product is performed according to customary methods known to the skilled person which include, for example, quenching of a reaction mixture with water, adjustment of a certain pH, precipitation, extraction, drying, concentration, crystallization, distillation and chromatography. As further examples of methods applicable in the synthesis of the compounds of the invention, microwave assistance for speeding-up, facilitating or enabling reactions, may be mentioned, and modern separation techniques like preparative high-pressure liquid chromatography (HPLC), which can be used for separating mixtures of positional isomers which may occur in any reactions. Also, for the characterization of the product, customary methods are used such as NMR, IR and mass spectroscopy.

Another subject of the present invention are the novel starting compounds and intermediates occurring in the synthesis of the compounds of the formula 1, 1a, 2, 3, 4, 4a, 5, 6, 6a, 7 or 8, including the compounds of the formulae S1, S2, S3, S4 and S5 wherein the groups R1, R2, R3 and LG according to the general synthesis scheme in any of their stereoisomeric forms or a mixture of stereoisomeric forms in any ratio, and their salts, and their use as synthetic intermediates or starting compounds. All general explanations, specifications of embodiments and definitions of numbers and groups given above with respect to the compounds of the invention apply correspondingly to the said intermediates and starting compounds. Subject of the invention are in particular the novel specific starting compounds and intermediates described herein. Independently thereof whether they are described as a free compound and/or as a specific salt, they are a subject of the invention both in the form of the free compounds and in the form of their salts, and if a specific salt is described, additionally in the form of this specific salt.

The starting materials employed in the synthesis of the compounds of the invention are commercially available or can be prepared according to procedures, or in analogy to procedures, described in the literature or herein.

Abbreviations:

| | |
|---|---|
| DCM | Dichloromethane |
| DIPEA | N,N-Diisopropylethylamine |
| DMF | N,N-Dimethylformamide |
| LCMS | Liquid chromatography-mass spectrometry |
| NMR | Nuclear magnetic resonance spectroscopy |
| RT | Retention time |
| Sat. | Saturated |
| TFA | Trifluoroacetic acid |
| HATU | 1-[Bis(dimethylamino)methylene]-1H-1,2,3-triazolo[4,5-b]pyridinium 3-oxide hexafluorophosphate |

Reactions were generally performed under argon as protective gas. Solvents such as dichloromethane, ethanol, dimethylformamide, methanol, tetrahydrofuran and the like were generally employed as commercially available dry solvents. "Room temperature" means a temperature of 20° C. to 25° C. Solvents were generally evaporated under reduced pressure at temperatures ranging from 35° C. to 45° C. on a rotary evaporator. Chromatography over silica gel was carried out by semiautomatic cartridge systems such as Companion (CombiFlash) or biotage systems.

The example compounds were generally characterized by analytical HPLC with ultraviolet detection at 220 nm and 254 nm and mass spectrometry (MS) detection with electrospray ionization (ESI) (LCUV/ESI-MS coupling; LC/MS), and by 1H nuclear magnetic resonance spectroscopy (1H NMR). The LCMS analyses were based on the UV chromatograms at 220 nm and 254 nm and the ion current from the mass spectrometer at different ionisation modes (e.g. ESI+, ESI−) with the help of ion extracts of the expected ion masses. 1H NMR spectra were recorded at 300 MHz or 600 MHz or 750 MHz in DMSO-$d_6$ as solvent at 298 K, unless specified otherwise. In the NMR characterization, the chemical shift δ (in ppm) and the multiplicities (s=singlet, d=doublet, t=triplet, q=quartet, dd=doublet of doublets, br=broad) and the number of hydrogen atoms (H) of the peaks are given. In the LC/MS characterization, the HPLC method specified below, the retention time (RT) in minutes, and generally the mass-to-charge-ratio m/z of the peak of the molecular ion representing the monoisotopic mass, or of a related ion which was formed depending on the ionization mode, is given. In most cases, the ionization mode was positive electrospray ionization (ESI+), and the mass-to-charge-ratio of the ion [M+H]+ is given. When no significant [M+H]+ peak was obtained, the mass-to-charge-ratio of another characteristic mass signal such as [M+2H]++ or an ion of an addition compound with a solvent molecule or [M−H]", which was formed depending on the ionization mode, such as negative electrospray ionization (ESI−) in the case of the latter ion, is given.

The particular HPLC method in the LC/MS characterization is as follows. LCMS method: instrument: Agilent Technologies 6120 Quadrupole LC/MS linked to Agilent Technologies HPLC 1290 Infinity; column: Thermo Accuore RP-MS; particle size: 2.6 µM dimension: 30×2.1 mm; Eluent A: $H_2O$ with 0.1% TFA Eluent B: MeCN with 0.1% TFA; gradient: 0.00 min 95% A, 0.2 min 95% A, 1.1 min 1% A, 2.5 min stop time, 1.3 min post time; flow rate: 0.8 ml $min^{-1}$; UV-detection: 220 nm, 254 nm, 300 nm.

Example Compound 1: N-(4-(3-Hydroxyphenyl)thiazol-2-yl)-2-((4-oxo-3-phenethyl-3,4-dihydropteridin-2-yl)thio)acetamide (i) Methyl 3-isothiocyanatopyrazine-2-carboxylate

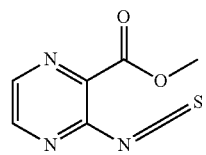

To a solution of methyl 3-aminopyrazine-2-carboxylate (5.0 g) in 60 mL dry DCM under nitrogen atmosphere was added a suspension of Na₂CO₃ (13.2 g) in 30 mL dry DCM. A solution of thiophosgene (4.6 g) in 30 mL dry DCM was added slowly. The reaction was stirred for 48 h at room temperature. After completion of the reaction as monitored by LCMS the precipitate was filtered and washed with DCM and the combined organic phases were washed with water followed by a sat. NaHCO₃ solution and brine. The organic phase was dried over Na₂SO₄, filtered and concentrated under reduced pressure. The crude product was dissolved in ethyl acetate/diisopropyl ether (v/v=1/10) and impurities were removed by filtration. The filtrate was concentrated under reduced pressure to obtain the product as a solid.

Yield: 5.4 g MS (ES+) [M+H]⁺: m/e=196.1, Retention Time: 1.006 min.

(ii) 3-Phenethyl-2-thioxo-2,3-dihydropteridin-4(1H)-one

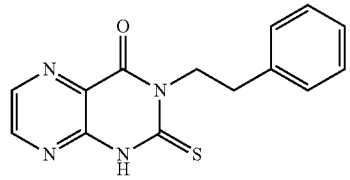 [SMILES: O=c1c2nccnc2[nH]c(=S)n1CCc1ccccc1]

To a solution of methyl 3-isothiocyanatopyrazine-2-carboxylate (2.0 g) in 10 mL dry dioxane over 4 Å molsieve was added a solution of 2-phenylethan-1-amine (1.3 g) in 10 mL dry dioxane. The reaction was refluxed overnight. After completion of the reaction as monitored by LCMS the reaction was cooled to room temperature and the resulting precipitate was filtered, washed three times with diisopropylether followed by ethyl acetate/diisopropylether (v/v=1.5/10) and the resulting solids were dried under reduced pressure.

Yield: 2.0 g MS (ES+) [M+H]⁺: m/e=285.3, RT: 1.090 min

(iii) 3-(2-Aminothiazol-4-yl)phenol

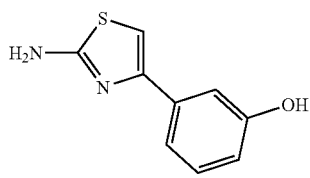 [SMILES: Nc1nc(-c2cccc(O)c2)cs1]

To a solution of 2-bromo-1-(3-hydroxyphenyl)ethan-1-one (620 mg) in 8 mL dry EtOH was added thiourea (220 mg) in portions and heated to reflux for 1 h. After completion of the reaction as monitored by LCMS the solvent was removed under reduced pressure and a sat. solution of NaHCO₃ was added. The resulting solution was extracted three times with ethyl acetate and the combined organic phases were washed with brine, dried over Na₂SO₄ and the solvents were removed under reduced pressure. The crude product was used without further purification.

Yield: 550 mg MS (ES+) [M+H]⁺: m/e=193.3, RT: 0.695 min

(iv) 2-Bromo-N-(4-(3-hydroxyphenyl)thiazol-2-yl)acetamide

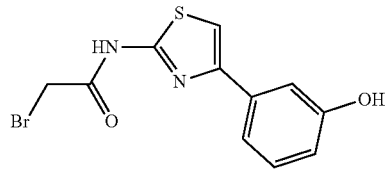 [SMILES: O=C(CBr)Nc1nc(-c2cccc(O)c2)cs1]

To a solution of 2-bromoacetic acid (481 mg), 3-(2-aminothiazol-4-yl)phenol (550 mg) and DIPEA (895 mg) in 8 mL dry DMF was added dropwise a 50% solution 1-propanephosphonic acid anhydride in ethyl acetate (3.1 mL) at 0° C. and stirred at room temperature overnight. After completion of the reaction as monitored by LCMS the solvent was removed under reduced pressure and a sat. solution of NaHCO₃ was added. The resulting solution was extracted three times with ethyl acetate and the combined organic phases were washed with brine, dried over Na₂SO₄ and the solvent was removed under reduced pressure. The crude product was purified by silica gel chromatography using a gradient of ethyl acetate/cyclohexane as eluent.

Yield: 90 mg MS (ES+) [M+H]⁺: m/e=313.2, RT: 1.101 min

(v) N-(4-(3-Hydroxyphenyl)thiazol-2-yl)-2-((4-oxo-3-phenethyl-3,4-dihydropteridin-2-yl)thio)acetamide

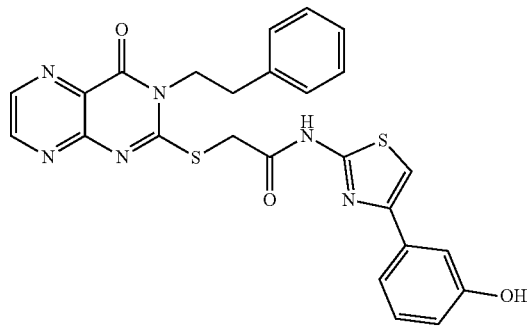 [SMILES: O=C(CSc1nc2nccnc2c(=O)n1CCc1ccccc1)Nc1nc(-c2cccc(O)c2)cs1]

To a solution of 3-phenethyl-2-thioxo-2,3-dihydropteridin-4(1H)-one (74 mg) in 3 mL dry DMF was added dry triethylamine (58 mg) followed by dropwise addition of 2-bromo-N-(4-(3-hydroxyphenyl)thiazol-2-yl)acetamide (90 mg) in 3 mL dry DMF. The reaction mixture was stirred overnight at 80° C. After completion of reaction as monitored by LCMS the DMF was removed under reduced pressure and to the crude product was added water. The water phase was extracted three times with DCM and the combined organic phases were washed with brine, dried over Na₂SO₄ and concentrated under reduced pressure. The crude product was purified by silica gel chromatography using a gradient of DCM/MeOH as eluent. The product was obtained as a beige solid.

Yield: 62 mg MS (ES+) [M+H]⁺: m/e=517.5, RT: 1.128 min

¹H NMR (300 MHz, DMSO-d₆): δ 12.72 (s, 1H), 9.51 (s, 1H), 8.89 (d, J=2.1 Hz, 1H), 8.76 (d, J=2.1 Hz, 1H), 7.54 (s,

1H), 7.39-7.30 (m, 7H), 7.22 (t, J=7.7 Hz, 1H), 6.76-6.70 (m, 1H), 4.49 (s, 2H), 4.31 (dd, J=9.7, 6.8 Hz, 2H), 3.11-3.03 (m, 2H).

Example Compound 2: N-(4-(4-(Methylsulfonamido)phenyl)thiazol-2-yl)-2-((4-oxo-3-phenethyl-3,4-dihydropteridin-2-yl)thio)acetamide (i) N-(4-(2-Aminothiazol-4-yl)phenyl)methanesulfonamid

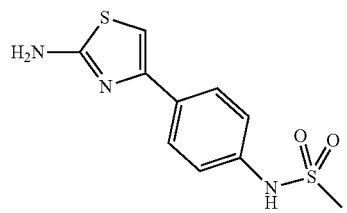 [SMILES: CS(=O)(=O)Nc1ccc(-c2csc(N)n2)cc1]

To a solution of N-(4-(2-bromoacetyl)phenyl)methanesulfonamide (255 mg) in 8 mL dry EtOH was added thiourea (69 mg) in portions and heated to reflux for 1 h. After completion of the reaction as monitored by LCMS the solvent was removed under reduced pressure and a sat. solution of NaHCO$_3$ was added. The resulting solution was extracted three times with ethyl acetate and the combined organic phases were washed with brine, dried over Na$_2$SO$_4$ and the solvent was removed under reduced pressure. The crude product was used without further purification.

Yield: 208 mg MS (ES+) [M+H]$^+$: m/e=270.1, RT: 0.752 min (ii) 2-Bromo-N-(4-(4-(methylsulfonamido)phenyl)thiazol-2-yl)acetamide

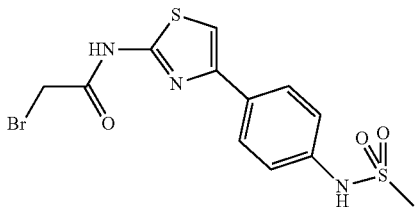 [SMILES: CS(=O)(=O)Nc1ccc(-c2csc(NC(=O)CBr)n2)cc1]

To a solution of 2-bromoacetic acid (484 mg), N-(4-(2-aminothiazol-4-yl)phenyl)methanesulfonamid (152 mg) and Et$_3$N (385 mg) in 12 mL dry DCM and 5 mL dry MeCN at 0° C. and stirred at room temperature overnight. After completion of the reaction as monitored by LCMS the solvent was removed under reduced pressure and a sat. solution of NaHCO$_3$ was added. The resulting solution was extracted three times with ethyl acetate and the combined organic phases were washed with brine, dried over Na$_2$SO$_4$ and the solvent was removed under reduced pressure. The crude product was purified by silica gel chromatography using a gradient of ethyl acetate/cyclohexane as eluent.

Yield: 60 mg MS (ES+) [M+H]$^+$: m/e=390.0, RT: 0.930 min (iii) N-(4-(4-(Methylsulfonamido)phenyl)thiazol-2-yl)-2-((4-oxo-3-phenethyl-3,4-dihydropteridin-2-yl)thio)acetamide

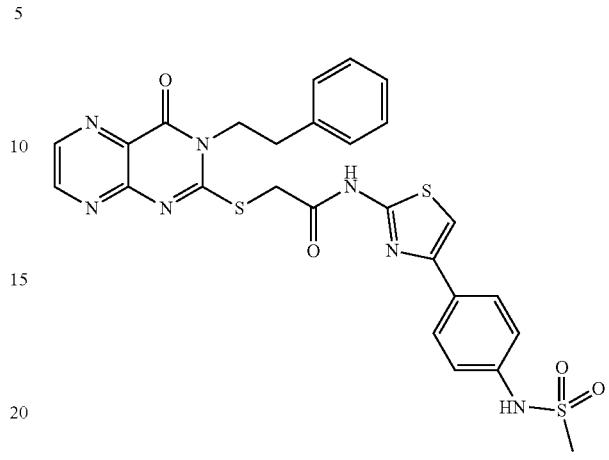

To a solution of 3-phenethyl-2-thioxo-2,3-dihydropteridin-4(1H)-one (27 mg) in 3 mL dry DMF was added dry triethylamine (17 mg) followed by dropwise addition of 2-bromo-N-(4-(4-(methylsulfonamido)phenyl)thiazol-2-yl)acetamide (30 mg) in 3 mL dry DMF. The reaction mixture was stirred overnight at 80° C. After completion of reaction as monitored by LCMS the DMF was removed under reduced pressure and to the crude product was added water. The water phase was extracted three times with DCM and the combined organic phases were washed with brine, dried over Na$_2$SO$_4$ and concentrated under reduced pressure. The crude product was purified by silica gel chromatography using a gradient of DCM/MeOH as eluent. The product was obtained as a beige solid.

Yield: 23 mg MS (ES+) [M+H]$^+$: m/e=594.1, RT: 1.133 min $^1$H NMR (300 MHz, DMSO-d$_6$): δ 12.76 (s, 1H), 9.88 (s, 1H), 8.89 (d, J=2.1 Hz, 1H), 8.76 (d, J=2.1 Hz, 1H), 7.87 (d, J=8.5 Hz, 2H), 7.55 (s, 1H), 7.38-7.31 (m, 4H), 7.27 (d, J=8.6 Hz, 3H), 4.49 (s, 2H), 4.36-4.25 (m, 2H), 3.13-3.04 (m, 2H), 3.04 (d, J=4.6 Hz, 3H).

Example Compound 3: 2-((3-(3-Fluorophenethyl)-4-oxo-3,4-dihydropteridin-2-yl)thio)-N-(oxazol-2-yl)acetamide (i) 3-(3-Fluorophenethyl)-2-thioxo-2,3-dihydropteridin-4(1H)-one

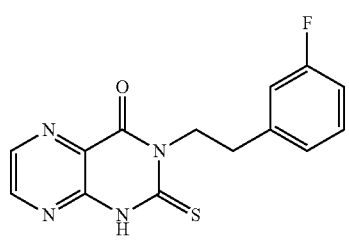 [SMILES: O=c1c2nccnc2[nH]c(=S)n1CCc1cccc(F)c1]

To a solution of methyl 3-isothiocyanatopyrazine-2-carboxylate (110 mg) in 10 mL dry dioxane over 4 Å molsieve was added a solution of 2-(3-fluorophenyl)ethan-1-amine (79 mg) in 10 mL dry dioxane. The reaction was refluxed overnight. After completion of the reaction as monitored by LCMS the reaction was cooled to room temperature and the resulting precipitate was filtered, washed three times with diisopropylether and the resulting solid product was dried under reduced pressure.

Yield: 145 mg MS (ES+) [M+H]$^+$: m/e=303.2, RT: 1.062 min (ii) 2-Bromo-N-(oxazol-2-yl)acetamide

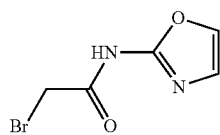

To a solution of 2-bromoacetic acid (200 mg), oxazol-2-amine (83 mg) and Et$_3$N (130 mg) in 12 mL dry DCM at 0° C. and stirred at room temperature overnight. After completion of the reaction as monitored by LCMS the precipitating product was filtered and washed three times with DCM. The solid product was dried and used without further purification.

Yield: 84 mg MS (ES+) [M+H]$^+$: m/e=205.0, RT: 0.247 min (iii) 2-((3-(3-Fluorophenethyl)-4-oxo-3,4-dihydropteridin-2-yl)thio)-N-(oxazol-2-yl)acetamide

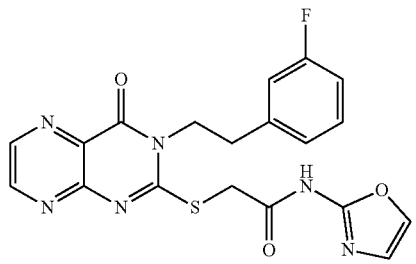 [SMILES: O=C(CSc1nc2nccnc2c(=O)n1CCc1cccc(F)c1)Nc1ncco1]

To a solution of 3-(3-fluorophenethyl)-2-thioxo-2,3-dihydropteridin-4(1H)-one (50 mg) in 3 mL dry DMF was added dry triethylamine (38 mg) followed by dropwise addition of 2-bromo-N-(oxazol-2-yl)acetamide (36 mg) in 3 mL dry DMF. The reaction mixture was stirred overnight at 80° C. After completion of reaction as monitored by LCMS the DMF was removed under reduced pressure and to the crude product was added water. The water phase was extracted three times with DCM and the combined organic phases were washed with brine, dried over Na$_2$SO$_4$ and concentrated under reduced pressure. The crude product was purified by silica gel chromatography using a gradient of DCM/MeOH as eluent. The product was obtained as a beige solid.

Yield: 12 mg MS (ES+) [M+H]$^+$: m/e=427.1, RT: 0.992 min $^1$H NMR (300 MHz, DMSO-d$_6$): δ 11.74 (s, 1H), 8.92 (s, 1H), 8.76 (s, 1H), 7.86 (s, 1H), 7.26 (m, 5H), 4.35 (m, 4H), 3.16-3.01 (m, 2H).

Example Compound 4: 2-((3-(3-Fluorophenethyl)-4-oxo-3,4-dihydropteridin-2-yl)thio)-N-(thiazol-2-yl)acetamide (i) 2-Bromo-N-(thiazol-2-yl)acetamide

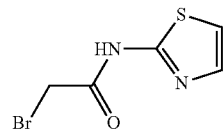

2-Bromo-N-(thiazol-2-yl)acetamide was prepared by adapting the procedures described in example 3 for the synthesis of 2-bromo-N-(oxazol-2-yl)acetamide.

Yield: 98 mg $^1$H NMR (300 MHz, Chloroform-d): δ 7.56 (d, J=3.6 Hz, 1H), 7.08 (d, J=3.6 Hz, 1H), 4.07 (s, 2H).

(ii) 2-((3-(3-Fluorophenethyl)-4-oxo-3,4-dihydropteridin-2-yl)thio)-N-(thiazol-2-yl)acetamide

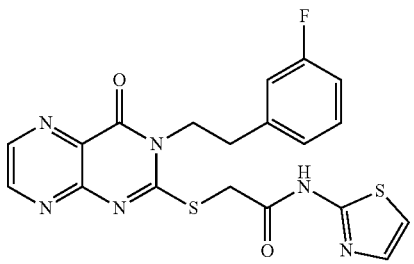

To a solution of 3-(3-fluorophenethyl)-2-thioxo-2,3-dihydropteridin-4(1H)-one (50 mg) in 3 mL dry DMF was added dry triethylamine (38 mg) followed by dropwise addition of 2-bromo-N-(thiazol-2-yl)acetamide (38 mg) in 3 mL dry DMF. The reaction mixture was stirred overnight at 80° C. After completion of reaction as monitored by LCMS the DMF was removed under reduced pressure and to the crude product was added water. The water phase was extracted three times with DCM and the combined organic phases were washed with brine, dried over Na$_2$SO$_4$ and concentrated under reduced pressure. The crude product was purified by silica gel chromatography using a gradient of DCM/MeOH as eluent. The product was obtained as a beige solid.

Yield: 23 mg MS (ES+) [M+H]$^+$: m/e=443.1, RT: 1.068 min $^1$H NMR (300 MHz, DMSO-d$_6$): δ 12.57 (s, 1H), 8.89 (d, J=2.0 Hz, 1H), 8.75 (d, J=2.0 Hz, 1H), 7.69-6.88 (m, 6H), 4.46 (s, 2H), 4.41-4.24 (m, 2H), 3.19-2.99 (m, 2H).

Example Compound 5: 2-((3-(3-Fluorophenethyl)-4-oxo-3,4-dihydropteridin-2-yl)thio)-N-(5-methyl-1,3,4-thiadiazol-2-yl)acetamide (i) 2-Bromo-N-(5-methyl-1,3,4-thiadiazol-2-yl)acetamide

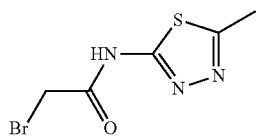

2-Bromo-N-(5-methyl-1,3,4-thiadiazol-2-yl)acetamide was prepared by adapting the procedures described in example 3 for the synthesis of 2-bromo-N-(oxazol-2-yl)acetamide.

Yield: 174 mg MS (ES+) [M+H]$^+$: m/e=236.0, RT: 0.799 min (ii) 2-((3-(3-Fluorophenethyl)-4-oxo-3,4-dihydropteridin-2-yl)thio)-N-(5-methyl-1,3,4-thiadiazol-2-yl)acetamide

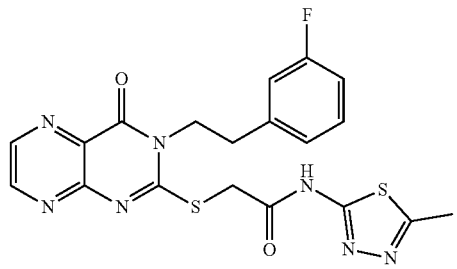 [SMILES: Cc1nnc(NC(=O)CSc2nc3nccnc3c(=O)n2CCc2cccc(F)c2)s1]

To a solution of 3-(3-fluorophenethyl)-2-thioxo-2,3-dihydropteridin-4(1H)-one (50 mg) in 3 mL dry DMF was added dry triethylamine (38 mg) followed by dropwise addition of 2-bromo-N-(5-methyl-1,3,4-thiadiazol-2-yl)acetamide (41 mg) in 3 mL dry DMF. The reaction mixture was stirred overnight at 80° C. After completion of reaction as monitored by LCMS the DMF was removed under reduced pressure and to the crude product was added water. The water phase was extracted three times with DCM and the combined organic phases were washed with brine, dried over Na$_2$SO$_4$ and concentrated under reduced pressure. The crude product was purified by silica gel chromatography using a gradient of DCM/MeOH as eluent. The product was obtained as a grey solid.

Yield: 19 mg MS (ES+) [M+H]$^+$: m/e=458.2, RT: 1.036 min $^1$H NMR (300 MHz, DMSO-d$_6$): δ 12.85 (s, 1H), 8.89 (d, J=2.1 Hz, 1H), 8.75 (d, J=2.1 Hz, 1H), 7.38 (m, 1H), 7.20-7.07 (m, 3H), 4.47 (s, 2H), 4.39-4.26 (m, 2H), 3.14-3.04 (m, 2H), 2.60 (s, 3H).

Example Compound 6: 2-((3-(3-Fluorophenethyl)-4-oxo-3,4-dihydropteridin-2-yl)thio)-N-(4-(4-fluorophenyl)thiazol-2-yl)acetamide (i) 4-(4-Fluorophenyl)thiazol-2-amine

To a solution of 2-bromo-1-(4-fluorophenyl)ethan-1-one (1.14 g) in 15 mL dry EtOH was added thiourea (220 mg) in portions and heated to reflux for 1 h. After completion of the reaction as monitored by LCMS the solvent was removed under reduced pressure and a sat. solution of NaHCO$_3$ was added. The resulting solution was extracted three times with ethyl acetate and the combined organic phases were washed with brine, dried over Na$_2$SO$_4$ and the solvent was removed under reduced pressure. The crude product was used without further purification.

Yield: 1.03 g MS (ES+) [M+H]$^+$: m/e=195.2, RT: 0.849 min (ii) 2-Bromo-N-(4-(4-fluorophenyl)thiazol-2-yl)acetamide

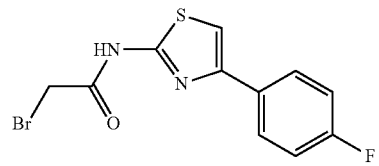 [SMILES: O=C(CBr)Nc1nc(-c2ccc(F)cc2)cs1]

2-Bromo-N-(4-(4-fluorophenyl)thiazol-2-yl)acetamide was prepared by adapting the procedures described in example 3 for the synthesis of 2-bromo-N-(oxazol-2-yl)acetamide. The crude product was purified by silica gel chromatography using a gradient of DCM/MeOH as eluent.

Yield: 1.225 g MS (ES+) [M+H]$^+$: m/e=315.0, RT: 1.138 min

(iii) 2-((3-(3-Fluorophenethyl)-4-oxo-3,4-dihydropteridin-2-yl)thio)-N-(4-(4-fluorophenyl)thiazol-2-yl)acetamide

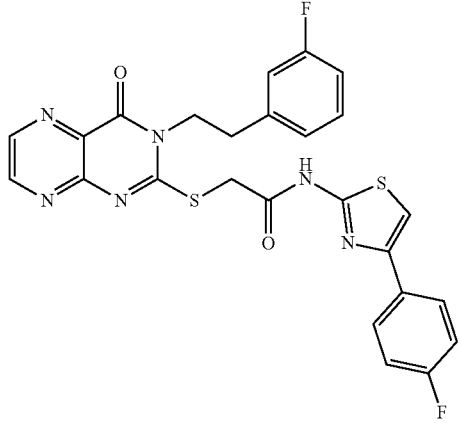 [SMILES: O=C(CSc1nc2nccnc2c(=O)n1CCc1cccc(F)c1)Nc1nc(-c2ccc(F)cc2)cs1]

To a solution of 3-(3-fluorophenethyl)-2-thioxo-2,3-dihydropteridin-4(1H)-one (55 mg) in 3 mL dry DMF was added dry triethylamine (40 mg) followed by dropwise addition of 2-bromo-N-(4-(4-fluorophenyl)thiazol-2-yl)acetamide (60 mg) in 3 mL dry DMF. The reaction mixture was stirred overnight at 80° C. After completion of reaction as monitored by LCMS the DMF was removed under reduced pressure and to the crude product was added water. The water phase was extracted three times with DCM and the combined organic phases were washed with brine, dried over $Na_2SO_4$ and concentrated under reduced pressure. The crude product was purified by silica gel chromatography using a gradient of DCM/MeOH as eluent. The product was obtained as a beige solid.

Yield: 43 mg MS (ES+) [M+H]$^+$: m/e=537.2, RT: 1.226 min $^1$H NMR (300 MHz, DMSO-d$_6$): δ 12.74 (s, 1H), 8.89 (d, J=2.1 Hz, 1H), 8.75 (d, J=2.1 Hz, 1H), 8.03-7.89 (m, 2H), 7.63 (s, 1H), 7.51-6.95 (m, 6H), 4.49 (s, 2H), 4.45-4.16 (m, 2H), 3.13-3.08 (m, 2H).

Example Compound 7: N-Cyclopropyl-2-((3-(3-fluorophenethyl)-4-oxo-3,4-dihydropteridin-2-yl)thio)acetamide

(i) 2-Bromo-N-cyclopropylacetamide

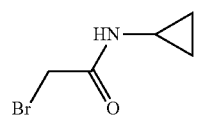

2-Bromo-N-cyclopropylacetamide was prepared by adapting the procedures described in example 3 for the synthesis of 2-bromo-N-(oxazol-2-yl)acetamide.

Yield: 126 mg MS (ES+) [M+H]$^+$: m/e=178.1, RT: 0.348 min

(ii) N-Cyclopropyl-2-((3-(3-fluorophenethyl)-4-oxo-3,4-dihydropteridin-2-yl)thio)acetamide

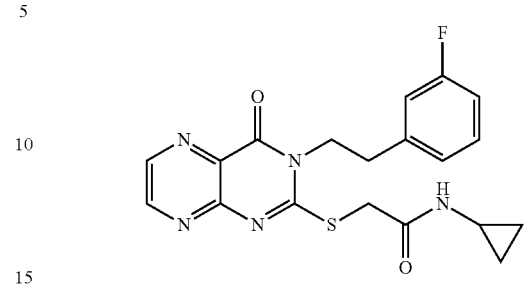

To a solution of 3-(3-fluorophenethyl)-2-thioxo-2,3-dihydropteridin-4(1H)-one (50 mg) in 3 mL dry DMF was added dry triethylamine (38 mg) followed by dropwise addition of 2-bromo-N-cyclopropylacetamide (31 mg) in 3 mL dry DMF. The reaction mixture was stirred overnight at 80° C. After completion of reaction as monitored by LCMS the DMF was removed under reduced pressure and to the crude product was added water. The water phase was extracted three times with DCM and the combined organic phases were washed with brine, dried over $Na_2SO_4$ and concentrated under reduced pressure. The crude product was purified by silica gel chromatography using a gradient of DCM/MeOH as eluent. The product was obtained as a beige solid.

Yield: 20 mg MS (ES+) [M+H]$^+$: m/e=400.2, RT: 1.020 min $^1$H NMR (300 MHz, DMSO-d$_6$): δ 8.94 (d, J=2.1 Hz, 1H), 8.77 (d, J=2.1 Hz, 1H), 8.42 (d, J=4.1 Hz, 1H), 7.38 (td, J=8.0, 6.2 Hz, 1H), 7.26-6.92 (m, 3H), 4.47-4.19 (m, 2H), 4.07 (s, 2H), 3.24-2.91 (m, 2H), 2.63 (tt, J=7.6, 3.8 Hz, 1H), 0.62 (td, J=7.0, 4.6 Hz, 2H), 0.53-0.34 (m, 2H).

Example Compound 8: 2-((4-Oxo-3-(2-(thiophen-2-yl)ethyl)-3,4-dihydropteridin-2-yl)thio)-N-(thiazol-2-yl)acetamide

(i) 3-(2-(Thiophen-2-yl)ethyl)-2-thioxo-2,3-dihydropteridin-4(1H)-one

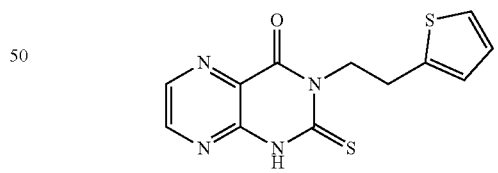

To a solution of methyl 3-isothiocyanatopyrazine-2-carboxylate (110 mg) in 10 mL dry dioxane over 4 Å molsieve was added a solution of 2-(thiophen-2-yl)ethan-1-amine (71 mg) in 10 mL dry dioxane. The reaction was refluxed overnight. After completion of the reaction as monitored by LCMS the reaction was cooled to room temperature and the resulting precipitate was filtered, washed three times with diisopropylether and the resulting solid product was dried under reduced pressure.

Yield: 102 mg MS (ES+) [M+H]$^+$: m/e=291.0, RT: 1.045 min

(ii) 2-((4-Oxo-3-(2-(thiophen-2-yl)ethyl)-3,4-dihydropteridin-2-yl)thio)-N-(thiazol-2-yl)acetamide

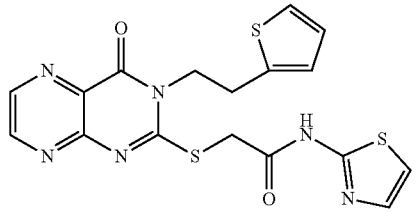 [SMILES: O=C(CSc1nc2nccnc2c(=O)n1CCc1cccs1)Nc1nccs1]

To a solution of 3-(2-(thiophen-2-yl)ethyl)-2-thioxo-2,3-dihydropteridin-4(1H)-one (60 mg) in 3 mL dry DMF was added dry triethylamine (49 mg) followed by dropwise addition of 2-bromo-N-(thiazol-2-yl)acetamide (48 mg) in 3 mL dry DMF. The reaction mixture was stirred overnight at 80° C. After completion of reaction as monitored by LCMS the DMF was removed under reduced pressure and to the crude product was added water. The water phase was extracted three times with DCM and the combined organic phases were washed with brine, dried over $Na_2SO_4$ and concentrated under reduced pressure. The crude product was purified by silica gel chromatography using a gradient of DCM/MeOH as eluent. The product was obtained as a beige solid.

Yield: 60 mg MS (ES+) $[M+H]^+$: m/e=431.1, RT: 1.041 min $^1$H NMR (300 MHz, DMSO-$d_6$): δ 12.60 (s, 1H), 8.90 (s, 1H), 8.76 (s, 1H), 7.46 (d, J=18.7 Hz, 2H), 7.23 (s, 1H), 7.02 (s, 2H), 4.47 (s, 2H), 4.33 (s, 2H), 3.32-3.23 (m, 2H).

Example Compound 9: 2-((4-Oxo-3-(3-(trifluoromethyl)phenethyl)-3,4-dihydropteridin-2-yl)thio)-N-(thiazol-2-yl)acetamide

(i) 2-Thioxo-3-(3-(trifluoromethyl)phenethyl)-2,3-dihydropteridin-4(1H)-one

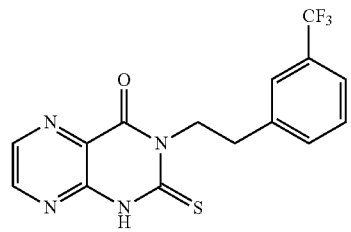 [SMILES: O=c1c2nccnc2[nH]c(=S)n1CCc1cccc(C(F)(F)F)c1]

To a solution of methyl 3-isothiocyanatopyrazine-2-carboxylate (300 mg) in 10 mL dry dioxane over 4 Å molsieve was added a solution of 2-(3-(trifluoromethyl)phenyl)ethan-1-amine (291 mg) in 10 mL dry dioxane. The reaction was refluxed overnight. After completion of the reaction as monitored by LCMS the reaction was cooled to room temperature and the resulting precipitate was filtered, washed three times with diisopropylether and the resulting solids were dried under reduced pressure.

Yield: 505 mg MS (ES+) $[M+H]^+$: m/e=353.1, RT: 1.166 min

(ii) 2-((4-Oxo-3-(3-(trifluoromethyl)phenethyl)-3,4-dihydropteridin-2-yl)thio)-N-(thiazol-2-yl)acetamide

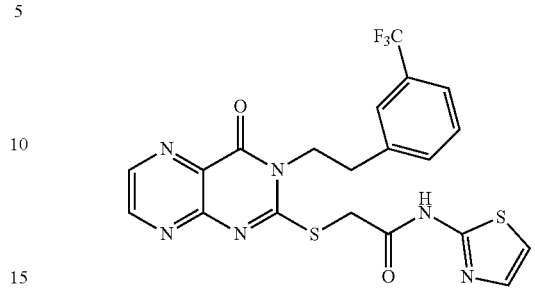

To a solution of 2-thioxo-3-(3-(trifluoromethyl)phenethyl)-2,3-dihydropteridin-4(1H)-one (60 mg) in 3 mL dry DMF was added dry triethylamine (38 mg) followed by dropwise addition of 2-bromo-N-(thiazol-2-yl)acetamide (38 mg) in 3 mL dry DMF. The reaction mixture was stirred overnight at 80° C. After completion of reaction as monitored by LCMS the DMF was removed under reduced pressure and to the crude product was added water. The water phase was extracted three times with DCM and the combined organic phases were washed with brine, dried over $Na_2SO_4$ and concentrated under reduced pressure. The crude product was purified by silica gel chromatography using a gradient of DCM/MeOH as eluent. The product was obtained as a beige solid.

Yield: 53 mg MS (ES+) $[M+H]^+$: m/e=493.1, RT: 1.132 min $^1$H NMR (300 MHz, DMSO-$d_6$): δ 12.55 (s, 1H), 8.97-8.82 (m, 1H), 8.75 (s, 1H), 7.62 (d, J=10.6 Hz, 4H), 7.49 (s, 1H), 7.22 (s, 1H), 4.46 (s, 2H), 4.37 (d, J=15.2 Hz, 2H), 3.20 (d, J=15.1 Hz, 2H).

Example Compound 10: 2-((4-Oxo-3-phenethyl-3,4-dihydropteridin-2-yl)thio)-N-(4-phenylthiazol-2-yl)acetamide

(i) 4-Phenylthiazol-2-amine

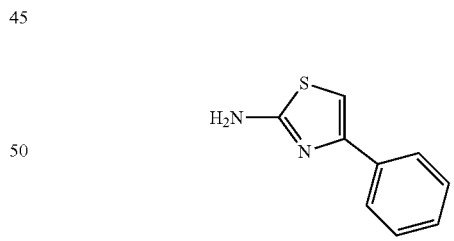

To a solution of 2-bromoacetophenone (500 mg) in 8 mL dry EtOH was added thiourea (191 mg) in portions and heated to reflux for 1 h. After completion of the reaction as monitored by LCMS the solvent was removed under reduced pressure and a sat. solution of $NaHCO_3$ was added. The resulting solution was extracted three times with ethyl acetate and the combined organic phases were washed with brine, dried over $Na_2SO_4$ and the solvent was removed under reduced pressure. The crude product was used without further purification.

Yield: 441 mg MS (ES+) $[M+H]^+$: m/e=177.3, RT: 0.781 min (ii) 2-Bromo-N-(4-phenylthiazol-2-yl)acetamide

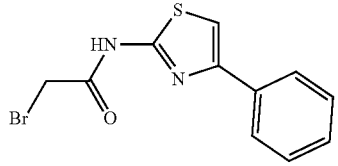 [SMILES: O=C(CBr)Nc1nc(-c2ccccc2)cs1]

2-Bromo-N-(4-phenylthiazol-2-yl)acetamide was prepared by adapting the procedures described in example 3 for the synthesis of 2-bromo-N-(oxazol-2-yl)acetamide.

Yield: 438 mg MS (ES+) [M+H]$^+$: m/e=297.2, RT: 1.154 min (iii) 2-((4-Oxo-3-phenethyl-3,4-dihydropteridin-2-yl)thio)-N-(4-phenylthiazol-2-yl)acetamide

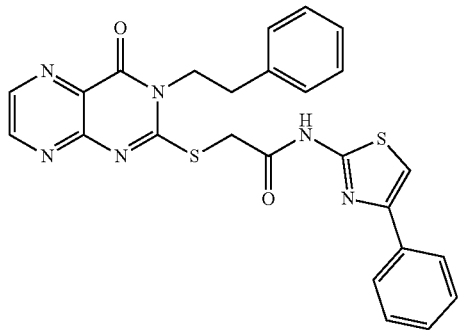 [SMILES: O=C(CSc1nc2nccnc2c(=O)n1CCc1ccccc1)Nc1nc(-c2ccccc2)cs1]

To a solution of 3-(3-fluorophenethyl)-2-thioxo-2,3-dihydropteridin-4(1H)-one (55 mg) in 3 mL dry DMF was added dry triethylamine (40 mg) followed by dropwise addition of 2-bromo-N-(4-(4-fluorophenyl)thiazol-2-yl)acetamide (60 mg) in 3 mL dry DMF. The reaction mixture was stirred overnight at 80° C. After completion of reaction as monitored by LCMS to the solution was added water. After treating the resulting solution with ethyl acetate a white precipitate could be filtered and the precipitating product was washed two times with ethyl acetate. The product was obtained as a colorless solid.

Yield: 58 mg MS (ES+) [M+H]$^+$: m/e=501.4, RT: 1.224 min $^1$H NMR (300 MHz, DMSO-d$_6$): δ 12.75 (s, 1H), 9.01-8.63 (m, 2H), 7.92 (d, J=7.6 Hz, 2H), 7.64 (s, 1H), 7.57-7.10 (m, 8H), 4.49 (s, 2H), 4.31 (d, J=16.0 Hz, 2H), 3.15-2.94 (m, 2H).

Example Compound 11: 2-((4-Oxo-3-phenethyl-3,4-dihydropteridin-2-yl)thio)-N-(thiazol-2-yl)acetamide

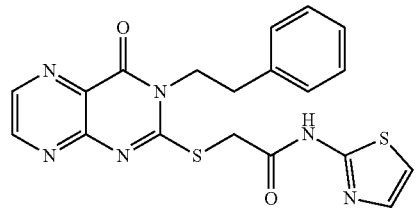 [SMILES: O=C(CSc1nc2nccnc2c(=O)n1CCc1ccccc1)Nc1nccs1]

2-((4-Oxo-3-phenethyl-3,4-dihydropteridin-2-yl)thio)-N-(thiazol-2-yl)acetamide was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=425.1, RT: 1.073 min $^1$H NMR (300 MHz, DMSO-d$_6$): δ 12.57 (s, 1H), 8.90 (d, J=2.1 Hz, 1H), 8.76 (d, J=2.1 Hz, 1H), 7.50 (d, J=3.6 Hz, 1H), 7.36 (d, J=6.4 Hz, 4H), 7.28 (dt, J=6.3, 2.8 Hz, 1H), 7.23 (d, J=3.6 Hz, 1H), 4.47 (s, 2H), 4.36-4.23 (m, 2H), 3.12-3.01 (m, 2H).

Example Compound 12: N-(4-(3-(Methylsulfonamido)phenyl)thiazol-2-yl)-2-((4-oxo-3-phenethyl-3,4-dihydropteridin-2-yl)thio)acetamide

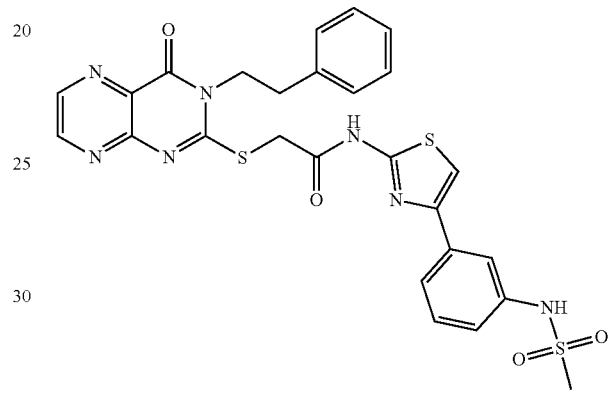

N-(4-(3-(Methylsulfonamido)phenyl)thiazol-2-yl)-2-((4-oxo-3-phenethyl-3,4-dihydropteridin-2-yl)thio)acetamide was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=594.1, RT: 1.122 min $^1$H NMR (300 MHz, DMSO-d$_6$): δ 12.79 (s, 1H), 9.85 (s, 1H), 8.89 (d, J=2.1 Hz, 1H), 8.76 (d, J=2.1 Hz, 1H), 7.82 (t, J=1.9 Hz, 1H), 7.64 (dt, J=7.8, 1.2 Hz, 1H), 7.60 (s, 1H), 7.42-7.33 (m, 5H), 7.28 (ddd, J=8.4, 4.5, 2.5 Hz, 1H), 7.19-7.13 (m, 1H), 4.50 (s, 2H), 4.35-4.26 (m, 2H), 3.12-3.03 (m, 2H), 3.02 (s, 3H).

Example Compound 13: 2-((4-Oxo-3-phenethyl-3,4-dihydropyrido[3,2-d]pyrimidin-2-yl)thio)-N-(thiazol-2-yl)acetamide

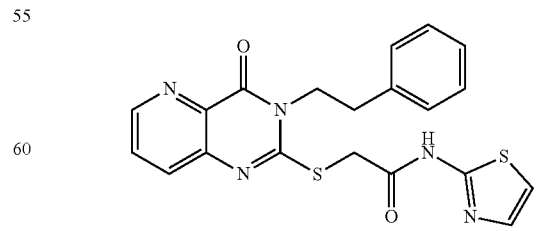

2-((4-Oxo-3-phenethyl-3,4-dihydropyrido[3,2-d]pyrimidin-2-yl)thio)-N-(thiazol-2-yl)acetamide was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=424.1, RT: 1.061 min

1H NMR (300 MHz, Chloroform-d): δ 8.85-8.79 (m, 1H), 8.01-7.94 (m, 1H), 7.65 (dd, J=8.4, 4.3 Hz, 1H), 7.45 (d, J=3.6 Hz, 1H), 7.31 (d, J=4.3 Hz, 4H), 7.26 (s, 1H), 7.00 (d, J=3.6 Hz, 1H), 4.44-4.33 (m, 2H), 4.15-4.08 (m, 2H), 3.16-3.06 (m, 2H).

Example Compound 14: N-(Oxazol-2-yl)-2-((4-oxo-3-phenethyl-3,4-dihydropteridin-2-yl)thio)acetamide

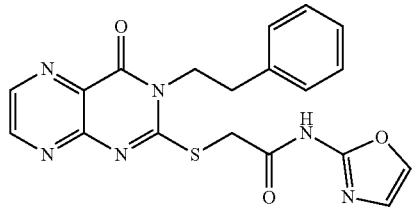

N-(Oxazol-2-yl)-2-((4-oxo-3-phenethyl-3,4-dihydropteridin-2-yl)thio)acetamide was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=409.2, RT: 0.982 min

1H NMR (300 MHz, DMSO-d6): δ 11.73 (s, 1H), 8.92 (d, J=2.1 Hz, 1H), 8.77 (d, J=2.1 Hz, 1H), 7.87 (d, J=1.0 Hz, 1H), 7.51-7.21 (m, 5H), 7.11 (d, J=1.0 Hz, 1H), 4.43 (s, 2H), 4.36-4.22 (m, 2H), 3.11-2.98 (m, 2H).

Example Compound 15: N-(2-Fluorophenyl)-2-((4-oxo-3-phenethyl-3,4-dihydropteridin-2-yl)thio)acetamide

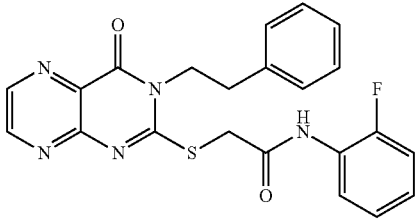 [SMILES: O=C(CSc1nc2nccnc2c(=O)n1CCc1ccccc1)Nc1ccccc1F]

N-(2-Fluorophenyl)-2-((4-oxo-3-phenethyl-3,4-dihydropteridin-2-yl)thio)acetamide was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=436.1, RT: 1.115 min

1H NMR (300 MHz, DMSO-d6): δ 10.24 (s, 1H), 8.94 (d, J=2.1 Hz, 1H), 8.78 (d, J=2.1 Hz, 1H), 8.01-7.80 (m, 1H), 7.44-7.09 (m, 8H), 4.45 (s, 2H), 4.39-4.16 (m, 2H), 3.25-2.83 (m, 2H).

Example Compound 16: 2-((3-(3-Fluorophenethyl)-4-oxo-3,4-dihydropteridin-2-yl)thio)-N-(thiazol-2-yl)propenamide

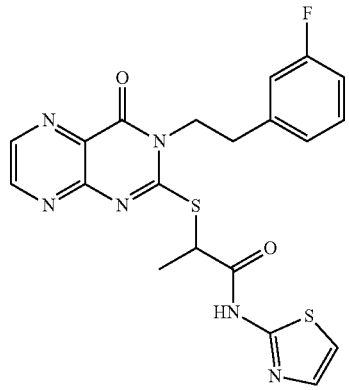 [SMILES: CC(Sc1nc2nccnc2c(=O)n1CCc1cccc(F)c1)C(=O)Nc1nccs1]

2-((3-(3-Fluorophenethyl)-4-oxo-3,4-dihydropteridin-2-yl)thio)-N-(thiazol-2-yl)propanamide was prepared by adapting the procedures described in example 4 for the synthesis of 2-((3-(3-fluorophenethyl)-4-oxo-3,4-dihydropteridin-2-yl)thio)-N-(thiazol-2-yl)acetamide.

MS (ES+) [M+H]+: m/e=457.2, RT: 1.110 min

1H NMR (300 MHz, DMSO-d6): δ 12.61 (s, 1H), 8.92 (d, J=2.1 Hz, 1H), 8.77 (d, J=2.1 Hz, 1H), 7.60-6.90 (m, 6H), 5.00 (q, J=7.1 Hz, 1H), 4.28 (tt, J=9.2, 4.5 Hz, 2H), 3.06 (t, J=7.8 Hz, 2H), 1.66 (d, J=7.2 Hz, 3H).

Example Compound 17: 2-((3-([1,1'-Biphenyl]-3-yl)-4-oxo-3,4-dihydropteridin-2-yl)thio)-N-(thiazol-2-yl)acetamide

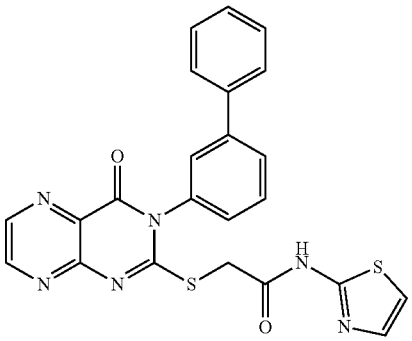 [SMILES: O=C(CSc1nc2nccnc2c(=O)n1-c1cccc(-c2ccccc2)c1)Nc1nccs1]

2-((3-([1,1'-Biphenyl]-3-yl)-4-oxo-3,4-dihydropteridin-2-yl)thio)-N-(thiazol-2-yl)acetamide was prepared by adapting the procedures described in example 4 for the synthesis of 2-((3-(3-fluorophenethyl)-4-oxo-3,4-dihydropteridin-2-yl)thio)-N-(thiazol-2-yl)acetamide.

MS (ES+) [M+H]+: m/e=473.1, RT: 1.107 min

1H NMR (300 MHz, DMSO-d6): δ 12.49 (s, 1H), 8.95 (d, J=2.1 Hz, 1H), 8.79 (d, J=2.1 Hz, 1H), 7.95 (dd, J=4.5, 2.6 Hz, 2H), 7.81-7.17 (m, 9H), 4.30 (d, J=2.2 Hz, 2H).

Example Compound 18: 2-((3-(2,2-Difluoro-2-phenylethyl)-4-oxo-3,4-dihydropteridin-2-yl)thio)-N-(thiazol-2-yl)acetamide

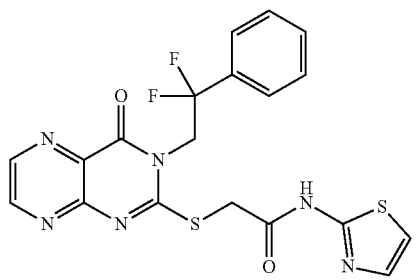 [SMILES: O=C(CSc1nc2nccnc2c(=O)n1CC(F)(F)c1ccccc1)Nc1nccs1]

2-((3-(2,2-Difluoro-2-phenylethyl)-4-oxo-3,4-dihydropteridin-2-yl)thio)-N-(thiazol-2-yl)acetamide was prepared by adapting the procedures described in example 4 for the synthesis of 2-((3-(3-fluorophenethyl)-4-oxo-3,4-dihydropteridin-2-yl)thio)-N-(thiazol-2-yl)acetamide.

MS (ES+) [M+H]$^+$: m/e=461.2, RT: 1.072 min
$^1$H NMR (300 MHz, DMSO-d$_6$): δ 12.56 (s, 1H), 8.93 (d, J=2.1 Hz, 1H), 8.78 (d, J=2.1 Hz, 1H), 7.81-7.40 (m, 6H), 7.23 (d, J=3.6 Hz, 1H), 4.93 (t, J=14.9 Hz, 2H), 4.47 (s, 2H).

Example Compound 19: 2-((3-(2,3-Dihydro-1H-inden-1-yl)-4-oxo-3,4-dihydropteridin-2-yl)thio)-N-(thiazol-2-yl)acetamide

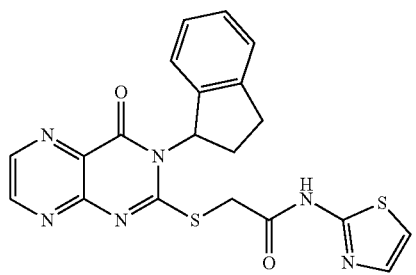 [SMILES: O=C(CSc1nc2nccnc2c(=O)n1C1CCc2ccccc21)Nc1nccs1]

2-((3-(2,3-Dihydro-1H-inden-1-yl)-4-oxo-3,4-dihydropteridin-2-yl)thio)-N-(thiazol-2-yl)acetamide was prepared by adapting the procedures described in example 4 for the synthesis of 2-((3-(3-fluorophenethyl)-4-oxo-3,4-dihydropteridin-2-yl)thio)-N-(thiazol-2-yl)acetamide.

MS (ES+) [M+H]$^+$: m/e=437.2, RT: 1.072 min
$^1$H NMR (300 MHz, DMSO-d$_6$): δ 12.61 (s, 1H), 8.88 (t, J=3.7 Hz, 1H), 8.82-8.64 (m, 1H), 7.59-7.09 (m, 6H), 6.29-5.41 (m, 2H), 4.52 (s, 2H), 4.22 (d, J=42.7 Hz, 1H), 3.29-2.87 (m, 2H).

Example Compound 20: 2-((4-Oxo-3-phenethyl-3,4-dihydropteridin-2-yl)thio)-N-(pyrimidin-2-yl)acetamide

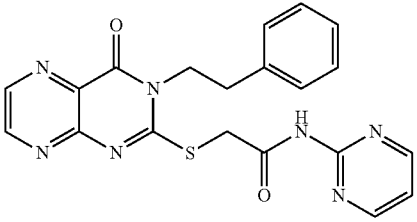 [SMILES: O=C(CSc1nc2nccnc2c(=O)n1CCc1ccccc1)Nc1ncccn1]

2-((4-Oxo-3-phenethyl-3,4-dihydropteridin-2-yl)thio)-N-(pyrimidin-2-yl)acetamide was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=420.2, RT: 0.977 min
$^1$H NMR (300 MHz, DMSO-d$_6$): δ 11.05 (s, 1H), 8.91 (d, J=2.0 Hz, 1H), 8.76 (d, J=2.0 Hz, 1H), 8.69 (d, J=4.8 Hz, 2H), 7.42-7.17 (m, 6H), 4.61 (s, 2H), 4.39-4.24 (m, 2H), 3.14-3.00 (m, 2H).

Example Compound 21: 2-((4-Oxo-3-(2-phenylcyclopropyl)-3,4-dihydropteridin-2-yl)thio)-N-(thiazol-2-yl)acetamide

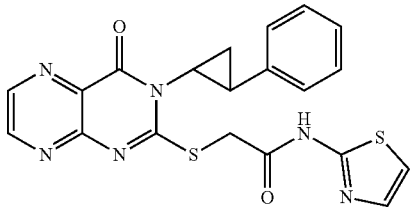 [SMILES: O=C(CSc1nc2nccnc2c(=O)n1C1CC1c1ccccc1)Nc1nccs1]

2-((4-Oxo-3-(2-phenylcyclopropyl)-3,4-dihydropteridin-2-yl)thio)-N-(thiazol-2-yl)acetamide was prepared by adapting the procedures described in example 4 for the synthesis of 2-((3-(3-fluorophenethyl)-4-oxo-3,4-dihydropteridin-2-yl)thio)-N-(thiazol-2-yl)acetamide.

MS (ES+) [M+H]$^+$: m/e=437.1, RT: 1.078 min

Example Compound 22: 2-((4-Oxo-3-phenethyl-3,4-dihydropteridin-2-yl)thio)-N-phenylacetamide

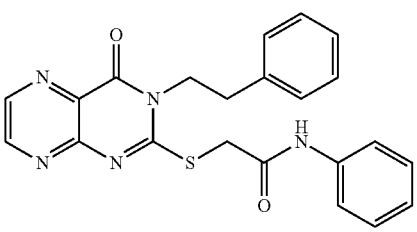

2-((4-Oxo-3-phenethyl-3,4-dihydropteridin-2-yl)thio)-N-phenylacetamide was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=418.1, RT: 1.137 min

Example Compound 23: 2-((4-Oxo-3-phenethyl-3,4-dihydropteridin-2-yl)thio)-N-(4-(thiophen-3-yl)thiazol-2-yl)acetamide

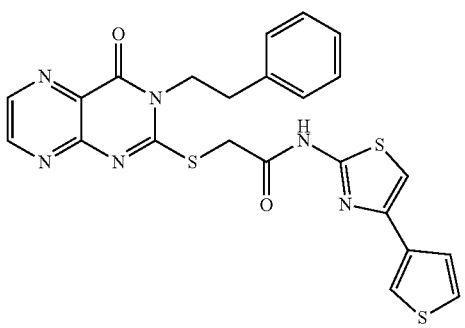 [SMILES: O=C(CSc1nc2nccnc2c(=O)n1CCc1ccccc1)Nc1nc(-c2ccsc2)cs1]

2-((4-Oxo-3-phenethyl-3,4-dihydropteridin-2-yl)thio)-N-(4-(thiophen-3-yl)thiazol-2-yl)acetamide was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=507.1, RT: 1.193 min $^1$H NMR (300 MHz, DMSO-d$_6$): δ 12.76 (s, 1H), 8.89 (d, J=2.1 Hz, 1H), 8.76 (d, J=2.1 Hz, 1H), 7.81 (dd, J=2.9, 1.3 Hz, 1H), 7.56 (s, 2H), 7.52-7.18 (m, 6H), 4.48 (s, 2H), 4.30 (dd, J=10.2, 6.3 Hz, 2H), 3.15-2.96 (m, 2H).

Example Compound 24: Methyl 2-(2-(2-((4-oxo-3-phenethyl-3,4-dihydropteridin-2-yl)thio)acetamido)thiazol-4-yl)acetate

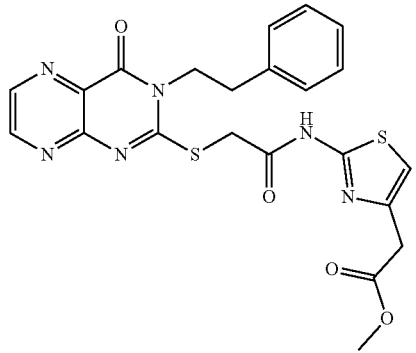 [SMILES: COC(=O)Cc1csc(NC(=O)CSc2nc3nccnc3c(=O)n2CCc2ccccc2)n1]

Methyl 2-(2-(2-((4-oxo-3-phenethyl-3,4-dihydropteridin-2-yl)thio)acetamido)thiazol-4-yl)acetate was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=497.2, RT: 1.094 min $^1$H NMR (300 MHz, DMSO-d$_6$): δ 12.62 (s, 1H), 8.90 (d, J=2.1 Hz, 1H), 8.76 (d, J=2.1 Hz, 1H), 7.47-7.15 (m, 5H), 7.00 (s, 1H), 4.44 (s, 2H), 4.30 (dd, J=10.1, 6.3 Hz, 2H), 3.73 (s, 2H), 3.63 (s, 3H), 3.06 (dd, J=10.0, 6.3 Hz, 2H).

Example Compound 25: N-(4-(Morpholine-4-carbonyl)thiazol-2-yl)-2-((4-oxo-3-phenethyl-3,4-dihydropteridin-2-yl)thio)acetamide

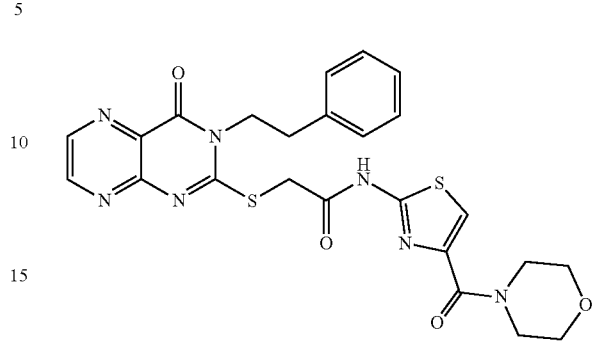

N-(4-(Morpholine-4-carbonyl)thiazol-2-yl)-2-((4-oxo-3-phenethyl-3,4-dihydropteridin-2-yl)thio)acetamide was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=538.4, RT: 1.043 min $^1$H NMR (300 MHz, DMSO-d$_6$): δ 12.75 (s, 1H), 8.89 (d, J=2.1 Hz, 1H), 8.76 (d, J=2.1 Hz, 1H), 7.63 (s, 1H), 7.48-6.99 (m, 5H), 4.48 (s, 2H), 4.30 (dd, J=10.1, 6.3 Hz, 2H), 3.63 (s, 8H), 3.07 (dd, J=9.7, 6.5 Hz, 2H).

Example Compound 26: N-(4-(3-Fluorophenyl)thiazol-2-yl)-2-((4-oxo-3-phenethyl-3,4-dihydropteridin-2-yl)thio)acetamide

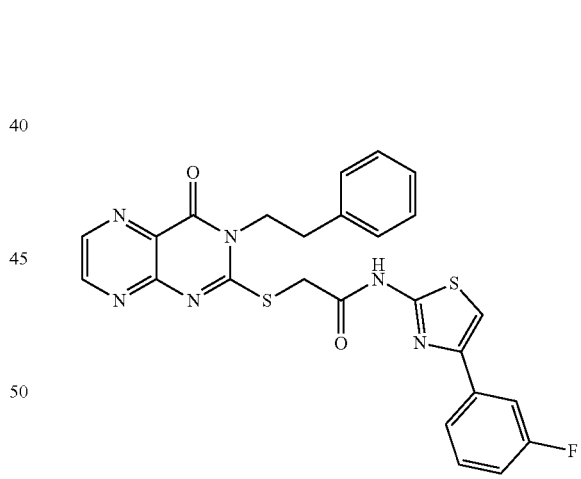

N-(4-(3-Fluorophenyl)thiazol-2-yl)-2-((4-oxo-3-phenethyl-3,4-dihydropteridin-2-yl)thio)acetamide was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=519.4, RT: 1.229 min $^1$H NMR (300 MHz, DMSO-d$_6$): δ 12.78 (s, 1H), 8.89 (d, J=2.1 Hz, 1H), 8.76 (d, J=2.1 Hz, 1H), 7.81-7.75 (m, 2H), 7.71 (dt, J=10.5, 2.2 Hz, 1H), 7.49 (td, J=8.0, 6.1 Hz, 1H), 7.41-7.32 (m, 4H), 7.31-7.24 (m, 1H), 7.17 (td, J=8.6, 2.6 Hz, 1H), 4.50 (s, 2H), 4.31 (dd, J=10.2, 6.2 Hz, 2H), 3.07 (dd, J=9.6, 6.6 Hz, 2H).

Example Compound 27: 2-((4-Oxo-3-phenethyl-3,4-dihydropteridin-2-yl)thio)-N-(4-phenylthiophen-2-yl)acetamide

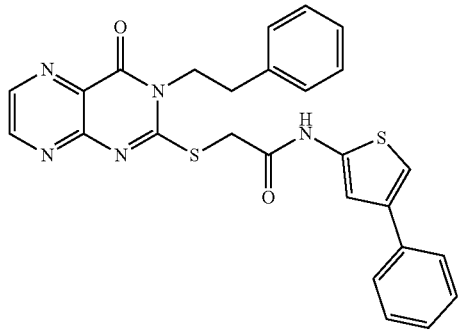 [SMILES: O=C(CSc1nc2nccnc2c(=O)n1CCc1ccccc1)Nc1cc(-c2ccccc2)cs1]

2-((4-Oxo-3-phenethyl-3,4-dihydropteridin-2-yl)thio)-N-(4-phenylthiophen-2-yl)acetamide was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=500.4, RT: 1.230 min $^1$H NMR (300 MHz, DMSO-$d_6$): δ 11.77 (s, 1H), 8.92 (d, J=2.1 Hz, 1H), 8.77 (d, J=2.1 Hz, 1H), 7.70-7.55 (m, 2H), 7.46-7.23 (m, 9H), 7.08 (d, J=1.8 Hz, 1H), 4.43 (s, 2H), 4.31 (dd, J=10.2, 6.3 Hz, 2H), 3.12-3.01 (m, 2H).

Example Compound 28: N-(5-Cyanopyridin-2-yl)-2-((4-oxo-3-phenethyl-3,4-dihydropteridin-2-yl)thio)acetamide (i) 2-Bromo-N-(5-cyanopyridin-2-yl)acetamide

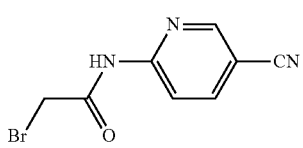 [SMILES: N#Cc1ccc(NC(=O)CBr)nc1]

To a solution of 2-amino-5-cyanopyridine (300 mg) in 7 mL dry DCM was added dropwise dry Et$_3$N (332 mg). After stirring for 10 min was added 2-bromoacetyl bromide (508 mg) and the resulting mixture was additional stirred for 5 h at RT. After completion of the reaction as monitored by LCMS water was added and the organic phase was separated. The water phase was extracted three times with DCM and the combined organic layers were dried with Na$_2$SO$_4$, the solvents were removed under reduced pressure and the crude product was purified by silica gel chromatography using a gradient of ethyl acetate/cyclohexane as eluent.

Yield: 126 mg MS (ES+) [M+H]$^+$: m/e=241.1, RT: 0.940 min (ii) N-(5-Cyanopyridin-2-yl)-2-((4-oxo-3-phenethyl-3,4-dihydropteridin-2-yl)thio)acetamide

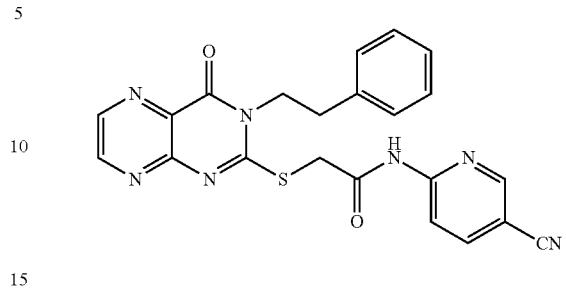

To a solution of 3-phenethyl-2-thioxo-2,3-dihydropteridin-4(1H)-one (55 mg) in 3 mL dry DMF was added dry triethylamine (45 mg) followed by dropwise addition of 2-bromo-N-(4-phenylthiazol-2-yl)acetamide (49 mg) in 3 mL dry DMF. The reaction mixture was stirred overnight at 80° C. After completion of reaction as monitored by LCMS the DMF was removed under reduced pressure and to the crude product was added water. The water phase was extracted three times with DCM and the combined organic phases were washed with brine, dried over Na$_2$SO$_4$ and concentrated under reduced pressure. The crude product was purified by silica gel chromatography using a gradient of DCM/MeOH as eluent. The product was obtained as a beige solid.

Yield: 18 mg MS (ES+) [M+H]$^+$: m/e=444.1, RT: 1.100 min $^1$H NMR (300 MHz, DMSO-$d_6$): δ 11.48 (s, 1H), 8.89 (d, J=1.9 Hz, 1H), 8.83 (d, J=1.5 Hz, 1H), 8.75 (d, J=1.8 Hz, 1H), 8.22 (dt, J=21.4, 5.4 Hz, 2H), 7.40-7.23 (m, 5H), 4.49 (s, 2H), 4.37-4.24 (m, 2H), 3.11-2.99 (m, 2H).

Example Compound 29: N-(5-Bromothiazol-2-yl)-2-((4-oxo-3-phenethyl-3,4-dihydropteridin-2-yl)thio)acetamide

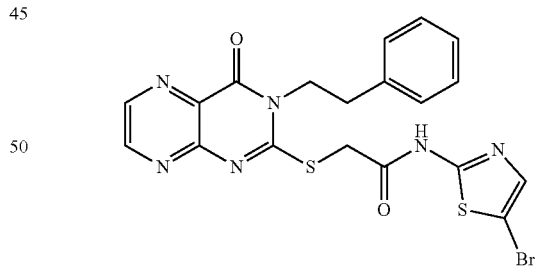

N-(5-Bromothiazol-2-yl)-2-((4-oxo-3-phenethyl-3,4-dihydropteridin-2-yl)thio)acetamide was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=503.2, RT: 1.165 min

1H NMR (300 MHz, DMSO-$d_6$): δ 12.86 (s, 1H), 8.90 (d, J=2.1 Hz, 1H), 8.76 (d, J=2.1 Hz, 1H), 7.60 (s, 1H), 7.39-7.25 (m, 5H), 4.46 (s, 2H), 4.36-4.15 (m, 2H), 3.18-2.86 (m, 2H).

Example Compound 30: N-(4-(5-Methylthiophen-2-yl)thiazol-2-yl)-2-((4-oxo-3-phenethyl-3,4-dihydropteridin-2-yl)thio)acetamide

(i) 4-(5-methylthiophen-2-yl)thiazol-2-amine

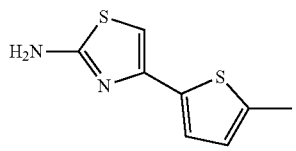

To a solution of 2-bromo-1-(5-methylthiophen-2-yl)ethan-1-one (304 mg) in 8 mL dry EtOH was added thiourea (206 mg) in portions and heated to reflux for 1 h. After completion of the reaction as monitored by LCMS the solvent was removed under reduced pressure and a sat. solution of NaHCO$_3$ was added. The resulting solution was extracted three times with ethyl acetate and the combined organic phases were washed with brine, dried over Na$_2$SO$_4$ and the solvents were removed under reduced pressure. The crude product was used without further purification.

Yield: 285 mg MS (ES+) [M+H]$^+$: m/e=197.1, RT: 0.994 min

(ii) 2-Bromo-N-(4-(5-methylthiophen-2-yl)thiazol-2-yl)acetamide

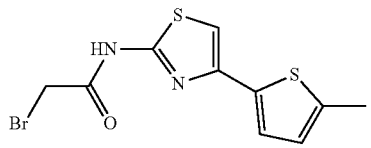 [SMILES: Cc1ccc(-c2csc(NC(=O)CBr)n2)s1]

To a solution of 4-(5-methylthiophen-2-yl)thiazol-2-amine (102 mg) in 7 mL dry DCM was added dropwise dry Et$_3$N (67 mg). After stirring for 10 min was added 2-bromoacetyl bromide (113 mg) and the resulting mixture was additional stirred for 5 h at RT. After completion of the reaction as monitored by LCMS water was added and the organic phase was separated. The water phase was extracted three times with DCM and the combined organic layers were dried with Na$_2$SO$_4$, the solvents were removed under reduced pressure and the crude product was purified by silica gel chromatography using a gradient of ethyl acetate/cyclohexane as eluent.

Yield: 51 mg MS (ES+) [M+H]$^+$: m/e=317.0, RT: 1.178 min

(iii) N-(4-(5-Methylthiophen-2-yl)thiazol-2-yl)-2-((4-oxo-3-phenethyl-3,4-dihydropteridin-2-yl)thio)acetamide

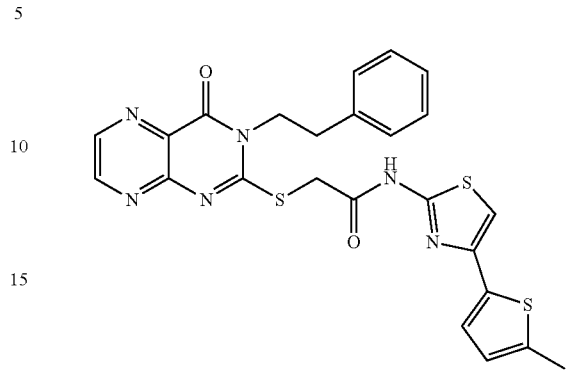

To a solution of 3-phenethyl-2-thioxo-2,3-dihydropteridin-4(1H)-one (42 mg) in 3 mL dry DMF was added dry triethylamine (66 mg) followed by dropwise addition of 2-bromo-N-(4-phenylthiazol-2-yl)acetamide (52 mg) in 3 mL dry DMF. The reaction mixture was stirred overnight at 80° C. After completion of reaction as monitored by LCMS the DMF was removed under reduced pressure and to the crude product was added water. The water phase was extracted three times with DCM and the combined organic phases were washed with brine, dried over Na$_2$SO$_4$ and concentrated under reduced pressure. The crude product was purified by silica gel chromatography using a gradient of DCM/MeOH as eluent. The product was obtained as a beige solid.

Yield: 46 mg MS (ES+) [M+H]$^+$: m/e=521.0, RT: 1.238 min $^1$H NMR (300 MHz, DMSO-d$_6$) δ 12.81 (s, 1H), 8.89 (d, J=2.0 Hz, 1H), 8.76 (d, J=2.0 Hz, 1H), 7.41-7.24 (m, 7H), 6.80 (d, J=3.2 Hz, 1H), 4.46 (s, 2H), 4.35-4.26 (m, 2H), 3.14-3.01 (m, 2H), 2.46 (s, 3H).

Example Compound 31: N-(4-(3-Methoxyphenyl)thiazol-2-yl)-2-((4-oxo-3-phenethyl-3,4-dihydropteridin-2-yl)thio)acetamide

(i) 4-(3-Methoxyphenyl)thiazol-2-amine

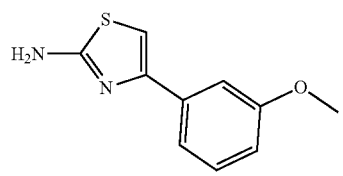

To a solution of 2-bromo-1-(3-methoxyphenyl)ethan-1-one (305 mg) in 8 mL dry EtOH was added thiourea (106 mg) in portions and heated to reflux for 1 h. After completion of the reaction as monitored by LCMS the solvent was removed under reduced pressure and a sat. solution of NaHCO$_3$ was added. The resulting solution was extracted three times with ethyl acetate and the combined organic phases were washed with brine, dried over Na$_2$SO$_4$ and the solvents were removed under reduced pressure. The crude product was used without further purification.

Yield: 232 mg MS (ES+) [M+H]$^+$: m/e=207.1, RT: 0.897 min

(ii) 2-Bromo-N-(4-(3-methoxyphenyl)thiazol-2-yl) acetamide

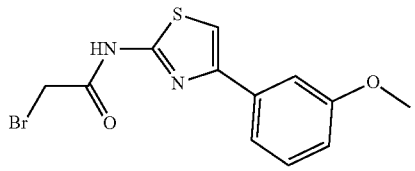 [SMILES: COc1cccc(-c2csc(NC(=O)CBr)n2)c1]

To a solution of 4-(3-methoxyphenyl)thiazol-2-amine (100 mg) in 7 mL dry DCM was added dropwise dry Et₃N (54 mg). After stirring for 10 min was added 2-bromoacetyl bromide (97 mg) and the resulting mixture was additional stirred for 5 h at RT. After completion of the reaction as monitored by LCMS water was added and the organic phase was separated. The water phase was extracted three times with DCM and the combined organic layers were dried with Na₂SO₄, the solvent were removed under reduced pressure and the crude product was purified by silica gel chromatography using a gradient of ethyl acetate/cyclohexane as eluent.

Yield: 64 mg MS (ES+) [M+H]⁺: m/e=327.0, RT: 1.150 min

(iii) N-(4-(3-Methoxyphenyl)thiazol-2-yl)-2-((4-oxo-3-phenethyl-3,4-dihydropteridin-2-yl)thio)acetamide

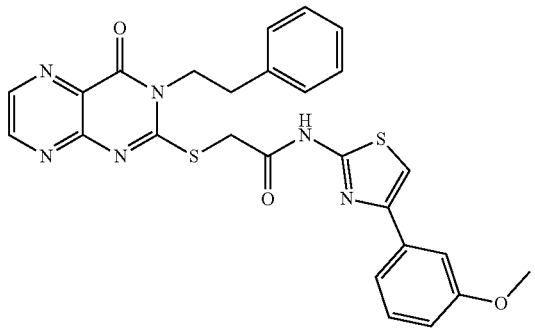 [SMILES: COc1cccc(-c2csc(NC(=O)CSc3nc4nccnc4c(=O)n3CCc3ccccc3)n2)c1]

To a solution of 3-phenethyl-2-thioxo-2,3-dihydropteridin-4(1H)-one (50 mg) in 3 mL dry DMF was added dry triethylamine (40 mg) followed by dropwise addition of 2-bromo-N-(4-(3-methoxyphenyl)thiazol-2-yl)acetamide (60 mg) in 3 mL dry DMF. The reaction mixture was stirred overnight at 80° C. After completion of reaction as monitored by LCMS the DMF was removed under reduced pressure and to the crude product was added water. The water phase was extracted three times with DCM and the combined organic phases were washed with brine, dried over Na₂SO₄ and concentrated under reduced pressure. The crude product was purified by silica gel chromatography using a gradient of DCM/MeOH as eluent. The product was obtained as a beige solid.

Yield: 45 mg MS (ES+) [M+H]⁺: m/e=531.1, RT: 1.214 min

¹H NMR (300 MHz, DMSO-d₆): δ 12.76 (s, 1H), 8.89 (d, J=1.8 Hz, 1H), 8.76 (d, J=1.9 Hz, 1H), 7.68 (s, 1H), 7.53-7.23 (m, 8H), 6.95-6.88 (m, 1H), 4.49 (s, 2H), 4.36-4.26 (m, 2H), 3.81 (s, 3H), 3.11-3.02 (m, 2H).

Example Compound 32: 2-((3-(Furan-2-ylmethyl)-4-oxo-3,4-dihydropteridin-2-yl)thio)-N-(thiazol-2-yl)acetamide

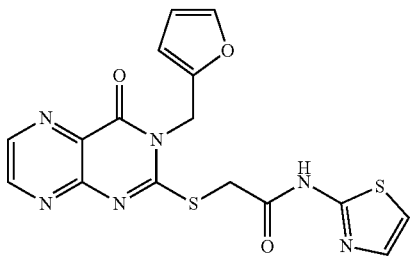 [SMILES: O=C(CSc1nc2nccnc2c(=O)n1Cc1ccco1)Nc1nccs1]

2-((3-(Furan-2-ylmethyl)-4-oxo-3,4-dihydropteridin-2-yl)thio)-N-(thiazol-2-yl)acetamide was prepared by adapting the procedures described in example 1 for the synthesis of N-(4-(3-Hydroxyphenyl)thiazol-2-yl)-2-((4-oxo-3-phenethyl-3,4-dihydropteridin-2-yl)thio)acetamide.

MS (ES+) [M+H]⁺: m/e=401.0, RT: 0.964 min

¹H NMR (300 MHz, DMSO-d₆): δ 12.55 (s, 1H), 8.90 (d, J=2.1 Hz, 1H), 8.76 (d, J=2.1 Hz, 1H), 7.65 (dd, J=1.9, 0.8 Hz, 1H), 7.49 (d, J=3.6 Hz, 1H), 7.22 (d, J=3.6 Hz, 1H), 6.57-6.51 (m, 1H), 6.47 (dd, J=3.3, 1.9 Hz, 1H), 5.37 (s, 2H), 4.45 (s, 2H).

Example Compound 33: N-(2-Fluorophenyl)-2-((3-(furan-2-ylmethyl)-4-oxo-3,4-dihydropteridin-2-yl)thio)acetamide

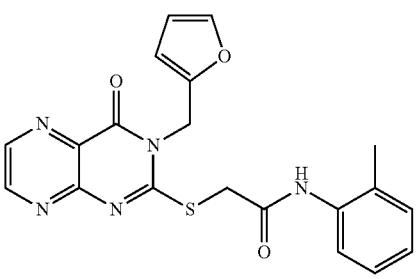 [SMILES: Cc1ccccc1NC(=O)CSc1nc2nccnc2c(=O)n1Cc1ccco1]

N-(2-Fluorophenyl)-2-((3-(furan-2-ylmethyl)-4-oxo-3,4-dihydropteridin-2-yl)thio)acetamide was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]⁺: m/e=412.2, RT: 1.026 min

¹H NMR (300 MHz, DMSO-d₆): δ 10.24 (s, 1H), 8.94 (d, J=2.1 Hz, 1H), 8.78 (d, J=2.1 Hz, 1H), 7.97-7.82 (m, 1H), 7.64 (dd, J=1.8, 0.9 Hz, 1H), 7.36-7.05 (m, 3H), 6.49 (ddd, J=22.2, 3.3, 1.4 Hz, 2H), 5.38 (s, 2H), 4.43 (s, 2H).

Example Compound 34: 2-((4-Oxo-3-phenethyl-3,4-dihydropyrido[3,2-d]pyrimidin-2-yl)thio)-N-(5-(trifluoromethyl)-1,3,4-thiadiazol-2-yl)acetamide

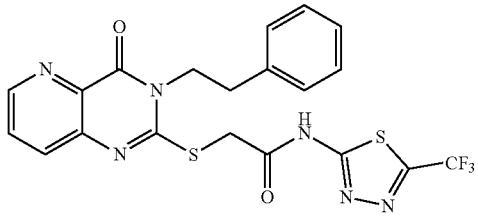 [SMILES: O=C(CSc1nc2cccnc2c(=O)n1CCc1ccccc1)Nc1nnc(C(F)(F)F)s1]

2-((4-Oxo-3-phenethyl-3,4-dihydropyrido[3,2-d]pyrimidin-2-yl)thio)-N-(5-(trifluoromethyl)-1,3,4-thiadiazol-2-yl)acetamide was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=493.1, RT: 1.162 min
$^1$H NMR (300 MHz, DMSO-d$_6$): δ 8.70 (dd, J=4.1, 1.8 Hz, 1H), 7.88-7.59 (m, 2H), 7.50-7.18 (m, 5H), 4.44 (s, 2H), 4.32-4.16 (m, 2H), 3.15-2.91 (m, 2H).

Example Compound 35: 2-((2-(Indolin-1-yl)-2-oxoethyl)thio)-3-phenethylpteridin-4(3H)-one

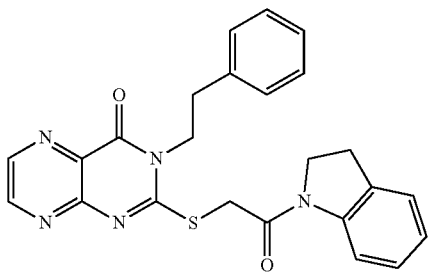 [SMILES: O=C(CSc1nc2nccnc2c(=O)n1CCc1ccccc1)N1CCc2ccccc21]

2-((2-(Indolin-1-yl)-2-oxoethyl)thio)-3-phenethylpteridin-4(3H)-one was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=444.2, RT: 1.153 min
$^1$H NMR (300 MHz, DMSO-d$_6$): δ 8.91 (d, J=2.1 Hz, 1H), 8.76 (d, J=2.1 Hz, 1H), 8.03 (d, J=7.9 Hz, 1H), 7.58-6.90 (m, 8H), 4.63-4.39 (m, 4H), 4.40-4.17 (m, 2H), 3.19 (s, 2H), 3.18-2.92 (m, 2H).

Example Compound 36: N-(Oxazol-2-yl)-2-((4-oxo-3-phenethyl-3,4-dihydropyrido[3,2-d]pyrimidin-2-yl)thio)acetamide

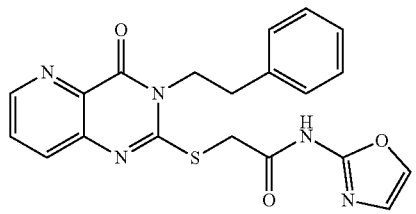

N-(Oxazol-2-yl)-2-((4-oxo-3-phenethyl-3,4-dihydropyrido[3,2-d]pyrimidin-2-yl)thio)acetamide was prepared by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=408.2, RT: 0.993 min
$^1$H NMR (300 MHz, DMSO-d$_6$): δ 11.64 (s, 1H), 8.72 (dd, J=4.1, 1.8 Hz, 1H), 7.92-7.73 (m, 3H), 7.37-7.12 (m, 6H), 4.38-4.13 (m, 4H), 3.14-2.89 (m, 2H).

Example Compound 37: 2-Methyl-2-((4-oxo-3-phenethyl-3,4-dihydropteridin-2-yl)thio)-N-(thiazol-2-yl)propanamide

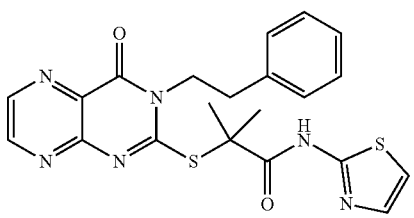 [SMILES: CC(C)(Sc1nc2nccnc2c(=O)n1CCc1ccccc1)C(=O)Nc1nccs1]

2-Methyl-2-((4-oxo-3-phenethyl-3,4-dihydropteridin-2-yl)thio)-N-(thiazol-2-yl)propanamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=453.2, RT: 1.104 min
$^1$H NMR (300 MHz, DMSO-d$_6$): δ 11.93 (s, 1H), 8.86 (d, J=2.1 Hz, 1H), 8.72 (d, J=2.1 Hz, 1H), 7.70-6.90 (m, 7H), 4.55-3.91 (m, 2H), 3.21-2.91 (m, 2H), 1.85 (s, 6H).

Example Compound 38: N-Methyl-2-((4-oxo-3-phenethyl-3,4-dihydropteridin-2-yl)thio)-N-phenylacetamide

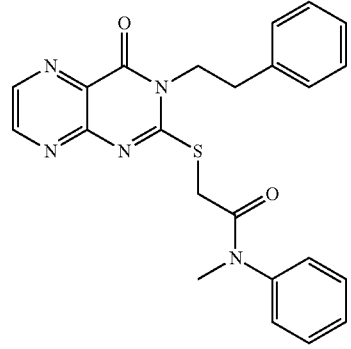 [SMILES: CN(C(=O)CSc1nc2nccnc2c(=O)n1CCc1ccccc1)c1ccccc1]

N-Methyl-2-((4-oxo-3-phenethyl-3,4-dihydropteridin-2-yl)thio)-N-phenylacetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=432.2, RT: 1.125 min
$^1$H NMR (300 MHz, DMSO-d$_6$): δ 8.97 (d, J=2.1 Hz, 1H), 8.77 (d, J=2.1 Hz, 1H), 7.87-7.05 (m, 10H), 4.25 (dd, J=10.0, 6.3 Hz, 2H), 4.02 (s, 2H), 3.23 (s, 3H), 3.01 (dd, J=10.1, 6.4 Hz, 2H).

Example Compound 39: 2-((2-(4-Methoxyphenyl)-2-oxoethyl)thio)-3-phenethylpteridin-4(3H)-one

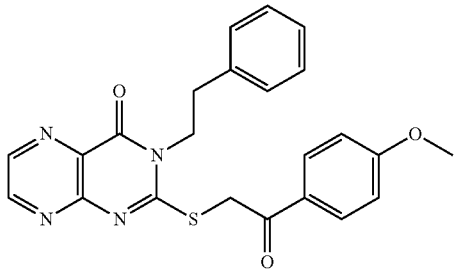 [SMILES: COc1ccc(C(=O)CSc2nc3nccnc3c(=O)n2CCc2ccccc2)cc1]

2-((2-(4-Methoxyphenyl)-2-oxoethyl)thio)-3-phenethylpteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=433.2, RT: 1.160 min
$^1$H NMR (300 MHz, DMSO-d$_6$): δ 8.85 (d, J=2.1 Hz, 1H), 8.74 (d, J=2.1 Hz, 1H), 8.20-7.96 (m, 2H), 7.48-7.20 (m, 5H), 7.17-7.00 (m, 2H), 5.04 (s, 2H), 4.51-4.17 (m, 2H), 3.88 (s, 3H), 3.19-2.98 (m, 2H).

Example Compound 40: 2-((4-Oxo-3-phenyl-3,4-dihydropteridin-2-yl)thio)-N-(thiazol-2-yl)acetamide

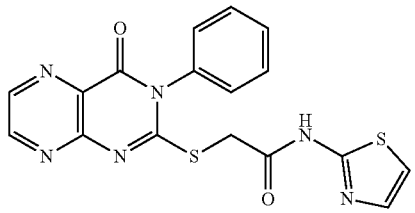 [SMILES: O=C(CSc1nc2nccnc2c(=O)n1-c1ccccc1)Nc1nccs1]

2-((4-Oxo-3-phenyl-3,4-dihydropteridin-2-yl)thio)-N-(thiazol-2-yl)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=397.2, RT: 0.968 min
$^1$H NMR (300 MHz, DMSO-d$_6$): δ 12.49 (s, 1H), 8.94 (d, J=2.1 Hz, 1H), 8.77 (d, J=2.1 Hz, 1H), 7.93-7.06 (m, 7H), 4.29 (s, 2H).

Example Compound 41: 4-(4-Oxo-2-((2-oxo-2-(thiazol-2-ylamino)ethyl)thio)pteridin-3(4H)-yl)benzamide

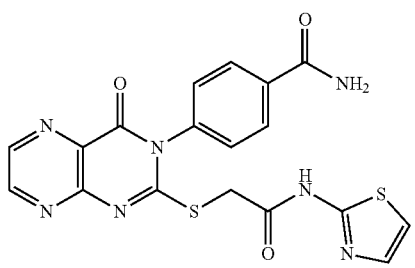 [SMILES: NC(=O)c1ccc(-n2c(SCC(=O)Nc3nccs3)nc3nccnc3c2=O)cc1]

4-(4-Oxo-2-((2-oxo-2-(thiazol-2-ylamino)ethyl)thio)pteridin-3(4H)-yl)benzamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=440.0, RT: 0.856 min
$^1$H NMR (300 MHz, DMSO-d$_6$): δ 12.49 (s, 1H), 8.94 (d, J=2.1 Hz, 1H), 8.78 (d, J=2.1 Hz, 1H), 8.17 (s, 1H), 8.13-8.01 (m, 2H), 7.72-7.61 (m, 2H), 7.59 (s, 1H), 7.48 (d, J=3.5 Hz, 1H), 7.22 (d, J=3.6 Hz, 1H), 4.31 (s, 2H).

Example Compound 42: 2-((3-Benzyl-4-oxo-3,4-dihydropteridin-2-yl)thio)-N-(thiazol-2-yl)acetamide

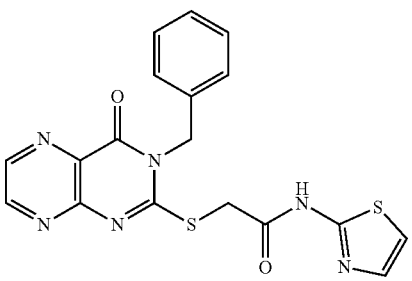 [SMILES: O=C(CSc1nc2nccnc2c(=O)n1Cc1ccccc1)Nc1nccs1]

2-((3-Benzyl-4-oxo-3,4-dihydropteridin-2-yl)thio)-N-(thiazol-2-yl)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=411.1, RT: 1.016 min
$^1$H NMR (300 MHz, DMSO-d$_6$): δ 12.54 (s, 1H), 8.92 (d, J=2.1 Hz, 1H), 8.78 (d, J=2.1 Hz, 1H), 7.49 (d, J=3.6 Hz, 1H), 7.42-7.16 (m, 6H), 5.40 (s, 2H), 4.41 (s, 2H).

Example Compound 43: 2-((3-(2-(Adamantan-1-yl)ethyl)-4-oxo-3,4-dihydropteridin-2-yl)thio)-N-(thiazol-2-yl)acetamide

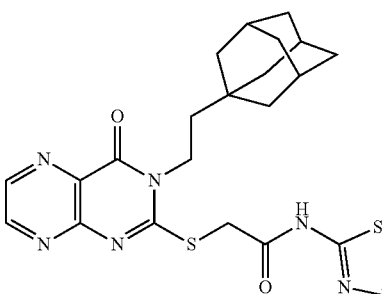

2-((3-(2-(Adamantan-1-yl)ethyl)-4-oxo-3,4-dihydropteridin-2-yl)thio)-N-(thiazol-2-yl)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=483.3, RT: 1.238 min
$^1$H NMR (300 MHz, DMSO-d$_6$): δ 12.56 (s, 1H), 8.88 (d, J=2.1 Hz, 1H), 8.74 (d, J=2.1 Hz, 1H), 7.49 (d, J=3.5 Hz, 1H), 7.23 (d, J=3.6 Hz, 1H), 4.44 (s, 2H), 4.24-4.04 (m, 2H), 1.98 (d, J=4.3 Hz, 3H), 1.78-1.57 (m, 12H), 1.51-1.49 (m, 2H).

Example Compound 44: 2-((3-(2-Cyclohexylethyl)-4-oxo-3,4-dihydropteridin-2-yl)thio)-N-(thiazol-2-yl)acetamide

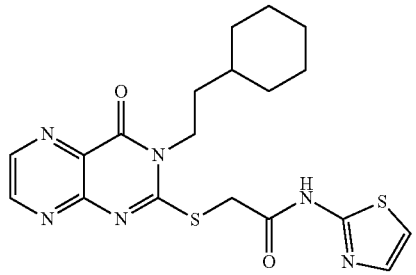 [SMILES: O=C(CSc1nc2nccnc2c(=O)n1CCC1CCCCC1)Nc1nccs1]

2-((3-(2-Cyclohexylethyl)-4-oxo-3,4-dihydropteridin-2-yl)thio)-N-(thiazol-2-yl)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=431.2, RT: 1.152 min $^1$H NMR (300 MHz, DMSO-d$_6$): δ 12.55 (s, 1H), 8.88 (s, 1H), 8.74 (s, 1H), 7.49 (s, 1H), 7.22 (s, 1H), 4.44 (s, 2H), 4.13 (s, 2H), 1.79 (d, J=11.0 Hz, 2H), 1.66 (s, 5H), 1.39 (s, 1H), 1.32-1.13 (m, 3H), 1.08-0.96 (m, 2H).

Example Compound 45: N-(5-Chlorothiazol-2-yl)-2-((4-oxo-3-phenethyl-3,4-dihydropteridin-2-yl)thio)acetamide

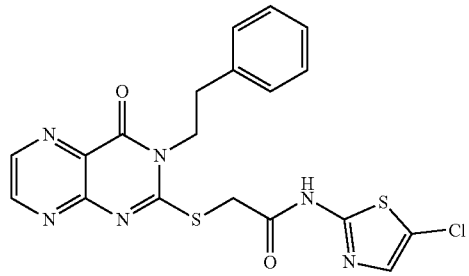 [SMILES: O=C(CSc1nc2nccnc2c(=O)n1CCc1ccccc1)Nc1ncc(Cl)s1]

N-(5-Chlorothiazol-2-yl)-2-((4-oxo-3-phenethyl-3,4-dihydropteridin-2-yl)thio)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=459.0, RT: 1.165 min $^1$H NMR (300 MHz, DMSO-d$_6$): δ 12.84 (s, 1H), 8.90 (s, 1H), 8.76 (s, 1H), 7.55 (s, 1H), 7.32 (d, J=27.9 Hz, 5H), 4.46 (s, 2H), 4.37-4.19 (m, 2H), 3.17-2.96 (m, 2H).

Example Compound 46: 2-((6-Methyl-4-oxo-3-phenethyl-3,4-dihydropteridin-2-yl)thio)-N-(thiazol-2-yl)acetamide

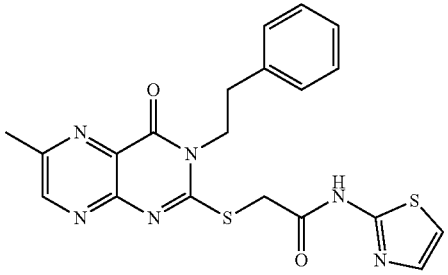 [SMILES: Cc1cnc2nc(SCC(=O)Nc3nccs3)n(CCc3ccccc3)c(=O)c2n1]

2-((6-Methyl-4-oxo-3-phenethyl-3,4-dihydropteridin-2-yl)thio)-N-(thiazol-2-yl)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=439.1, RT: 1.092 min $^1$H NMR (300 MHz, DMSO-d$_6$) δ 12.56 (s, 1H), 8.80 (s, 1H), 8.11-6.90 (m, 7H), 4.38 (d, J=45.0 Hz, 4H), 3.05 (s, 2H), 2.62 (s, 3H).

Example Compound 47: N-(4-(4-Methoxyphenyl)thiazol-2-yl)-2-((4-oxo-3-phenethyl-3,4-dihydropteridin-2-yl)thio)acetamide

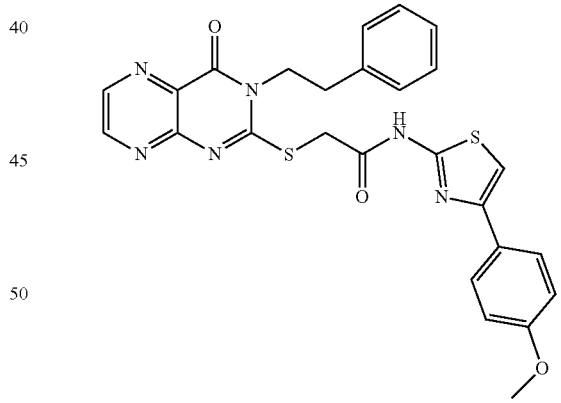

N-(4-(4-Methoxyphenyl)thiazol-2-yl)-2-((4-oxo-3-phenethyl-3,4-dihydropteridin-2-yl)thio)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=531.1, RT: 1.209 min $^1$H NMR (300 MHz, Chloroform-d): δ 11.35 (s, 1H), 8.93 (d, J=2.1 Hz, 1H), 8.87-8.74 (m, 1H), 7.69 (d, J=8.4 Hz, 2H), 7.38-7.24 (m, 5H), 7.00 (s, 1H), 6.88 (d, J=8.4 Hz, 2H), 4.43-4.29 (m, 2H), 4.18 (s, 2H), 3.80 (s, 3H), 3.15-3.03 (m, 2H), 2.92 (d, J=21.3 Hz, 1H).

Example Compound 48: N-(4-(Naphthalen-2-yl)thiazol-2-yl)-2-((4-oxo-3-phenethyl-3,4-dihydropteridin-2-yl)thio)acetamide

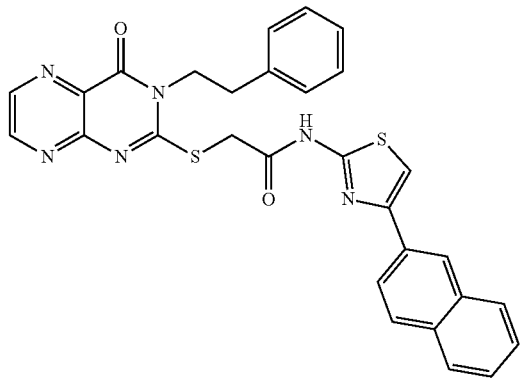 [SMILES: O=C(CSc1nc2nccnc2c(=O)n1CCc1ccccc1)Nc1nc(-c2ccc3ccccc3c2)cs1]

N-(4-(Naphthalen-2-yl)thiazol-2-yl)-2-((4-oxo-3-phenethyl-3,4-dihydropteridin-2-yl)thio)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=551.1, RT: 1.279 min $^1$H NMR (300 MHz, DMSO-d$_6$): δ 12.83 (s, 1H), 8.89 (d, J=2.1 Hz, 1H), 8.75 (d, J=2.1 Hz, 1H), 8.48-8.44 (m, 1H), 8.01-7.89 (m, 3H), 7.80 (s, 1H), 7.53 (dt, J=6.3, 2.9 Hz, 2H), 7.41-7.28 (m, 6H), 4.51 (s, 2H), 4.31 (dd, J=10.3, 6.1 Hz, 2H), 3.11-3.05 (m, 2H). 4.18 (s, 2H), 3.80 (s, 3H), 3.15-3.03 (m, 2H), 2.92 (d, J=21.3 Hz, 1H).

Example Compound 49: N-(4-(4-Chlorophenyl)thiazol-2-yl)-2-((4-oxo-3-phenethyl-3,4-dihydropteridin-2-yl)thio)acetamide

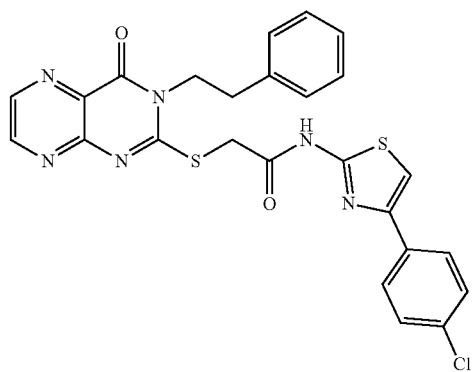 [SMILES: O=C(CSc1nc2nccnc2c(=O)n1CCc1ccccc1)Nc1nc(-c2ccc(Cl)cc2)cs1]

N-(4-(4-Chlorophenyl)thiazol-2-yl)-2-((4-oxo-3-phenethyl-3,4-dihydropteridin-2-yl)thio)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=535.0, RT: 1.267 min $^1$H NMR (300 MHz, DMSO-d$_6$) δ 8.89 (d, J=2.1 Hz, 1H), 8.76 (d, J=2.1 Hz, 1H), 7.94 (d, J=8.5 Hz, 3H), 7.71 (s, 1H), 7.51 (d, J=8.5 Hz, 2H), 7.36 (d, J=6.0 Hz, 4H), 4.49 (s, 2H), 4.37-4.25 (m, 2H), 3.12-3.02 (m, 2H).

Example Compound 50: N-(4-(4-Cyanophenyl)thiazol-2-yl)-2-((4-oxo-3-phenethyl-3,4-dihydropteridin-2-yl)thio)acetamide

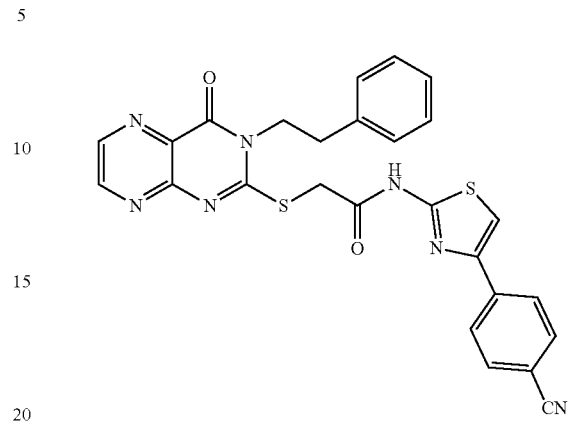

N-(4-(4-Cyanophenyl)thiazol-2-yl)-2-((4-oxo-3-phenethyl-3,4-dihydropteridin-2-yl)thio)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

$^1$H NMR (300 MHz, DMSO-d$_6$) δ 12.83 (s, 1H), 8.89 (d, J=2.1 Hz, 1H), 8.75 (d, J=2.1 Hz, 1H), 8.10 (d, J=8.3 Hz, 2H), 7.94 (d, J=4.0 Hz, 2H), 7.90 (s, 1H), 7.40-7.29 (m, 5H), 4.50 (s, 2H), 4.37-4.25 (m, 2H), 3.11-3.02 (m, 2H).

Example Compound 51: N-(4-(tert-Butyl)thiazol-2-yl)-2-((4-oxo-3-phenethyl-3,4-dihydropteridin-2-yl)thio)acetamide

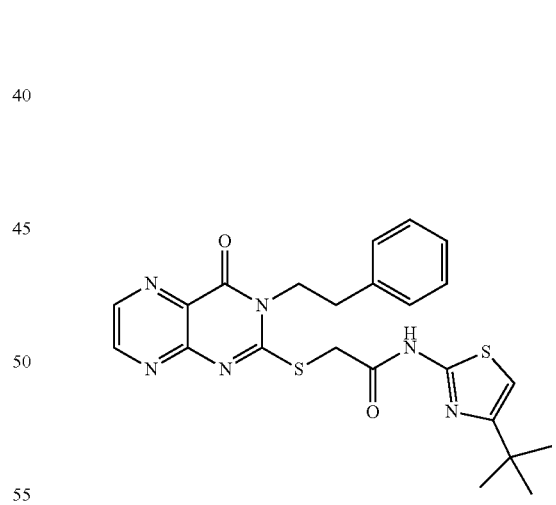

N-(4-(tert-Butyl)thiazol-2-yl)-2-((4-oxo-3-phenethyl-3,4-dihydropteridin-2-yl)thio)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=481.2, RT: 1.236 min $^1$H NMR (300 MHz, DMSO-d$_6$): δ 12.56 (s, 1H), 8.89 (d, J=2.1 Hz, 1H), 8.76 (d, J=2.1 Hz, 1H), 7.43-7.24 (m, 5H), 6.75 (s, 1H), 4.45 (s, 2H), 4.29 (dd, J=7.2, 4.0 Hz, 2H), 3.12-2.99 (m, 2H), 1.27 (s, 9H).

Example Compound 52: N-(4-(5-Chlorothiophen-2-yl)thiazol-2-yl)-2-((4-oxo-3-phenethyl-3,4-dihydropteridin-2-yl)thio)acetamide

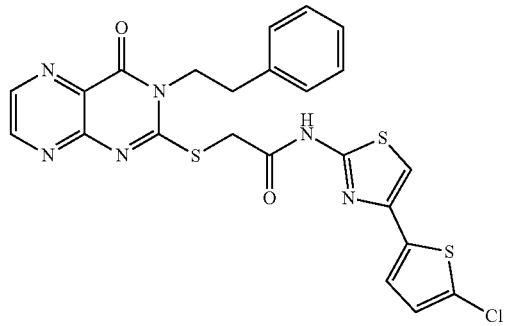 [SMILES: O=C(CSc1nc2nccnc2c(=O)n1CCc1ccccc1)Nc1nc(-c2ccc(Cl)s2)cs1]

N-(4-(5-Chlorothiophen-2-yl)thiazol-2-yl)-2-((4-oxo-3-phenethyl-3,4-dihydropteridin-2-yl)thio)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=541.1, RT: 1.268 min

Example Compound 53: N-(4-(4-(Methylsulfonyl)phenyl)thiazol-2-yl)-2-((4-oxo-3-phenethyl-3,4-dihydropteridin-2-yl)thio)acetamide

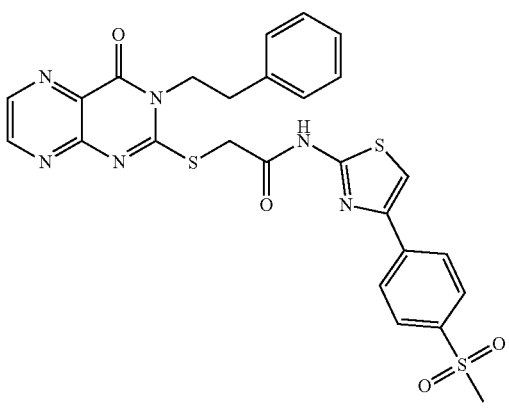 [SMILES: CS(=O)(=O)c1ccc(-c2csc(NC(=O)CSc3nc4nccnc4c(=O)n3CCc3ccccc3)n2)cc1]

N-(4-(4-(Methylsulfonyl)phenyl)thiazol-2-yl)-2-((4-oxo-3-phenethyl-3,4-dihydropteridin-2-yl)thio)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=579.1, RT: 1.137 min $^1$H NMR (300 MHz, DMSO-d$_6$): δ 12.86 (s, 1H), 8.88 (d, J=2.1 Hz, 1H), 8.77-8.74 (m, 1H), 8.17 (d, J=8.4 Hz, 2H), 8.00 (d, J=8.5 Hz, 2H), 7.94 (d, J=5.2 Hz, 1H), 7.37-7.32 (m, 5H), 4.50 (s, 2H), 4.36-4.25 (m, 2H), 3.25 (s, 3H), 3.12-3.03 (m, 2H).

Example Compound 54: 2-((4-Oxo-3-phenethyl-3,4-dihydropyrido[2,3-d]pyrimidin-2-yl)thio)-N-(thiazol-2-yl)acetamide

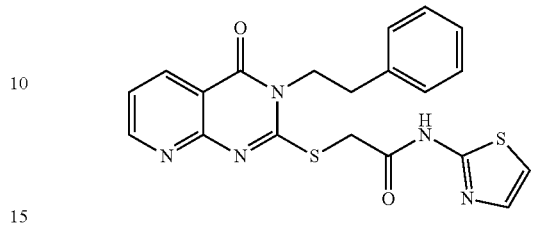

2-((4-Oxo-3-phenethyl-3,4-dihydropyrido[2,3-d]pyrimidin-2-yl)thio)-N-(thiazol-2-yl)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

$^1$H NMR (300 MHz, DMSO-d$_6$): δ 12.56 (s, 1H), 8.85 (dd, J=4.6, 2.0 Hz, 1H), 8.46 (dd, J=7.9, 2.0 Hz, 1H), 7.51-7.43 (8, 2H), 7.39-7.20 (m, 6H), 4.45 (s, 2H), 4.35-4.22 (m, 2H), 3.09-3.00 (m, 2H). 130 NMR (75 MHz, DMSO-d$_6$) δ 165.6, 160.9, 159.7, 158.0, 156.0, 156.0, 137.7, 137.6, 136.3, 128.7, 128.7, 126.8, 121.9, 114.1, 113.7, 45.8, 35.6, 33.2.

Example Compound 55: N-(4-(3-(N-(Methylsulfonyl)methylsulfonamido)phenyl)thiazol-2-yl)-2-((4-oxo-3-phenethyl-3,4-dihydropteridin-2-yl)thio-acetamide

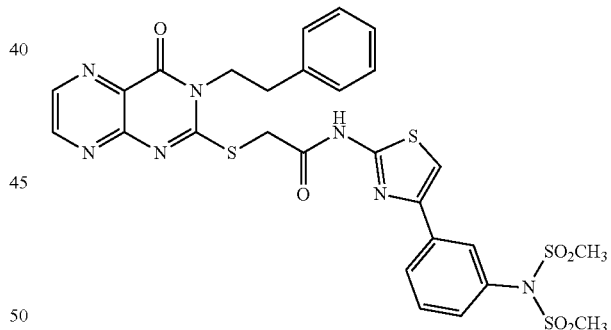

N-(4-(3-(N-(Methylsulfonyl)methylsulfonamido)phenyl)thiazol-2-yl)-2-((4-oxo-3-phenethyl-3,4-dihydropteridin-2-yl)thio)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=672.0, RT: 1.151 min $^1$H NMR (300 MHz, DMSO-d$_6$): δ 12.81 (s, 1H), 8.89 (d, J=2.1 Hz, 1H), 8.75 (d, J=2.1 Hz, 1H), 8.06 (dt, J=7.8, 1.4 Hz, 1H), 7.99 (t, J=1.9 Hz, 1H), 7.83 (s, 1H), 7.58 (t, J=7.8 Hz, 1H), 7.49 (dt, J=8.2, 1.4 Hz, 1H), 7.41-7.24 (m, 5H), 4.49 (s, 2H), 4.37-4.22 (m, 2H), 3.57 (s, 6H), 3.13-3.02 (m, 2H).

Example Compound 56: N-(7-Methoxybenzo[d]thiazol-2-yl)-2-((4-oxo-3-phenethyl-3,4-dihydropteridin-2-yl)thio)acetamide i) 2-Chloro-N-(7-methoxybenzo[d]thiazol-2-yl)acetamide

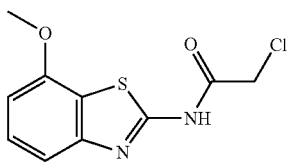 [SMILES: COc1cccc2nc(NC(=O)CCl)sc12]

To a solution of 7-methoxybenzo[d]thiazol-2-amine (102 mg) and dry Et₃N (80 mg) in 3 mL of dry DCM were added 2-chloroacetyl chloride (77 mg) at 0° C. After stirring 15 min at this temperature, the mixture was additionally stirred for 2 h at RT. After completion of the reaction as monitored by LCMS water was added and the organic phase was separated. The water phase was extracted two times with DCM and the combined organic layers were dried with MgSO₄, the solvent were removed under reduced pressure and the crude product was purified by silica gel chromatography using a gradient of ethyl acetate/cyclohexane as eluent.

Yield: 70 mg MS (ES−) [M−H]⁻: m/e=255.0, RT: 1.043 min

¹H NMR (300 MHz, DMSO-d₆): δ 12.86 (s, 1H), 7.55 (dd, J=8.0, 0.9 Hz, 1H), 7.28 (t, J=8.0 Hz, 1H), 7.01 (dd, J=8.1, 1.0 Hz, 1H), 4.43 (s, 2H), 3.91 (s, 3H).

ii) N-(7-Methoxybenzo[d]thiazol-2-yl)-2-((4-oxo-3-phenethyl-3,4-dihydropteridin-2-yl)thio)acetamide

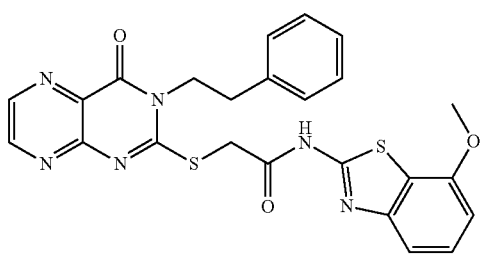 [SMILES: COc1cccc2nc(NC(=O)CSc3nc4nccnc4c(=O)n3CCc3ccccc3)sc12]

N-(7-Methoxybenzo[d]thiazol-2-yl)-2-((4-oxo-3-phenethyl-3,4-dihydropteridin-2-yl)thio)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]⁺: m/e=550.0, RT: 1.146 min

¹H NMR (300 MHz, DMSO-d₆): δ 12.93 (s, 1H), 8.88 (d, J=2.1 Hz, 1H), 8.75 (d, J=2.1 Hz, 1H), 7.50 (dd, J=8.0, 0.9 Hz, 1H), 7.40-7.32 (m, 4H), 7.31-7.22 (m, 2H), 7.01 (dd, J=8.2, 1.0 Hz, 1H), 4.50 (s, 2H), 4.36-4.24 (m, 2H), 3.93 (s, 3H), 3.12-3.02 (m, 2H).

Example Compound 57: N-(4,6-Difluorobenzo[d]thiazol-2-yl)-2-((4-oxo-3-phenethyl-3,4-dihydropteridin-2-yl)thio)acetamide i) 2-Chloro-N-(4,6-difluorobenzo[d]thiazol-2-yl)acetamide

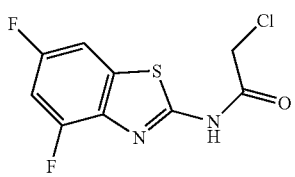 [SMILES: O=C(CCl)Nc1nc2c(F)cc(F)cc2s1]

To a solution of 4,6-difluorobenzo[d]thiazol-2-amine (186 mg) and dry Et₃N (141 mg) in 5 mL of dry DCM were added 2-chloroacetyl chloride (135 mg) dropwise at 0° C. After stirring 15 min at this temperature, the mixture was additionally stirred for 2 h at RT. After completion of the reaction as monitored by LCMS water was added and the organic phase was separated. The water phase was extracted two times with DCM and the combined organic layers were dried with MgSO₄, the solvent were removed under reduced pressure and the crude product was purified by silica gel chromatography using a gradient of ethyl acetate/cyclohexane as eluent.

Yield: 186 mg MS (ES−) [M−H]⁻: m/e=261.0, RT: 1.101 min ii) N-(4,6-Difluorobenzo[d]thiazol-2-yl)-2-((4-oxo-3-phenethyl-3,4-dihydropteridin-2-yl)thio)acetamide

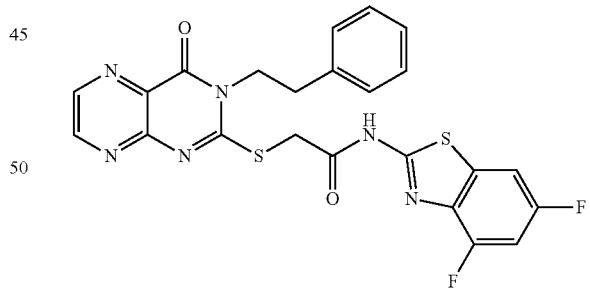

N-(4,6-Difluorobenzo[d]thiazol-2-yl)-2-((4-oxo-3-phenethyl-3,4-dihydropteridin-2-yl)thio)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]⁺: m/e=511.1, RT: 1.187 min

¹H NMR (300 MHz, DMSO-d₆): δ 8.88 (d, J=2.1 Hz, 1H), 8.75 (d, J=2.1 Hz, 1H), 7.78 (ddd, J=8.4, 2.5, 1.0 Hz, 1H), 7.45-7.23 (m, 6H), 4.52 (s, 2H), 4.36-4.24 (m, 2H), 3.12-3.01 (m, 2H).

Example Compound 58: N-(4-(3-Nitrophenyl)thiazol-2-yl)-2-((4-oxo-3-phenethyl-3,4-dihydropteridin-2-yl)thio)acetamide (i) 4-(3-Nitrophenyl)thiazol-2-amine hydrobromide salt

To a solution of 2-bromo-1-(3-nitrophenyl)ethan-1-one (2 g) in 32 mL dry EtOH was added thiourea (624 mg) in portions and heated to reflux for h. After completion of the reaction as monitored by LCMS, the product was collected by filtration and washed with DCM.

Yield: 2.2 g MS (ES+) [M+H]$^+$: m/e=222.0, RT: 0.934 min $^1$H NMR (300 MHz, DMSO-d$_6$): δ 8.58 (t, J=2.0 Hz, 1H), 8.26-8.19 (m, 2H), 7.75 (t, J=8.0 Hz, 1H), 7.49 (s, 1H).

(ii) 2-Chloro-N-(4-(3-nitrophenyl)thiazol-2-yl)acetamide

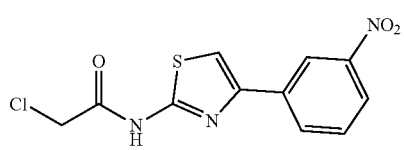 [SMILES: O=C(CCl)Nc1nc(-c2cccc([N+](=O)[O-])c2)cs1]

To a solution of 4-(3-nitrophenyl)thiazol-2-amine hydrobromide salt (2.2 g) and dry Et$_3$N (1.7 g) in 36 mL of dry DCM were added 2-chloroacetyl chloride (0.98 g) dropwise at 0° C. After stirring 15 min at this temperature, the mixture was stirred overnight at RT. Due to incomplete conversion of the starting amine, additional dry Et$_3$N (0.8 g) and 2-chloroacetyl chloride (0.7 g) were added and the reaction mixture was further stirred overnight at RT. After completion of the reaction as monitored by LCMS, the product was collected by filtration and washed with water, EtOH, and DCM.

Yield: 1.5 g MS (ES+) [M+H]$^+$: m/e=298.0, RT: 1.124 min (iii) N-(4-(3-Nitrophenyl)thiazol-2-yl)-2-((4-oxo-3-phenethyl-3,4-dihydropteridin-2-yl)thio)acetamide

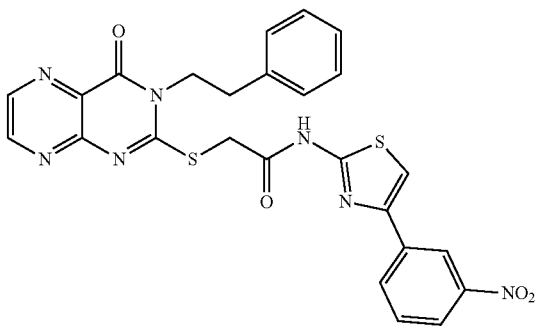 [SMILES: Nc1cccc(-c2csc(NC(=O)CSc3nc4nccnc4c(=O)n3CCc3ccccc3)n2)c1]

To a solution of 3-phenethyl-2-thioxo-2,3-dihydropteridin-4(1H)-one (500 mg) in 6 mL dry DMF was added dry triethylamine (360 mg) followed by dropwise addition of 2-chloro-N-(4-(3-nitrophenyl)thiazol-2-yl)acetamide (580 mg) in 3 mL dry DMF. The reaction mixture was stirred overnight at 80° C. After completion of reaction as monitored by LCMS, the DMF was removed under reduced pressure and to the crude product was added water. The water phase was extracted three times with DCM and the combined organic phases were washed with brine, dried over MgSO$_4$ and concentrated under reduced pressure. The crude product was purified by silica gel chromatography using a gradient of DCM/MeOH as eluent. The product was obtained as an orange solid.

Yield: 770 mg MS (ES+) [M+H]$^+$: m/e=546.1, RT: 1.196 min $^1$H NMR (300 MHz, DMSO): δ 12.87 (s, 1H), 8.89 (d, J=2.1 Hz, 1H), 8.80-8.72 (m, 2H), 8.42-8.32 (m, 1H), 8.24-8.14 (m, 1H), 7.96 (d, J=5.4 Hz, 1H), 7.75 (t, J=8.0 Hz, 1H), 7.42-7.22 (m, 5H), 4.50 (s, 2H), 4.37-4.25 (m, 2H), 3.13-3.01 (m, 2H).

Example Compound 59: N-(4-(3-Aminophenyl)thiazol-2-yl)-2-((4-oxo-3-phenethyl-3,4-dihydropteridin-2-yl)thio)acetamide

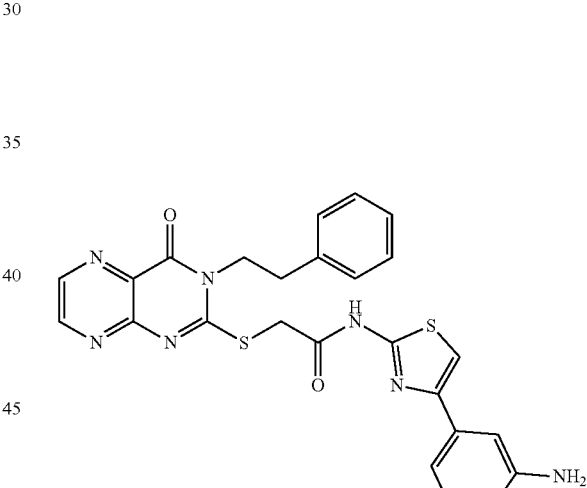

A solution of N-(4-(3-nitrophenyl)thiazol-2-yl)-2-((4-oxo-3-phenethyl-3,4-dihydropteridin-2-yl)thio)acetamide (610 mg) and SnCl$_2$·2H$_2$O (1.2 g) in EtOH (10 mL) was stirred for 2 h at 70° C. The mixture was poured on ice and quenched with sat. NaHCO$_3$ solution. The resulting solution was extracted three times with DCM and the combined organic phases were washed with brine, dried over MgSO$_4$ and concentrated under reduced pressure. The crude product was purified by silica gel chromatography using a gradient of DCM/MeOH as eluent. The product (206 mg) was obtained as a red solid.

MS (ES+) [M+H]$^+$: m/e=516.1, RT: 1.038 min $^1$H NMR (300 MHz, DMSO-d$_6$): δ 12.72 (s, 1H), 8.90 (d, J=2.1 Hz, 1H), 8.76 (d, J=2.1 Hz, 1H), 7.47-7.22 (m, 6H), 7.16-6.92 (m, 3H), 6.54 (dt, J=8.0, 3.1 Hz, 1H), 5.16 (s, 2H), 4.49 (s, 2H), 4.39-4.26 (m, 2H), 3.16-3.02 (m, 2H).

Example Compound 60: N-Cyclobutyl-2-((4-oxo-3-phenethyl-3,4-dihydropteridin-2-yl)thio)acetamide i) 2-Chloro-N-cyclobutylacetamidemide

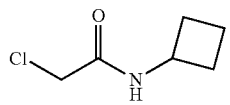

To a solution of cyclobutylamine (200 mg) and dry Et₃N (683 mg) in 5.6 mL of dry DCM were added 2-chloroacetyl chloride (381 mg) dropwise at 0° C. After stirring 15 min at this temperature, the mixture was additionally stirred for 2 h at RT. After completion of the reaction as monitored by LCMS water was added and the organic phase was separated. The water phase was extracted 2-times with DCM and the combined organic layers were dried with MgSO₄, the solvents were removed under reduced pressure and the crude product was purified by silica gel chromatography using a gradient of ethyl acetate/cyclohexane as eluent.

Yield: 247 mg MS (ES+) [M+H]⁺: m/e=148.1, RT: 0.657 min ii) N-Cyclobutyl-2-((4-oxo-3-phenethyl-3,4-dihydropteridin-2-yl)thio)acetamide

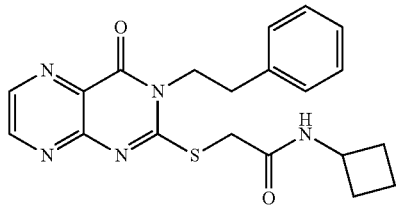 [SMILES: O=C(CSc1nc2nccnc2c(=O)n1CCc1ccccc1)NC1CCC1]

N-Cyclobutyl-2-((4-oxo-3-phenethyl-3,4-dihydropteridin-2-yl)thio)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]⁺: m/e=396.1, RT: 1.049 min

¹H NMR (300 MHz, DMSO-d₆): δ 8.94 (d, J=2.1 Hz, 1H), 8.77 (d, J=2.1 Hz, 1H), 8.62 (d, J=7.7 Hz, 1H), 7.40-7.22 (m, 5H), 4.34-4.08 (m, 5H), 3.10-2.96 (m, 2H), 2.23-2.07 (m, 2H), 2.01-1.84 (m, 2H), 1.71-1.56 (m, 2H).

Example Compound 61: N-Isopropyl-2-((4-oxo-3-phenethyl-3,4-dihydropteridin-2-yl)thio)acetamide i) 2-Chloro-N-isopropylacetamide

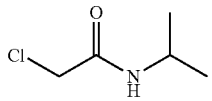

To a solution of isopropylamine (200 mg) and dry Et₃N (821 mg) in 6.8 mL of dry DCM were added 2-chloroacetyl chloride (458 mg) dropwise at 0° C. After stirring 15 min at this temperature, the mixture was additionally stirred for 2 h at RT. After completion of the reaction as monitored by LCMS water was added and the organic phase was separated. The water phase was extracted two times with DCM and the combined organic layers were dried with MgSO₄, the solvents were removed under reduced pressure and the crude product was purified by silica gel chromatography using a gradient of ethyl acetate/cyclohexane as eluent.

Yield: 299 mg MS (ES+) [M+H]⁺: m/e=136.0, RT: 0.428 min ii) N-Isopropyl-2-((4-oxo-3-phenethyl-3,4-dihydropteridin-2-yl)thio)acetamide

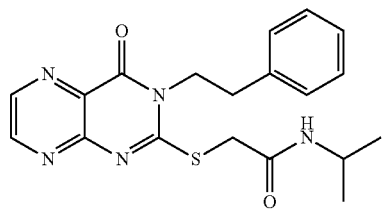 [SMILES: CC(C)NC(=O)CSc1nc2nccnc2c(=O)n1CCc1ccccc1]

N-Isopropyl-2-((4-oxo-3-phenethyl-3,4-dihydropteridin-2-yl)thio)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]⁺: m/e=384.1, RT: 1.026 min

¹H NMR (300 MHz, DMSO-d₆): δ 8.94 (d, J=2.1 Hz, 1H), 8.77 (d, J=2.1 Hz, 1H), 8.25 (d, J=7.6 Hz, 1H), 7.47-7.14 (m, 5H), 4.34-4.22 (m, 2H), 3.96-3.74 (dsept, J=7.6, 6.6 Hz, 1H), 3.09-2.98 (m, 2H), 1.08 (d, J=6.6 Hz, 6H).

Example Compound 62: 2-((Benzo[d]thiazol-2-ylmethyl)thio)-3-phenethylpteridin-4(3H)-one

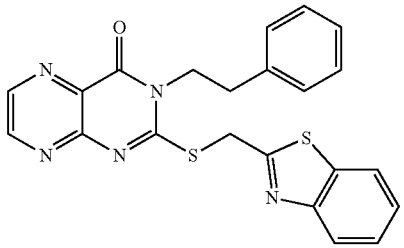 [SMILES: O=c1c2nccnc2nc(SCc2nc3ccccc3s2)n1CCc1ccccc1]

2-((Benzo[d]thiazol-2-ylmethyl)thio)-3-phenethylpteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]⁺: m/e=432.1, RT: 1.166 min

¹H NMR (300 MHz, DMSO-d₆): δ 8.98 (d, J=2.1 Hz, 1H), 8.81 (d, J=2.1 Hz, 1H), 8.10-8.00 (m, 1H), 8.03-7.93 (m, 1H), 7.51 (ddd, J=8.2, 7.2, 1.4 Hz, 1H), 7.48-7.36 (m, 1H), 7.33-7.27 (m, 4H), 7.23-7.16 (m, 1H), 5.10 (s, 2H), 4.34-4.22 (m, 2H), 3.10-2.95 (m, 2H).

Example Compound 63: 2-((Benzo[d]oxazol-2-ylmethyl)thio)-3-phenethylpteridin-4(3H)-one

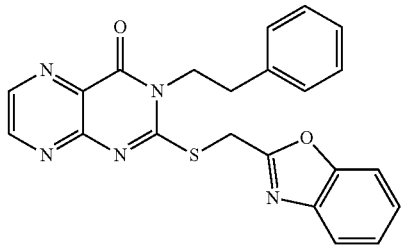 [SMILES: O=c1c2nccnc2nc(SCc2nc3ccccc3o2)n1CCc1ccccc1]

2-((Benzo[d]oxazol-2-ylmethyl)thio)-3-phenethylpteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=416.1, RT: 1.142 min $^1$H NMR (300 MHz, DMSO-d$_6$): δ 8.92 (d, J=2.1 Hz, 1H), 8.77 (d, J=2.1 Hz, 1H), 7.76-7.69 (m, 2H), 7.45-7.35 (m, 2H), 7.35-7.29 (m, 4H), 7.27-7.18 (m, 1H), 5.01 (s, 2H), 4.35-4.25 (m, 2H), 3.10-3.00 (m, 2H).

Example Compound 64: 2-((2-(2-Fluorophenyl)-2-oxoethyl)thio)-3-phenethylpteridin-4(3H)-one

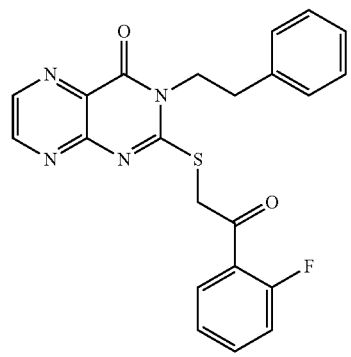 [SMILES: O=C(CSc1nc2nccnc2c(=O)n1CCc1ccccc1)c1ccccc1F]

2-((2-(2-Fluorophenyl)-2-oxoethyl)thio)-3-phenethylpteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=421.1, RT: 1.165 min $^1$H NMR (300 MHz, DMSO-d$_6$): δ 8.87 (d, J=2.1 Hz, 1H), 8.74 (d, J=2.1 Hz, 1H), 7.96 (td, J=7.7, 1.9 Hz, 1H), 7.80-7.68 (m, 1H), 7.50-7.21 (m, 7H), 4.95 (d, J=2.4 Hz, 2H), 4.41-4.25 (m, 2H), 3.15-2.96 (m, 2H).

Example Compound 65: 2-(((1H-Benzo[d]imidazol-2-yl)methyl)thio)-3-phenethylpteridin-4(3H)-one

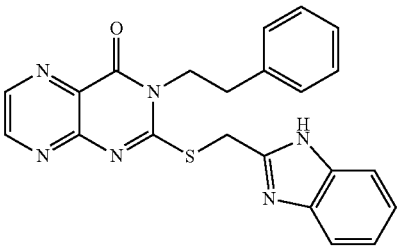

2-(((1H-Benzo[d]imidazol-2-yl)methyl)thio)-3-phenethylpteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=415.1, RT: 0.912 min $^1$H NMR (300 MHz, DMSO-d$_6$): δ 12.46 (s, 1H), 8.96 (d, J=2.1 Hz, 1H), 8.79 (d, J=2.1 Hz, 1H), 7.58-7.46 (m, 2H), 7.39-7.21 (m, 5H), 7.20-7.13 (m, 2H), 4.91 (s, 2H), 4.38-4.19 (m, 2H), 3.11-2.97 (m, 2H).

Example Compound 66: N,N-Diethyl-2-(((4-oxo-3-phenethyl-3,4-dihydropteridin-2-yl)thio)methyl)-1H-benzo[d]imidazole-6-sulfonamide

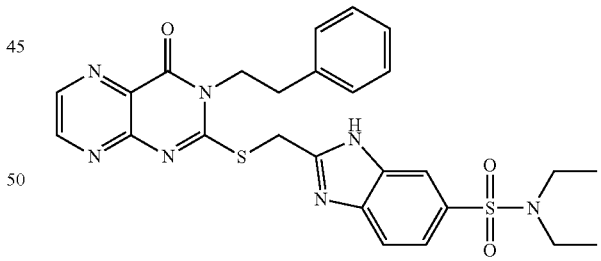

N,N-Diethyl-2-(((4-oxo-3-phenethyl-3,4-dihydropteridin-2-yl)thio)methyl)-1H-benzo[d]imidazole-6-sulfonamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=550.1, RT: 1.103 min $^1$H NMR (300 MHz, DMSO-d$_6$): δ 12.89 (s, 1H), 8.95 (d, J=2.1 Hz, 1H), 8.80 (d, J=2.1 Hz, 1H), 7.95 (dd, J=1.7, 0.7 Hz, 1H), 7.70 (d, J=8.5 Hz, 1H), 7.59 (dd, J=8.5, 1.8 Hz, 1H), 7.38-7.29 (m, 4H), 7.29-7.20 (m, 1H), 4.96 (s, 2H), 4.37-4.22 (m, 2H), 3.14 (q, J=7.1 Hz, 4H), 3.09-3.01 (m, 2H), 1.01 (t, J=7.1 Hz, 6H).

Example Compound 67: 2-(((4-Oxo-3,4-dihydroquinazolin-2-yl)methyl)thio)-3-phenethylpteridin-4(3H)-one

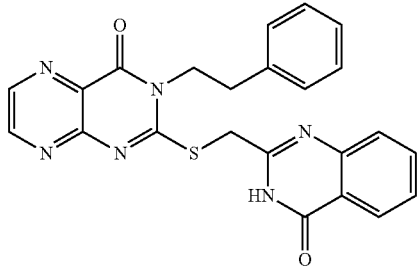 [SMILES: O=c1[nH]c(CSc2nc3nccnc3c(=O)n2CCc2ccccc2)nc2ccccc12]

2-(((4-Oxo-3,4-dihydroquinazolin-2-yl)methyl)thio)-3-phenethylpteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=443.0, RT: 1.070 min $^1$H NMR (300 MHz, DMSO-d$_6$): δ 12.56 (s, 1H), 8.94 (d, J=2.1 Hz, 1H), 8.78 (d, J=2.1 Hz, 1H), 8.11 (dd, J=8.0, 1.5 Hz, 1H), 7.80 (ddd, J=8.5, 7.1, 1.5 Hz, 1H), 7.67-7.59 (m, 1H), 7.50 (ddd, J=8.1, 7.2, 1.2 Hz, 1H), 7.38-7.30 (m, 4H), 7.29-7.21 (m, 1H), 4.69 (s, 2H), 4.41-4.24 (m, 2H), 3.17-3.00 (m, 2H).

Example Compound 68: 1,3-Dimethyl-8-(((4-oxo-3-phenethyl-3,4-dihydropteridin-2-yl)thio)methyl)-3,9-dihydro-1H-purine-2,6-dione

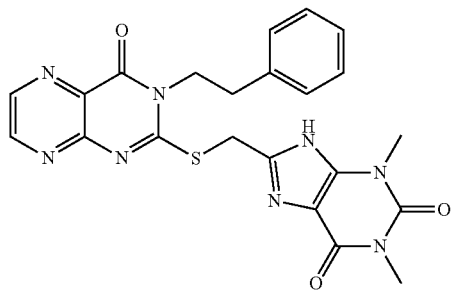 [SMILES: Cn1c(=O)c2nc(CSc3nc4nccnc4c(=O)n3CCc3ccccc3)[nH]c2n(C)c1=O]

1,3-Dimethyl-8-(((4-oxo-3-phenethyl-3,4-dihydropteridin-2-yl)thio)methyl)-3,9-dihydro-1H-purine-2,6-dione by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=477.1, RT: 1.006 min $^1$H NMR (300 MHz, DMSO-d$_6$): δ 8.95 (d, J=2.1 Hz, 1H), 8.79 (d, J=2.1 Hz, 1H), 7.39-7.29 (m, 5H), 4.78 (s, 2H), 4.32-4.21 (m, 2H), 3.42 (s, 3H), 3.22 (s, 3H), 3.10-2.98 (m, 2H).

Example Compound 69: 2-(((5-Chloro-1H-benzo[d]imidazol-2-yl)methyl)thio)-3-phenethylpteridin-4(3H)-one

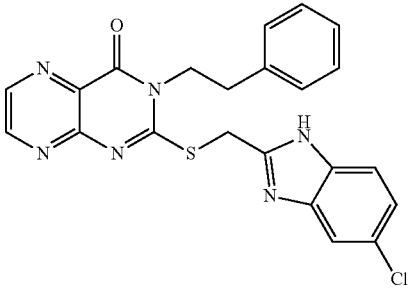 [SMILES: O=c1c2nccnc2nc(SCc2nc3cc(Cl)ccc3[nH]2)n1CCc1ccccc1]

2-(((5-Chloro-1H-benzo[d]imidazol-2-yl)methyl)thio)-3-phenethylpteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=449.1, RT: 1.060 min $^1$H NMR (300 MHz, DMSO-d$_6$): δ 12.65 (s, 1H), 8.95 (d, J=2.1 Hz, 1H), 8.79 (d, J=2.1 Hz, 1H), 7.59 (d, J=2.0 Hz, 1H), 7.53 (d, J=8.6 Hz, 1H), 7.37-7.28 (m, 4H), 7.28-7.22 (m, 1H), 7.19 (dd, J=8.6, 2.1 Hz, 1H), 4.91 (s, 2H), 4.37-4.23 (m, 2H), 3.11-2.99 (m, 2H).

Example Compound 70: 2-(((7-Methyl-3H-imidazo[4,5-b]pyridin-2-yl)methyl)thio)-3-phenethylpteridin-4(3H)-one

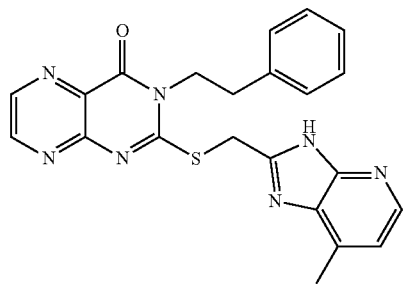 [SMILES: Cc1ccnc2[nH]c(CSc3nc4nccnc4c(=O)n3CCc3ccccc3)nc12]

2-(((7-Methyl-3H-imidazo[4,5-b]pyridin-2-yl)methyl)thio)-3-phenethylpteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=430.1, RT: 0.921 min $^1$H NMR (300 MHz, DMSO-d$_6$): δ 12.96 (s, 1H), 8.96 (d, J=2.1 Hz, 1H), 8.80 (d, J=2.1 Hz, 1H), 8.16 (d, J=4.9 Hz, 1H), 7.37-7.29 (m, 4H), 7.29-7.20 (m, 1H), 7.04 (dd, J=4.9, 1.0 Hz, 1H), 4.93 (s, 2H), 4.36-4.22 (m, 2H), 3.13-3.00 (m, 2H), 2.53 (s, 3H).

Example Compound 71: 2-(((1-Methyl-4-oxo-4,5-dihydro-1H-pyrazolo[3,4-d]pyrimidin-6-yl)methyl)thio)-3-phenethylpteridin-4(3H)-one

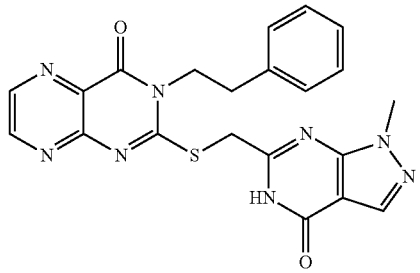 [SMILES: Cn1ncc2c(=O)[nH]c(CSc3nc4nccnc4c(=O)n3CCc3ccccc3)nc21]

2-(((1-Methyl-4-oxo-4,5-dihydro-1H-pyrazolo[3,4-d]pyrimidin-6-yl)methyl)thio)-3-phenethylpteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=447.1, RT: 1.005 min $^1$H NMR (300 MHz, DMSO-d$_6$): δ 12.41 (s, 1H), 8.93 (d, J=2.1 Hz, 1H), 8.77 (d, J=2.1 Hz, 1H), 8.02 (s, 1H), 7.38-7.29 (m, 4H), 7.29-7.20 (m, 1H), 4.69 (s, 2H), 4.43-4.20 (m, 2H), 3.85 (s, 3H), 3.16-3.00 (m, 2H).

Example Compound 72: 2-(((5-Bromo-1H-benzo[d]imidazol-2-yl)methyl)thio)-3-phenethylpteridin-4(3H)-one

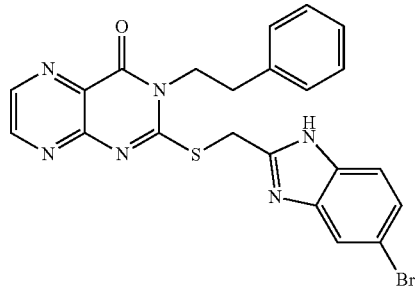 [SMILES: O=c1c2nccnc2nc(SCc2nc3cc(Br)ccc3[nH]2)n1CCc1ccccc1]

2-(((5-Bromo-1H-benzo[d]imidazol-2-yl)methyl)thio)-3-phenethylpteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=493.0, RT: 1.070 min $^1$H NMR (300 MHz, DMSO-d$_6$): δ 8.95 (d, J=2.1 Hz, 1H), 8.79 (d, J=2.1 Hz, 1H), 7.73 (d, J=1.9 Hz, 1H), 7.49 (d, J=8.5 Hz, 1H), 7.39-7.18 (m, 6H), 4.91 (s, 2H), 4.39-4.18 (m, 2H), 3.14-2.94 (m, 2H).

Example Compound 73: 2-(((3H-Imidazo[4,5-b]pyridin-2-yl)methyl)thio)-3-phenethylpteridin-4(3H)-one

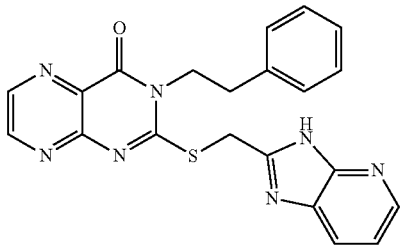 [SMILES: O=c1c2nccnc2nc(SCc2nc3cccnc3[nH]2)n1CCc1ccccc1]

2-(((3H-Imidazo[4,5-b]pyridin-2-yl)methyl)thio)-3-phenethylpteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=416.0, RT: 0.932 min $^1$H NMR (300 MHz, DMSO-d$_6$): δ 8.94 (d, J=2.1 Hz, 1H), 8.79 (d, J=2.1 Hz, 1H), 8.30 (dd, J=4.8, 1.5 Hz, 1H), 7.95 (dd, J=8.0, 1.5 Hz, 1H), 7.38-7.30 (m, 4H), 7.29-7.18 (m, 2H), 4.94 (s, 2H), 4.36-4.22 (m, 2H), 3.12-2.98 (m, 2H).

Example Compound 74: 2-(((6-Bromo-3H-imidazo[4,5-b]pyridin-2-yl)methyl)thio)-3-phenethylpteridin-4(3H)-one

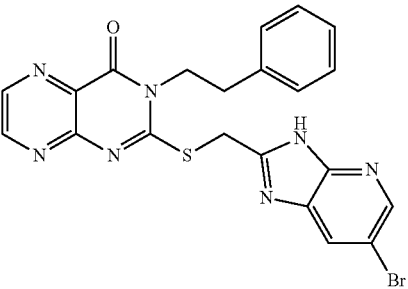

2-(((6-Bromo-3H-imidazo[4,5-b]pyridin-2-yl)methyl)thio)-3-phenethylpteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=494.0, RT: 1.067 min $^1$H NMR (300 MHz, DMSO-d$_6$): δ 8.94 (d, J=2.1 Hz, 1H), 8.79 (d, J=2.1 Hz, 1H), 8.39 (d, J=2.1 Hz, 1H), 8.23 (d, J=2.2 Hz, 1H), 7.38-7.30 (m, 4H), 7.29-7.20 (m, 1H), 4.93 (s, 2H), 4.36-4.24 (m, 2H), 3.11-2.99 (m, 2H).

Example Compound 75: Methyl 2-(((4-oxo-3-phenethyl-3,4-dihydropteridin-2-yl)thio)methyl)-1H-benzo[d]imidazole-5-carboxylate

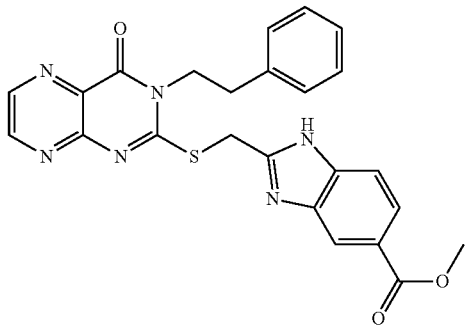 [SMILES: COC(=O)c1ccc2[nH]c(CSc3nc4nccnc4c(=O)n3CCc3ccccc3)nc2c1]

Methyl 2-(((4-oxo-3-phenethyl-3,4-dihydropteridin-2-yl)thio)methyl)-1H-benzo[d]imidazole-5-carboxylate by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=473.0, RT: 1.023 min $^1$H NMR (300 MHz, DMSO-$d_6$): δ 8.95 (d, J=2.1 Hz, 1H), 8.79 (d, J=2.1 Hz, 1H), 8.14 (dd, J=1.6, 0.7 Hz, 1H), 7.81 (dd, J=8.5, 1.6 Hz, 1H), 7.61 (dd, J=8.4, 0.7 Hz, 1H), 7.37-7.30 (m, 4H), 7.29-7.20 (m, 1H), 4.95 (s, 2H), 4.36-4.21 (m, 2H), 3.85 (s, 3H), 3.10-2.99 (m, 2H).

Example Compound 76: 2-(((1H-Imidazol-2-yl)methyl)thio)-3-phenethylpteridin-4(3H)-one

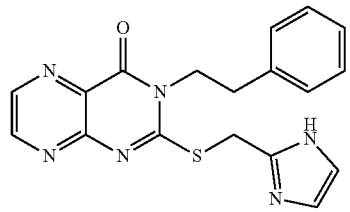 [SMILES: O=c1c2nccnc2nc(SCc2ncc[nH]2)n1CCc1ccccc1]

2-(((1H-Imidazol-2-yl)methyl)thio)-3-phenethylpteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=365.0, RT: 0.854 min $^1$H NMR (300 MHz, DMSO-$d_6$): δ 12.05 (s, 1H), 8.97 (d, J=2.1 Hz, 1H), 8.80 (d, J=2.1 Hz, 1H), 7.40-7.21 (m, 5H), 7.11 (s, 1H), 6.87 (s, 1H), 4.70 (s, 2H), 4.31-4.19 (m, 2H), 3.07-2.95 (m, 2H).

Example Compound 77: 2-(((4,5-Dimethyl-1H-imidazol-2-yl)methyl)thio)-3-phenethylpteridin-4(3H)-one

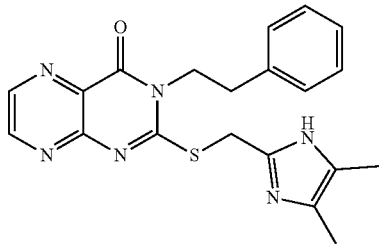 [SMILES: Cc1nc(CSc2nc3nccnc3c(=O)n2CCc2ccccc2)[nH]c1C]

2-(((4,5-Dimethyl-1H-imidazol-2-yl)methyl)thio)-3-phenethylpteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=393.2, RT: 0.903 min $^1$H NMR (300 MHz, DMSO-$d_6$): δ 11.70 (s, 1H), 8.96 (d, J=2.1 Hz, 1H), 8.79 (d, J=2.1 Hz, 1H), 7.40-7.19 (m, 5H), 4.59 (s, 2H), 4.32-4.18 (m, 2H), 3.07-2.94 (m, 2H), 2.03 (s, 6H) ppm.

Example Compound 78: 2-((3-(4-(Methylsulfonyl)phenyl)-4-oxo-3,4-dihydropteridin-2-yl)thio)-N-(thiazol-2-yl)acetamide i) 3-(4-(Methylsulfonyl)phenyl)-2-thioxo-2,3-dihydropteridin-4(1H)-one

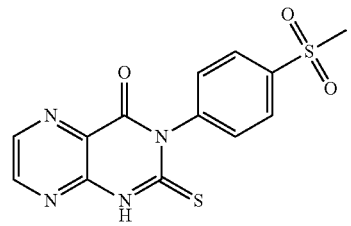

To a solution of methyl 3-isothiocyanatopyrazine-2-carboxylate (80 mg, 0.39 mmol) in dry dioxane (2-4 mL) was added a primary amine (0.39 mmol). The reaction was refluxed overnight. The product (30 mg) was isolated by filtration.

MS (ES+) [M+H]+: m/e=334.9, RT: 0.838 min.

ii) 2-((3-(4-(Methylsulfonyl)phenyl)-4-oxo-3,4-dihydropteridin-2-yl)thio)-N-(thiazol-2-yl)acetamide

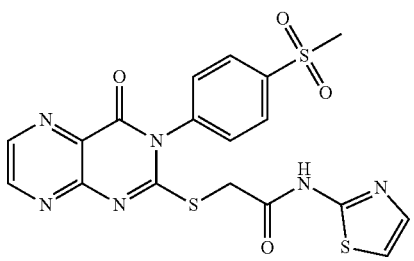 [SMILES: CS(=O)(=O)c1ccc(-n2c(SCC(=O)Nc3nccs3)nc3nccnc3c2=O)cc1]

3-(4-(Methylsulfonyl)phenyl)-2-thioxo-2,3-dihydropteridin-4(1H)-one was dissolved in DMF (1-3 mL). Triethylamine (1.2 equiv.) and 2-chloro-N-(thiazol-2-yl)acetamide (1 equiv.) were added. The reaction mixture stirred overnight at room temperature. DMF was removed under reduced pressure. The residue was dissolved in DCM and washed with water. After separating phases, product was further extracted with DCM (twice) from aqueous phase. Combined organic phases were dried over $MgSO_4$ and filtered. The solvent was removed under reduced pressure. The resulting solid was washed with methanol to obtain colorless solid (8.3 mg, 39% yield).

MS (ES+) [M+H]$^+$: m/e=474.9, RT: 0.931 min.

$^1$H NMR (600 MHz, DMSO-d$_6$) δ 12.49 (s, 1H), 8.95 (d, J=2.2 Hz, 1H), 8.78 (d, J=2.2 Hz, 1H), 8.25-8.20 (m, 2H), 7.92-7.88 (m, 2H), 7.48 (d, J=3.5 Hz, 1H), 7.22 (d, J=3.5 Hz, 1H), 4.33 (s, 2H), 3.37 (s, 3H) ppm.

$^{13}$C NMR (151 MHz, DMSO-d$_6$) δ 165.8, 161.3, 160.3, 153.5, 150.7, 144.0, 143.0, 140.3, 138.2, 132.7, 131.1, 129.1, 114.2, 43.7, 36.6 ppm.

HRMS (ESI) (m/z): [M+H]$^+$ calcd for $C_{18}H_{15}N_6O_4S_3$, 475.0311; found, 475.0306.

Example Compound 79: 2-(((1H-Benzo[d]imidazol-2-yl)methyl)thio)-3-(4-(methylsulfonyl)phenyl)pteridin-4(3H)-one

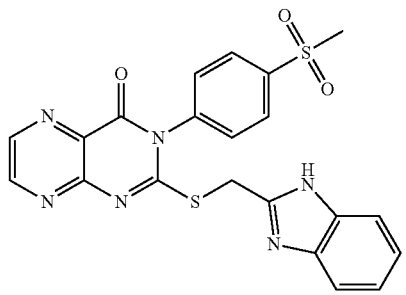 [SMILES: CS(=O)(=O)c1ccc(-n2c(SCc3nc4ccccc4[nH]3)nc3nccnc3c2=O)cc1]

3-(4-(Methylsulfonyl)phenyl)-2-thioxo-2,3-dihydropteridin-4(1H)-one was dissolved in DMF (1-3 mL). Triethylamine (1.2 equiv.) and 2-(chloromethyl)-1H-benzimidazole (1 equiv.) were added. The reaction stirred overnight at room temperature. DMF was removed under reduced pressure. The residue was dissolved in DCM and washed with water. After separating phases, product was further extracted with DCM (twice) from aqueous phase. Combined organic phases were dried over $MgSO_4$ and filtered. The solvent was removed under reduced pressure. The resulting solid was washed with methanol to obtain colorless solid (4.1 mg, 20% yield).

MS (ES+) [M+H]$^+$: m/e=465.0, RT: 0.854 min.

$^1$H NMR (600 MHz, DMSO-d$_6$) δ 12.40 (s, 1H), 9.02 (d, J=2.2 Hz, 1H), 8.83 (d, J=2.1 Hz, 1H), 8.19 (d, J=8.4 Hz, 2H), 7.88 (d, J=8.4 Hz, 2H), 7.53 (d, J=7.9 Hz, 1H), 7.43 (d, J=8.2 Hz, 1H), 7.17 (td, J=7.3, 1.3 Hz, 1H), 7.13 (td, J=7.6, 1.3 Hz, 1H), 4.77 (s, 2H), 3.36 (s, 3H) ppm.

$^{13}$C-NMR (151 MHz, DMSO-d$_6$) δ 161.1, 160.4, 153.6, 150.7, 149.3, 144.1, 143.4, 143.0, 140.2, 134.8, 132.8, 131.1, 129.1, 122.8, 121.9, 119.0, 111.7, 43.7, 30.7 ppm.

HRMS (ESI) (m/z): [M+H]$^+$ calcd for $C_{21}H_{17}N_6O_3S_2$, 465.0798; found, 465.0796.

Example Compound 80: 2-((3-(4-(N-(5-Methyl-1,3,4-thiadiazol-2-yl)sulfamoyl)phenyl)-4-oxo-3,4-dihydropteridin-2-yl)thio)-N-(thiazol-2-yl)acetamide

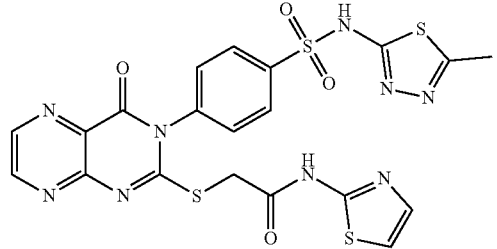 [SMILES: Cc1nnc(NS(=O)(=O)c2ccc(-n3c(SCC(=O)Nc4nccs4)nc4nccnc4c3=O)cc2)s1]

2-((3-(4-(N-(5-Methyl-1,3,4-thiadiazol-2-yl)sulfamoyl)phenyl)-4-oxo-3,4-dihydropteridin-2-yl)thio)-N-(thiazol-2-yl)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [$C_{20}H_{15}N_9O_4S_4$+H]$^+$: m/e=574.0, RT: 0.988 min.

$^1$H NMR (600 MHz, DMSO-d$_6$) δ 12.46 (s, 1H), 8.94 (d, J=2.1 Hz, 1H), 8.77 (d, J=2.1 Hz, 1H), 8.04 (d, J=8.4 Hz, 2H), 7.82-7.75 (m, 2H), 7.48 (d, J=3.6 Hz, 1H), 7.21 (d, J=3.6 Hz, 1H), 4.31 (s, 2H) ppm.

$^{13}$C NMR (151 MHz, DMSO-d$_6$) δ 168.3, 165.4, 160.9, 159.8, 157.8, 155.0, 153.0, 150.2, 143.9, 143.5, 138.6, 137.7, 132.3, 130.4, 127.2, 113.7, 69.8, 36.1, 16.1 ppm.

HRMS (ESI) (m/z): [M+H]$^+$ calcd for $C_{20}H_{16}N_9O_4S_4$, 574.0203; found, 574.0201.

Example Compound 81: 4 N-Methyl-4-(4-oxo-2-((2-oxo-2-(thiazol-2-ylamino)ethyl)thio)pteridin-3(4H)-yl)benzamide

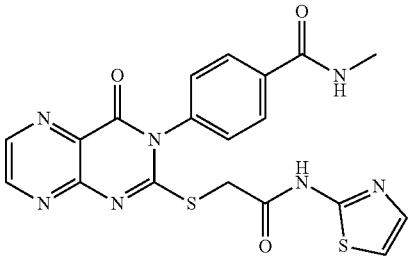 [SMILES: CNC(=O)c1ccc(-n2c(SCC(=O)Nc3nccs3)nc3nccnc3c2=O)cc1]

4 N-Methyl-4-(4-oxo-2-((2-oxo-2-(thiazol-2-ylamino)ethyl)thio)pteridin-3(4H)-yl)benzamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=454.1, RT: 0.892 min.

$^1$H NMR (600 MHz, DMSO-d$_6$) δ 12.47 (s, 1H), 8.94 (d, J=2.2 Hz, 1H), 8.78 (d, J=2.2 Hz, 1H), 8.62 (q, J=4.5 Hz, 1H), 8.05-8.01 (m, 2H), 7.68-7.64 (m, 2H), 7.48 (d, J=3.6 Hz, 1H), 7.21 (d, J=3.6 Hz, 1H), 4.31 (s, 2H), 2.84 (d, J=4.5 Hz, 3H) ppm.

$^{13}$C-NMR (151 MHz, DMSO-d$_6$) δ 165.9, 165.4, 161.4, 159.8, 157.8, 153.1, 150.2, 143.5, 137.7, 137.5, 136.4, 132.2, 129.3, 128.4, 113.7, 36.2, 26.3 ppm.

HRMS (ESI) (m/z): [M+H]+ calcd for $C_{19}H_{16}N_7O_3S_2$, 454.0751; found, 454.0762.

Example Compound 82: 4-(2-(((1H-Benzo[d]imidazol-2-yl)methyl)thio)-4-oxopteridin-3(4H)-yl)-N-methylbenzamide

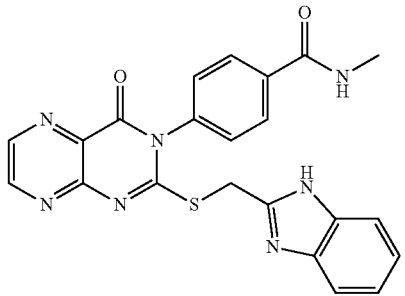 [SMILES: CNC(=O)c1ccc(-n2c(SCc3nc4ccccc4[nH]3)nc3nccnc3c2=O)cc1]

4-(2-(((1H-Benzo[d]imidazol-2-yl)methyl)thio)-4-oxopteridin-3(4H)-yl)-N-methylbenzamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=444.1, RT: 0.835 min.

$^1$H NMR (600 MHz, DMSO-$d_6$) δ 12.38 (s, 1H), 9.01 (d, J=2.2 Hz, 1H), 8.82 (d, J=2.2 Hz, 1H), 8.59 (q, J=4.5 Hz, 1H), 8.00 (d, J=8.4 Hz, 2H), 7.64 (d, J=8.4 Hz, 2H), 7.53 (d, J=7.8 Hz, 1H), 7.43 (d, J=7.8 Hz, 1H), 7.20-7.09 (m, 2H), 4.74 (s, 2H), 2.82 (d, J=4.5 Hz, 3H) ppm.

$^{13}$C-NMR (151 MHz, DMSO-$d_6$) δ 165.9, 161.3, 159.9, 153.2, 150.2, 148.9, 143.5, 143.0, 137.4, 136.5, 134.3, 132.3, 129.3, 128.5, 122.3, 121.4, 118.5, 111.2, 30.2, 26.3 ppm.

HRMS (ESI) (m/z): [M+H]+ calcd for $C_{22}H_{18}N_7O_2S$, 444.1237; found, 444.1251.

Example Compound 83: 2-((3-(3-(1H-Tetrazol-5-yl)phenyl)-4-oxo-3,4-dihydropteridin-2-yl)thio)-N-(thiazol-2-yl)acetamide

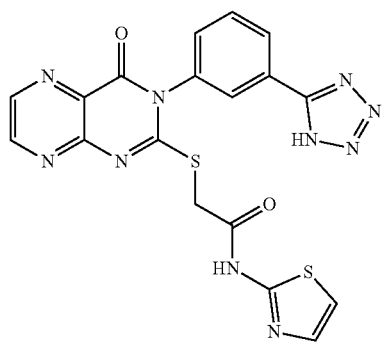 [SMILES: O=C(CSc1nc2nccnc2c(=O)n1-c1cccc(-c2nnn[nH]2)c1)Nc1nccs1]

2-((3-(3-(1H-Tetrazol-5-yl)phenyl)-4-oxo-3,4-dihydropteridin-2-yl)thio)-N-(thiazol-2-yl)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=465.0, RT: 0.931 min.

$^1$H NMR (600 MHz, DMSO-$d_6$) δ 12.45 (s, 1H), 8.93 (d, J=2.2 Hz, 1H), 8.77 (d, J=2.2 Hz, 1H), 8.19 (dt, J=7.8, 1.4 Hz, 1H), 8.10 (t, J=1.8 Hz, 1H), 7.65 (t, J=7.8 Hz, 1H), 7.47 (d, J=3.6 Hz, 1H), 7.46-7.43 (m, 1H), 7.20 (d, J=3.6 Hz, 1H), 4.32 (d, J=15.9 Hz, 1H), 4.26 (d, J=16.0 Hz, 1H) ppm.

$^{13}$C-NMR (151 MHz, DMSO-$d_6$) δ 166.0, 162.3, 160.4, 159.8, 158.4, 153.6, 150.5, 143.8, 138.1, 136.1, 132.8, 130.4, 128.2, 127.9, 126.9, 114.1, 36.6 ppm.

HRMS (ESI) (m/z): [M+H]+ calcd for $C_{18}H_{13}N_{10}O_2S_2$, 466.0681; found, 466.0678.

Example Compound 84: 2-(((1H-Benzo[d]imidazol-2-yl)methyl)thio)-3-(3-(1H-tetrazol-5-yl)phenyl)pteridin-4(3H)-one

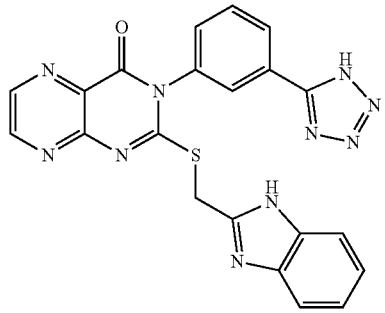

2-(((1H-Benzo[d]imidazol-2-yl)methyl)thio)-3-(3-(1H-tetrazol-5-yl)phenyl)pteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=455.0, RT: 0.835 min.

$^1$H-NMR (600 MHz, DMSO-$d_6$) δ 12.38 (s, 1H), 11.99 (s, 1H), 8.99 (d, J=2.2 Hz, 1H), 8.80 (d, J=2.2 Hz, 1H), 8.16 (dt, J=7.8, 1.3 Hz, 1H), 8.11-8.07 (m, 1H), 7.60 (t, J=7.8 Hz, 1H), 7.51 (s, 1H), 7.42 (s, 1H), 7.41-7.38 (m, 1H), 7.13 (s, 2H), 4.75 (d, J=14.8 Hz, 1H), 4.72 (d, J=14.8 Hz, 1H) ppm.

$^{13}$C-NMR (151 MHz, DMSO-$d_6$) δ 172.1, 161.7, 160.0, 159.8, 153.4, 150.0, 149.1, 143.4, 135.5, 134.4, 132.4, 129.7, 127.3, 127.2, 126.2, 122.2, 121.4, 118.6, 111.2, 30.2, 21.1 ppm.

HRMS (ESI) (m/z): [M+H]+ calcd for $C_{21}H_{15}N_{10}OS$, 455.1146; found, 455.1141.

Example Compound 85: 2-((3-(4-Cyanophenyl)-4-oxo-3,4-dihydropteridin-2-yl)-thio)-N-(thiazol-2-yl)acetamide

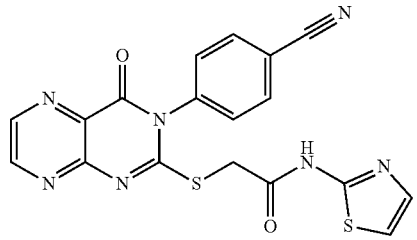 [SMILES: N#Cc1ccc(-n2c(SCC(=O)Nc3nccs3)nc3nccnc3c2=O)cc1]

2-((3-(4-Cyanophenyl)-4-oxo-3,4-dihydropteridin-2-yl)-thio)-N-(thiazol-2-yl)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=422.0, RT: 1.007 min.
HRMS (ESI) (m/z): [M+H]+ calcd for $C_{18}H_{12}N_7O_2S_2$, 422.0488; found, 422.0481.

Example Compound 86: 4-(2-(((1H-Benzo[d]imidazol-2-yl)methyl)thio)-4-oxopteridin-3(4H)-yl)benzonitrile

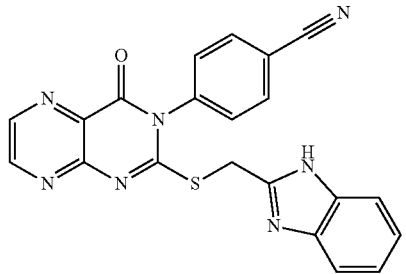 [SMILES: N#Cc1ccc(-n2c(SCc3nc4ccccc4[nH]3)nc3nccnc3c2=O)cc1]

4-(2-(((1H-Benzo[d]imidazol-2-yl)methyl)thio)-4-oxopteridin-3(4H)-yl)benzonitrile by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=412.0, RT: 0.892 min.
$^1$H NMR (600 MHz, DMSO-$d_6$) δ 12.40 (s, 1H), 9.01 (d, J=2.1 Hz, 1H), 8.82 (d, J=2.1 Hz, 1H), 8.16-8.11 (m, 2H), 7.85-7.80 (m, 2H), 7.57-7.40 (m, 4H), 7.16 (m, 2H), 4.77 (s, 2H) ppm.
$^{13}$C-NMR (151 MHz, DMSO-$d_6$) δ 161.1, 160.3, 153.7, 150.8, 149.3, 144.1, 143.5, 139.9, 134.8, 134.4, 132.8, 131.2, 122.8, 121.9, 119.0, 118.5, 113.8, 111.7, 30.7 ppm.
HRMS (ESI) (m/z): [M+H]+ calcd for $C_{21}H_{14}N_7OS$, 412.0975; found, 412.0978.

Example Compound 87: 2-((3-(2,3-Dihydro-1H-inden-2-yl)-4-oxo-3,4-dihydropteridin-2-yl)thio)-N-(thiazol-2-yl)acetamide

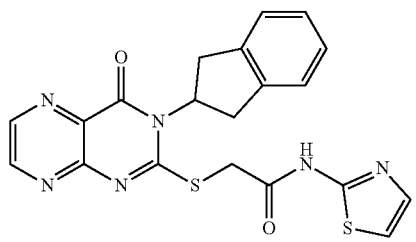 [SMILES: O=C(CSc1nc2nccnc2c(=O)n1C1Cc2ccccc2C1)Nc1nccs1]

2-((3-(2,3-Dihydro-1H-inden-2-yl)-4-oxo-3,4-dihydropteridin-2-yl)thio)-N-(thiazol-2-yl)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=436.9, RT: 1.084 min.
$^1$H NMR (600 MHz, DMSO-$d_6$) δ 8.88 (d, J=2.1 Hz, 1H), 8.72 (d, J=2.1 Hz, 1H), 7.48 (d, J=3.5 Hz, 1H), 7.26 (dt, J=7.2, 3.5 Hz, 2H), 7.22-7.18 (m, 3H), 5.49 (tt, J=9.6, 7.3 Hz, 1H), 4.45 (s, 2H), 3.65 (dd, J=16.1, 7.3 Hz, 2H), 3.39-3.33 (m, 2H) ppm.

$^{13}$C-NMR (151 MHz, DMSO-$d_6$) δ 166.1, 161.6, 160.3, 158.8, 152.5, 150.6, 144.1, 141.3, 138.2, 132.2, 126.9, 124.8, 114.0, 58.4, 36.9, 35.6 ppm.
HRMS (ESI) (m/z): [M+H]+ calcd for $C_{20}H_{17}N_6O_2S_2$, 437.0849; found, 437.0846.

Example Compound 88: 2-(((1H-Benzo[d]imidazol-2-yl)methyl)thio)-3-(2,3-dihydro-1H-inden-2-yl) pteridin-4(3H)-one

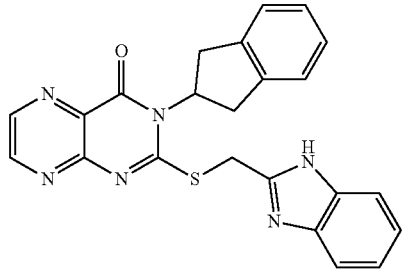 [SMILES: O=c1c2nccnc2nc(SCc2nc3ccccc3[nH]2)n1C1Cc2ccccc2C1]

2-(((1H-Benzo[d]imidazol-2-yl)methyl)thio)-3-(2,3-dihydro-1H-inden-2-yl)pteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=427.1, RT: 0.969 min.
HRMS (ESI) (m/z): [M+H]+ calcd for $C_{23}H_{19}N_6OS$, 427.1336; found, 427.1334.

Example Compound 89: (S)-2-((4-Oxo-3-(1-phenylethyl)-3,4-dihydropteridin-2-yl)-thio)-N-(thiazol-2-yl) acetamide

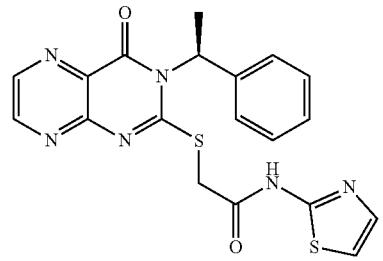 [SMILES: C[C@@H](c1ccccc1)n1c(SCC(=O)Nc2nccs2)nc2nccnc2c1=O]

(S)-2-((4-Oxo-3-(1-phenylethyl)-3,4-dihydropteridin-2-yl)-thio)-N-(thiazol-2-yl) acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=425.0, RT: 1.080 min.
$^1$H NMR (600 MHz, DMSO-$d_6$) δ 12.53 (s, 1H), 8.88 (d, J=2.1 Hz, 1H), 8.72 (d, J=2.1 Hz, 1H), 7.50 (d, J=3.6 Hz, 1H), 7.42 (dt, J=8.3, 1.1 Hz, 2H), 7.40-7.36 (m, 2H), 7.32-7.28 (m, 1H), 7.22 (d, J=3.6 Hz, 1H), 6.12 (br s, 1H), 4.46 (d, J=15.9 Hz, 1H), 4.41 (d, J=15.9 Hz, 1H), 2.01 (d, J=6.9 Hz, 3H) ppm.
$^{13}$C NMR (151 MHz, DMSO-$d_6$) δ 165.4, 161.0, 157.9, 152.1, 150.3, 143.7, 138.6, 137.7, 131.6, 128.3, 127.2, 126.3, 113.6, 36.4, 15.8 ppm.
HRMS (ESI) (m/z): [M+H]+ calcd for $C_{19}H_{17}N_6O_2S_2$, 425.0849; found, 425.0855.

Example Compound 90: (S)-2-(((1H-Benzo[d]imidazol-2-yl)methyl)thio)-3-(1-phenylethyl)pteridin-4(3H)-one

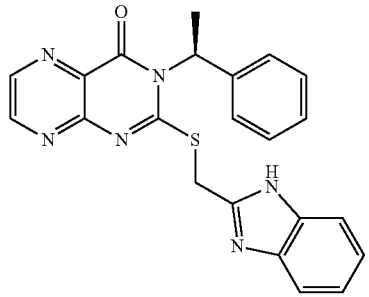 [SMILES: C[C@@H](c1ccccc1)n1c(SCc2nc3ccccc3[nH]2)nc2nccnc2c1=O]

(S)-2-(((1H-Benzo[d]imidazol-2-yl)methyl)thio)-3-(1-phenylethyl)pteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=415.0, RT: 0.950 min.

$^1$H NMR (600 MHz, DMSO-d$_6$) δ 8.95 (d, J=2.1 Hz, 1H), 8.77 (d, J=2.1 Hz, 1H), 7.53 (dt, J=5.9, 3.5 Hz, 2H), 7.42 (d, J=7.6 Hz, 2H), 7.35 (dd, J=8.5, 6.4 Hz, 2H), 7.28 (t, J=7.3 Hz, 1H), 7.21-7.16 (m, 2H), 4.93 (d, J=14.8 Hz, 1H), 4.87 (d, J=14.8 Hz, 1H), 1.99 (d, J=6.9 Hz, 3H) ppm.

$^{13}$C NMR (151 MHz, DMSO-d$_6$) δ 160.9, 159.6, 152.3, 150.3, 149.1, 143.8, 142.3, 138.7, 131.8, 128.3, 128.0, 127.2, 126.3, 122.0, 40.1, 30.5, 15.8 ppm.

HRMS (ESI) (m/z): [M+H]$^+$ calcd for C$_{22}$H$_{19}$N$_6$OS, 415.1336; found, 415.1347.

Example Compound 91: trans-Methyl 3-(4-oxo-2-((2-oxo-2-(thiazol-2-ylamino)ethyl)thio)pteridin-3(4H)-yl)cyclobutane-1-carboxylate

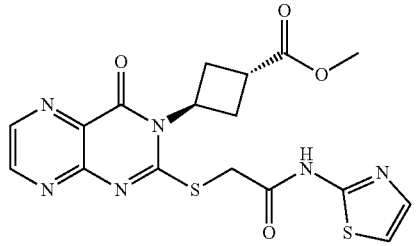 [SMILES: COC(=O)[C@H]1C[C@H](n2c(SCC(=O)Nc3nccs3)nc3nccnc3c2=O)C1]

trans-Methyl 3-(4-oxo-2-((2-oxo-2-(thiazol-2-ylamino)ethyl)thio)pteridin-3(4H)-yl)cyclobutane-1-carboxylate by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=433.0, RT: 0.988 min.

$^1$H NMR (600 MHz, DMSO-d$_6$) δ 12.51 (s, 1H), 8.86 (d, J=2.1 Hz, 1H), 8.74 (d, J=2.1 Hz, 1H), 7.48 (d, J=3.6 Hz, 1H), 7.21 (d, J=3.6 Hz, 1H), 5.22-5.15 (m, 1H), 4.40 (s, 2H), 3.70 (s, 3H), 2.67-2.60 (m, 2H) ppm (signals of three hydrogens of cyclobutyl group are overlapped with DMSO and water signals). $^{13}$C-NMR (151 MHz, DMSO-d$_6$) δ 175.9, 166.0, 161.2, 160.9, 158.5, 152.4, 150.6, 144.1, 138.2, 132.2, 114.1, 52.3, 52.0, 36.6, 32.3, 30.1 ppm.

HRMS (ESI) (m/z): [M+H]$^+$ calcd for C$_{17}$H$_{17}$N$_6$O$_4$S$_2$, 433.0747; found, 433.0748.

Example Compound 92: trans-Methyl-3-(2-(((1H-benzo[d]imidazol-2-yl)methyl)thio)-4-oxo-pteridin-3(4H)-yl)cyclobutane-1-carboxylate

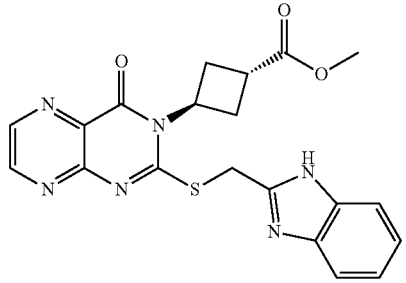 [SMILES: COC(=O)[C@H]1C[C@H](n2c(SCc3nc4ccccc4[nH]3)nc3nccnc3c2=O)C1]

trans-Methyl-3-(2-(((1H-benzo[d]imidazol-2-yl)methyl)thio)-4-oxo-pteridin-3(4H)-yl)cyclobutane-1-carboxylate by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=423.0, RT: 0.893 min.

$^1$H NMR (600 MHz, DMSO-d$_6$) δ 12.43 (s, 1H), 8.93 (d, J=2.1 Hz, 1H), 8.78 (d, J=2.1 Hz, 1H), 7.58 (br s, 1H), 7.47 (br s, 1H), 7.18 (d, 2H), 5.18 (dd, J=8.9, 7.0 Hz, 1H), 4.86 (s, 2H), 3.69 (s, 3H), 2.79-2.55 (m, 2H) ppm.

$^{13}$C NMR (151 MHz, DMSO-d$_6$) δ 175.4, 160.6, 160.5, 152.0, 150.1, 149.1, 143.7, 131.8, 122.3, 121.4, 118.5, 111.2, 51.8, 51.5, 31.8, 30.2, 29.6 ppm.

HRMS (ESI) (m/z): [M+H]$^+$ calcd for C$_{20}$H$_{19}$N$_6$O$_3$S, 423.1234; found, 423.1228.

Example Compound 93: tert-Butyl 4-(4-oxo-2-((2-oxo-2-(thiazol-2-ylamino)ethyl)thio)pteridin-3(4H)-yl)piperidine-1-carboxylate

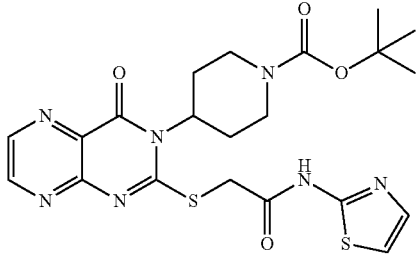 [SMILES: CC(C)(C)OC(=O)N1CCC(n2c(SCC(=O)Nc3nccs3)nc3nccnc3c2=O)CC1]

tert-Butyl 4-(4-oxo-2-((2-oxo-2-(thiazol-2-ylamino)ethyl)thio)pteridin-3(4H)-yl)piperidine-1-carboxylate by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=504.1, RT: 1.084 min.

$^1$H NMR (600 MHz, DMSO-d$_6$) δ 8.84 (d, J=2.1 Hz, 1H), 8.69 (d, J=2.1 Hz, 1H), 7.43 (d, J=3.6 Hz, 1H), 7.11 (d, J=3.6 Hz, 1H), 4.41 (s, 2H), 4.15 (s, 2H), 2.86 (s, 3H), 2.69 (tt, J=12.6, 6.2 Hz, 2H), 1.79 (dd, J=12.4, 4.1 Hz, 2H), 1.43 (s, 9H) ppm.

$^{13}$C NMR (151 MHz, DMSO-d$_6$) δ 163.6, 159.1, 158.5, 156.3, 152.2, 150.3, 148.5, 141.9, 135.9, 130.1, 111.0, 77.2, 68.2, 34.7, 27.4, 26.5, 25.3 ppm.

HRMS (ESI) (m/z): [M+H]+ calcd for $C_{21}H_{26}N_7O_4S_2$, 504.1482; found, 504.1477.

Example Compound 94: tert-Butyl 4-(2-(((1H-benzo[d]imidazol-2-yl)methyl)thio)4-oxopteridin-3(4H)-yl)piperidine-1-carboxylate

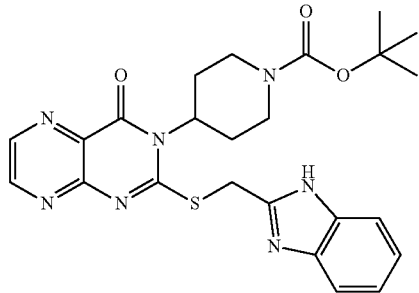 [SMILES: CC(C)(C)OC(=O)N1CCC(n2c(SCc3nc4ccccc4[nH]3)nc3nccnc3c2=O)CC1]

tert-Butyl 4-(2-(((1H-benzo[d]imidazol-2-yl)methyl)thio)4-oxopteridin-3(4H)-yl)piperidine-1-carboxylate by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=494.1, RT: 0.988 min.

$^1$H NMR (300 MHz, DMSO-$d_6$) δ 12.31 (s, 1H), 8.87 (br s, 1H), 8.70 (br s, 1H), 7.46 (m, 2H), 7.13 (br s, 1H), 4.85 (s, 2H), 4.15 (br s, 1H), 1.76 (d, J=8.6 Hz, 2H), 1.41 (s, 12H), 1.20 (s, 4H) ppm.

HRMS (ESI) (m/z): [M+H]+ calcd for $C_{24}H_{28}N_7O_3S$, 494.1969; found, 494.196.

Example Compound 95: 2-((3-(4-Hydroxyphenethyl)-4-oxo-3,4-dihydropteridin-2-yl) thio)-N-(thiazol-2-yl)acetamide

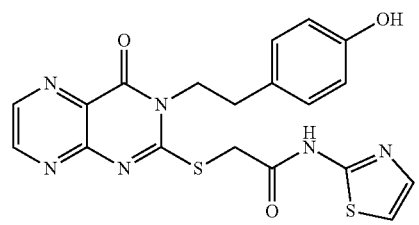 [SMILES: O=C(CSc1nc2nccnc2c(=O)n1CCc1ccc(O)cc1)Nc1nccs1]

2-((3-(4-Hydroxyphenethyl)-4-oxo-3,4-dihydropteridin-2-yl) thio)-N-(thiazol-2-yl)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=441.0, RT: 0.937 min.

$^1$H NMR (600 MHz, DMSO-$d_6$) δ 12.54 (s, 1H), 9.29 (s, 1H), 8.89 (d, J=2.1 Hz, 1H), 8.75 (d, J=2.1 Hz, 1H), 7.49 (d, J=3.6 Hz, 1H), 7.22 (d, J=3.6 Hz, 1H), 7.19-7.06 (m, 2H), 6.87-6.65 (m, 2H), 4.47 (s, 2H), 4.32-4.16 (m, 2H), 3.02-2.88 (m, 2H) ppm.

$^{13}$C NMR (151 MHz, DMSO-$d_6$) δ 165.9, 161.1, 160.0, 158.4, 156.6, 152.9, 150.8, 144.2, 138.2, 131.5, 130.1, 128.0, 115.9, 114.2, 47.0, 36.2, 32.7 ppm.

HRMS (ESI) (m/z): [M+H]+ calcd for $C_{19}H_{17}N_6O_3S_2$, 441.0798; found, 441.0795.

Example Compound 96: 2-(((1H-Benzo[d]imidazol-2-yl)methyl)thio)-3-(4-hydroxyphenethyl)pteridin-4(3H)-one

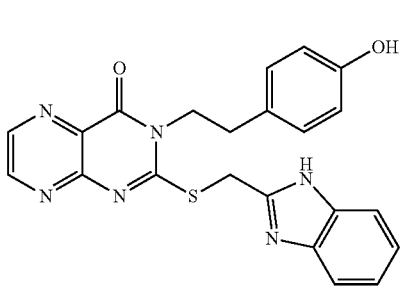 [SMILES: O=c1c2nccnc2nc(SCc2nc3ccccc3[nH]2)n1CCc1ccc(O)cc1]

2-(((1H-Benzo[d]imidazol-2-yl)methyl)thio)-3-(4-hydroxyphenethyl)pteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]+: m/e=431.0, RT: 0.892 min.

$^1$H NMR (600 MHz, DMSO-$d_6$) δ 12.45 (s, 1H), 9.28 (s, 1H), 8.95 (d, J=2.0 Hz, 1H), 8.79 (d, J=2.0 Hz, 1H), 7.58 (d, J=7.8 Hz, 1H), 7.46 (d, J=7.7 Hz, 1H), 7.16 (dt, J=15.0, 7.9 Hz, 2H), 7.10 (d, J=8.0 Hz, 2H), 6.76-6.68 (m, 2H), 4.91 (s, 2H), 4.33-4.14 (m, 2H), 3.06-2.80 (m, 2H) ppm.

$^{13}$C NMR (151 MHz, DMSO-$d_6$) δ 161.0, 160.1, 156.6, 153.0, 150.8, 149.6, 144.3, 143.5, 134.9, 131.6, 130.1, 128.0, 122.8, 121.9, 119.1, 115.9, 111.8, 46.9, 32.6, 30.2 ppm.

HRMS (ESI) (m/z): [M+H]+ calcd for $C_{22}H_{19}N_6O_2S$, 431.1285; found, 431.1284.

Example Compound 97: 2-((3-(9H-Fluoren-9-yl)-4-oxo-3,4-dihydropteridin-2-yl)-thio)-N-(thiazol-2-yl)acetamide

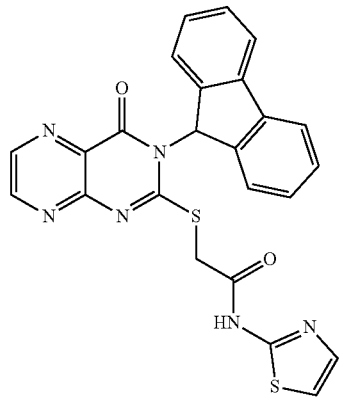 [SMILES: O=C(CSc1nc2nccnc2c(=O)n1C1c2ccccc2-c2ccccc21)Nc1nccs1]

2-((3-(9H-Fluoren-9-yl)-4-oxo-3,4-dihydropteridin-2-yl)-thio)-N-(thiazol-2-yl)acetamide by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=485.0, RT: 1.141 min.

$^1$H NMR (600 MHz, DMSO-d$_6$) δ 12.64 (s, 1H), 12.23 (s, 1H), 8.93 (d, J=2.2 Hz, 1H), 8.88 (d, J=2.1 Hz, 1H), 8.83 (d, J=2.2 Hz, 1H), 8.65 (d, J=2.1 Hz, 1H), 8.01 (dd, J=7.6, 1.0 Hz, 2H), 7.97 (dt, J=7.7, 0.8 Hz, 2H), 7.59-7.57 (m, 3H), 7.55 (dd, J=7.6, 1.0 Hz, 2H), 7.52 (d, J=4.2 Hz, 1H), 7.51 (t, J=7.6 Hz, 2H), 7.46 (t, J=7.5 Hz, 1H), 7.43 (d, J=3.5 Hz, 1H), 7.37 (td, J=7.6, 1.1 Hz, 2H), 7.32 (td, J=7.5, 1.1 Hz, 1H), 7.25 (d, J=3.6 Hz, 1H), 7.15 (d, J=3.6 Hz, 1H), 6.56 (s, 1H), 4.64 (s, 2H), 3.96 (s, 2H) ppm.

$^{13}$C NMR (151 MHz, DMSO-d$_6$) δ 165.9, 165.6, 162.2, 162.1, 160.8, 158.4, 158.3, 158.2, 152.8, 150.8, 150.7, 144.3, 141.0, 140.7, 144.3, 144.2, 140.8, 140.4, 138.3, 138.1, 131.8, 131.7, 129.5, 128.9, 128.3, 127.9, 124.9, 123.5, 121.4, 121.0, 114.2, 113.9, 63.5, 57.9, 37.2, 36.5 ppm.

HRMS (ESI) (m/z): [M+H]$^+$ calcd for $C_{24}H_{17}N_6O_2S_2$, 485.0849; found, 485.087.

Example Compound 98: 2-(((1H-Benzo[d]imidazol-2-yl)methyl)thio)-3-(9H-fluoren-9-yl)pteridin-4(3H)-one

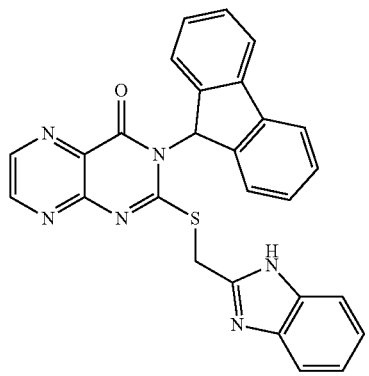 [SMILES: O=c1c2nccnc2nc(SCc2nc3ccccc3[nH]2)n1C1c2ccccc2-c2ccccc21]

2-(((1H-Benzo[d]imidazol-2-yl)methyl)thio)-3-(9H-fluoren-9-yl)pteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=475.1, RT: 1.007 min.

$^1$H NMR (600 MHz, DMSO-d$_6$) δ 12.52 (s, 1H), 12.02 (s, 1H), 9.02 (d, J=2.2 Hz, 1H), 8.95 (d, J=2.1 Hz, 1H), 8.90 (d, J=2.2 Hz, 1H), 8.70 (d, J=2.1 Hz, 1H), 7.95 (ddt, J=7.6, 4.4, 0.9 Hz, 4H), 7.60 (d, J=7.9 Hz, 1H), 7.50 (d, J=7.9 Hz, 1H), 7.35 (d, J=7.9 Hz, 1H), 7.23-7.19 (m, 1H), 7.19-7.15 (m, 1H), 7.12 (t, J=7.5 Hz, 1H), 7.08 (t, J=7.6 Hz, 1H), 6.55 (s, 1H), 5.08 (s, 2H), 4.46 (s, 2H) ppm.

$^{13}$C NMR (151 MHz, DMSO-d$_6$) δ 162.3, 162.1, 160.6, 158.3, 153.0, 152.9, 150.9, 150.8, 149.6, 149.1, 144.4, 144.3, 143.5, 143.3, 141.1, 140.7, 140.6, 140.4, 135.0, 134.6, 131.9, 131.9, 129.4, 128.8, 128.2, 127.9, 124.7, 123.6, 122.9, 122.8, 121.9, 121.8, 121.5, 120.9, 119.1, 119.0, 111.8, 111.7, 63.4, 57.9, 31.4, 30.5 ppm.

HRMS (ESI) (m/z): [M+H]$^+$ calcd for $C_{27}H_{19}N_6OS$, 475.1336; found, 475.1332.

Example Compound 99: trans-2-(((1H-Benzo[d]imidazol-2-yl)methyl)thio)-3-(2-phenylcyclopropyl)pteridin-4(3H)-one

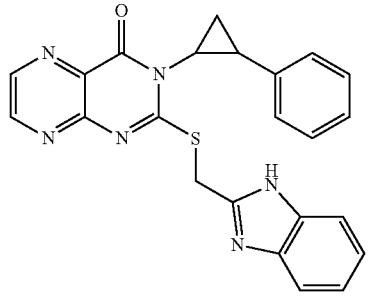 [SMILES: O=c1c2nccnc2nc(SCc2nc3ccccc3[nH]2)n1C1CC1c1ccccc1]

trans-2-(((1H-Benzo[d]imidazol-2-yl)methyl)thio)-3-(2-phenylcyclopropyl)pteridin-4(3H)-one by adapting the procedures described in example 1 for the synthesis of N-(4-(3-hydroxyphenyl)thiazol-2-yl)-2-((4-oxo-3-phenethyl-3,4-dihydropteridin-2-yl)thio)acetamide.

MS (ES+) [M+H]$^+$: m/e=427.0, RT: 0.988 min.

$^1$H NMR (300 MHz, DMSO-d$_6$) δ 12.38 (s, 1H), 8.92 (d, J=2.1 Hz, 1H), 8.77 (d, J=2.1 Hz, 1H), 7.56 (d, J=6.4 Hz, 1H), 7.44 (d, J=7.2 Hz, 1H), 7.32 (d, J=4.3 Hz, 4H), 7.24 (d, J=4.5 Hz, 1H), 7.16 (dd, J=7.4, 3.9 Hz, 2H), 4.86 (d, J=14.9 Hz, 1H), 4.80 (d, J=14.9 Hz, 1H), 3.13 (dd, J=7.0, 3.8 Hz, 1H), 2.58 (dt, J=7.5, 4.2 Hz, 1H), 1.82 (q, J=6.9 Hz, 1H), 1.68 (dt, J=10.2, 5.3 Hz, 1H) ppm.

$^{13}$C NMR (151 MHz, DMSO-d$_6$) δ 163.8, 161.0, 152.9, 150.4, 150.0, 143.9, 139.8, 132.2, 128.7, 127.0, 126.8, 122.7, 121.8, 119.0, 111.7, 36.3, 30.2, 27.7, 19.5 ppm.

HRMS (ESI) (m/z): [M+H]$^+$ calcd for $C_{23}H_{19}N_6OS$, 427.1336; found, 427.1332.

Example Compound 100: 3-(4-Oxo-3-phenethyl-3,4-dihydropteridin-2-yl)-N-phenylpropanamide i) 3-Amino-N-phenethylpyrazine-2-carboxamide

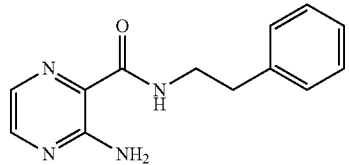 [SMILES: Nc1nccnc1C(=O)NCCc1ccccc1]

Methyl 3-aminopyrazine-2-carboxylate (117 mg, 0.77 mmol) was dissolved in phenethylamine (1.15 mL) at RT. To the resulting mixture was added 1,8-diazabicyclo[5.4.0]undec-7-ene,DBU, (1.93 g, 12.8 mmol) dropwise. The mixture was stirred at RT overnight. The reaction was quenched with H$_2$O and extracted with chloroform (three times). Combined organic phases were washed with brine solution, dried over Na$_2$SO$_4$, filtered, and concentrated under vacuum. The crude product was purified by column chromatography (0 to 5% MeOH in DCM).

Yield: 170 mg, 91%

MS (ES+) [M+H]$^+$: m/e=243.1, RT: 1.082 min.

ii) Methyl 4-oxo-4-((3-(phenethylcarbamoyl)pyrazin-2-yl)amino)butanoate

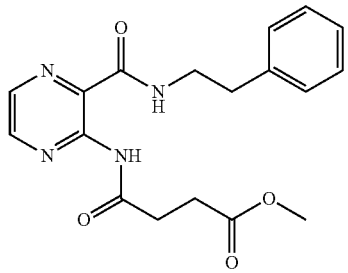 [SMILES: COC(=O)CCC(=O)Nc1nccnc1C(=O)NCCc1ccccc1]

To a solution of 3-amino-N-phenethylpyrazine-2-carboxamide (2.58 g, 10.7 mmol) in dry DCM (30 mL) was added pyridine (4.3 mL) under nitrogen atmosphere. At 0° C., methyl 4-chloro-4-oxobutanoate (1.93 g, 12.8 mmol) was added to the reaction mixture dropwise. The mixture was stirred for 30 min at 0° C., then for 1 h at RT. The reaction was quenched with water and extracted with DCM (three times). Combined organic phases were dried over $Na_2SO_4$, filtered, and concentrated under reduced pressure. The crude product was purified by column chromatography (0 to 10% MeOH in DCM).

Yield: 3.19 g, 84%

MS (ES+) [M+H]$^+$: m/e=357.1, RT: 1.090 min.

iii) Methyl 3-(4-oxo-3-phenethyl-3,4-dihydropteridin-2-yl)propanoate

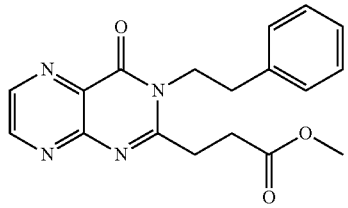 [SMILES: COC(=O)CCc1nc2nccnc2c(=O)n1CCc1ccccc1]

To a solution of methyl 4-oxo-4-((3-(phenethylcarbamoyl)pyrazin-2-yl)amino)butanoate (865 mg, 2.43 mmol) and $Et_3N$ (3.38 mL, 24.3 mmol) in dry toluene (18 mL) was added chlorotrimethylsilane (3.71 mL, 29.2 mmol) dropwise. The mixture was refluxed overnight. The reaction was stopped and cooled down to RT before quenching with $H_2O$. It was extracted with ethyl acetate (three times). Combined organic phases were washed with HCl (1 M), water, and brine solution. The organic phase was dried over $Na_2SO_4$, filtered, and concentrated under reduced pressure. The crude product was purified by column chromatography (0 to 5% MeOH in DCM).

Yield: 501 mg, 61%

MS (ES+) [M+H]$^+$: m/e=339.1, RT: 1.009 min.

iv) 3-(4-Oxo-3-phenethyl-3,4-dihydropteridin-2-yl)propanoic acid

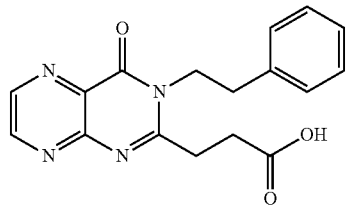 [SMILES: O=C(O)CCc1nc2nccnc2c(=O)n1CCc1ccccc1]

A 5-mL microwave vessel was charged with lithium iodide (3 g, 22.4 mmol) and it was heated with a heat gun under vacuum. Methyl 3-(4-oxo-3-phenethyl-3,4-dihydropteridin-2-yl)propanoate (470 mg, 1.4 mmol) and dry pyridine (1 mL) were added under nitrogen atmosphere. The mixture was stirred at 140° C. for 3 h under microwave irradiation. The reaction mixture was quenched with water and extracted with chloroform (three times). The combined organic phases were washed with HCl (1 M) and water. then dried over $Na_2SO_4$. The solution was filtered, concentrated under vacuum and the product was purified by column chromatography (0 to 10% MeOH in DCM).

Yield: 44 mg, 10%

MS (ES+) [M+H]$^+$: m/e=325.0, RT: 0.930 min.

v) 3-(4-Oxo-3-phenethyl-3,4-dihydropteridin-2-yl)-N-phenylpropanamide

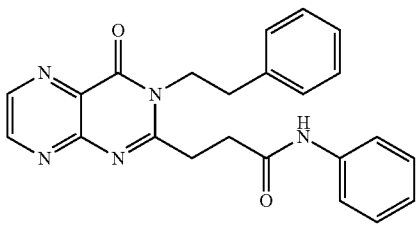 [SMILES: O=C(CCc1nc2nccnc2c(=O)n1CCc1ccccc1)Nc1ccccc1]

To a solution of 3-(4-oxo-3-phenethyl-3,4-dihydropteridin-2-yl)propanoic acid (25 mg, 0.077 mmol) in dry DMF (2 mL) was added HATU (59 mg, 0.154 mmol) and the mixture was stirred for 15 min under nitrogen atmosphere. In a separate flask, aniline (7 mg, 0.077 mmol) and DIPEA (20 mg, 0.154 mmol) were dissolved in 1 mL of dry DMF and the resulting solution was added to the reaction mixture dropwise at rt. It was then stirred overnight. All volatiles were evaporated under reduced pressure and the the product was purified by column chromatography (0 to 100% ethyl acetate in cyclohexane).

Yield: 6 mg, 20%

MS (ES+) [M+H]$^+$: m/e=400.0, RT: 1.074 min.

$^1$H NMR (300 MHz, DMSO-d$_6$) δ 10.13 (s, 1H), 8.97 (d, J=2.0 Hz, 1H), 8.83 (d, J=2.0 Hz, 1H), 7.60 (d, J=8.0 Hz, 2H), 7.40-7.21 (m, 7H), 7.01 (t, J=7.3 Hz, 1H), 4.42-4.29 (m, 2H), 3.24 (t, J=6.7 Hz, 2H), 3.11-3.00 (m, 2H), 2.96 (t, J=6.7 Hz, 2H).

Example Compound 101: N-Benzyl-3-(4-oxo-3-phenethyl-3,4-dihydropteridin-2-yl)propanamide

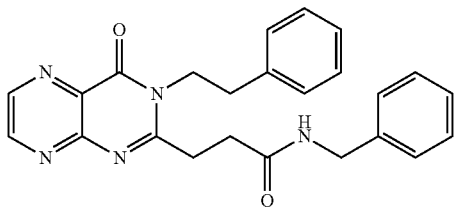 [SMILES: O=C(CCc1nc2nccnc2c(=O)n1CCc1ccccc1)NCc1ccccc1]

N-Benzyl-3-(4-oxo-3-phenethyl-3,4-dihydropteridin-2-yl)propanamide by adapting the procedures described in example 100 for the synthesis of 3-(4-oxo-3-phenethyl-3,4-dihydropteridin-2-yl)-N-phenylpropanamide.

MS (ES+) [M+H]$^+$: m/e=414.1, RT: 1.061 min.

Example Compound 102: 3-(4-Oxo-3-phenethyl-3,4-dihydropteridin-2-yl)-N-phenethylpropanamide

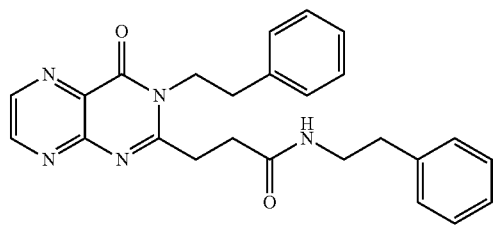 [SMILES: O=C(CCc1nc2nccnc2c(=O)n1CCc1ccccc1)NCCc1ccccc1]

3-(4-Oxo-3-phenethyl-3,4-dihydropteridin-2-yl)-N-phenethylpropanamide by adapting the procedures described in example 100 for the synthesis of 3-(4-oxo-3-phenethyl-3,4-dihydropteridin-2-yl)-N-phenylpropanamide.

MS (ES+) [M+H]$^+$: m/e=428.1, RT: 1.096 min.
$^1$H NMR (300 MHz, DMSO-d$_6$) δ 8.99 (d, J=2.0 Hz, 1H), 8.83 (d, J=2.0 Hz, 1H), 8.09 (t, J=5.6 Hz, 1H), 7.38-7.11 (m, 9H), 4.37-4.25 (m, 2H), 3.31-3.22 (m, 2H), 3.12 (t, J=6.9 Hz, 2H), 3.06-2.96 (m, 2H), 2.75-2.62 (m, 4H).

The invention claimed is:
1. A compound according to Formula 1,

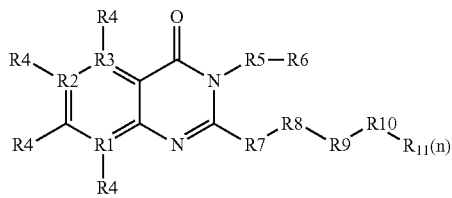

Formula 1 wherein
R1: N;
R2: C;
R3: N;
R4: can be the same or different, H, halogen, C1-C5 alkyl, C1-C5 haloalkyl, hydroxyl, alkoxy, cycloalkyl, —CN, carbonyl, carboxyl, carboxy ester, alkoxy, aldehyde, trihalide methyl ester, primary, secondary or tertiary amine, amide, imide, carbamate, carboxamide, nitro, sulfide, sulfurtrihalide, sulfurpentahalide, sulfinyl, sulfonyl, sulfino, sulfo, sulfonamide, or —OCF$_3$;
wherein R4 attached to R1 and R3 is absent;
R5: absent (covalent bond to R6), C1-C5 alkyl, cycloalkyl, aryl, C1-C5 alkyl-cycloalkyl, C1-C5 alkyl-aryl, or a partially saturated bicyclic aryl;
wherein R5 is optionally substituted with one or more halogens, C1-C5 alkyl, C1-C5 haloalkyl, hydroxyl, or alkoxy;
wherein R5 is optionally substituted with at least two substituents, said two substituents forming R6, attached to adjacent atoms of R5, to form as R6 a 5- to 8-membered saturated, partially unsaturated or aromatic cyclic group comprising said adjacent two atoms of R5;
R6: cycloalkyl, aryl, heterocyclyl, or heteroaryl, wherein R6 is optionally substituted with one or more halogens, C1-C5 alkyl, C1-C5 haloalkyl, hydroxyl, alkoxy, C2-C10 alkynyl, C3-C8 cycloalkyl, a 5- or 6-membered heterocyclyl or heteroaryl comprising one or more of N, O and/or S, carbonyl, C1-C5 alkyl carboxyester, carboxamide, C1-C5 alkyl carboxamide, primary, secondary or tertiary amine, carbamate, amide amine, nitro, —CN, O, sulfide, amine sulfoxide, sulfonamide amine, sulfoxide, sulfone, sulfonamide haloalkyl, cyano, —OCF$_3$, carbamate, imide, —SF$_3$, —SF$_5$, or sulfonamide, said sulfonamide optionally substituted with a 5- or 6-membered heterocyclyl or heteroaryl comprising one or more of N, O and/or S, wherein said heteroaryl is optionally substituted with alkyl;
R7: S;
R8: C1 alkyl, optionally substituted with C1 alkyl;
R9: absent (covalent bond to R10) or amide;
R10: 5-membered heteroaryl, except for pyrazolyl, or tetrahydrofurfuryl, wherein optionally a C1-C5 alkyl is positioned between R9 and R10; and
R11 (n): n is 0-5, may be the same or different, halogen, C1-C5 alkyl, CN, C1-C5 haloalkyl, hydroxyl, alkoxy, alkoxycarbonyl, cycloalkyl, aryl, C1-C5 alkyl-cycloalkyl, C1-C5 alkyl-aryl, heterocyclyl, heteroaryl, carboxamide, or C1-C5 alkyl carboxamide;
wherein optionally, two R11 form, together with two carbon atoms of R10 to which they are attached, a 5-, 6-, 7- or 8-membered cyclic residue, comprising two carbon atoms of R10 and optionally further comprising 0, 1, 2, 3 or 4 heteroatoms, said heteroatoms selected independently from nitrogen, sulfur or oxygen, wherein said cyclic residue as R11 is saturated, partially unsaturated or aromatic, and optionally substituted by one or more substituents,
wherein optionally, when R11 is aryl, heterocyclyl or heteroaryl and R11 is substituted with at least two substituents, two substituents of R11 attached to adjacent atoms of R11 form a 5- to 8-membered saturated, partially unsaturated or aromatic cyclic group comprising two atoms of R11 and further comprising 0, 1, 2, 3 or 4 heteroatoms, said heteroatoms selected independently from nitrogen, sulfur or oxygen, wherein said saturated, partially unsaturated or aromatic cyclic group is optionally substituted by one or more of R, wherein R is independently selected from the group consisting of H, alkyl, haloalkyl, alkoxy, or amine, and
wherein R11 is optionally substituted with one or more substituents selected from the group consisting of one or more halogens, C1-C5 alkyl, C1-C5 haloalkyl, hydroxyl, alkoxy, C2-C10 alkynyl, C3-C8 cycloalkyl, carbonyl, C1-C5 alkyl carboxyester, carboxamide, C1-C5 alkyl carboxamide, primary, secondary or tertiary amine, carbamate, amide amine, nitro, —CN, O, sulfide, amine sulfoxide, sulfonamide, alkyl sulfonamide, sulfonamide amine, sulfoxide, sulfone, sulfonamide haloalkyl, —OCF$_3$, carbamate, imide, —SF$_3$, and —SF$_5$.

2. The compound according to claim 1, according to Formula 2b,

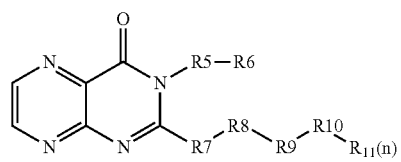

Formula 2b wherein R5, R6, R7, R8, R9, R10 and R11 are according to claim 1.

3. The compound according to claim 1, wherein R5-R6 is one of:

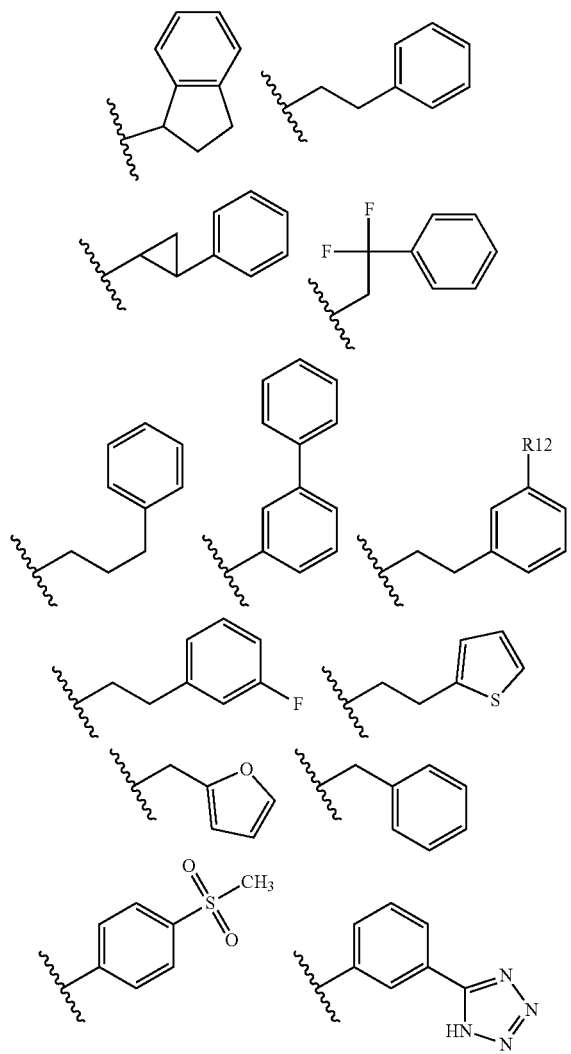

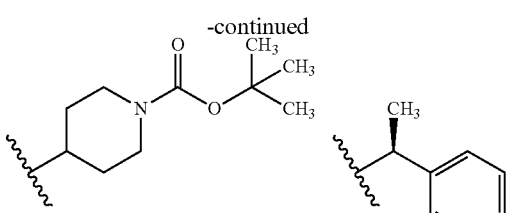

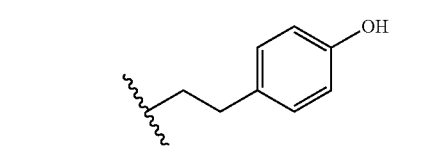

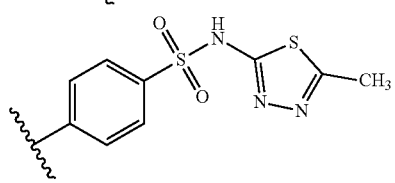

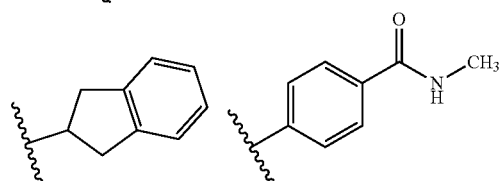

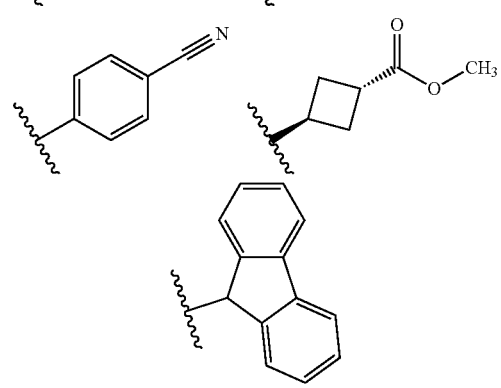

wherein R12: halogen, or C1-C5 haloalkyl.

4. The compound according to claim 1, according to Formula 3,

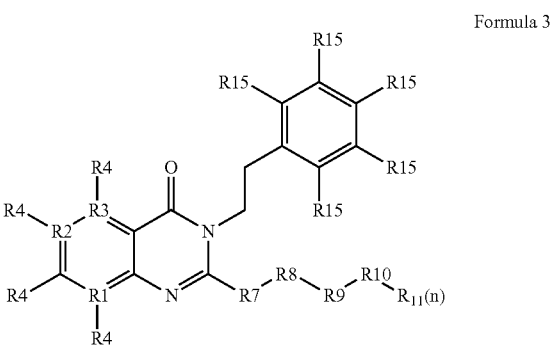

Formula 3 wherein
R15: may be the same or different, H, halogen C1-C5 alkyl, C1-C5 haloalkyl, hydroxyl, or alkoxy;
and R1, R2, R3, R4, R7, R8, R9, R10 and R11 are according to claim 1.

5. The compound according to claim 1, according to Formula 4,
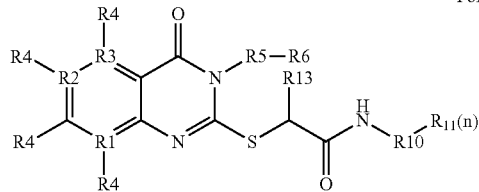
Formula 4
wherein
R13: H or CH₃, and
R1, R2, R3, R4, R5 and R6 and R10 and R11 are according to claim 1.
6. The compound according to claim 1, wherein R10-R11 is one of:
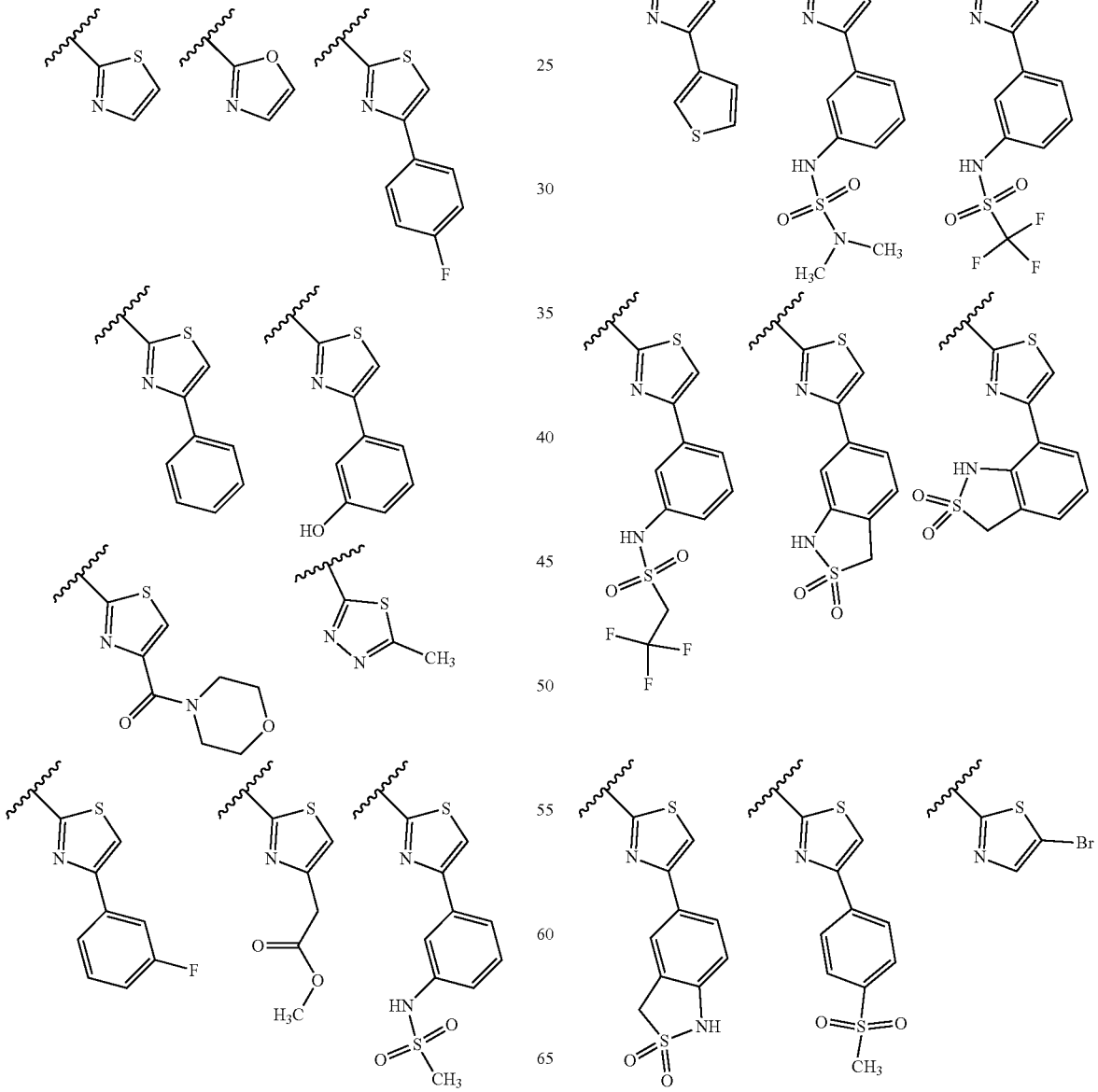
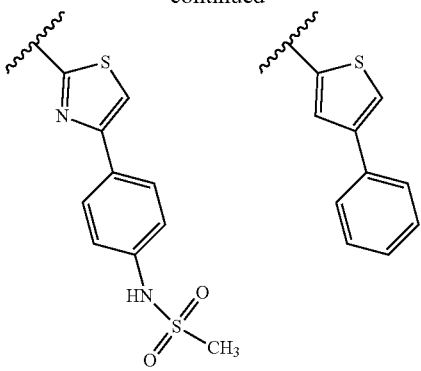

175
-continued
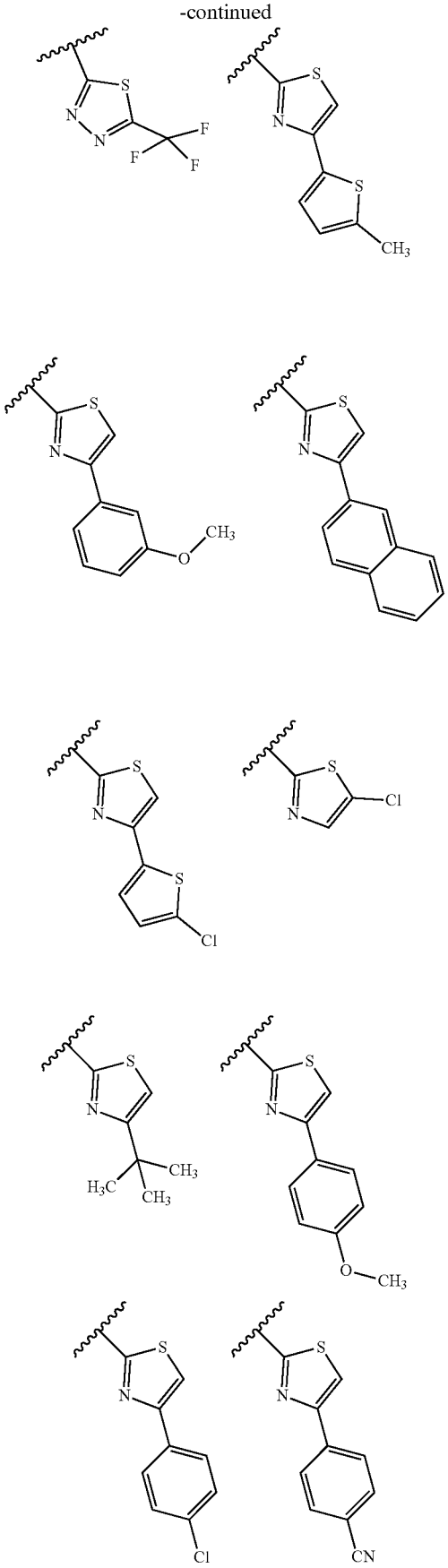
176
-continued
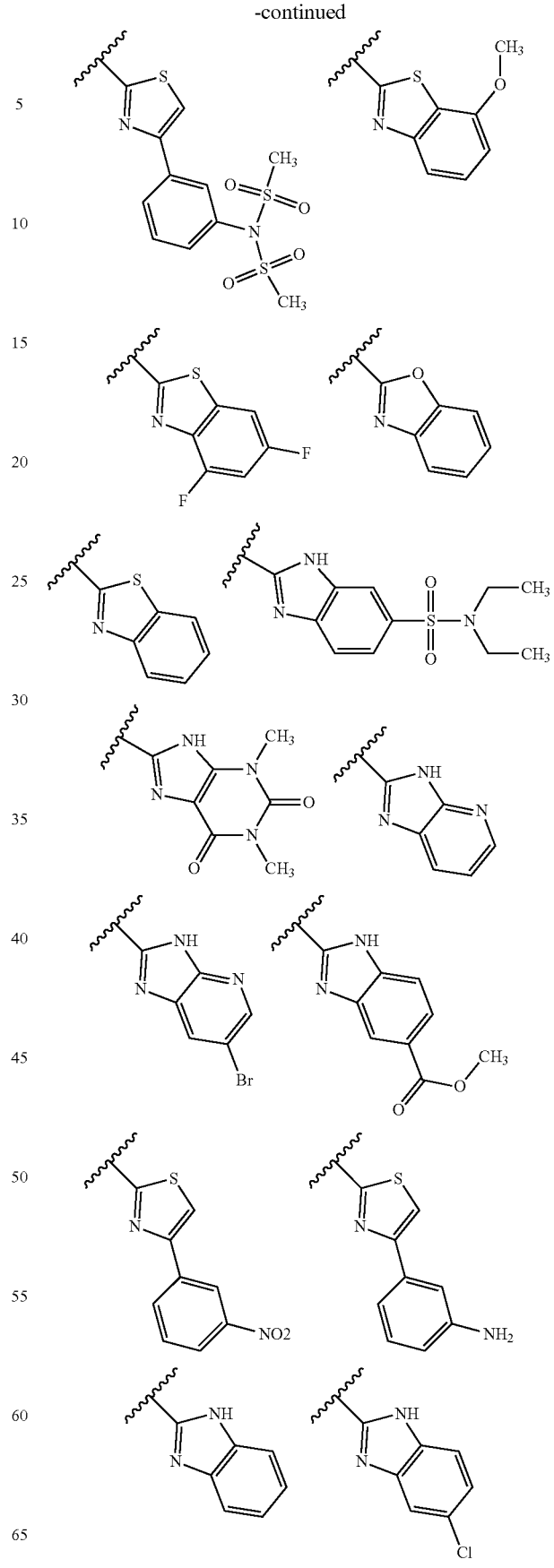

-continued

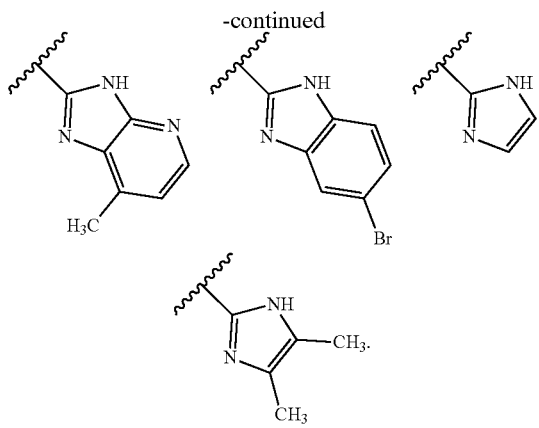

7. The compound according to claim 1, according to Formula 5,

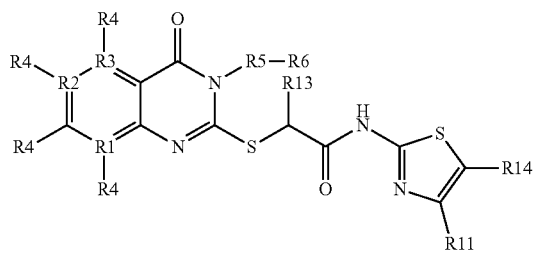

Formula 5 wherein R1, R2, R3, R4, R5 and R6 are according to claim 1;
R14: H, halogen, or C1-C5 alkyl; and
R11: halogen, C1-C5 alkyl, CN, C1-C5 haloalkyl, hydroxyl, alkoxy, alkoxycarbonyl, cycloalkyl, aryl, C1-C5 alkyl-cycloalkyl, C1-C5 alkyl-aryl, heterocyclyl, heteroaryl, carboxamide, or C1-C5 alkyl carboxamide;
wherein R11 is optionally substituted with one or more substituents selected from the group consisting of one or more halogens, C1-C5 alkyl, C1-C5 haloalkyl, hydroxyl, alkoxy, C2-C10 alkynyl, C3-C8 cycloalkyl, carbonyl, C1-C5 alkyl carboxyester, carboxamide, C1-C5 alkyl carboxamide, primary, secondary or tertiary amine, carbamate, amide amine, nitro, —CN, O, sulfide, amine sulfoxide, sulfonamide, sulfonamide amine, sulfoxide, sulfone, sulfonamide haloalkyl, —OCF₃, carbamate, imide, —SF₃, and —SF₅,
wherein optionally, when R11 is aryl, heterocyclyl or heteroaryl and R11 is substituted with at least two substituents, two substituents of R11 attached to adjacent atoms of R11 form a 5- to 8-membered saturated, partially unsaturated or aromatic cyclic group comprising two atoms of R11 and further comprising 0, 1, 2, 3 or 4 heteroatoms, said heteroatoms selected independently from nitrogen, sulfur or oxygen, wherein said saturated, partially unsaturated or aromatic cyclic group is optionally substituted by one or more of R, wherein R is independently selected from the group consisting of H, alkyl, haloalkyl, alkoxy, and amine,
wherein optionally, R11 and R14 form, together with the two carbon atoms of the adjacent 5-membered ring structure to which they are attached, a 5-, 6-7- or 8-membered cyclic residue, optionally further comprising 0, 1, 2, 3 or 4 heteroatoms, said heteroatoms selected independently from nitrogen, sulfur or oxygen, wherein said cyclic residue is saturated, partially unsaturated or aromatic, and optionally substituted with the substituents above for R11.

8. The compound according to claim 1, according to Formula 7,

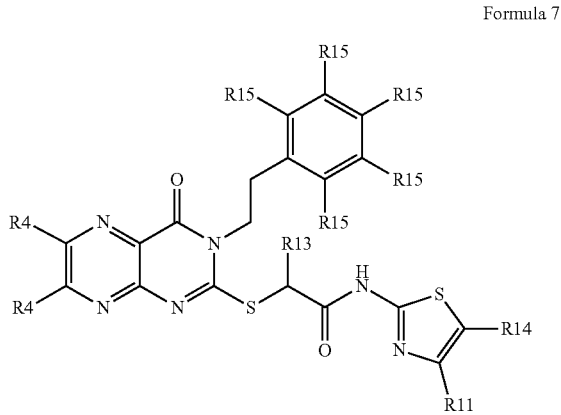

Formula 7 wherein
R4 is according to claim 1;
R13: H or CH₃;
R14: H, halogen, or C1-C5 alkyl;
R15: may be the same or different, H, halogen C1-C5 alkyl, C1-C5 haloalkyl, hydroxyl, or alkoxy; and
R11: halogen, C1-C5 alkyl, CN, C1-C5 haloalkyl, hydroxyl, alkoxy, alkoxycarbonyl, cycloalkyl, aryl, C1-C5 alkyl-cycloalkyl, C1-C5 alkyl-aryl, heterocyclyl, heteroaryl, carboxamide, or C1-C5 alkyl carboxamide;
wherein R11 is optionally substituted with one or more substituents selected from the group consisting of one or more halogens, C1-C5 alkyl, C1-C5 haloalkyl, hydroxyl, alkoxy, C2-C10 alkynyl, C3-C8 cycloalkyl, carbonyl, C1-C5 alkyl carboxyester, carboxamide, C1-C5 alkyl carboxamide, primary, secondary or tertiary amine, carbamate, amide amine, nitro, —CN, O, sulfide, amine sulfoxide, sulfonamide, sulfonamide amine, sulfoxide, sulfone, sulfonamide haloalkyl, —OCF₃, carbamate, imide, —SF₃, and —SF 5,
wherein optionally, when R11 is aryl, heterocyclyl or heteroaryl and R11 is substituted with at least two substituents, two substituents of R11 attached to adjacent atoms of R11 form a 5- to 8-membered saturated, partially unsaturated or aromatic cyclic group comprising two atoms of R11 and further comprising 0, 1, 2, 3 or 4 heteroatoms, said heteroatoms selected independently from nitrogen, sulfur or oxygen, wherein said saturated, partially unsaturated or aromatic cyclic group is optionally substituted by one or more of R, wherein R is independently selected from the group consisting of H, alkyl, haloalkyl, alkoxy, and amine,
wherein optionally, R11 and R14 form, together with the two carbon atoms of the adjacent 5-membered ring structure to which they are attached, a 5-, 6-7- or 8-membered cyclic residue, optionally further comprising 0, 1, 2, 3 or 4 heteroatoms, said heteroatoms selected independently from nitrogen, sulfur or oxygen, wherein said cyclic residue is saturated, partially unsaturated or aromatic, and optionally substituted with the substituents above for R11.
9. The compound according to claim 1, selected from the group consisting of:
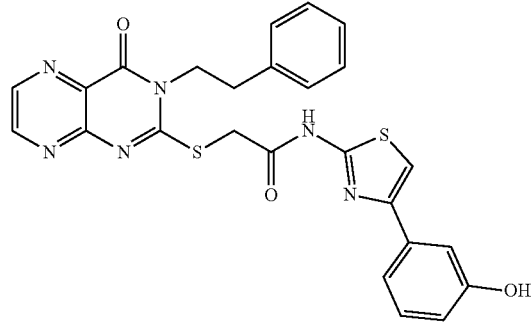
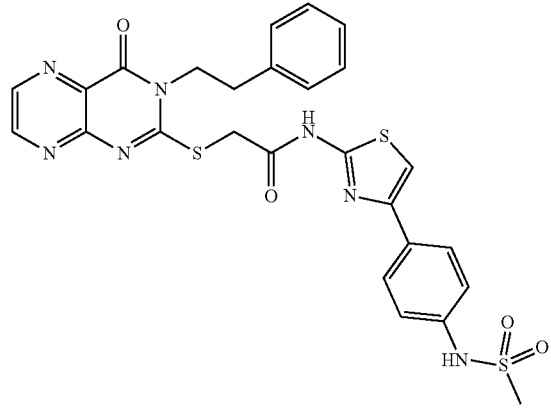
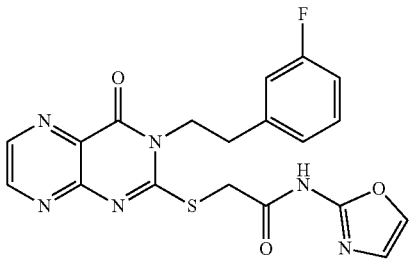
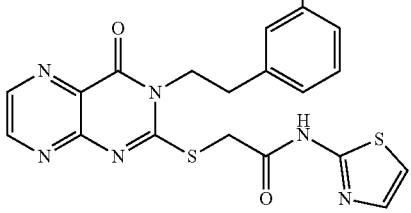
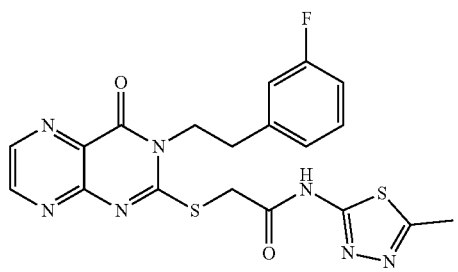
-continued
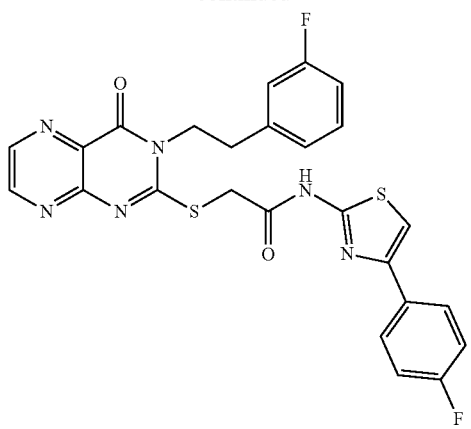
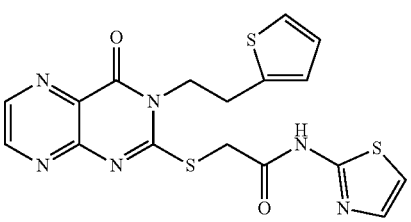
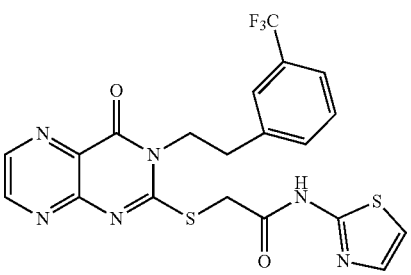
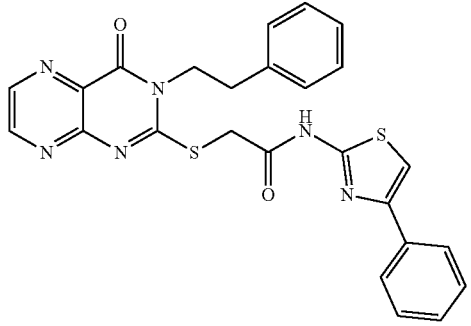
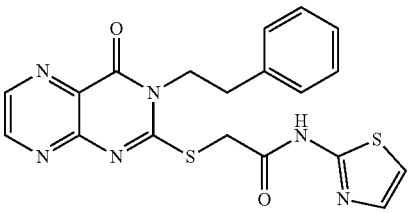

181
-continued
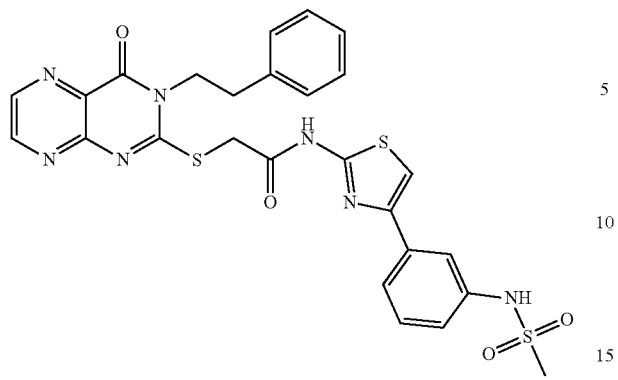
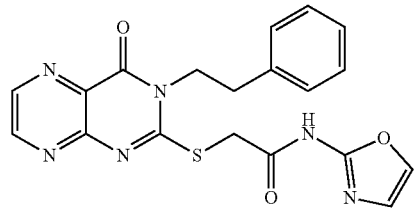
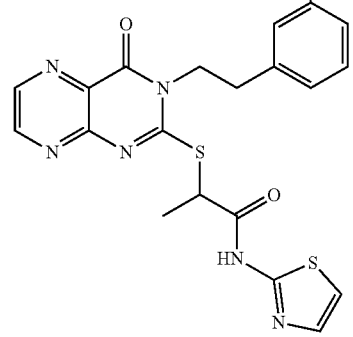
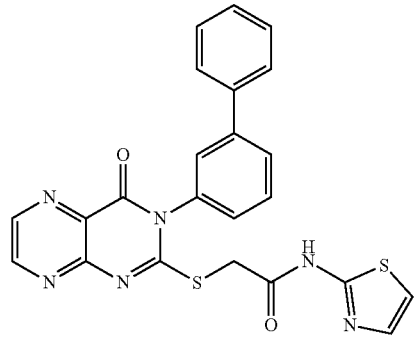
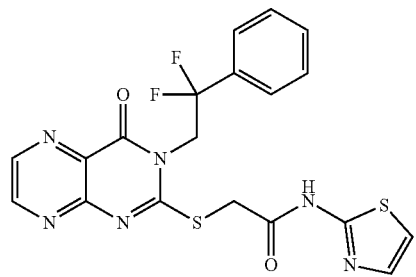
182
-continued
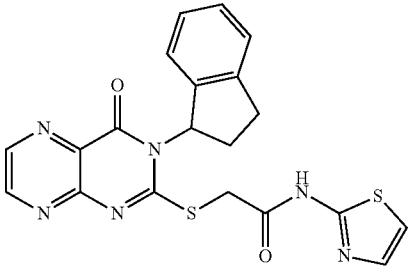
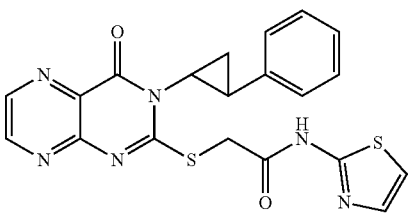
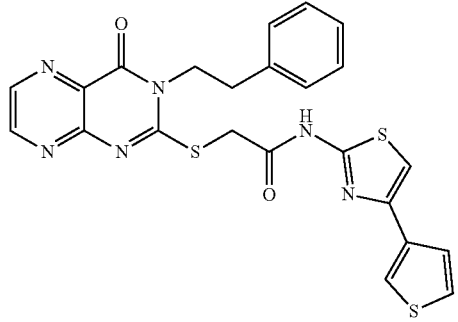
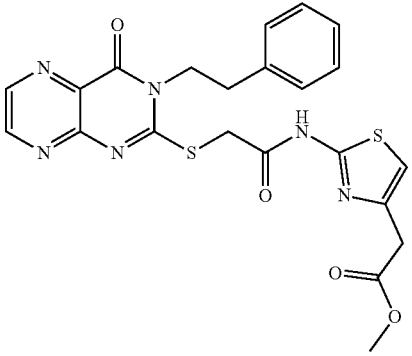
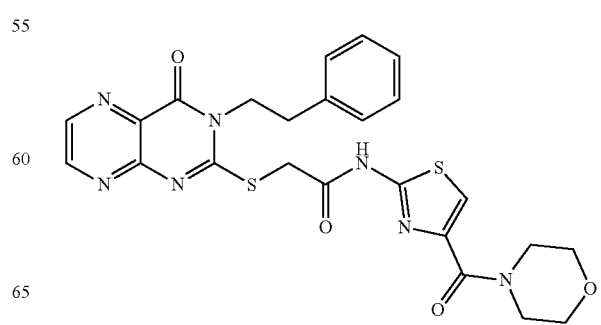

183
-continued
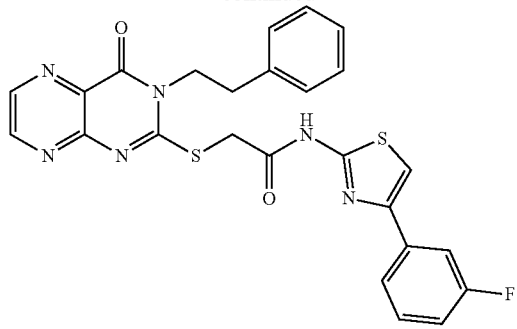
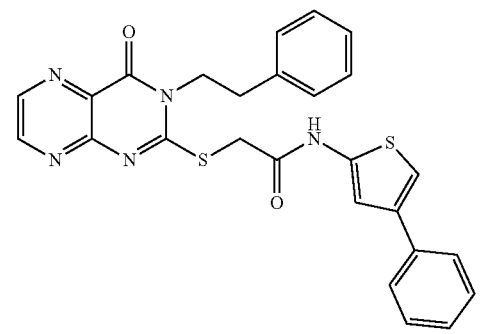
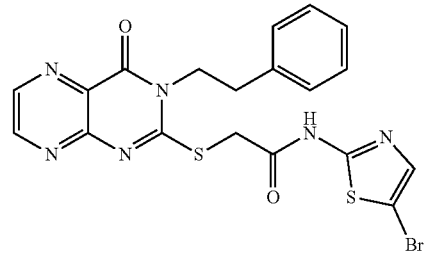
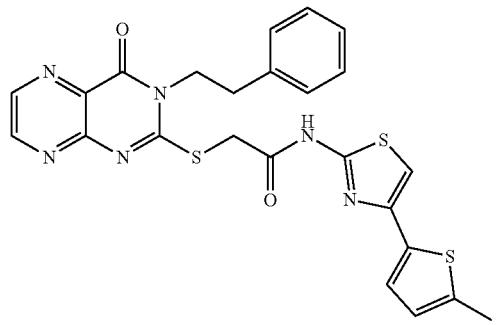
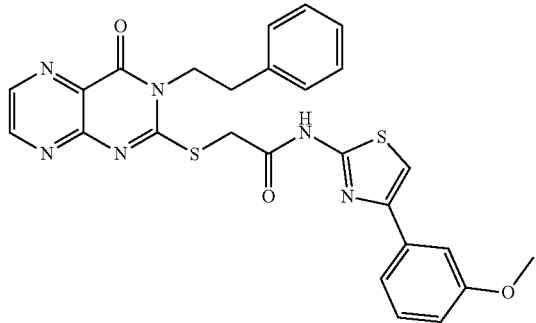
184
-continued
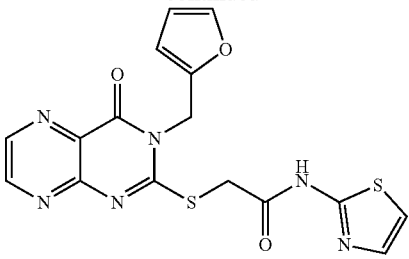
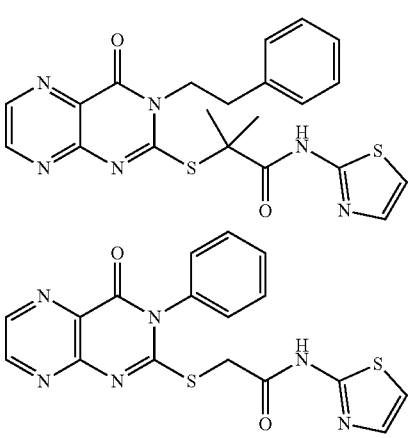
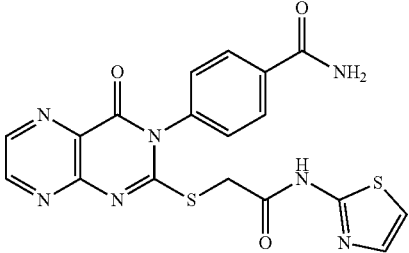
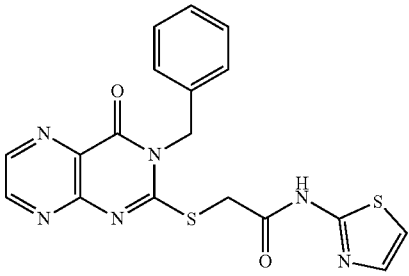
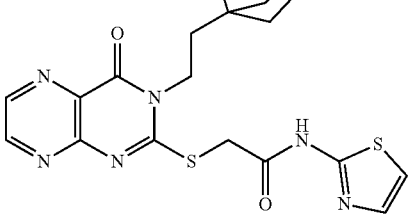

185
-continued
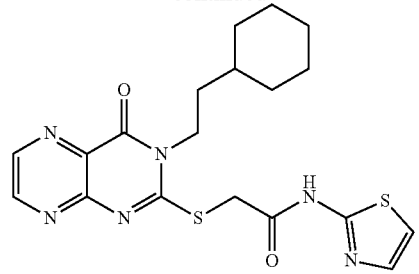
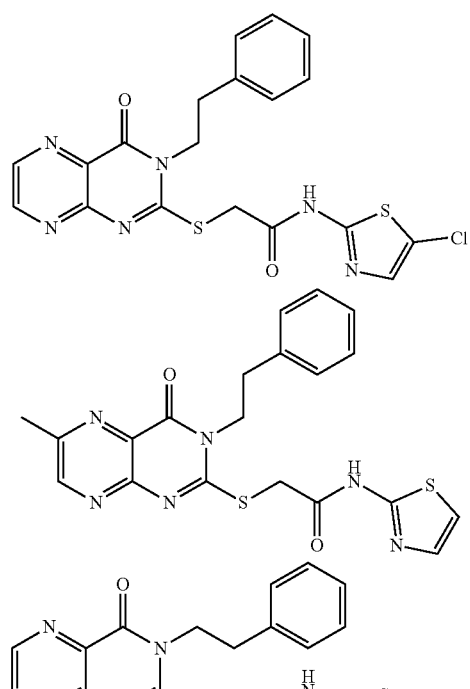
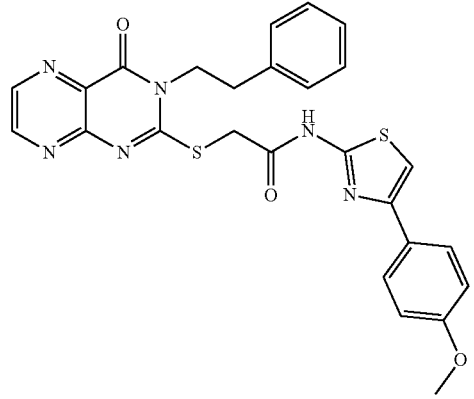
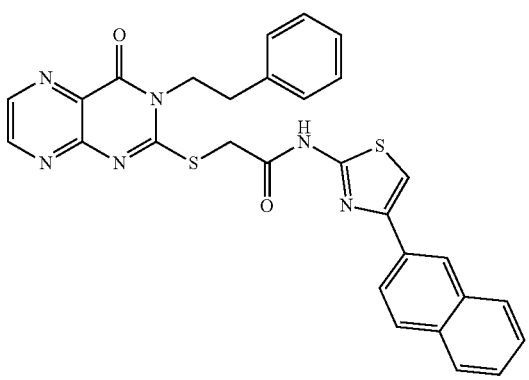
186
-continued
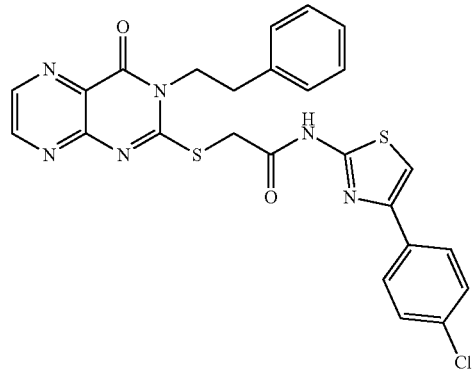
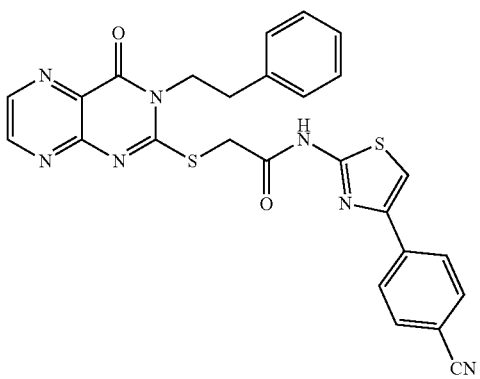
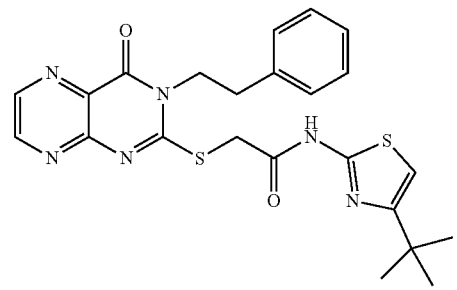
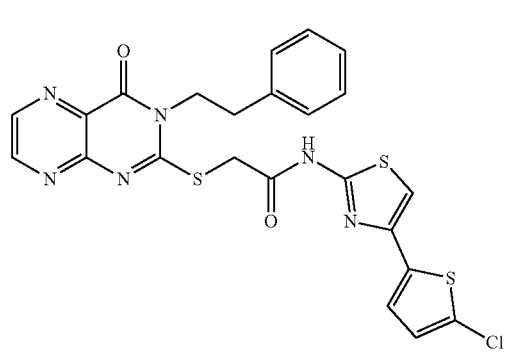

187
-continued
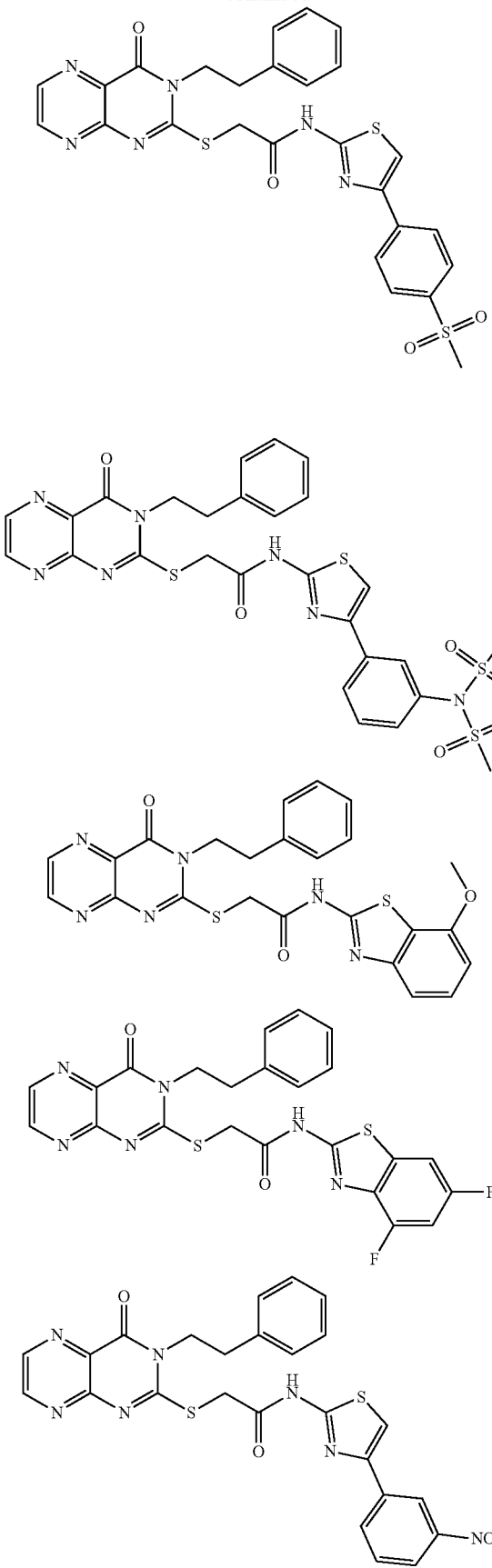
188
-continued
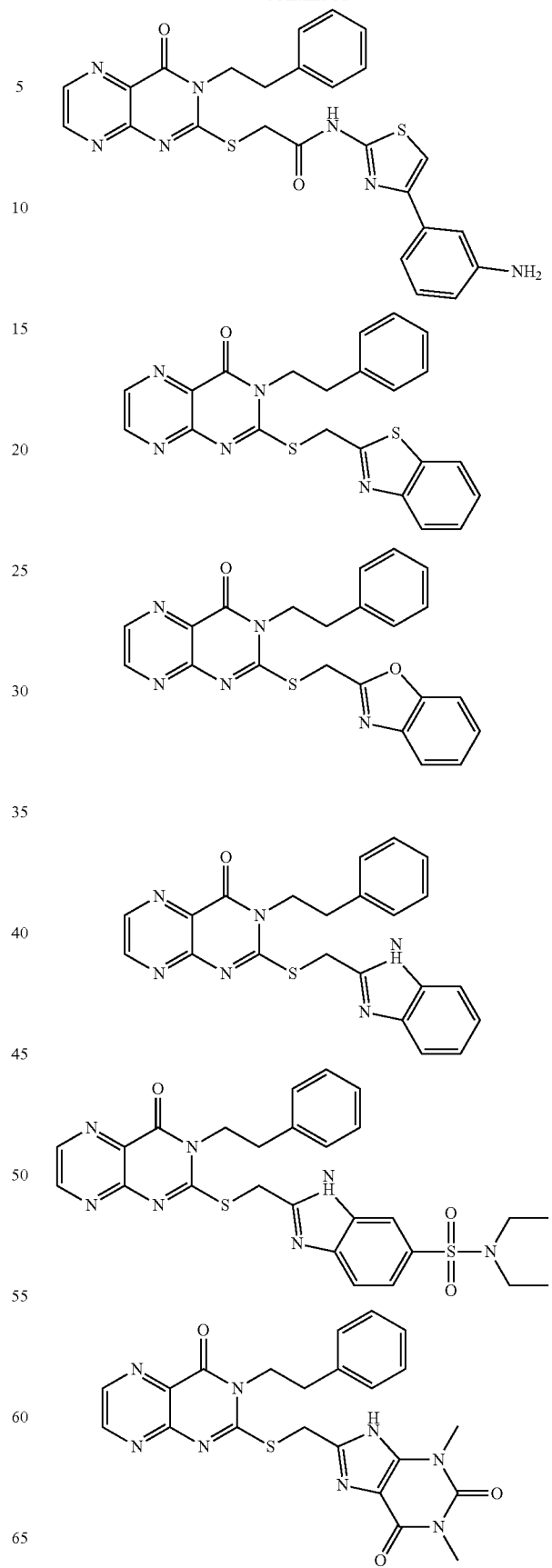

189
-continued
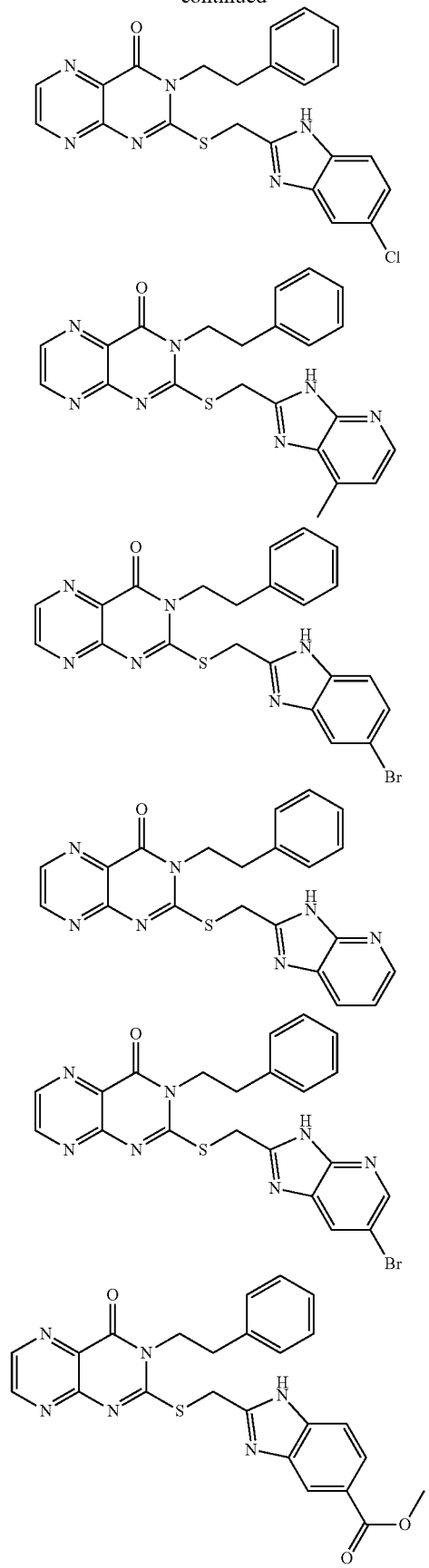
190
-continued
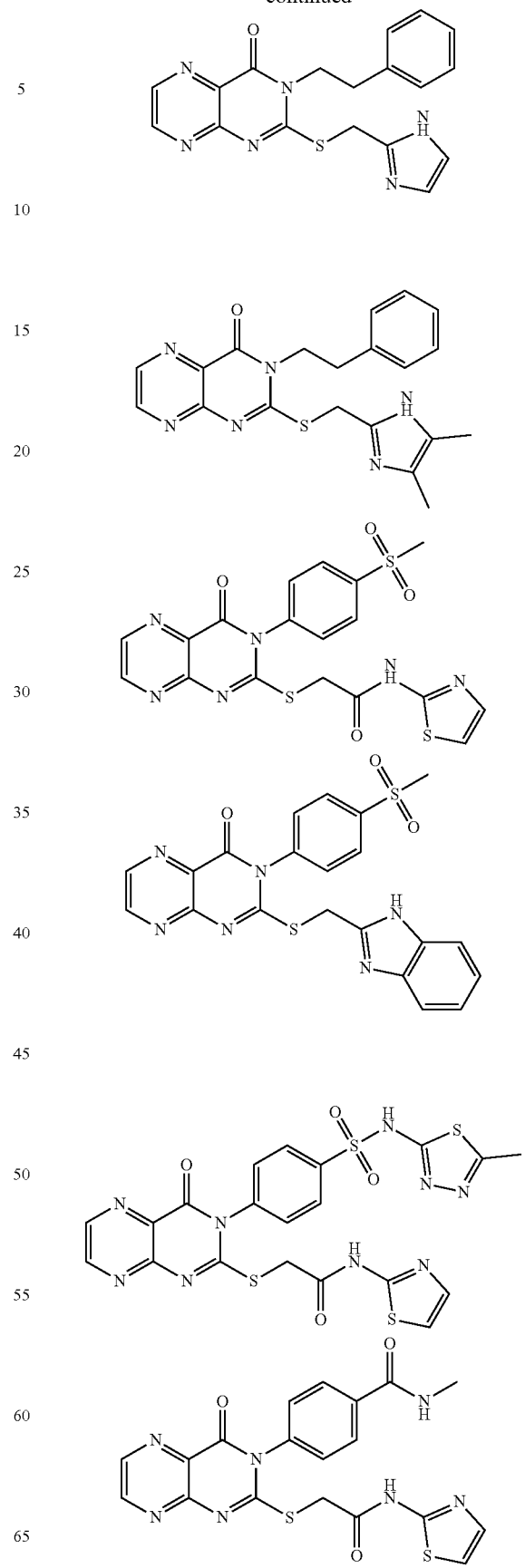

191
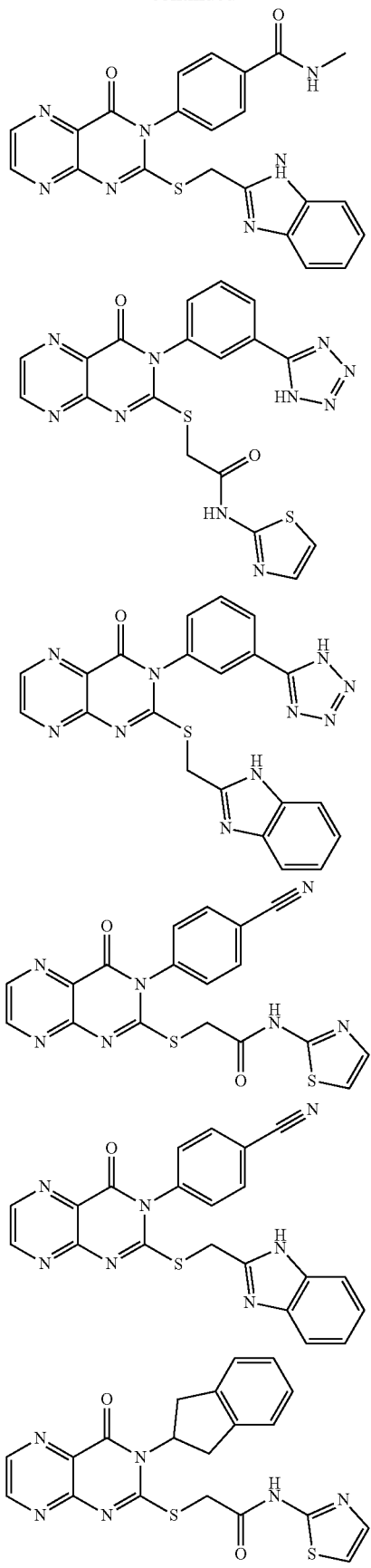
192
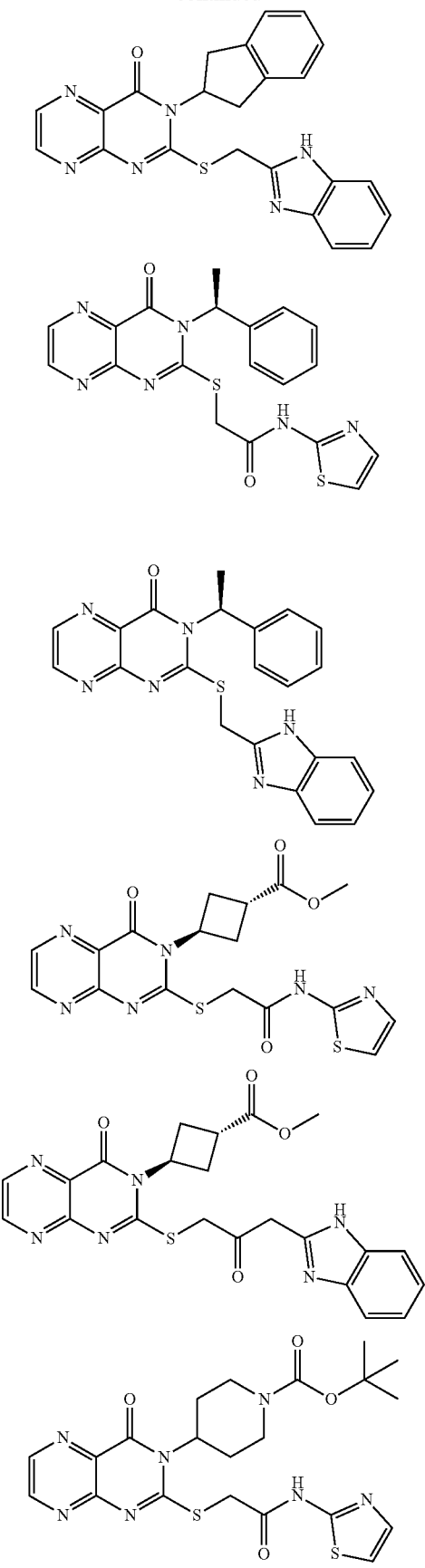

193
-continued

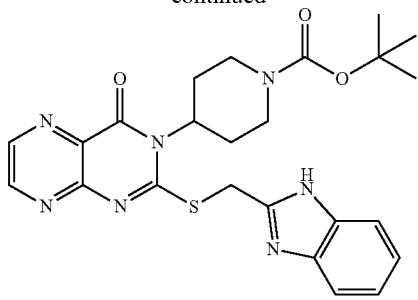

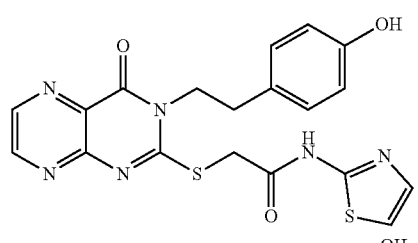

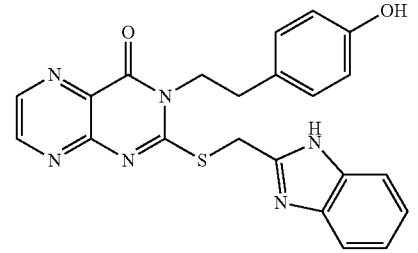

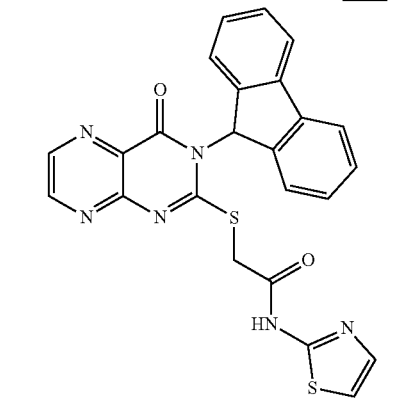

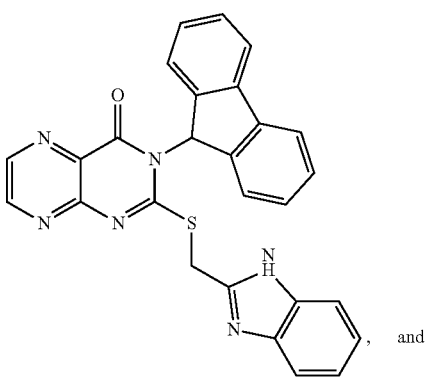
, and

194
-continued

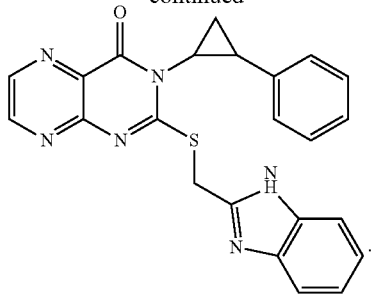

10. A method for inhibiting class II phosphoinositide 3-kinase (PI3K) signaling in a cell, comprising administering a compound according to claim 1, or a composition comprising said compound, to the cell in which PI3K signaling is to be inhibited.

11. The method of claim 10, wherein the cell is in a subject, wherein the subject is treated for a medical condition associated with defective and/or pathologic class II phosphoinositide 3-kinase (PI3K) signaling, and wherein the medical condition is selected from the group consisting of myopathy, a tumor, cancer, diabetes, thrombosis and cardiovascular disease.

12. The method according to claim 11, wherein the compound is according to Formula 2b, Formula 2b

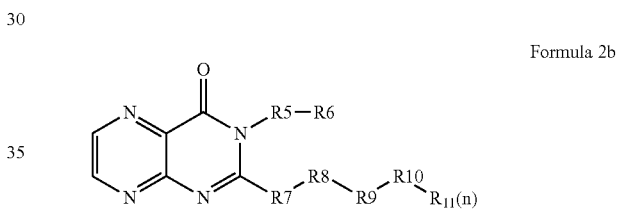

wherein:
R5: absent (covalent bond to R6), C1-C5 alkyl, cycloalkyl, aryl, C1-C5 alkyl-cycloalkyl, C1-C5 alkyl-aryl, or partially saturated bicyclic aryl;
wherein R5 is optionally substituted with one or more halogens, C1-C5 alkyl, C1-C5 haloalkyl, hydroxyl, alkoxy
wherein R5 is optionally substituted with at least two substituents, said two substituents forming R6, attached to adjacent atoms of R5, to form as R6 a 5- to 8-membered saturated, partially unsaturated or aromatic cyclic group comprising said adjacent two atoms of R5;
R6: cycloalkyl, aryl, heterocyclyl, or heteroaryl,
wherein R6 is optionally substituted with one or more halogens, C1-C5 alkyl, C1-C5 haloalkyl, hydroxyl, alkoxy, C2-C10 alkynyl, C3-C8 cycloalkyl, a 5- or 6-membered heterocyclyl or heteroaryl comprising one or more of n, o and/or s, carbonyl, C1-C5 alkyl carboxyester, carboxamide, C1-C5 alkyl carboxamide, primary, secondary or tertiary amine, carbamate, amide amine, nitro, —CN, O, sulfide, amine sulfoxide, sulfonamide amine, sulfoxide, sulfone, sulfonamide haloalkyl, cyano, —OCF$_3$, carbamate, imide, —SF$_3$, —SF$_5$, or sulfonamide, said sulfonamide optionally substituted with a 5- or 6-membered heterocyclyl or heteroaryl, comprising one or more of N, O and/or S, wherein said heteroaryl is optionally substituted with alkyl, R7: S;
R8: C1 alkyl, optionally substituted with C1 alkyl;
R9: absent (covalent bond to R10) or amide;
R10: 5-membered heteroaryl, except for pyrazolyl, or tetrahydrofurfuryl;
wherein optionally a C1-C5 alkyl is positioned between R9 and R10; and
R11 (n): n is 0-5, may be the same or different, halogen, C1-C5 alkyl, CN, C1-C5 haloalkyl, hydroxyl, alkoxy, alkoxycarbonyl, cycloalkyl, aryl, C1-C5 alkyl-cycloalkyl, C1-C5 alkyl-aryl, heterocyclyl, heteroaryl, carboxamide, or C1-C5 alkyl carboxamide;
wherein optionally, two R11 form, together with two carbon atoms of R10 to which they are attached, a 5-, 6-, 7- or 8-membered cyclic residue, comprising two carbon atoms of R10 and optionally further comprising 0, 1, 2, 3 or 4 heteroatoms, said heteroatoms selected independently from nitrogen, sulfur or oxygen, wherein said cyclic residue as R11 is saturated, partially unsaturated or aromatic, and optionally substituted by one or more substituents,
wherein optionally, when R11 is aryl, heterocyclyl or heteroaryl and R11 is substituted with at least two substituents, two substituents of R11 attached to adjacent atoms of R11 form a 5- to 8-membered saturated, partially unsaturated or aromatic cyclic group comprising two atoms of R11 and further comprising 0, 1, 2, 3 or 4 heteroatoms, said heteroatoms selected independently from nitrogen, sulfur or oxygen, wherein said saturated, partially unsaturated or aromatic cyclic group is optionally substituted by one or more of R, wherein R is independently selected from the group consisting of H, alkyl, haloalkyl, alkoxy, or amine, and
wherein R11 is optionally substituted with one or more substituents selected from the group consisting of one or more halogens, C1-C5 alkyl, C1-C5 haloalkyl, hydroxyl, alkoxy, C2-C10 alkynyl, C3-C8 cycloalkyl, carbonyl, C1-C5 alkyl carboxyester, carboxamide, C1-C5 alkyl carboxamide, primary, secondary or tertiary amine, carbamate, amide amine, nitro, —CN, O, sulfide, amine sulfoxide, sulfonamide, alkyl sulfonamide, sulfonamide amine, sulfoxide, sulfone, sulfonamide haloalkyl, —OCF$_3$, carbamate, imide, —SF$_3$, and —SF$_5$.

13. The method according to claim 10, wherein the compound is according to Formula 4a,

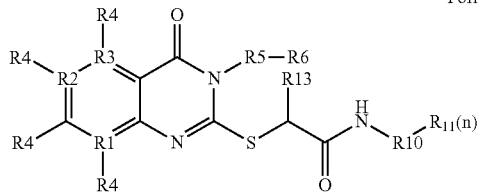

wherein R13: H or CH$_3$, and
R1: N;
R2: C;
R3: N;
R4: can be the same or different, H, halogen, C1-C5 alkyl, C1-C5 haloalkyl, hydroxyl, alkoxy, cycloalkyl, —CN, carbonyl, carboxyl, carboxy ester, alkoxy, aldehyde, trihalide methyl ester, primary, secondary or tertiary amine, amide, imide, carbamate, carboxamide, nitro, sulfide, sulfurtrihalide, sulfurpentahalide, sulfinyl, sulfonyl, sulfino, or sulfo, sulfonamide, or —OCF$_3$;
wherein R4 attached to R1 and R3 is absent;
R5: absent (covalent bond to R6), C1-C5 alkyl, cycloalkyl, aryl, C1-C5 alkyl-cycloalkyl, C1-C5 alkyl-aryl, or partially saturated bicyclic aryl;
wherein R5 is optionally substituted with one or more halogens, C1-C5 alkyl, C1-C5 haloalkyl, hydroxyl, or alkoxy
wherein R5 is optionally substituted with at least two substituents, said two substituents forming R6, attached to adjacent atoms of R5, to form as R6 a 5- to 8-membered saturated, partially unsaturated or aromatic cyclic group comprising said adjacent two atoms of R5;
R6: cycloalkyl, aryl, heterocyclyl, or heteroaryl,
wherein R6 is optionally substituted with one or more halogens, C1-C5 alkyl, C1-C5 haloalkyl, hydroxyl, alkoxy, C2-C10 alkynyl, C3-C8 cycloalkyl, a 5- or 6-membered heterocyclyl or heteroaryl comprising one or more of n, o and/or s, carbonyl, C1-C5 alkyl carboxyester, carboxamide, C1-C5 alkyl carboxamide, primary, secondary or tertiary amine, carbamate, amide amine, nitro, —CN, O, sulfide, amine sulfoxide, sulfonamide amine, sulfoxide, sulfone, sulfonamide haloalkyl, cyano, —OCF$_3$, carbamate, imide, —SF$_3$, —SF$_5$, or sulfonamide, said sulfonamide optionally substituted with a 5- or 6-membered heterocyclyl or heteroaryl comprising one or more of N, O and/or S, wherein said heteroaryl is optionally substituted with alkyl,
R10: 5-membered heteroaryl, except for pyrazolyl, or tetrahydrofurfuryl;
wherein optionally a C1-C5 alkyl is positioned between R9 and R10; and
R11 (n): n is 0-5, may be the same or different, halogen, C1-C5 alkyl, CN, C1-C5 haloalkyl, hydroxyl, alkoxy, alkoxycarbonyl, cycloalkyl, aryl, C1-C5 alkyl-cycloalkyl, C1-C5 alkyl-aryl, heterocyclyl, heteroaryl, carboxamide, or C0-C5 alkyl carboxamide;
wherein optionally, two R11 form, together with two carbon atoms of R10 to which they are attached, a 5-, 6-, 7- or 8-membered cyclic residue, comprising two carbon atoms of R10 and optionally further comprising 0, 1, 2, 3 or 4 heteroatoms, said heteroatoms selected independently from nitrogen, sulfur or oxygen, wherein said cyclic residue as R11 is saturated, partially unsaturated or aromatic, and optionally substituted by one or more substituents,
wherein optionally, when R11 is aryl, heterocyclyl or heteroaryl and R11 is substituted with at least two substituents, two substituents of R11 attached to adjacent atoms of R11 form a 5- to 8-membered saturated, partially unsaturated or aromatic cyclic group comprising two atoms of R11 and further comprising 0, 1, 2, 3 or 4 heteroatoms, said heteroatoms selected independently from nitrogen, sulfur or oxygen, wherein said saturated, partially unsaturated or aromatic cyclic group is optionally substituted by one or more of R, wherein R is independently selected from the group consisting of H, alkyl, haloalkyl, alkoxy, or amine, and
wherein R11 is optionally substituted with one or more substituents selected from the group consisting of one or more halogens, C1-C5 alkyl, C1-C5 haloalkyl, hydroxyl, alkoxy, C2-C10 alkynyl, C3-C8 cycloalkyl, carbonyl, C1-C5 alkyl carboxyester, carboxamide, C1-C5 alkyl carboxamide, primary, secondary or tertiary amine, carbamate, amide amine, nitro, —CN, O, sulfide, amine sulfoxide, sulfonamide, alkyl sulfonamide, sulfonamide amine, sulfoxide, sulfone, sulfonamide haloalkyl, —OCF$_3$, carbamate, imide, —SF$_3$, and —SF$_5$.

14. The method according to claim 11, wherein the compound is according to Formula 6a

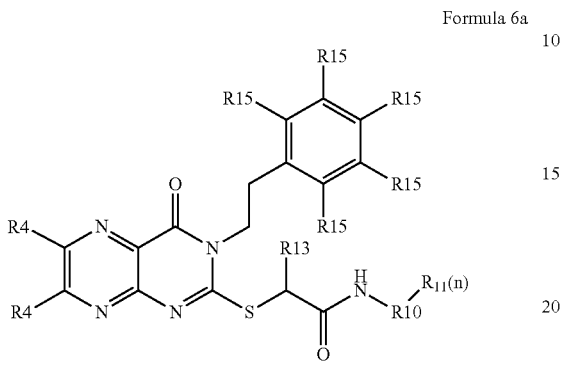

Formula 6a wherein

R4: can be the same or different, H, halogen, C1-C5 alkyl, C1-C5 haloalkyl, hydroxyl, alkoxy, cycloalkyl, —CN, carbonyl, carboxyl, carboxy ester, alkoxy, aldehyde, trihalide methyl ester, primary, secondary or tertiary amine, amide, imide, carbamate, carboxamide, nitro, sulfide, sulfurtrihalide, sulfurpentahalide, sulfinyl, sulfonyl, sulfino, sulfo, sulfonamide, or —OCF$_3$;

R10: 5-membered heteroaryl, except for pyrazolyl, or tetrahydrofurfuryl;

wherein optionally a C1-C5 alkyl is positioned between R9 and R10; and

R11 (n): n is 0-5, may be the same or different, halogen, C1-C5 alkyl, CN, C1-C5 haloalkyl, hydroxyl, alkoxy, alkoxycarbonyl, cycloalkyl, aryl, C1-C5 alkyl-cycloalkyl, C1-C5 alkyl-aryl, heterocyclyl, heteroaryl, carboxamide, or C1-C5 alkyl carboxamide;

wherein optionally, two R11 form, together with two carbon atoms of R10 to which they are attached, a 5-, 6-, 7- or 8-membered cyclic residue, comprising two carbon atoms of R10 and optionally further comprising 0, 1, 2, 3 or 4 heteroatoms, said heteroatoms selected independently from nitrogen, sulfur or oxygen, wherein said cyclic residue as R11 is saturated, partially unsaturated or aromatic, and optionally substituted by one or more substituents, wherein optionally, when R11 is aryl, heterocyclyl or heteroaryl and R11 is substituted with at least two substituents, two substituents of R11 attached to adjacent atoms of R11 form a 5- to 8-membered saturated, partially unsaturated or aromatic cyclic group comprising two atoms of R11 and further comprising 0, 1, 2, 3 or 4 heteroatoms, said heteroatoms selected independently from nitrogen, sulfur or oxygen, wherein said saturated, partially unsaturated or aromatic cyclic group is optionally substituted by one or more of R, wherein R is independently selected from the group consisting of H, alkyl, haloalkyl, alkoxy, or amine, wherein R11 is optionally substituted with one or more substituents selected from the group consisting of one or more halogens, C1-C5 alkyl, C1-C5 haloalkyl, hydroxyl, alkoxy, C2-C10 alkynyl, C3-C8 cycloalkyl, carbonyl, C1-C5 alkyl carboxyester, carboxamide, C1-C5 alkyl carboxamide, primary, secondary or tertiary amine, carbamate, amide amine, nitro, —CN, O, sulfide, amine sulfoxide, sulfonamide, alkyl sulfonamide, sulfonamide amine, sulfoxide, sulfone, sulfonamide haloalkyl, —OCF$_3$, carbamate, imide, —SF$_3$, and —SF$_5$;

R13: H or CH$_3$; and

R15: may be the same or different, H, halogen C1-C5 alkyl, C1-C5 haloalkyl, hydroxyl, alkoxy.

15. The method according to claim 11, comprising administering a pharmaceutical composition to the subject, the composition comprising a pharmaceutically acceptable carrier.

* * * * *